United States Patent [19]
Baker et al.

[11] Patent Number: 6,071,927
[45] Date of Patent: Jun. 6, 2000

[54] SPIRO-PIPERIDINE DERIVATIVES AND THEIR USE AS THERAPEUTIC AGENTS

[75] Inventors: Raymond Baker, Uley; Neil Roy Curtis, Puckeridge; Jason Matthew Elliott, Felsted; Timothy Harrison, Great Dunmow; Gregory John Hollingworth, Brentwood; Philip Stephen Jackson, Grantham; Janusz Jozef Kulagowski, Sawbridgeworth; Eileen Mary Seward, Bishops Stortford; Christopher John Swain, Duxford; Brian John Williams, Great Dunmow, all of United Kingdom

[73] Assignee: Merck Sharp & Dohme Ltd., Hoddesdon, United Kingdom

[21] Appl. No.: 09/202,493

[22] PCT Filed: Jun. 17, 1997

[86] PCT No.: PCT/GB97/01630

§ 371 Date: Dec. 16, 1998

§ 102(e) Date: Dec. 16, 1998

[87] PCT Pub. No.: WO97/49710

PCT Pub. Date: Dec. 31, 1997

[30] Foreign Application Priority Data

Jun. 21, 1996 [GB] United Kingdom .................... 9613108
Dec. 2, 1996 [GB] United Kingdom .................... 9625051
Dec. 20, 1996 [GB] United Kingdom .................... 9626593
Jan. 24, 1997 [GB] United Kingdom .................... 9701459
May 23, 1997 [GB] United Kingdom .................... 9710743
May 23, 1997 [GB] United Kingdom .................... 9710747
May 23, 1997 [GB] United Kingdom .................... 9710748

[51] Int. Cl.$^7$ ........................ A61K 31/435; C07D 211/06
[52] U.S. Cl. .............................................. 514/278; 546/16
[58] Field of Search ................................ 514/278; 546/16

[56] References Cited

FOREIGN PATENT DOCUMENTS

| WO 94/17045 | 8/1994 | WIPO . |
| WO 94/20500 | 9/1994 | WIPO . |
| WO 94/29309 | 12/1994 | WIPO . |
| WO 96/07649 | 3/1996 | WIPO . |
| WO 96/20197 | 7/1996 | WIPO . |
| WO 97/19084 | 5/1997 | WIPO . |

*Primary Examiner*—John Kight
*Assistant Examiner*—Charanjit S. Aulakh
*Attorney, Agent, or Firm*—J. Eric Thies; David L. Rose

[57] ABSTRACT

The present invention relates to certain spiro-piperdine derivatives which are tachykinnin antagonists and are useful, for example, in the treatment or prevention of pain, inflammation, migraine, emesis and postherpetic neuralgia.

24 Claims, No Drawings

SPIRO-PIPERIDINE DERIVATIVES AND THEIR USE AS THERAPEUTIC AGENTS

This application claims priority from PCT/GB97/01630, filed Jun. 17, 1997, now WO97/49710 published Dec. 31, 1997 which claims priority under from Great Britain Application No. 9613108.1, filed Jun. 21, 1996, Great Britain Application No. 9625051.9 filed Dec. 2, 1996, Great Britain Application No. 9626593.9, filed Dec. 20, 1996, Great Britain Application No. 9701459.1, filed Jan. 24, 1997, Great Britain Application No. 9710743.7 filed May 23, 1997, Great Britain Application No. 9710747.8, filed May 23, 1997, and Great Britian Application No. 9710748.6, filed May 23, 1997.

This invention relates to a class of azacyclic compounds which are useful as tachykinin antagonists. More particularly, the compounds of the invention are spiro-substituted azacyclic derivatives.

International (PCT) patent specification no. WO 94/20500 (published Sep. 15, 1994) discloses spiroazacyclic derivatives as substance P antagonists. In particular, WO 94/20500 relates to spirocyclic piperidine derivatives containing a 1,8-diazaspiro[5.5]undecane core.

We have now found a further class of non-peptides which are potent antagonists of tachykinins, especially of substance P. In addition, the compounds of the present invention exhibit a high level of hepatic stability as measured by, for example, conventional liver microsome analysis.

Furthermore, by virtue of their unique cyclopropyl ether moiety, a preferred sub-class of the compounds of the present invention possess a high degree of oral bioavailabilty together with high affinity for the human $NK_1$ receptor.

The present invention provides compounds of the formula (I):

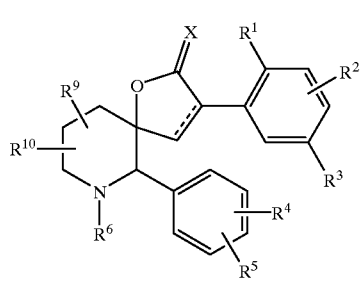

(I)

wherein $R^1$ represents hydrogen hydroxy, $C_{1-6}$alkyl, $C_{2-6}$alkenyl, $C_{3-7}$cycloalkyl, $C_{3-7}$cycloalkylC$_{1-4}$alkyl, $C_{1-6}$alkoxy, fluoroC$_{1-6}$alkoxy, $C_{1-6}$alkoxyC$_{1-4}$alkyl, $C_{1-6}$alkoxyC$_{1-4}$alkoxy, fluoroC$_{1-6}$alkoxyC$_{1-4}$alkyl, $C_{2-6}$alkenyloxy, $C_{3-7}$cycloalkoxy, $C_{3-7}$cycloalkylC$_{1-4}$alkoxy, phenoxy, benzyloxy, cyano, halogen, $NR^aR^a$, $SR^a$, $SOR^a$, $SO_2R^a$, $OSO_2R^a$, $NR^aCOR^{14}$, $COR^a$, $CO_2R^a$ or $CONR^aR^b$ where $R^a$ and $R^b$ each independently represent hydrogen, $C_{1-4}$alkyl or fluoroC$_{1-4}$alkyl;

$R^2$ represents hydrogen, halogen, $C_{1-6}$alkyl or $C_{1-6}$alkoxy;

or when $R^2$ is adjacent to $R^1$, they may be joined together such that there is formed a 5- or 6-membered saturated or unsaturated ring containing one or two atoms selected from nitrogen, oxygen and sulfur, which ring is optionally substituted by a group selected from $C_{1-4}$alkyl, $CF_3$, =O or =S;

$R^3$ represents hydrogen halogen $C_{1-6}$alkyl, fluoroC$_{1-6}$alkyl, $C_{1-6}$alkoxy, fluoroC$_{1-6}$alkoxy, $C_{3-7}$cycloalkyl, $C_{3-7}$cycloalkylC$_{1-4}$alkyl, cyano, $SR^a$, $SOR^a$, $SO_2R^a$, $NR^aR^b$, $NR^aCOR^{14}$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

$R^4$ represents hydrogen, halogen, $C_{1-6}$alkyl, $C_{1-6}$alkoxy, $CF_3$, $OCF_3$, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ are as previously defined;

$R^5$ represents hydrogen, halogen, $C_{1-6}$alkyl, $CF_3$ or $C_{1-6}$alkoxy substituted by $C_{1-4}$alkoxy;

$R^6$ represents hydrogen, $COR^a$, $CO_2R^a$, $COCONR^aR^b$, $COCO_2R^a$, $C_{1-6}$alkyl optionally substituted by a group selected from ($CO_2R^a$, $CONR^aR^b$, hydroxy, CN, $COR^a$, $NR^aR^b$, $C(NOH)NR^aR^b$, $CONHphenyl(C_{1-4}alkyl)$, $COCO_2R^a$, $CONHNR^aR^b$, $C(S)NR^aR^b$, $CONR^aC_{1-6}alkylR^{12}$, $CONR^{13}C_{2-6}$alkenyl, $CONR^{13}C_{2-6}$alkynyl, $COCONR^aR^b$, $CONR^aC(NR^b)NR^aR^b$, $CONR^a$heteroaryl, and phenyl optionally substituted by one, two or three substituents selected from $C_{1-6}$alkyl, $C_{1-6}$alkoxy, halogen and trifluoromethyl);

or $R^6$ represents a group of the formula —CH$_2$C≡CCH$_2$NR$^7$R$^8$ where $R^7$ and $R^8$ are as defined below;

or $R^6$ represents $C_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula $ZNR^7R^8$ where Z is $C_{1-6}$alkylene or $C_{3-6}$cycloalkyl;

$R^7$ is hydrogen or $C_{1-4}$alkyl, $C_{3-7}$cycloalkyl, $C_{3-7}$cycloalkylC$_{1-4}$alkyl, or $C_{2-4}$alkyl substituted by $C_{1-4}$alkoxy or hydroxyl;

$R^8$ is hydrogen or $C_{1-4}$alkyl, $C_{3-7}$cycloalkyl, $C_{3-7}$cycloalkylC$_{1-4}$alkyl, or $C_{2-4}$alkyl substituted by $C_{1-4}$alkoxy, hydroxyl or a 4, 5 or 6 membered heteroaliphatic ring containing one or two heteroatoms selected from N, O and S;

or $R^{7,}$ $R^8$ and the nitrogen atom to which they are attached form a heteroaliphatic ring of 4 to 7 ring atoms, optionally substituted by one or two groups selected from hydroxy or $C_{1-4}$alkoxy optionally substituted by a $C_{1-4}$alkoxy or hydroxyl group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring to 4 to 7 ring atoms which may optionally contain an oxygen ring atom;

$R^9$ and $R^{10}$ each independently represent hydrogen, halogen, $C_{1-6}$alkyl, $CH_2OR^e$, oxo, $CO_2R^a$ or $CONR^aR^b$ where $R^a$ and $R^b$ are as previously defined and $R^e$ represents hydrogen, $C_{1-6}$alkyl or phenyl;

$R^{12}$ represents $OR^a$, $CONR^aR^b$ or heteroaryl;

$R^{13}$ represents hydrogen or $C_{1-6}$alkyl;

$R^{14}$ represents $C_{1-6}$alkyl, $C_{1-6}$alkoxy, fluoroC$_{1-6}$alkyl or phenyl;

X is an oxygen atom or two hydrogen atoms; and the broken line represents an optional double bond; and pharmaceutically acceptable salts thereof.

One particular sub-class of compound of formula (I) is that wherein:

$R^1$ represents $C_{1-6}$alkoxy, fluoroC$_{1-6}$alkoxy, $C_{1-6}$alkoxyC$_{1-4}$alkyl, fluoroC$_{1-6}$alkoxyC$_{1-4}$alkyl, $C_{2-6}$alkenyloxy, $C_{3-7}$cycloalkoxy, phenoxy, benzyloxy, cyano, halogen or $NR^aR^b$, where $R^a$ and $R^b$ each independently represent hydrogen or $C_{1-4}$alkyl;

$R^3$ represents halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl or cyano;

$R^4$ represents hydrogen, halogen, $C_{1-6}$alkyl, $C_{1-6}$alkoxy, $CF_3$, $OCF_3$, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

X is two hydrogen atoms; and
and pharmaceutically acceptable salts thereof.

A preferred class of compound of formula (I) is that wherein $R^1$ is hydroxy, $C_{1-6}$alkyl, $C_{2-6}$alkenyl, $C_{1-6}$alkoxy, fluoro$C_{1-6}$alkoxy, $C_{2-6}$alkenyloxy, $C_{3-7}$cycloalkoxy, $C_{3-7}$cycloalkyl$C_{1-4}$alkoxy, cyano, $NR^aR^b$, $SR^a$, $OSO_2R^a$, or $R^1$ together with the group $R^2$ form a 5-membered saturated ring containing one oxygen atom.

A particularly preferred class of compound of formula (I) is that wherein $R^1$ is a $C_{1-6}$alkoxy, fluoro$C_{1-6}$alkoxy or $C_{3-7}$cycloalkoxy group, especially methoxy, trifluoromethoxy, 2,2,2-trifluoroethoxy, 2,2-difluoroethoxy, 2-fluoroethoxy, cyclopropoxy or cyclobutoxy. Most especially, $R^1$ is methoxy or cyclopropoxy.

A yet further preferred class of compound of the present invention is that wherein $R^1$ is a cyclopropoxy group.

Another preferred class of compound of formula (I) is that wherein $R^2$ is a hydrogen, fluorine or chlorine atom, especially a hydrogen atom.

A further preferred class of compound of formula (I) is that wherein $R^3$ is hydrogen, halogen, fluoro$C_{1-6}$alkyl, fluoro$C_{1-6}$alkoxy, cyano, $NR^aR^b$, or $NR^aCOR^{14}$ (where $R^{14}$ is preferably methyl, methoxy, trifluoromethyl or phenyl).

Also preferred is the class of compound of formula (I) in which $R^3$ is a halogen atom or a fluoro$C_{1-6}$alkoxy group, especially fluorine, trifluoromethoxy or 2,2,2-trifluoroethoxy. Most especially, $R^3$ is trifluoromethoxy.

A further preferred class of compound of formula (I) is that wherein $R^4$ is a hydrogen atom or a fluorine atom.

Another preferred class of compound of formula (I) is that wherein $R^5$ is a hydrogen atom.

A further preferred class of compound of formula (I) is that wherein $R^6$ is a hydrogen atom.

Also preferred is the class of compound of formula (I) in which $R^6$ is a $C_{1-6}$alkyl group, in particular $CH_2$, $CH(CH_3)$ and $CH_3CH_2$ and especially $CH_2$, substituted by a 5-membered heterocyclic ring containing 2 or 3 nitrogen atoms as previously defined.

In particular, the 5-membered ring is a heterocyclic ring selected from:

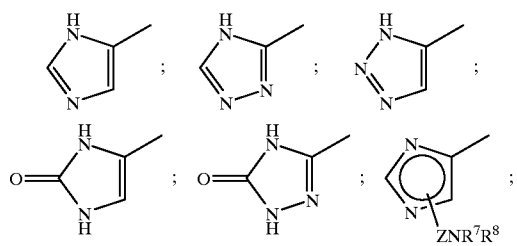

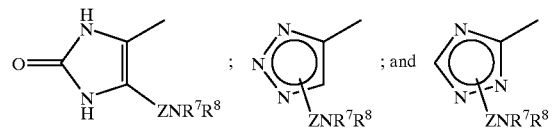

Particularly preferred heterocyclic rings are selected from:

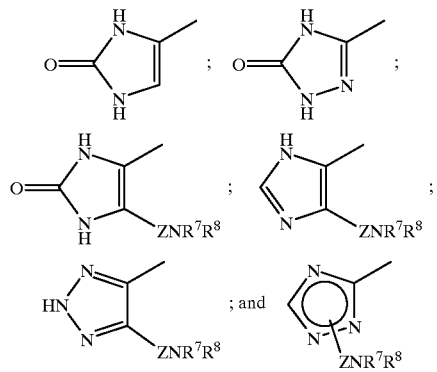

Another preferred class of compound of formula (I) is that wherein one of $R^9$ and $R^{10}$ is hydrogen, and especially wherein $R^9$ and $R^{10}$ are both hydrogen atoms.

A further preferred class of compound of formula (I) is that wherein X represents two hydrogen atoms.

Preferably the double bond represented by the broken line is absent.

One favoured group of compounds of the present invention are of the formula (Ia) and pharmaceutically acceptable salts thereof:

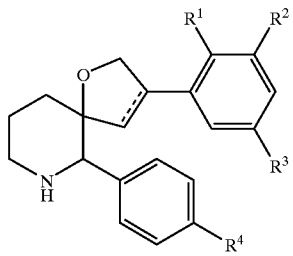

(Ia)

wherein $R^1$, $R^2$, $R^3$, $R^4$ and the broken line are as defined in relation to formula (I).

With respect to compounds of the formula (I), Z (where present), may be a linear, branched or cyclic group. Favourably Z contains 1 to 4 carbon atoms and most favourably 1 or 2 carbon atoms. A particularly favourable group Z is $CH_2$.

With respect to compounds of the formula (I), $R^7$ may aptly be a $C_{1-4}$alkyl group or a $C_{2-4}$alkyl group substituted by a hydroxyl or $C_{1-2}$alkoxy group, $R^8$ may aptly be a $C_{1-4}$alkyl group or a $C_{2-4}$alkyl group substituted by a hydroxyl or $C_{1-2}$alkoxy group, or $R^7$ and $R^8$ may be linked so that, together with the nitrogen atom to which they are attached, they form an azetidinyl, pyrrolidinyl, piperidyl, morpholino, thiomorpholino, piperazino or piperazino group substituted on the nitrogen atom by a $C_{1-4}$alkyl group or a $C_{2-4}$alkyl group substituted by a hydroxy or $C_{1-2}$alkoxy group.

Where the group $NR^7R^8$ represents a heteroaliphatic ring of 4 to 7 ring atoms and said ring contains a double bond, a particularly preferred group is 3-pyrroline.

Where the group $NR^7R^8$ represents a non-aromatic azabicyclic ring system, such a system may contain between 6 and 12, and preferably between 7 and 10, ring atoms. Suitable rings include 5-azabicyclo[2.1.1]hexyl, 5-azabicyclo[2.2.1]heptyl, 6-azabicyclo[3.2.1]octyl, 2-azabicyclo[2.2.2]octyl, 6-azabicyclo[3.2.2]nonyl, 6-azabicyclo[3.3.1]nonyl, 6-azabicyclo[3.2.2]decyl, 7-azabicyclo[4.3.1]decyl, 7-azabicyclo[4.4.1]undecyl and 8-azabicyclo[5.4.1]dodecyl, especially 5-azabicyclo[2.2.1] heptyl and 6-azabicyclo[3.2.1]octyl.

Where $R^8$ represents a $C_{2-4}$alkyl group substituted by a 5 or 6 membered heteroaliphatic ring containing one or two heteroatoms selected from N, O and S, suitable rings include pyrrolidino, piperidino, piperazino, morpholino, or thiomorpholino. Particularly preferred are nitrogen containing heteroaliphatic rings, especially pyrrolidino and morpholino rings.

Particularly suitable moieties $ZNR^7R^8$ include those wherein Z is $CH_2$or azetidinyl, pyrrolidino and morpholino.

In particular, Z is preferably $CH_2$and $NR^7R^8$ is preferably dimethylamino, azetidinyl or pyrrolidino, especially dimethylamino.

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the terms "fluoro$C_{1-6}$alkyl" and "fluoro$C_{1-6}$alkoxy" means a $C_{1-6}$alkyl or $C_{1-6}$alkoxy group in which one or more (in particular 1 to 3) hydrogen atoms have been replaced by fluoro atoms. Similarly, the term "fluoro$C_{1-4}$alkyl" means a $C_{1-4}$alkyl group in which one or more (in particular 1 to 3) hydrogen atoms have been replaced by fluorine atoms. Particularly preferred are fluoro$C_{1-3}$alkyl and fluoro$C_{1-3}$alkoxy groups, for example $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. A suitable cycloalkylalkyl group may be, for example, cyclopropylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is propargyl.

As used herein, the term "heteroaryl" as a group or part of a group means a 5- or 6-membered heteroaromatic ring containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridizinyl, triazolyl, oxadiazolyl, thiadiazolyl, triazinyl, and tetrazolyl.

When used herein the term "halogen" means fluorine, chlorine, bromine and iodine. The most apt halogens are fluorine and chlorine of which fluorine is preferred, unless otherwise stated.

Specific compounds within the scope of this invention include:
(6S,5R)-3-(2-methoxy-5-trifluoromethoxyphenyl)-6-phenyl-1-oxa-7-aza-spiro[4.5]dec-3-ene;
(6S,5R,3S)-3-(2-methoxy-5-trifluoromethoxyphenyl-6-phenyl-1-oxa-7-aza-spiro[4.5]decane;
(±)(6S*,5R*,3S*)-3-(2-methoxy-5-trifluoromethoxyphenyl)-6-phenyl-1-oxa-7-aza-spiro[4.5]decane;
(6S,5R,3S)-3-(2-methoxy-5-trifluoromethoxyphenyl)-6-phenyl-7-(1,2,4-triazolyl-3-methylene)-1-oxa-7-aza-spiro[4.5]decane;
(6S,5R)-3-(2-isopropoxy-5-trifluoromethoxyphenyl)-6-phenyl-1-oxa-7-aza-spiro[4.5]decane;
(6S,5R)-3-(2-allyloxy-5-trifluoromethoxyphenyl)-6-phenyl-1-oxa-7-aza-spiro[4.5]dec-3-ene;
(6S,5R)-3-(5-trifluoromethoxy-2,3-dihydrobenzofuran-7-yl)-6-phenyl-1-oxa-7-aza-spiro[4.5]dec-3-ene;
(6S,5R,3S)-3-(2-isopropoxy-5-trifluoromethoxyphenyl)-6-phenyl-1-oxa-7-aza-spiro[4.5]dec-3-ene;
(6S,5R,3S)-3-(5-trifluoromethoxy-2,3-dihydrobenzofuran-7-yl)-6-phenyl-1-oxa-7-aza-spiro[4.5]decane;
(6S,5R)-3-(2-methoxy-5-(2,2,2-trifluoroethoxy)phenyl)-6-phenyl-1-oxa-7-aza-spiro[4.5]dec-3-ene;
(6S,5R,3S)-3-(2-methoxy-5-(2,2,2-trifluoroethoxy)phenyl)-6-phenyl-1-oxa-7-aza-spiro[4.5]decane;
(6S,5R)-3-(2,5-bis(2,2,2-trifluoroethoxy)phenyl)-6-phenyl-1-oxa-7-aza-spiro[4.5]dec-3-ene;
(6S,5R,3S)-3-(2,5-bis(2,2,2-trifluoroethoxy)phenyl)-6-phenyl-1-oxa-7-aza-spiro[4.5]decane;
(6S,5R,3S)-3-(2-difluoromethoxy-5-trifluoromethoxyphenyl)-6-phenyl-1-oxa-7-aza-spiro[4.5]decane;
(6S,5R)-3-(2-(2,2,2-trifluoroethoxy)-5-trifluoromethoxyphenyl)-6-phenyl-1-oxa-7-aza-spiro[4.5]dec-3-ene;
(6S,5R,3S)-3-(2-(2,2,2-trifluoroethoxy)-5-trifluoromethoxyphenyl)-6-phenyl-1-oxa-7-aza-spiro[4.5]decane;
(6S,5R,3S)-3-(2-(2,2,2-trifluoroethoxy)-5-fluorophenyl)-6-phenyl-1-oxa-7-aza-spiro[4.5]decane;
and pharmaceutically acceptable salts thereof.

Further specific compounds within the scope of this invention include:
(3R,5R,6S)-3-(2-methoxy-5-(trifluoromethoxy)phenyl)-6-phenyl-1-oxa-7-aza-spiro[4.5]decane;
(3R,5R,6S)-7-benzyl-3-(2-methoxy-5-(trifluoromethoxy)phenyl)-6-phenyl-1-oxa-7-aza-spiro[4.5]decane;
(3R,5R,6S)-7-benzyl-3-[2-methoxy-5-(trifluoromethoxy)phenyl]-6-phenyl-1-oxa-7-aza-spiro[4.5]decane;
(3R,5R,6S)-3-(2-methoxy-5-trifluoromethoxyphenyl)-6-phenyl-1-oxa-7-aza-spiro[4.5]decane;
(3R,5R,6S)-3,6-bis(phenyl)-1-oxa-7-aza-spiro[4.5]decane;
(3R,5R,6S)-7-benzyl-3-(2-methoxy-5-trifluoromethoxyphenyl)-6-phenyl-1-oxa-7-aza-spiro[4.5]decane;
(±)-(3R*,5R*,6S*)-3-(2-methoxyphenyl-6-phenyl-1-oxa-7-(phenylmethoxycarbonyl)aza-spiro[4.5]decane;
(3R,5R,6S)-3-(2-methoxyphenyl)-6-phenyl-1-oxa-7-aza-spiro[4.5]decane;
(3R,5R,6S)-3-(2-methoxy-5-trifluoromethoxyphenyl)-6-phenyl-1-oxa-7-(tert-butoxycarbonyl)aza-spiro[4.5]decan-2-one;
and pharmaceutically acceptable salts thereof.

Yet further specific compounds within the scope of this invention include:
(3S,5R,6S)-3-(2-cyclopropoxy-5-(trifluoromethoxy)phenyl)-6-phenyl-1-oxa-7-aza-spiro[4.5]decane;
(3R,5R,6S)-3-[2-cyclopropoxy-5-(trifluoromethoxy)phenyl]-6-phenyl-1-oxa-7-aza-spiro[4.5]decane;
(3S,5R,6S)-3-[2-cyclopropoxy-5-(trifluoromethyl)phenyl]-6-phenyl-1-oxa-7-aza-spiro[4.5]decane;

and pharmaceutically acceptable salts thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I) and (Ia) where the optional double bond is absent will have the stereochemistry of the 3-, 5-, 6-positions that is possessed by the compound of Example 124 (i.e. 3-(S), 5-(R) and 6-(S)). Thus for example as shown in formula (Ib)

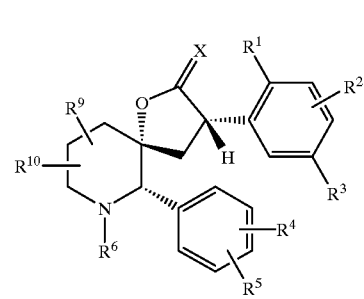

(Ib)

A particularly preferred class of compounds of the formula (I) and (a) where the optional double bond is absent is that with the stereochemistry 3-(R), 5-(R), 6-(S) (e.g. that possessed by the compound of Example 214), i.e. as shown in formula (Ic)

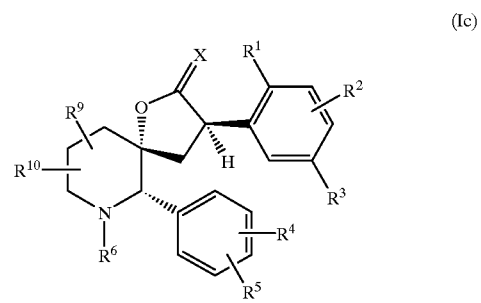

(Ic)

For instance, the 3(R) compound of Example 214 is more potent than its 3(S) epimer, Example 124.

It will be appreciated that the preferred definitions of the various substituents recited herein may be taken alone or in combination, and apply to the generic formula for compounds of the present invention as well as to the preferred classes of compound represented by formula (Ia), formula (Ib) and formula (Ic).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, solutions or suspensions, or suppositories, for oral, perenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethycellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithan) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention further provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity.

Thus, for example, an excess of tachykinin, and in particular substance P, activity is implicated in a variety of disorders of the central nervous system. Such disorders include mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder; anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders; schizophrenia and other psychotic disorders, for example, schizophreniform disorders, schizoaffective disorders, delusional disorders, brief psychotic disorders, shared psychotic disorders and psychotic disorders with delusions or hallucinations; delerium, dementia, and amnestic and other cognitive or neurodegenerative disorders, such as Alzheimer's disease, senile dementia, dementia of the Alzheimer's type, vascular dementia, and other dementias, for example, due to HIV disease, head trauma, Parkinson's disease, Huntington's disease, Pick's disease, Creutzfeldt-Jakob disease, or due to multiple aetiologies; Parkinson's disease and other extra-pyramidal movement disorders such as medication-induced movement disorders, for example, neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremour; substance-related disorders arising from the use of alcohol, amphetamines (or amphetamine-like substances) caffeine, cannabis, cocaine, hallucinogens, inhalants and aerosol propellants, nicotine, opioids, phenylglycidine derivatives, sedatives, hypnotics, and anxiolytics, which substance-related disorders include dependence and abuse, intoxication, withdrawal, intoxication delerium, withdrawal delerium, persisting dementia, psychotic disorders, mood disorders, anxiety disorders, sexual dysfunction and sleep disorders; epilepsy; Down's syndrome; demyelinating diseases such as MS and ALS and other neuropathological disorders such as peripheral neuropathy, for example diabetic and chemotheraphy-induced neuropathy, and postherpetic neuralgia, trigeminal neuralgia, segmental or intercostal neuralgia and other neuralgias; and cerebral vascular disorders due to acute or chronic cerebrovascular damage such as cerebral infarction, subarachnoid haemorrhage or cerebral oedema.

Tachykinin, and in particular substance P, activity is also involved in nociception and pain. The compounds of the present invention will therefore be of use in the prevention or treatment of diseases and conditions in which pain predominates, including soft tissue and peripheral damage, such as acute trauma, osteoarthritis, rheumatoid arthritis, musculo-skeletal pain, particularly after trauma, spinal pain, myofascial pain syndromes, headache, episiotomy pain, and burns; deep and visceral pain, such as heart pain, muscle pain, eye pain, orofacial pain, for example, odontalgia, abdominal pain, gynaecological pain, for example, dysmenorrhoea, and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; pain associated with carcinoma, often referred to as cancer pain; central nervous system pain, such as pain due to spinal cord or brain stem damage; low back pain; sciatica; ankylosing spondylitis, gout; and scar pain.

Tachykinin, and in particular substance P, antagonists may also be of use in the treatment of respiratory diseases, particularly those associated with excess mucus secretion, such as chronic obstructive airways disease, bronchopneumonia, chronic bronchitis, cystic fibrosis and asthma, adult respiratory distress syndrome, and bronchospasm; inflammatory diseases such as inflammatory bowel disease, psoriasis, fibrositis, osteoarthritis, rheumatoid arthritis, pruritis and sunburn; allergies such as eczema and rhinitis; hypersensitivity disorders such as poison ivy; opthalmic diseases such as conjunctivitis, vernal conjunctivitis, and the like; opthalmic conditions associated with cell proliferation such as proliferative vitreoretinopathy; cutaneous diseases such as contact dermatitis, atopic dermatitis, urticaria, and other eczematoid dermatitis.

Tachykinin, and in particular substance P, antagonists may also be of use in the treatment of neoplasms, including breast tumours, neuroganglioblastomas and small cell carcinomas such as small cell lung cancer.

Tachykinin, and in particular substance P, antagonists may also be of use in the treatment of gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcertive colitis, Crohn's disease, irritable bowel syndrome and emesis, including acute, delayed or anticipatory emesis such as emesis induced by chemotherapy, radiation, toxins, viral or bacterial infections, pregnancy, vestibular disorders, for example, motion sickness, vertigo, dizziness and Meniere's disease, surgery, migraine, variations in intercranial pressure, gastro-oesophageal reflux disease, acid indigestion, over indulgence in food or drink, acid stomach, waterbrash or regurgitation, heartburn, for example, episodic, nocturnal or meal-induced heartburn, and dyspepsia.

Tachykinin, and in particular substance P, antagonists may also be of use in the treatment of a variety of other conditions including stress related somatic disorder; reflex sympathetic dystrophy such as shoulder/hand syndrome; adverse immunological reactions such as rejection of transplanted tissues and disorders related to immune enhancement or suppression such as systemic lupus erythematosus; plasma extravasation resulting from cytokine chemotherapy, disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, vascular headache, migraine and Reynaud's disease; and pain or nociception attributable to or associated with any of the foregoing conditions, especially the transmission of pain in migraine.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed or anticipatory emesis, such as emesis induced by chemotherapy, radiation, toxins, pregnancy, vestibular disorders, motion, surgery, migraine, and variations in intercranial pressure. Most especially, the compounds of formula (I) are of use in the treatment of emesis induced by antineoplastic (cytotoxic) agents, including those routinely used in cancer chemotherapy, and emesis induced by other pharmacological agents, for example, rolipram.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in *Nausea and Vomiting: Recent Research and Clinical Advances*, Eds. J. Kucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, belomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT3 antagonist, such as ondanestron, granisetron or tropisetron, or other anti-emetic medicaments, for example, a dopamine antagonist such as metoclopramide or domperidone or GABAB receptor agonists such as baclofen. Additionally, a compound of formula (I), either alone or in combination with one or more other anti-emetic therapeutic agents, may be administered in combination with an anti-inflammatory corticosteroid, such as dexamethasone, betamethasone, triamcinolone, triamcinolone acetonide, flunisolide, budesonide, or others such as those disclosed in U.S. Pat. Nos. 2,789,118, 2,990,401, 3,048,581, 3,126,375, 3,929, 768, 3,996,359, 3,928,326 and 3,749,712. Desamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. Pharmacol.*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis and headache, including migraine, acute or chronic tension headache, cluster headache, temporomandibular pain, and maxillary sinus pain.

The compounds of formula (I) are also particularly useful in the treatment of depression including depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobia; seasonal affective disorder; or bipolar disorders or manic depression, for example, bipolar I disorder, bipolar II disorder and cyclothymic disorder.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the treatment or prevention of physiological disorders associated with an excess of tachykinins, especially substance P, which method comprises administration to a patient in need thereof of a tachykinin reducing amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination. Thus, for example, for the treatment of respiratory diseases such as asthma, a compound of formula (I) may be used in conjunction with a bronchodilator, such as a $\beta_2$-adrenergic receptor agonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D4 antagonist such as a compound selected from those disclosed in European patent specification nos. 0 480 717 and 0 604 114 and in U.S. Pat. Nos. 4,859,692 and 5,270,324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT1 agonists, especially sumatriptan, naratriptan, zolmatriptan or rizatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an anti-inflammatory agent such as a bradykinin receptor antagonist.

The present invention also provides a composition comprising a compound of formula (I), a bronchodilator, and a pharmaceutically acceptable carrier.

It will be appreciated that for the treatment or prevention of pain or nociception, a compound of the present invention may be used in conjunction with other analgesics, such as acetaminophen (paracetamol), aspiring and other NSAIDs and, in particular, opioid analgesics, especially morphine. Specific anti-inflammatory agents include diclofenac, ibuprofen, indomethacin, ketoprofen, naproxen, piroxicam and sulindac. Suitable opioid analgesics of use in conjunction with a compound of the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof. Preferred salts of these opioid analgesics include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of pain or nociception.

It will be appreciated that for the treatment of depression or anxiety, a compound of the present invention may be used in conjunction with other anti-depressant or anti-anxiety agents.

Suitable classes of anti-depressant agent include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical anti-depressants.

Suitable norepinephrine reuptake inhibitors include tertiary amine tricyclics and secondary amine tricyclics. Suitable examples of tertiary amine tricyclics include:

amitriptyline, clomipramine, doxepin, imipramine and trimipramine, and pharmaceutically acceptable salts thereof. Suitable examples of secondary amine tricyclics include: amoxapine, desipramine, maprotiline, nortriptyline and protriptyline, and pharmaceutically acceptable salts thereof.

Suitable selective serotonin reuptake inhibitors include: fluoxetine, fluvoxamine, paroxetine and sertraline, and pharmaceutically acceptable salts thereof.

Suitable monoamine oxidase inhibitors include: isocarboxazid, phenelzine, tranylcypromine and selegiline, and pharmaceutically acceptable salts thereof.

Suitable reversible inhibitors of monoamine oxidase include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists include those compounds described in International Patent Specification Nos. WO 94/13643, WO 94/13644, WO 94/13661, WO 94/13676 and WO 94/13677.

Suitable atypical anti-depressants include: bupropion, lithium, nefazodone, trazodone and viloxazine, and pharmaceutically acceptable salts thereof.

Suitable classes of anti-anxiety agent include benzodiazepines and 5-HT1A agonists or antagonists, especially 5-HT1A partial agonists, and corticotropin releasing factor (CRF) antagonists.

Suitable benzodiazepines include: alprazolam, chlordiazepoxide, clonazepam, chlorazepate, diazepam, halazepam, lorazepam, oxazepam and prazepam, and pharmaceutically acceptable salts thereof.

Suitable 5-HT1A receptor agonists or antagonists include, in particular, the 5-HT1A receptor partial agonists buspirone, flesinoxan, gepirone and ipsapirone, and pharmaceutically acceptable salts thereof.

Therefore, in a further aspect of the present invention, there is provided a pharmaceutical composition comprising a compound of the present invention and an anti-depressant or anti-anxiety agent, together with at least one pharmaceutically acceptable carrier or excipient.

In a further or alternative aspect of the present invention, there is provided a product comprising a compound of the present invention and an anti-depressant or anti-anxiety agent as a combined preparation for simultaneous, separate or sequential use for the treatment or prevention of depression and/or anxiety.

It will be appreciated that for the treatment or prevention of eating disorders, including obesity, bulimia nervosa and compulsive eating disorders, a compound of the present invention may be used in conjunction with other anorectic agents.

The present invention accordingly provides the use of a compound of formula (I) and an anorectic agent for the manufacture of a medicament for the treatment or prevention of eating disorders.

The present invention also provides a method for the treatment or prevention of eating disorders, which method comprises administration to a patient in need of such treatment an amount of a compound of formula (I) and an amount of an anorectic agent, such that together they give effective relief.

In a further aspect of the present invention, there is provided a pharmaceutical composition comprising a compound of formula (I) and an anorectic agent, together with at least one pharmaceutically acceptable carrier or excipient.

It will be appreciated that the compound of formula (I) and anorectic agent may be present as a combined preparation for simultaneous, separate or sequential use for the treatment or prevention of eating disorders. Such combined preparations may be, for example, in the form of a twin pack.

In a further or alternative aspect of the present invention, there is therefore provided a product comprising a compound of formula (I) and an anorectic agent as a combined preparation for simultaneous, separate or sequential use in the treatment or prevention of eating disorders.

In a further embodiment of the present invention there is provided the use of a compound of formula (I) and an anorectic agent for the manufacture of a medicament for the treatment or prevention of obesity.

The present invention also provides a method for the treatment or prevention of obesity, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for the treatment or prevention of bulimia nervosa.

The present invention also provides a method for the treatment or prevention of bulimia nervosa, which method comprises administration to a patient in need of such treatment an amount of a compound of formula (I) and an amount of an anorectic agent, such that together they give effective relief.

In a further embodiment of the present invention there is provided the use of a compound of formula (I) and an anorectic agent for the manufacture of a medicament for the treatment or prevention of compulsive eating disorders.

The present invention also provides a method for the treatment or prevention of compulsive eating disorders, which method comprises administration to a patient in need of such treatment an amount of a compound of formula (I) and an amount of an anorectic agent, such that together they give effective relief.

In an alternative embodiment of the present invention there is provided the use of a compound of formula (I) and an anorectic agent for the manufacture of a medicament for reducing the total body fat mass in an obese mammal, especially a human.

The present invention also provides a method for reducing the total body fat mass in an obese mammal, especially a human, which method comprises administration to a patient in need of such treatment an amount of a compound of formula (I) and an amount of an anorectic agent, such that together they give effective relief.

Suitable anoretic agents of use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

Particularly preferred anorectic agents include amphetamine and derivatives thereof such as amphetamine, benzphetamine, chlorphentermine, clobenzorex, cloforex, clotermine, dexfenfluramine, dextroamphetamine, diethylpropion, N-ethylamphetamine, fenfluramine, fenproporex, furfurylmethylamphetamine, levamfetamine, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof.

A particularly suitable class of anorectic agent are the halogenated amphetamine derivatives, including chlorphentermine, cloforex, clortermine, dexfenfluramine, fenfluramine, picilorex and sibutramine; and pharmaceutically acceptble salts thereof;

Particularly preferred halogenated amphetamine derivatives of use in combination with a compound of the present invention include: fenfluramine and dexfenfluramine, and pharmaceutically acceptable salts thereof.

It will be appreciated that for the treatment or prevention of obesity, the compounds of the present invention may also be used in combination with a selective serotonin reuptake inhibitor (SSRI).

The present invention accordingly provides the use of a compound of formula (I) and an SSRI for the manufacture of a medicament for the treatment or prevention of obesity.

The present invention also provides a method for the treatment or prevention of obesity, which method comprises administration to a patient in need of such treatment an amount of a compound of formula (I) and an amount of an SSRI, such that together they give effective relief.

In a further aspect of the present invention, there is provided a pharmaceutical composition for the treatment or prevention of obesity comprising a compound of formula (I) and an SSRI, together with at least one pharmaceutically acceptable carrier or excipient.

It will be appreciated that the compound of formula (I) and SSRI may be present as a combined preparation for simultaneous, separate or sequential use for the treatment or prevention of obesity. Such combined preparations may be, for example, in the form of a twin pack.

In a further or alternative aspect of the present invention, there is therefore provided a product comprising a compound of formula (I) and an SSRI as a combined preparation for simultaneous, separate or sequential use in the treatment or prevention of obesity.

In an alternative embodiment of the present invention, there is provided the use of a compound of formula (I) and an SSRI for the manufacture of a medicament for reducing the total body fat mass in an obese mammal, especially a human.

The present invention also provides a method for reducing the total body fat mass in an obese mammal, especially a human, which method comprises administration to the mammal an amount of a compound of formula (I) and an amount of an SSRI, such that together they give effective relief.

In a further aspect of the present invention, there is provided a pharmaceutical composition for reducing the total body fat mass in an obese mammal especially a human, comprising a compound of formula (I) and an SSRI, together with at least one pharmaceutically acceptable carrier or excipient.

Suitable selective serotonin reuptake inhibitors of use in combination with a compound of the present invention include: fluoxetine, fluvoxamine, paroxetine and sertraline, and pharmaceutically acceptable salts thereof.

As used herein "obesity" refers to a condition whereby a mammal has a Body Mass Index (BMI), which is calculated as weight per height squared ($kg/m^2$), of at least 25.9. Conventionally, those persons with normal weight, have a BMI of 19.9 to less than 25.9.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetes, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia.

"Treatment" (of obesity) refers to reducing the BMI of the mammal to less than about 25.9, and maintaining that weight for at least 6 months. The treatment suitably results in a reduction in food or calorie intake by the mammal.

"Prevention" (of obesity) refers to preventing obesity from occurring if the treatment is administered prior to the onset of the obese condition. Moreover, if treatment is commenced in already obese subjects, such treatment is expected to prevent, or to prevent the progression of, the medical sequelae of obesity, such as, e.g., arteriosclerosis, Type II diabetes, polycystic ovarian disease, cardiovascular diseases, osteroarthritis, dermatological disorder, hypertension, insulin resistance, hypercholesterolemia, hypertriglyceridemia, and cholelithiasis.

Thus, in one aspect, this invention relates to the inhibition and/or complete suppression of lipogenesis in obese mammals, i.e., the excessive accumulation of lipids in fat cells, which is one of the major features of human and animal obesity, as well as loss of total body weight. In another aspect, the invention ameliorates the conditions that are a consequence of the disease, such as preventing or arresting the progression of polycystic ovarian disease so that the patient is no longer infertile, and increasing the insulin sensitivity and/or decreasing or eliminating the need or usage of insulin in a diabetic patient, e.g., one with adult-onset diabetes or Type II diabetes.

A further aspect of the present invention comprises the use of a compound of formula (I) for achieving a chronobiologic (circadian rhythm phase-shifting effect and alleviating circadian rhythm disorders in a mammal. The present invention is further directed to the use of a compound of formula (I) for blocking the phase-shifting effects of light in a mammal.

The present invention further relates to the use of a compound of formula (I) for enhancing or improving sleep quality, in particular by increasing sleep efficiency and augmenting sleep maintenance, as well as for preventing and treating sleep disorders and sleep disturbances, in a mammal.

In a preferred embodiment, the present invention provides a method for the phase advance or phase delay in the circadian rhythm of a subject which comprises administering to the subject an appropriate amount of a compound of formula (I) or a pharmaceutically acceptable salt thereof.

The administration to a subject of an appropriate amount of a compound of formula (I) is useful, for example, in the prevention or treatment of the following conditions to achieve chronobiologic effects and/or to alleviate circadian rhythm phase disturbances: disorders of the sleep-wake schedule; jet lag; shift work; people who have a maladaption to work and off-work schedules; medical residents, nurses, firemen, policemen or those whose duties require alertness and wakefulness at evening or nighttime hours, or those deprived of sleep for various periods because of their duties or responsibilities; animal workers; the infantry, or other members of the armed forces whose duties require extreme levels of alertness and wakefulness, and those who may be sleep deprived in the performance of these duties; submariners, or people confined for research, exploration or industrial purposes below the seas; miners, spelunkers, researchers or those confined beneath the Earth; astronauts in orbit around the Earth, on missions in space to the Earth's moon or to the planets or out of the solar system, or in training for such missions; the blind or sight-impaired or those persons whose ability to distinguish differences in light and dark may be permanently or temporarily impaired; psychiatric patients; insomniacs; the comatose, or those who need to be maintained in a state of unconsciousness for medical, psychiatric or other reasons; residents of the far North or Antartica, or those persons who live in a climate or climates which possess abnormal amounts of light or darkness; those suffering from seasonal affective disorder (SAD), winter depression, or other forms of depression; the aged; Alzheimer's disease patients, or those suffering from other forms of dementia; patients who require dosages of medication at appropriate times in the circadian cycles; patients suffering from delayed sleep phase syndrome, advanced sleep phase syndrome, or non-24 hour sleep phase syndrome; and patients suffering from primary or secondary insomina or circadian rhythm-related insomnia. The present invention is useful, for example, in the prevention or treatment of conditions associated with circadian rhythmicity as well as mental and physical disorders associated with travel across time zones and with rotating shift-work schedules.

In a preferred embodiment, the present invention provides a method for the prevention or treatment of a circadian rhythm disorder in a mammal, including time-zone change (jet-lag) syndrome, shift-work sleep disorder, delayed sleep-phase syndrome, advanced sleep-phase syndrome, and non-24-hour sleep-wake wake disorder, which comprises administering to the mammal an effective amount of a compound of formula(I) or a pharmaceutically acceptable salt thereof.

In another preferred embodiment, the present invention provides a method for shortening the time of reintrainment of circadian rhythms in a subject following a shift in the sleep-wake cycle which comprises administering to the subject an appropriate amount of a compound of formula (I) or a pharmaceutically acceptable salt thereof.

In a more preferred embodiment, the present invention provides a method for alleviating the effects of jet lag in a traveller, especially a mammal, which comprises administering to the traveller an alertness increasing amount of a compound of formula (I) or a pharmaceutically acceptable salt thereof. The purpose of this embodiment is to assist the body to adjust physiologically to the changes in sleep and feeding patterns when crossing several time zones.

In another more preferred embodiment, the present invention provides a method for resetting the internal circadian clock in a subject, for example shift workers changing from a day to a night shift or vice versa, which comprises administering to the subject an appropriate amount of a compound of formula (I) or a pharmaceutically acceptable salt thereof.

The present invention is further directed to the use of a compound of formula (I) or a pharmaceutically acceptable salt thereof, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a compound of formula (I) or a pharmaceutically acceptable salt thereof. The present invention is useful for the treatment of sleep disorders, including Disorders of Initiating and Maintaining Sleep (insomnias) ("DIMS") which can arise from psychophysiological causes, as a consequence of psychiatric disorder (particularly related to anxiety), from drugs and alcohol use and abuse (particularly during withdrawal states), childhood onset DIMS, nocturnal myoclonus and restless legs and non specific REM disturbances as seen in ageing.

The following outcomes in a subject which are provided by the present invention may be correlated to enhancement in sleep quality: an increase in the value which is calculated from the time that a subject sleeps divided by the time that a subject is attempting to sleep; a decrease in sleep latency (the time it takes to fall asleep); a decrease in the number of awakenings during sleep; a decrease in the time spent awake following the initial onset of sleep; an increase in the total amount of sleep; an increase the amount and percentage of REM sleep; an increase in the duration and occurrence of REM sleep; a reduction in the fragmentation of REM sleep; an increase in the amount and percentage of slow-wave (i.e. stage 3 or 4) sleep; an increase in the amount and percentage of stage 2 sleep; a decrease in the number of awakenings, especially in the early morning; an increase in daytime alertness; and increased sleep maintenance. Secondary outcomes which may be provided by the present invention include enhanced cognitive function and increased memory retention.

The present invention is further useful for the prevention and treatment of sleep disorders and sleep disturbances including sleep problems associated with insomnia, hypersomnia, sleep apnea, narcolepsy, nocturnal myoclonus, REM sleep interruptions, jet-lag, shift workers' sleep disturbances, dysomnias, night terror, insomnias associated with depression or with emotional/mood disorders, dysfunctions associated with sleep (parasomnias), as well as sleep walking and enuresis, as well as sleep disorders which accompany aging. Sleep disorders and sleep disturbances are generally characterized by difficulty in initiating or maintaining sleep or in obtaining restful or enough sleep.

In addition, certain drugs may also cause reductions in REM sleep as a side effect and the present invention may be used to correct those types of sleeping disorders as well. The present invention would also be of benefit in the treatment of syndromes such as fibromyalgia which are manifested by non-restorative sleep and muscle pain or sleep apnea which is associated with respiratory disturbances during sleep. It will be clear to one skilled in the art that the present invention is not limited to just sleep disorders and sleep disturbances, but it applicable to a wide variety of conditions which result from a diminished quality of sleep.

The compounds of formula (I) may be used alone or in combination with other agents which are known to be beneficial in altering circadian rhythms or in the enhancement of sleep efficiency. For example, the compounds of formula (I) may be administered in conjunction with other compounds which are known in the art to be useful for suppressing or stimulating melatonin production including melatonergic agents, noradrenergic and serotonergic re-uptake blockers, alpha-1-noradrenergic agonist, monamine oxidase inhibitors, beta-adrenergic blockers and benzodiazepines, such as atenolol; or with other compounds which are known in the art to be useful for stimulating melatonin production including tricyclic antidepressants and alpha-2-adrenergic antagonists; or with melatonin precursors such as tryptophan, 5-hydroxytryptophan, serotonin and N-acetylserotonin; as well as melatonin analogues, melatonin agonists and melatonin antagonists. In addition, the compounds of formula (I) may be administered in conjunction with other compounds which are known in the art to be useful for enhancing sleep quality and preventing and treating sleep disorders and sleep disturbances, including e.g., sedative, hypnotics, anxiolytics, antipsychotics, antianxiety agents, minor tranquilizers, melatonin agonists and antagonists, melatonin, melatonergic agents, benzodiazepines, barbituates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, valproate, venlafaxine, zaleplon, zolazepam, zolpidem, and salts thereof, and combinations thereof, and the like.

The compounds of formula (I) may be administered in conjunction with the use of physical methods such as with light therapy or electrical stimulation. In particular, the compounds of formula (I) may be administered in conjunction with scheduling bright light administration, ordinary-intensity light exposure, or exposure to dim-light or darkness (or even sleep). In one embodiment of the present invention, the compound of formula (I) is administered accompanied by having an individual wear dark or red goggles at the time of administration to provide additive effects of the treatment plus darkness. In another embodiment of the present invention, the individual wears dark goggles at times other than the time of administration of the compound of formula (I) to avoid the occurrence of an external zeitgeber with respect to the phase shift resulting from the compound of formula (I). Similarly, bright light exposure can be used in conjunction with administration of a compound of formula (I).

Accordingly, the present invention further includes within its scope the use of a compound of formula (I), alone or in combination with other agents, for altering circadian rhythms or for the prevention or treatment of sleep disorders and sleep disturbances in a mammal.

As used herein the term "mammals" includes animals of economic importance such as bovine, ovine, and porcine animals, especially those that produce meat, as well as domestic animals, sports animals, zoo animals, and humans, the latter being preferred.

It will be appreciated that when using any combination described herein, both the compound of formula (I) and the other active agent(s) will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, one active component may be administered as a tablet and then, within a reasonable period of time, the second active component may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the first active component is provided as a table, then within one hour, the second active component should be administered, either in the same type of dosage form, or another dosage form which provides effective delivery of the medicament.

The excellent pharmacological profile of the compounds of the present invention offers the opportunity for their use in therapy at low doses thereby minimising the risk of unwanted side effects.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regiment of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to a general process (A.1) compounds of formula (I), wherein the double bond represented by the broken line is absent, may be prepared by the reduction of a corresponding compound of formula (I) in which the broken line represents a double bond, hereinafter referred to as formula (IIA)

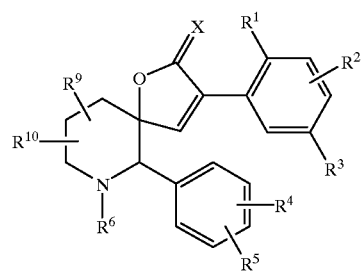

(IIA)

wherein $R^1$, $R^2$, $R^3$, $R^4$, $R^5$, $R^6$, $R^9$, $R^{10}$ and X are as defined in relation to formula (I).

Suitable reducing conditions include: catalytic hydrogenation using a metal catalyst such as palladium or platinum or hydroxides or oxides thereof, preferably in a suitable solvent such as alcohol, e.g. methanol or ethanol, or an ester, e.g. ethyl acetate, or an organic acid e.g. acetic acid, or a mixture thereof; or reduction using trifluoroacetic acid and triethylsilane.

Similarly, according to a general process (A.2), compounds of formula (I) wherein the double bond represented by the broken line is absent and X is two hydrogen atoms, may be prepared by the reduction of a compound of formula (IIB)

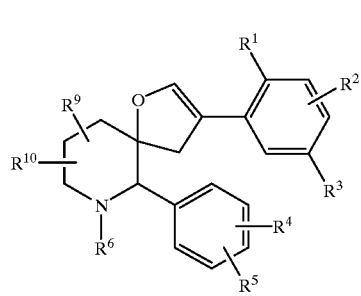

(IIB)

using the reaction conditions described in process (A.1), above.

According to another general process (B), compounds of formula (I) in which the broken line represents a double bond, (i.e. a compound of formula (IIA), above), may be prepared by the reaction of a compound of formula (III)

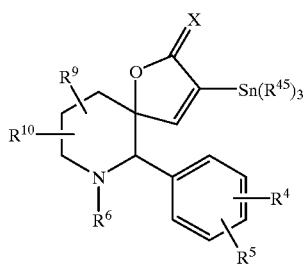

(III)

wherein each $R^{45}$ is a $C_{1-4}$alkyl group, preferably methyl or n-butyl groups, with a compound of formula (IV)

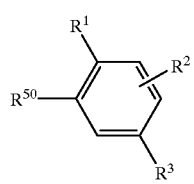

(IV)

wherein $R^{50}$ is a leaving group such as triflate (—$OSO_2CF_3$) or a halogen atom, for example, chlorine, bromine or iodine, especially triflate, bromine or iodine.

The reaction is conveniently effected in the presence of lithium chloride and a transition metal catalyst such as triphenylphosphine palladium (0). Suitable solvents for the reaction include an aromatic hydrocarbons, for example, toluene, polar aprotic solvents, for example, dimethylformamide, or ethers, for example, dioxan, the reaction being effected at a temperature between 80° C. and the reflux temperature of the solvent.

According to another general process (C), compounds of formula (I) may be prepared by the interconversion of a corresponding compound of formula (I) in which $R^6$ is H, hereinafter referred to as formula (V)

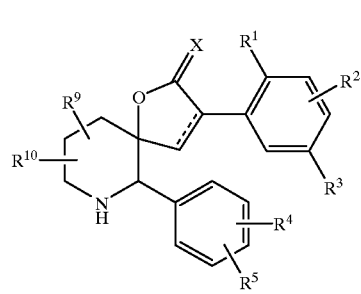

(V)

by reaction with a compound of formula (VI):

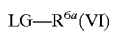

LG—$R^{6a}$(VI)

where $R^{6a}$ is a group of the formula $R^6$ as defined in relation to formula (I) (other than H) or a precursor therefor and LG is a leaving group such as an alkyl- or arylsulphonyloxy group (e.g. mesylate or tosylate) or a halogen atom (e.g. bromine, chlorine or iodine); and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

Suitable alternative methods for introducing the group $R^6$ are described, for instance, in International Patent Specification No. WO 95/18124.

According to another general process (D), compounds of formula (I) wherein $R^1$ is $C_{1-6}$alkoxy, fluoro$C_{1-6}$alkoxy, $C_{2-6}$alkoxy, $C_{3-7}$cycloalkoxy, $C_{3-7}$cycloalkyl$C_{1-4}$alkoxy or benzyloxy, may be prepared by the interconversion of a compound of formula (I) wherein $R^1$ is hydroxy, hereinafter referred to as formula (VI)

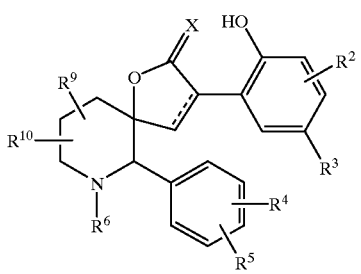

(VII)

by reaction with appropriate alkyl-, fluoroalkyl-, alkenyl-, cycloalkyl-, cycloalkylalkyl- or aralkyl-halide, especially the iodide, in the presence of a base.

Suitable bases include alkali metal hydrides, such as sodium hydride, in a suitable solvent such as dimethylformamide. The reaction is conveniently effected at about room temperature.

According to another general process (E), compounds of formula (I) may be prepared by the cyclisation of a compound of formula (VIII)

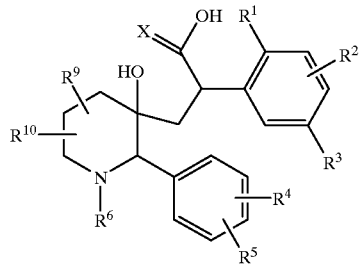

(VIII)

using suitable dehydrating reagents, for example, methanesulphonyl chloride or benzenesulphonyl chloride in pyridine or triethylamine. The reaction is conveniently effected at a temperature between 0° C. and 100° C., preferably at between room temperature and 80° C., using a suitable organic solvent such as dichloromethane, where necessary.

Intermediates of formula (VIII) are particularly preferred for controlling the stereochemistry of the 3-position in compounds of formula (I).

According to a further general process (F), compounds of formula (I) wherein the broken line represents a double bond (i.e. a compound of formula (IIA), above), may be prepared by the dehydration of a compound of formula (IX)

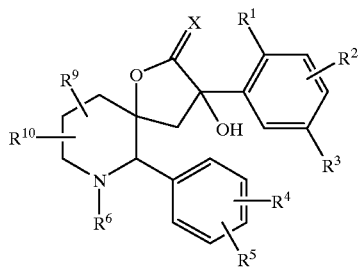

(IX)

using an acid such as trifluoroacetic acid. The reaction is conveniently effected at a temperature between 0° C. and room temperature, using a suitable organic solvent such as dichloromethane.

According to another general process (C), compounds of formula (I) wherein the double bond represented by the broken line is absent, may be prepared from a compound of formula (X)

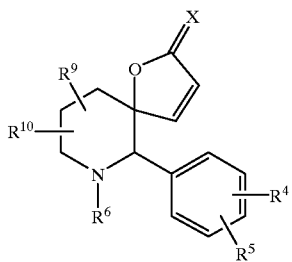

(X)

and a compound of formula (IV), where Hal in the compound of formula (IV) is chlorine, bromine or, preferably, iodine, by a reductive Heck reaction using a palladium catalyst such as palladium acetate with, for example, tri-o-tolylphosphine, dimethylformamide and tributylamine, or tetrabutylammonium chloride and dimethylformamide, and a reducing agent, preferably formic acid or a salt thereof, such as potassium formate.

According to another general process (H), compounds of formula (I) may be prepared from a compound of formula (XX)

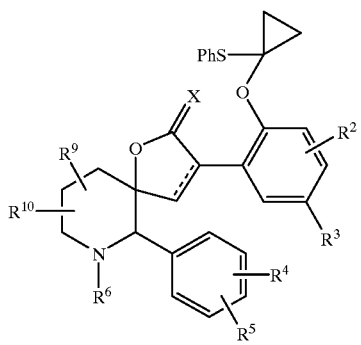

(XX)

by reaction with lithium naphthalenide in tetrahydrofuran. The reaction is preferably effected at reduced temperature, for example at about −78° C.

Further details of suitable procedures will be found in the accompanying Examples.

Compounds of formula (IIB) may be prepared using the method of general process (F) described above, provided that X in the compound of formula (IX) is two hydrogen atoms.

Intermediates of formula (V) may be prepared in a similar manner to that described in general process (B), preferably with a amino protecting group on the piperidine nitrogen in the compound of formula (III). Suitable amino protecting groups include alkoxycarbonyl groups such as tert-butoxycarbonyl and trichloroethoxycarbonyl, aralkyloxycarbonyl groups such as benzyloxycarbonyl, or aralkyl groups such as benzyl. Removal of the protecting group is effected by conventional procedures thus, for example, tert-butoxycarbonyl groups may be removed under acidic conditions using, for example, trifluoroacetic acid; tert-butoxycarbonyl groups, together with benzyloxycarbonyl and benzyl groups, may also be removed by hydrogenolysis in the presence of a catalyst, for example, palladium; and trichloroethoxycarbonyl groups may be removed with zinc dust.

Compounds of formula (III) may be prepared from a compound of formula (XII)

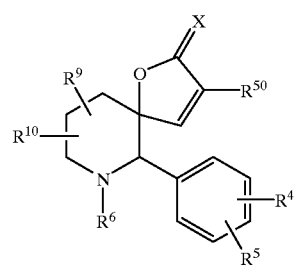

(XII)

wherein $R^{50}$ is as previously defined (and is preferably a triflate group or a bromine or iodine atom), by reaction with a compound of the formula $(R^{45})_3Sn-Sn(R^{45})_3$, for example, hexamethyl distannane. The reaction is conveniently effected in the presence of a base, for example, lithium carbonate, and a catalyst such as triphenylphosphine palladium(0). Suitable solvents for the reaction include ethers such as tetrahydrofuran, the reaction being effected at a temperature between room temperature and 100° C., for example, at about 60° C.

Compounds of formula (XII) where X is two hydrogen atoms may be prepared from a compound of formula (XIII).

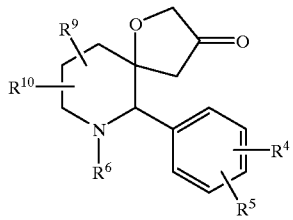
(XIII)

by enolisation of the ketone in the presence of a base, for example, sodium hexamethyldisilazide, followed by reaction with a reagent capable of introducing a suitable leaving group, for instance, where $R^{50}$ is —$OSO_2CF_3$, using 2-[N,N-bis(trifluoromethylsulphonyl)amino]-5-chloropyridine or triflic anhydride. The reaction is conveniently effected in a suitable solvent such as an ether, for example, tetrahydrofuran at a reduced temperature, for instance, −80° C.

Compounds of formula (XIII) may be prepared from a compound of formula (XIV) by the following reaction sequences (Scheme A or Scheme B) or by methods analogous thereto (with the proviso that $R^9$ and $R^{10}$ are not oxo):

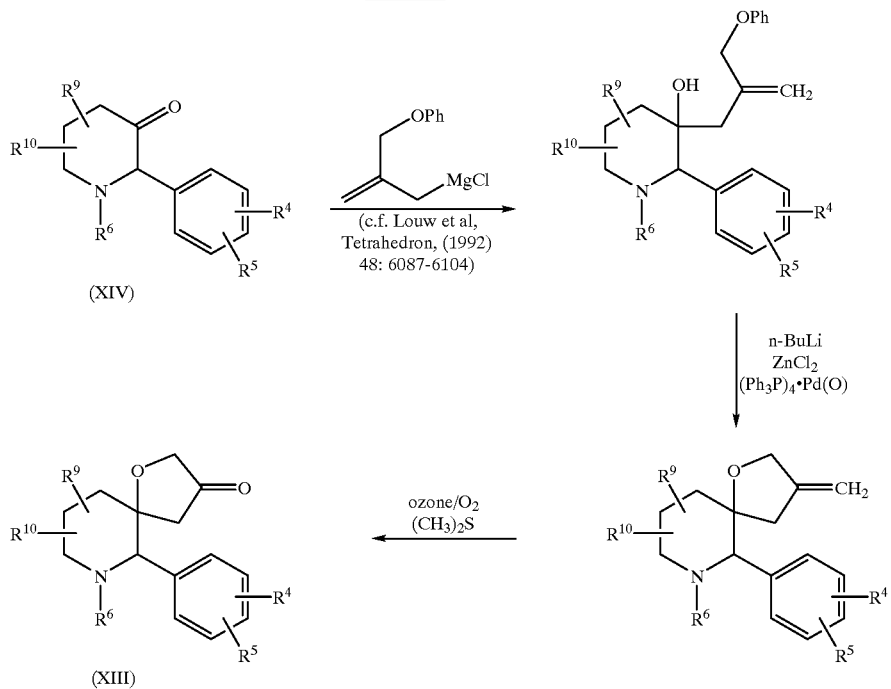

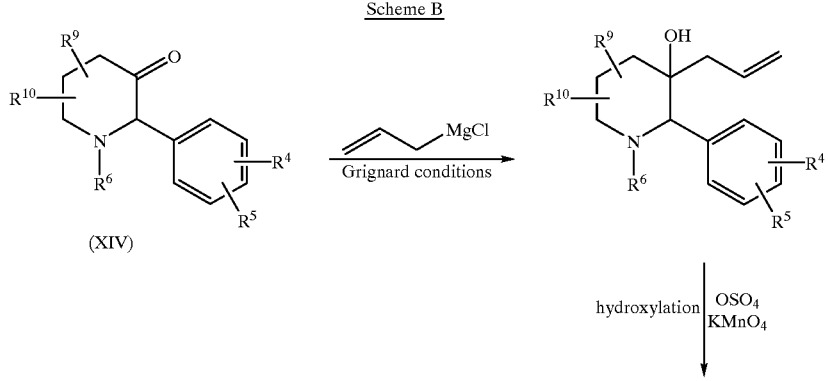

-continued

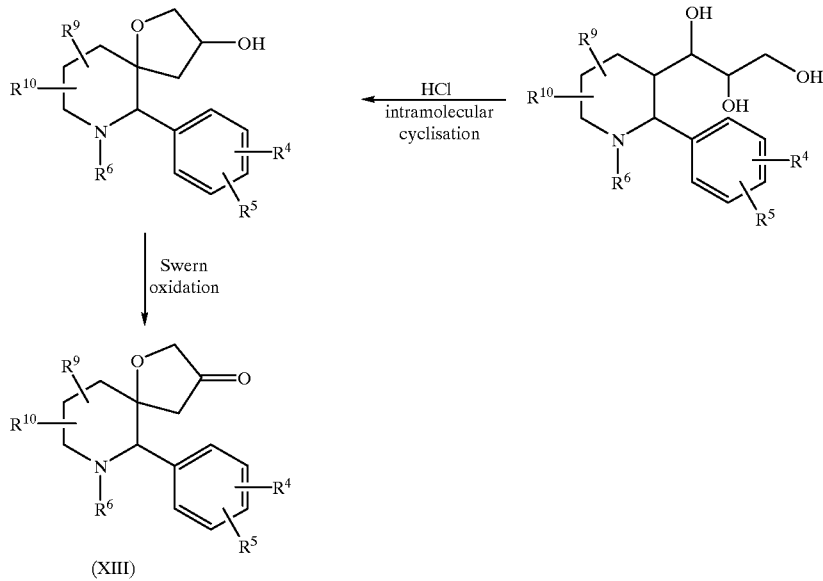

(XIII)

In a preferred embodiment of the aforementioned processes, $R^6$ is a benzyl group. The reduction reaction described as process (A) above for the preparation of compounds of formula (I) may conveniently replace the benzyl group with a hydrogen atom. It will be appreciated from the discussion above that compounds of formula (I) wherein $R^6$ is a hydrogen atom are particularly preferred precursors to other compounds of formula (I).

In an alternative method, compounds of formula (III) where X is two hydrogen atoms may be prepared by the following reaction sequence (Scheme C) or by methods analogous thereto (with the proviso that $R^9$ and $R^{10}$ are not oxo):

Scheme C

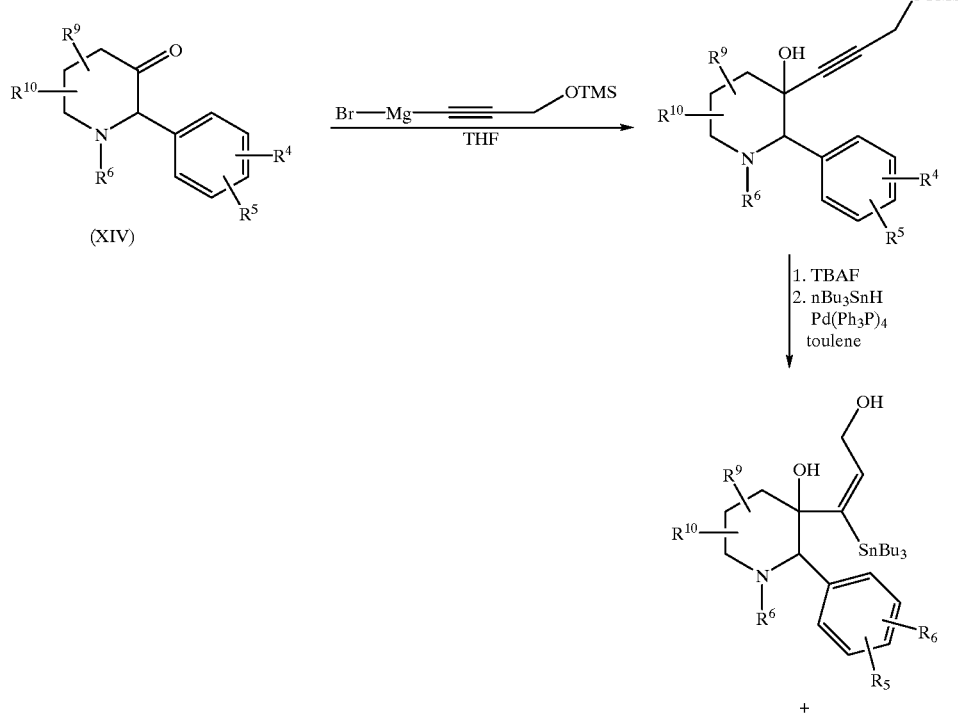

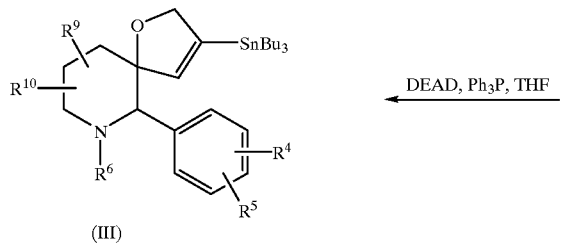

(III)

←—— DEAD, Ph₃P, THF ——

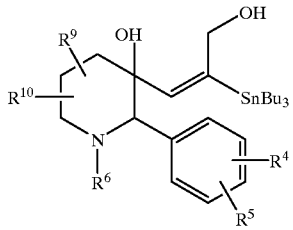

In another preferred embodiment of the aforementioned processes, $R^6$ is replaced with an amino protecting group, in particular tert-butoxycarbonyl which is conveniently removed prior to reduction of the 7-aza-spiro[4.5]dec-3-ene structure (general process (A)).

Compounds of formula (VII) may be prepared from the appropriate phenolic precursor (or a protected (e.g. benzyloxy) derivative thereof) using the methods of processes (A), (B) or (C).

Compounds of formula (VIII) where X is two hydrogen atoms may be prepared by reduction of a compound of formula (I) where X is an oxygen atom, using, for example, a borohydride such as lithium borohydride, or lithium triethylborohydride in tetrahydrofuran, or a hydride such as lithium aluminium hydride or diisobutylaluminium hydride.

Compounds of formula (I) where X is an oxygen atom may be prepared by the reduction of a compound of formula (IIA) where X is an oxygen atom, using, for example, palladium acetate and potassium formate in a suitable solvent such as dimethylformamide at elevated temperature, for example at about 80° C.; or using catalytic hydrogenation with palladium or platinum hydroxide on carbon, preferably in a suitable solvent such as an alcohol, for example methanol, or an ester, for example ethyl acetate, or an organic acid, for example acetic acid, or a mixture thereof; or using sodium borohydride and nickel chloride.

In an alternative method, compounds of formula (VIII) may be prepared by the reaction of a compound of formula (XIV) with a Grignard reagent of formula (XV)

(XV)

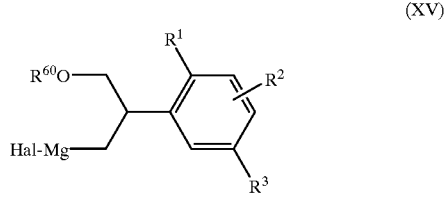

wherein $R^{60}$ is a suitable hydroxy protecting group, preferably benzyl, and Hal is a halogen atom, preferably chlorine, followed by removal of the protecting group $R^{50}$. Utilisation of a chiral intermediate of formula (XV) is particularly suitable for controlling the stereochemistry of the 3-position in compounds of formula (I).

Compounds of formula (XV) may be prepared by conventional methods well known in the art or based upon the methods described in the Examples herein.

In a further alternative method, compounds of formula (VIII) may be prepared by the reduction of a compound of formula (XVI)

(XVI)

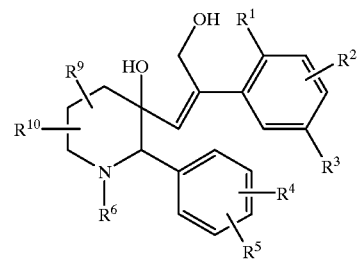

using, for example, catalytic hydrogenation in the presence of a metal catalyst such as palladium or platinum or hydroxides or oxides thereof, preferably in a suitable solvent such as an alcohol, e.g. methanol, an ester, e.g. ethyl acetate, or an organic acid, e.g. acetic acid, or a mixture thereof.

Compounds of formula (XVI) may be prepared from a compound of formula (XVII)

(XVII)

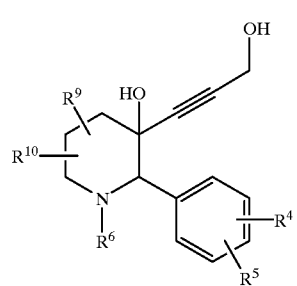

by reaction with a compound of formula (IV) using reductive Heck conditions as described in general process (G), above.

Compounds of formula (XVII) may be prepared from compounds of formula (XIV) and, for example, a Grignard reagent prepared from O-trimethylsilylpropargyl alcohol using conventional methodology, followed by removal of the hydroxy protecting group.

According to another method, compounds of formula (VIII) may be prepared from a compound of formula (XVIII)

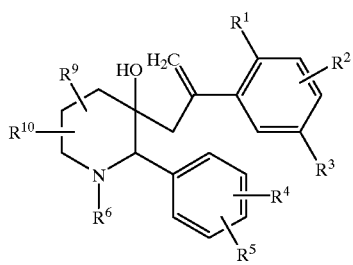

(XVIII)

by reaction with borane in tetrahydrofuran, followed by an oxidative work-up using, for example, hydrogen peroxide and sodium hydroxide.

Compounds of formula (XVIII) may be prepared from a compound of formula (XIV) and, for example, a Grignard reagent prepared from a 2-aryl-3-bromo-1-propene using conventional methodology.

Compounds of formula (IX) may be prepared by the reaction of a compound of formula (XIII) with Grignard reagent prepared from a compound of formula (IV), preferably using magnesium and a bromide of formula (IV). The coupling reaction is conveniently effected at reduced temperature, for example at about 0° C., using a suitable solvent such as an ether, for example, diethyl ether.

Compounds of formula (X) may be prepared, for example, by the conversion of a stannane of formula (III) to the corresponding iodide by treatment with iodine at reduced temperature, for example, at about −78° C., in a suitable solvent such as dichloromethane. The iodine may then be displaced to give the compound of formula (X) by treatment with, for example, α,α'-azo-isobutyronitrile and tributyltin hydride in a suitable solvent, for example, toluene, at an elevated temperature, for example, at about 100° C.

Alternatively, compounds of formula (X) may be prepared by the cyclisation of a compound of formula (XIX)

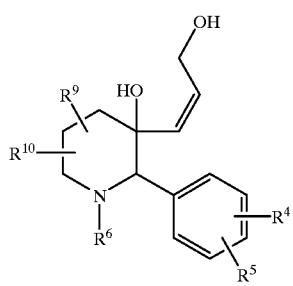

(XIX)

using the dehydrating conditions described above for general process (E) or using triphenylphosphine and diethylazodicarboxylate in a suitable solvent such as tetrahydrofuran.

Compounds of formula (XIX) may be prepared by the partial reduction of an acetylene compound of formula (XVII). The reaction is conveniently effected by catalytic hydrogenation using a metal catalyst such as palladium on calcium carbonate in the presence of a lead poison (e.g. Lindlar catalyst). Other suitable methods will be readily apparent to a person of ordinary skill in the art.

Compounds of formula (XX) may be prepared from a compound of formula (VII) by reaction with (1-iodo-cycloprop-1-yl)phenylsulfide.

It will be appreciated that compounds of the formula (I) wherein $R^6$ contains an =O or =S substituent can exist in tautomeric forms. All such tuatomeric forms and mixtures thereof are included within this invention. Most aptly the =O or =S substituent in $R^6$ is the =O substituent.

Where they are not commercially available, the intermediates of formula (IV) above may be prepared, for example, from the corresponding phenol derivative using, for example, the procedures described in the accompanying Examples, or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the $NK_1$ receptor of less than 100 nM on said test method. The particularly preferred 3(R) epimer sub-class of compounds of the present invention generally displayed a 2- to 5-fold improvement in affinity for the human NK-1 receptor over the corresponding 3(S) epimers.

For the avoidance of doubt, the nomenclature adhered to throughout this specification is based upon the following structures:

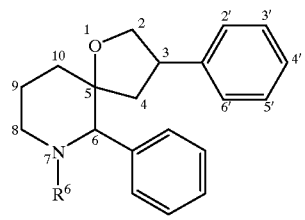

The following non-limiting Examples serve to illustrate the preparation of compounds of the present invention:

DESCRIPTION 1

(2S)-1-tert-Butoxycarbonyl-2-phenylpiperidin-3-one

Dimethyl sulfoxide (20.80 mL, 22.90 g, 29.3 mmol) in dichloromethane (75 mL) was added dropwise to a cooled (−70° C.) solution of oxalyl chloride (13.96 mL, 20.30 g, 160 mmol) in dichloromethane (350 mL). The mixture was stirred at −70° C. for 15 min., then (2S,3S)-1-tert-butoxycarbonyl-3-hydroxy-2-phenylpiperidine (prepared by the method described in European Patent Specification number 0 528 495-A; 36.91 g. 133 mmol) in dichloromethane (150 mL) was added dropwise. The mixture was stirred at −70° C. for 20 min., then allowed to warm to −30° C. The mixture was cooled to −50° C. and triethylamine (55.95 mL, 40.45 g, 400 mmol) was added slowly. The mixture was allowed to warm to 0° C. and diluted with ice-cooled dichloromethane (250 mL). The mixture was washed with ice cold aqueous citric acid solution (5%, 2×300 mL) and water (300 mL), dried (MgSO₄), and the solvent was evaporated under reduced pressure to give the title compound as a yellow oil (42.3 g), which was used immediately without further purification. $^1$H NMR (250 MHz, CDCl₃) δ7.5-7.3

(5H, m), 5.8 (1H, br s), 4.2(1H, br s), 3.4 (1H, m), 2.6 (2H, m), 2.0 (2H, m), and 1.54 (9H, s).

DESCRIPTION 2

(2S3R)-1-tert-Butoxycarbonyl-3-hydroxy-3-(2-methylene-3-phenoxypropyl)-2-phenylpiperidine A solution of 3-(chloromagnesio)-2-(phenoxymethyl)-1-propene in THF (0.91M, 3 ml) (Louw et. al. *Tetrahedron*, 48, 6087–6104, 1992, prepared from 2.74 mmol of 3-chloro-2-(phenoxymethyl)-1-propene) was slowly added to a solution of (2S)-1-tert-butoxycarbonyl-2-phenylpiperidin-3-one (Description 1) in THF (3 ml). The mixture was stirred at room temperature for 1 h., then saturated aqueous ammonium chloride (20 ml) was added and the mixture was extracted with ethyl acetate (20 ml). The organic phase was washed with brine, dried ($MgSO_4$) and the solvent was evaporated under reduced pressure. The residue was purified by column chromatography on silica gel, eluting with hexane/EtOAc (100:0 increasing to 80:20) to give the title compound. $^1$H NMR (360 MHz, $CDCl_3$) δ7.48 (2H, d, J6.9 Hz), 7.35-7.2 (6H, m), 6.9–6.88 (3H, m), 5.4 (1H, s), 5.15 (2H, d, J13.7 Hz), 4.61 (2H, s), 4.11 (2H, m), 3.17 (1H, m), 2.66 and 2.59 (2H, AB d, J 14.0 Hz), 1.95 (2H, m), 1.79 (2H, m), and 1.36 (9H, s), m/z ($ES^+$) 424 (M+1).

DESCRIPTION 3

(5R,6S)-3-Methylene-6-phenyl-1-oxa-7-(tert-butoxycarbonyl)aza-spiro[4.5]decane

To a cooled (–80° C.) solution of (2S,3R)-1-tert-butoxycarbonyl-3-hydroxy-3-(2-methylene-3-phenoxypropyl)-2-phenylpiperidine (Description 2, 1.53 g, 3.62 mmol) in THF (20 ml) was added n-butyl lithium (2.5M in hexanes. 1.45 ml, 3.62 mmol) followed by a solution of zinc chloride (0.5M in THF, 7.24 ml, 3.62 mmol). The solution was allowed to warm to room temperature and tetrakis(triphenylphosphine)palladium (0) (0.23 g, 0.2 mmol) was added. The mixture was degassed with bubbling nitrogen and heated under reflux for 16 h. The mixture was cooled and the solvent was evaporated under reduced pressure. The residue was partitioned between ethyl acetate and 2M NaOH. The organic phase was washed with saturated brine, dried ($MgSO_4$) and purified by chromatography on a column containing silica gel (eluting with hexane containing increasing proportions of ethyl acetate between 0% to 5%). Evaporation of the fractions gave (6S,5R)-3-methylene-6-phenyl-1-oxa-7-(tert-butoxycarbonyl)aza-spiro[4.5]decane. $^1$H NMR (360 MHz, $CDCl_3$) δ7.58 (2H, d, J 8.4 Hz), 7.32-7.21 (3H, m), 5.23 (1H, s), 5.06 (1H, m), 4.97 (1H, m), 4.39 (2H, AB d, J 13.3 Hz), 3.99 (1H, dd, J 13.3, 4.48 Hz), 2.83 (1H, ABd J 15.5 Hz), 2.7 (1H, td J 12.5, 3.93 Hz), 2.5 (1H, ABd, J 15.4 Hz), 2.15 (2H, td, J 12., .4 Hz), 1.69 (2H, m), and 1.46 (9H,s. m/z ($ES^+$) 329 (M+2H-$^t$BuOCO).

DESCRIPTION 4

(5R,6S)-3-Keto-6-phenyl-1-oxa-7-(tert-butoxycarbonyl)aza-spiro[4.5]decane

Through a cooled (–80° C.) solution of (5R,6S)-3-methylene-6-phenyl-1-oxa-7-(tert-butoxycarbonyl)aza-spiro[4.5]decane (Description 3; 0.665 g) in $CH_2Cl_2$ (5 ml) and methanol (5 ml) was bubbled a mixture of ozone and oxygen for 45 min. After the solution had been purged with nitrogen, dimethyl sulphide (0.5 ml) was added and then stirred under nitrogen at room temperature for 16 h. The solvent was removed in vacuo and the residue partitioned between ethyl acetate and water. The organic phase was dried ($MgSO_4$), evaporated and the residue purified by chromatography on a column containing silica gel (eluting with hexane containing increasing proportions of ethyl acetate between 0% to 10%). Evaporation of the fractions gave the title compound. $^1$H NMR (250 MHz, $CDCl_3$) δ7.58 (2H, d, J 6.2 Hz). 7.37-7.26 (3H, m), 5.3 (1H, s), 4.15 and 4.09 (2H, AB d, J 17.4 Hz), 3.97 (1H, m), 2.80 (1H, td. J 12.9, 4.0 Hz), 2.74 and 2.48 (2H, ABd, J18.1 Hz), 2.29 (2H, m), 1.88-1.63 (2H, m), and 1.44 (9H, s). m/z ($ES^+$) 332 (M+1).

DESCRIPTION 5

(5R,6S)-3-Trifluoromethylsulfonyloxy-6-phenyl-1-oxa-7-(tert-butoxycarbonyl)aza-spiro[4.5]dec-3-ene To a cooled (–80° C.) solution of 1M sodium hexamethyldisilazide (0.38 ml, 0.38 mmol) in THF was added a solution of (5R,6S)-3-keto-6-phenyl-1-oxa-7-(tert-butoxycarbonyl)aza-spiro[4.5]decane (Description 4: 0.105 mg, 0.319 mmol) in THF (3 ml). The solution was stirred for 1 h. at –80° C. then a solution of 2-[N,N-bis(trifluoromethylsulfonyl)amino]-5-chloropyridine (0.163 g, 0.415 mmol) in THF (3 ml) was added. The solution was stirred at –80° C. for 30 min. then at room temperature for 30 min. before being quenched by addition of saturated ammonium chloride solution and ethyl acetate. The dried ($MgSO_4$) organic phase was purified by chromatography on a column containing silica gel (eluting with hexane containing increasing proportions of ethyl acetate between 0% to 5%). Evaporation of the fractions gave the title compound. $^1$H NMR (360 MHz, $CDCl_3$) δ7.4 (2H, d, J 7.3 Hz). 7.3-7.22 (3H, m), 6.01 (1H, t, J 2.13 Hz), 5.13 (1H, s), 4.56 and 4.26 (2H, ABdd, J 12.4, 1.97 Hz), 4.10 (1H, dt, J 12.6, 4.22 Hz), 3.00 (1H, m), 2.28-2.04 (2H, m), 1.88-1.76 (2H, m), and 1.37 (9H, s). m/z ($ES^+$) 464 (M+1).

DESCRIPTION 6

(5R,6S)-3-Trimethylstannyl-6-phenyl-1-oxa-7-(tert-butoxycarbonyl)aza-spiro[4,5]dec-3-ene To a degassed solution of (5R,6S)-3-trifluoromethylsulfonyloxy-6-phenyl-1-oxa-7-(tert-butoxycarbonyl)aza-spiro[4.5]dec-3-ene (Description 5; 0.482 g, 1.04 mmol), lithium chloride (0.264 g, 6.25 mmol), lithium carbonate (0.076 g) and hexamethyl distannane (0.96 g, 2.9 mmol) in THF (10 ml) was added triphenylphosphine palladium (0) (0.06g). The solution wsa desgassed and then heated at 60° C. for 5 h. under nitrogen. Water (20 ml) and ethyl acetate (20 ml) were added and the dried organic phase was purified by chromatography on a column containing silica gel (eluting with hexane containing increasing proportions of ethyl acetate between 0% to 5%). Evaporation of the fractions gave the title compound as a crystalline solid. $^1$H NMR (360 MHz, $CDCl_3$) δ7.25 (2H, d, J 7.3 Hz), 7.1-7.0 (3H, m). 5.83 (1H. t, J 2.5 Hz), 4.78 (1H, s), 4.48 and 4.02 (2H, dd, J 12.9, 2.3 Hz), 3.96 (1H, dd, J 6.16, 13.4 Hz). 2.95 (1H, td, J 13.3, 4.5 Hz), 1.84 (1H, m), 1.68 (1H, m), 1.60 (2H, m), 1.19 (9H, s), and 0.0 (6H, s).

DESCRIPTION 7

(2S,3R)-1-tert-Butoxycarbonyl-3-(3-hydroxypyn-1-yl)-2-phenylpiperidin-3-ol

O-Trimethylsilylpropargyl alcohol (24.51 mL, 20.47 g, 160 mL) was added slowly to a cooled (–10° C.) solution of ethylmagnesium bromide (1M in tetrahydrofuran, 160 mL, 160 mmol). The mixture was stirred at 0° C. for 20 min., then at room temperature for 2 h. The mixture was cooled to −10° C. and a solution of (2S)-1-tert-butoxycarbonyl-2-phenylpiperidin-3-one (Description 1; 42.3 g) in tetrahydrofuran (200 mL) was added dropwise over 30 min. (Internal temperature below −5° C.). The mixture was stirred at room temperature for 14 h., poured into water (300 mL) and saturated aqueous ammonium chloride (300 mL) and extracted with ethyl acetate (2×300 mL). The combined organic fractions were washed with brine (300 mL), dried ($MgSO_4$) and the solvent was evaporated under reduced pressure. The residue was dissolved in ethyl acetate (500 mL) and a solution of tetrabutylammonium fluoride (1M in tetrahydrofuran, 160 mL, 160 mmol) was added dropwise. The mixture was stirred at room temperature for 30 min., water (300 mL) was added, and the layers were separated. The aqueous layer was extracted with ethyl acetate (2×300 mL) and the combined organic fractions were washed with water (300 mL) and brine (300 mL), dried ($MgSO_4$) and the solvent was evaporated under reduced pressure to give the crude title compound as an orange oil (45 g). The crude material was purified by flash column chromatography on silica gel, eluting with hexane/EtOAc (90:10 increasing to 25:75) to give the title compound as an amber oil (32.2 g). $^1$H NMR ($CDCl_3$) δ7.53–7.55 (2H, m), 7.19–7.35 (3H, m), 5.56 (1H, s), 4.27 (2H, s), 3.99–4.03 (1H, m), 3.25 (1H, br s), 2.77–2.81 (1H, m), 2.77 (1H, br s), 2.12–2.20 (1H, m), 1.91–1.99 (2H, m), 1.77–1.83 (1H, m), and 1.39 (9H, s).

DESCRIPTION 8

(5R,6S)-3-Tributylstannyl-6-phenyl-1-oxa-7-(tert-butoxycarbonyl)aza-spiro[4.5]dec-3-ene Crude (2S,3R)-1-tert-butoxycarbonyl-3-(3-hydroxypropyn-1-yl)-2-phenylpiperidin-3-ol (Description 7; 45 g) was dissolved in toluene (750 mL) and degassed with nitrogen. Tetrakis(triphenylphosphine)palladium (0) (2.30 g, 2.0 mmol) in toluene (600 mL) was added and the mixture was degassed. Tributyltin hydride (35.78 mL, 38.71 g, 133 mmol) was added dropwise over 15 min., with stirring and cooling (Internal temperature below 25° C.). The mixture was stirred at room temperature for 1 h., then the solvent was evaporated under reduced pressure. The residue was dissolved in tetrahydrofuran (600 mL) and triphenylphosphine (34.88 g, 133 mmol) was added. A solution of diethyl azodicarboxylate (20.94 mL, 23.16 g, 133 mmol) in tetrahydrofuran (150 mL) was added dropwise with stirring and cooling and the mixture was stirred at room temperature for 1 h. The solvent was evaporated under reduced pressure, acetonitrile (600 mL) was added and the mixture was extracted with hexane (8×150 mL). The hexane fractions were combined and the solvent was evaporated under reduced pressure. The residue was purified by flash column chromatography on silica gel, eluting with dichloromethane/ethyl acetate (100:0 increasing to 99:1)to give the title compound as a yellow oil (53.64 g, 67% from (2S,3S)-1-tert-butoxycarbonyl-3-hydroxy-2-phenylpiperidine). $^1$H NMR ($CDCl_3$) δ7.38–7.40 (1H, m), 7.15–7.25 (3H, m), 5.96 (1H, t, J 2.3 Hz), 4.93 (1H, s), 4.63 (1H, dd, J 2.23, 12.9 Hz), 4.22 (1H, dd, J 2.23, 12.9 Hz). 4.09–4.14 (1H, m), 3.09–3.17 (1H, m), 1.95–1.99 (1H, m), 1.83–1.86 (1H, m), 1.72–1.76 (2H, m), 1.40–1.51 (6H, m), 1.38 (9H, s), 1.25–1.32 (6H, m), and 0.86–0.99 (15H, m).

DESCRIPTION 9

(2S,3R)-Ethyl 3-(1-tert-Butoxycarbonyl-3-hydroxy-2-phenylpiperidin-3-yl)propynoate n-Butyl lithium (2.28 ml, 1.6M solution in hexanes, 3.64 mmol) was added slowly to a cooled (−78° C.) solution of ethyl propiolate (0.370 ml, 3.64 mmol) in tetrahydrofuran (10 ml). the soluton was stirred for 10 min. at −78° C. after addition was complete then (2S)-1-tert-butoxycarbonyl-2-phenylpiperidin-3-one (Description 1, 1,0 g, 3.64 mmol) in tetrahydrofuran (10 ml) was added, the temperature being maintained below −75° C. The mixture was stirred for a further 10 min, then warmed to −60° C. when glacial acetic acid (1 ml) was added. The mixture was warmed to room temperature and poured into saturated aqueous sodium hydrogen carbonate (20 ml). The organic phase was separated and the aqueous phase was extracted with ethyl acetate (20 ml). The combined organic fractions were dried ($Na_2SO_4$) and the solvent was evaporated under reduced pressure. The residue was purified by flash column chromatography on silica gel, eluting with hexane/EtOAc (90:10), to give the title compound as a gum (801 mg, 59%), $^1$H NMR (250 MHz, $CDCl_3$) δ7.50 (2H, m), 7.35 (3H, m), 5.49 (1H, s), 4.25 (2H, q, J 7.12 Hz), 4.15 (1H, m), 3.02 (1H, m), 2.23 (2H, m), 2.00 (2H, m), 1.78 (1H, m), 1.37 (9H, s), and 1.29 (3H, t, J 7.12 Hz), m/z ($ES^+$) 374 (M+1).

DESCRIPTION 10

(5R,6S)-7-tert-Butoxycarbonyl-6-phenyl-3-tributylstannyl-1-oxa-7-aza-spiro[4.5]dec-3-en-2-one A mixture of (2S,3R)-ethyl 3-(1-tert-butoxycarbonyl-3-hydroxy-2-phenylpiperidin-3-yl)propynoate (Description 9, 524 mg, 1.4 mmol) and tetrakis(triphenylphosphine) palladium (0) (50 mg) in toluene (10 ml) was degassed with nitrogen for 30 min. Tributyl tin hydride (0.405 mM, 1.5 mmol) was added dropwise and the resulting mixture was stirred at 23° C. for 2 h. The solvent was evaporated under reduced pressure and the residue was taken up in ethyl acetate (50 ml). The mixture was washed with saturated aqueous sodium hydrogen carbonate (50 ml), dried ($Na_2SO_4$) and the solvent was evaporated under reduced pressure. The residue was purified by flash column chromatography on silica gel to give the title compound as a gum (538 mg, 0.87 mmol, 62%). $^1$H NMR (250 MHz, $CDCl_3$) δ7.63 (1H, s), 7.30 (5H, m), 5.11 (1H, m, 310 (1H, m) 2.19 (1H, m), 1.80 (3H, m), 1.30–150 (12H, m), 1.40 (9H), s), 1.02 (6H), m), and 0.88 (9H), t, J 7.22 Hz), m/z ($ES^+$) 619 (M+1)

DESCRIPTION 11

2-Bromo-4-(trifluoromethoxy)phenol

To a cooled (0°) solution of 4-trifluoromethoxyphenol (35.6 g, 0.2 mol) in chloroform (280 ml) was added dropwise a solution of bromine (32 g, 0.2 mol) in chloroform (50 ml). The solution was stirred at 0° C. for 1 h. and at room temperature for 2 h. Dichloromethane (200 ml) and waster (400 ml) ware added and the organic phase was washed further with water (400 ml), brine (200 ml) and dried ($MgSO_4$). The solvent was removed and the residue was purified by distillation at reduced pressure to give the title compound. $^1$ H NMR (250 MHz, $CDCl_3$) δ7.38 (1H, d, J 2.1 Hz), 7.13 (1H, dd, J 9.1, 2.1 Hz), 7.03 (1H, d, J 9.1 Hz), and 5.53 (1H, s).

DESCRIPTION 12

2-Bromo-4-(trifluoromethoxy)anisole

To a solution of 2-bromo-4-trifluoromethoxyphenol (Description 11; 7.2 g) and potassium carbonate (11.6 g, 0.084 mol) in dimethylformamide (60 ml) was added methyl iodide (14.94 ml, 0.24 mol). The solution was stirred for 15 h. at room temperature under nitrogen whereupon water (400 ml) and diethyl ether (200 ml) were added and the organic phase washed with water (4×200 ml), saturated NaHCO$_3$ (2×200 ml), brine (200 ml), and the solvent removed in vacuo. The residue was purified by chromatography on silica gel eluting with ethyl acetate in hexane (0–2%), to give the title compound. $^1$H NMR (250 MHz, CDCl$_3$) δ7.45 (1H, d, J 2.8 Hz), 7.16 (1H, dd, J 9.0, 2.8 Hz), 6.88 (1H, d, J 9.0 Hz), and 3.90 (3H, s).

DESCRIPTION 13

2-Bromo-4-trifluoromethoxy-isopropoxybenzene

To a solution of 2-bromo-4-trifluoromethoxyphenol (Description 11; 1 g, 3.9 mmol) and K$_2$CO$_3$ (1.1 g, 7.8 mmol) in dimethylformamide (15 ml) was added 2-bromopropane (0.55 ml, 5.9 mmol). The solution was stirred for 14 h. at room temperature under an atmosphere of nitrogen. Waster (200 ml) and ethyl acetate (3×70 ml) was added to the solution and the organic phase washed with water (100 ml), brine (100 ml) and dried (MgSO$_4$). The solvent was removed in vacuo and the residue purified by chromatography on silica gel (eluting with 5% ethyl acetate in hexane) to give the title compound. $^1$H NMR (250 MHz, CDCl$_3$) δ1.38 (6H, d, J 6.1 Hz), 4.53 (1H, m), 6.88 (1H, d, J, 9 Hz), 7.12 (1H, dd, J 8.8, 2.6 Hz), and 7.43 (1H, d, J 2.8 Hz).

DESCRIPTION 14

2-Bromo-4-trifluoromethoxy-allyloxybenzene

To a solution of 2-bromo-4-trifluoromethoxyphenol (Description 11; 8 g, 0.03 mol) and K$_2$CO$_3$ (8.6 g, 0.06 mol) in dimethylformamide (100 ml) was added allyl bromide (4 ml, 0.045 mol). The solution was stirred for 4 h. at room temperature undre nitrogen whereupon water (400 ml) and ethyl acetate (3×100 ml) were added and the combined organic phase was washed with water (200 ml), saturated brine (200 ml), dried (MgSO$_4$) and the solvent removed in vacuo. The residue was purified by chromatography on silica gel (eluting with 5% ethyl acetate in hexane) to give the title compound as a yellow oil $^1$H NMR (250 MHz, CDCl$_3$) δ4.60 (2H, dt, J 5, 1.6 Hz), 5.33 (1H, dq, J 10.5, 1.4 Hz), 5.48 (1H, dq, J 17.3, 1.6 Hz), 6.04 (1H, m), 6.86 (1H, d, J 9 Hz), 7.13 (1H, dd, J 8.4, 2.7 Hz), and 7.45 (1H, d, J 2.8 Hz).

DESCRIPTION 15

2-Bromo-6-(prop-2-enyl)-4-trifluoromethoxyphenol

2-Bromo-4-trifluoromethoxy-allyloxybenzene (Desc 14.; 8.6 g) was heated at 200° C. for 7 h. and the cooled residue was purified by chromatography on silica gel (eluting with 1% ethyl acetate in hexane ) to give 2-bromo-6-(prop-2enyl)-4-trifluormethoxyphenol as a yellow oil $^1$H NMR (250 MHz, CDCl$_3$) δ3.43 (2H, d, J 6.6 Hz), 5.13 (2H, m), 5.60 (1H, s), 5.98 (1H, m), 6.98 (1H, d, J 2.4 Hz), and 7.24 (1H, d, 2.4 Hz).

DESCRIPTION 16

2-Bromo-6-(2-hydroxyethyl)-4-trifluoromethoxyphenol

Through a cooled (−78° C.) solution of 2-bromo-6-(prop-2-enyl)-4-trifluormethoxyphenol (Description 15.; 5.9 g, 0.02 mol) in dichloromethane (30 ml) and methanol (30 ml) was bubbled a mixture of ozone in oxygen for 4 h. After the solution had been purged with nitrogen for 1 h., sodium borohydride (0.755 g) was added and then stirred at room temperature for 15 h. The solvent was removed in vacuo and the residue partitioned between ethyl acetate and water containing (2M HCl (20 ml). The organic phase was washed with saturated brine, dried (MgSO$_4$) and the solvent evaporated in vacuo. The residue was chromatographed on silica gel (eluting with 20% ethyl acetate in hexane) to give the title compound. $^1$H NMR (250 MHz, CDCl$_3$) δ2.93 (2H, t, J 5.6 Hz), 3.98 (2H, t, J 5.4 Hz), 6.96 (1H, d, J 2.5 Hz), and 7.3 (1H, d, J 2.4 Hz).

DESCRIPTION 17

7-Bromo-5-trifluoromethoxy-2,3-dihydrobenzofuran

To a cooled (0° C.) of triphenylphosphine (6.11 g, 0.0234 mol) in tetrahydrofuran (40 ml) was added diethylazodicarboxylate (3.7 ml, 0.0234 mol). The solution was stirred for 30 min., whereupon a solution of 2-bromo-6-(2-hydroxyethyl)-4-trifluoromethoxyphenol (Desc 16.; 5.4 g, 0.018 mol) in tetrahydrofuran was added. The solution was stirred at room temperature for 15 h. and then the solvent was removed in vacuo. The residue was dissolved in ethyl acetate and the solution was washed with water, saturated brine, dried (MgSO4). After removal of the solvent in vacuo the residue was purified by chromatography on silica gel (eluting with 10% ethyl acetate in hexane) to give the title compound as a pink oil. $^1$H NMR (250 MHz, CDCl$_3$) δ2.93 (2H, t, J 5.6 Hz), 3.98 (2H, t, J 5.4 Hz), 6.96 (1H, d, J 2.5 Hz), and 7.30 (1H, d, J 2.4 Hz).

DESCRIPTION 18

1-Benzyloxy-4-(2,2,2-trifluoroethoxy)benzene

To a solution of 4-benzyloxyphenol (5 g) and 2,2,2-trifluoroethyl-p-toluenesulphonate (5 g) in dimethylformamide (50 ml) was added sodium hydride (60% dispersion in oil, 2.3 g) and the solution heated to 110° C. for 16 h. The mixture was cooled, diluted with water and the product extracted into ethyl acetate. The organic phase was washed with water, brine and dried (MgSO$_4$). The solvent was remove in vacuo and the residue chromatographed on silica gel (eluting with 10% diethyl ether/hexane) to give the the title compound as a solid, m.p. 72–74° C.

DESCRIPTION 19

4-(2,2,2-Trifluoroethoxy)phenol

A solution of 1-benzyloxy-4-(2,2,2-trifluoroethoxy) benzene (Description 18, 5 g) and palladium (10% on carbon; 0.1 g) in methanol (50 ml) was hydrogenated at 50 psi for 12 h. The solution was filtered and the solvent removed in vacuo to give the title compound as a colourless solid m.p. 60–64° C.

DESCRIPTION 20

2-Bromo-4-(2,2,2-trifluoroethoxy)phenol

To a cooled (0° C.) solution of 4-2,2,2-trifluoroethoxy) phenol (Description 19) in a mixture of acetic acid and chloroform (20 ml; 1:1), was added a solution of bromine (0.83 g) in chloroform (5 ml). The mixture was stirred for 10 min. and diluted with chloroform, then washed with water (2×50 ml), dried (MgSO$_4$) and evaporated to give the title compound as an oil. $^1$H NMR (250 MHz, CDCl$_3$) δ4.33 (2H, q, J 8 Hz), 6.83 (1H, dd, J 2.8, 8.8 Hz), 6.97 (1H, d, J 8.8 Hz), and 7.10 (1H, d, J 2.8 Hz).

DESCRIPTION 21

2-Bromo-4-(2,2,2-trifluoroethoxy)anisole

To a solution of 2-bromo-4-(2,2,2-trifluoroethoxy)phenol (Description 20, 0.6 g) in acetone was added added $K_2CO_3$ (1 g) and methyl iodide (1 ml). The solution was heated to reflux for 1 h. and then evaporated in vacuo. The residue was partitioned between ethyl acetate and water and the organic phase washed further with water and saturated brine. After drying ($MgSO_4$) the solvent was removed in vacuo to give the title compound as a yellow oil. $^1$H NMR (250 MHz, $CDCl_3$) δ3.87 (3H, s) 4.30 (2H, q, J 8 Hz), 6.82–6.92 (2H, m), and 7.20 (1H, d, J 3 Hz).

DESCRIPTION 22

2.5-Bis(2,2,2-trifluoroethoxy)bromobenzene

To a solution of 2-bromo-4-(2,2,2-trifluoroethoxyphenol (Description 20; 0.83 g, 3.06 mmol) and sodium hydride (60% in oil, 0.367 g, 9.18 mmol) in dimethylformamide (10 mol) was added 2,2,2-trifluoroethyl-p-toluenensulphonate (1.17 g, 4.6 mmol). The mixture was heated at 100° C. for 10 h., cooled and diluted with athyl acetate and water. The organic phase was washed with water, saturated brine, dried ($MgSO_4$) and evaporated in vacuo. The residue was purified by chromatography on silica gel (eluting with 2% ethyl acetate in hexane) to give the title compound as an oil $^1$H NMR (250 MHz, $CDCl_3$) δ4.32 (4H, m) 6.89 (2H, m), and 7.20 (1H, d, J 4.1 Hz).

DESCRIPTION 23

2-Bromo-1-(difluoromethoxy)-4-trifluoromethoxy)benzene

To a solution of 2-bromo-4-trifluoromethoxy)phenol (Description 11, 5.14 g) in dimethylformamide was slowly added sodium hydride (0.96 g, 60% in oil. After stirring for 20 min. a slow stream of chlorodifluoromethane was bubbled through the solution for 10 min. The mixture was heated at 60° C. for 2 h., cooled, diluted with water and the solution extracted with diethyl ether (2×100 ml). The organic phases were combined, washed with water, saturated brine, dried ($MgSO_40$ and evaporated in vacuo. The residue was chromatographed on silica gel (eluting with hexane) to give the title compound as a solid. $^1$H NMR (250 MHz, $CDCl_3$) δ6.53 (1H, t, J 7.2 Hz), 7.17–7.29 (2H, m), and 7.51 (1H, d, J 2.5 Hz).

DESCRIPTION 24

2-Bromo-1-(2,2,2-trifluoroethoxy)-4-trifluoromethoxy)benzene

To a solution of 2-bromo-4-trifluoromethoxyphenol (Description 11, 2 g) and 2,2,2-trifluoroethyl-p-toluene sulphonate in dimethylformamide (30 ml) was slowly added sodium hydride (2 g, 60% in oil) and the mixture heated to 110° C. for 12 h. The mixture was cooled, diluted with water (300 ml) and extracted with ethyl acetate (2×50 ml). The organic phases were washed with water, saturated brine and dried ($MgSO_4$). The solvent was removed in vacuo and the residue was chromatographed on silica gel(eluting with diethyl ether/hexane (1:10)) to give the title compound as a colourless oil. $^1$H NMR (250 MHz, $CDCl_3$) δ4.40 (2H, q, J 8 Hz), 6.95 (1H, d, J 9 Hz), 7.15–7.20 (1H, m), and 7.48–7.49 (1H, m).

DESCRIPTION 25

2-Bromo-4-fluoro-(2,2,2-trifluoroethoxy)benzene

To a solution of 2-bromo-4-fluorophenol (4 g) and 2,2,2-trifluoroethoxy-p-toluene sulphonate (5 g) in dimethylformamide (40 ml) was slowly added sodium hydride (1 g, 60% in oil) and the mixture then heated at 110° C. for 12 h. The solution was cooled, diluted with water (500 ml) and the product extracted into ethyl acetate (2×150 ml). The organic phase was washed with saturated $NaHCO_3$ solution, water, saturated brine and dried ($MgSO_4$). The solvent was removed in vacuo and the residue was chromatographed on silica gel (eluting with diethyl ether/hexane (1:5)) to give the title compound as a colourless oil. $^1$H NMR (250 MHz, $CDCl_3$) δ4.36 (2H, q, J 8 Hz), 6.91–7.05 (2H, m), and 7.33 (1H, dd, J 8, 3 Hz).

DESCRIPTION 26

4-(Methanesulfonyl)phenol

Oxone (65.8 g, 0.108 mol) in water (290 ml) was added to a cooled (ice-bath) solution of 4-(methylmercapto)phenol (5 g, 36 mmol) in methanol (290 ml). The resulting solution was stirred at ambient temperature for 48 h. and then concentrated in vacuo. The residue was diluted with water (100 ml) and extracted with dichloromethane (10×100 ml). The combined organic layers were dried over sodium sulphate and removal of the solvent in vacuo gave the title compound as a clear oil (5.66 g, 92%). $^1$H NMR (250 MHz, $CDCl_3$) δ7.80–7.75 (2H, d, J 11.7 Hz), 7.28 (1H, br s), 7.01–6.96 (2H, d, J 11.7 Hz), and 3.08 (3H, s).

DESCRIPTION 27

2-Bromo-4-(methanesulfonyl)phenol

A solution of bromine (0.9 ml, 17.45 mmol) in glacial acetic acid (10 ml) was added dropwise to a stirred solution of 4-(methanesulfonyl)phenol (Description 26; 3 g, 17.45 mmol). The resulting solution was stirred at ambient temperature for 16 h. Bromine (0.45 ml) in glacial acetic acid (5 ml) was added dropwise and the solution was stirred for 2 h. The excess acetic acid and bromine were removed in vacuo and the residue was azeotroped with toluene to give the desired compound as an off-white solid (3.54 g, 81%). $^1$H NMR (250 MHz, $CDCl_3$) δ8.06–8.05 (1H, d, J 2.3 Hz), 7.73–7.69 (1H, dd, J 8.6, 2.3 Hz), 7.06–7.02 (1H, d, J 8.6 Hz), and 3.06 (3H, s).

DESCRIPTION 28

2-Bromo-4-(methanesulfonyl)anisole

Potassium carbonate (2.31 g, 16.8 mmol) was added to a solution of 2-bromo-4-(methanesulfonyl)phenol (Description 27; 3.5 g, 14 mmol) in dimethylformamide (50 ml). The resulting solution was stirred for 30 min. and methyl iodide (1.04 ml, 16.8 mmol). After stirring for 1 h. the solution was poured into water (200 ml) and extracted with ethyl acetate (2×100 ml). The combined organics were washed with water and dried over sodium sulphate. Removal of the solvent in vacuo gave a white solid which was crystallised from diethyl ether to give the title compound (2.02 g). $^1$H NMR (250 MHz, $CDCl_3$) δ8.12–8.11 (1H, d, J 2.2 Hz), 7.90–7.86 (1H, dd, J 8.7, 2.2 Hz), 7.04–7.00 (1H, d, J 8.7 Hz), and 3.99 (3H, s), and 3.05 (3H, s).

DESCRIPTION 29

3-Bromo-4-(cyclobutyloxy)trifluoroanisole

2-Bromo-4-(trifluoromethoxy)phenol (Description 11; 1.5 g, 5.83 mmol) and cyclobutyl bromide (3.0 g, 17.5 mmol) were dissolved in dimethylformamide (10 ml). Potassium carbonate (4.85 g, 35 mmol) was added and the solution was stirred at 50° C. for 16 h. The solution was allowed to cool to ambient temperature, poured into a 10% citric acid solution (50 ml) and extracted with ethyl acetate (2×100 ml). The combined organic layers were washed with water and dried over sodium sulphate. Removal of the solvent in vacuo gave an oil which was chromatographed on silica in 10% ethyl acetate/hexane to give the title compound as an oil (1.65 g, 91%). $^1$H NMR (250 MHz, CDCl$_3$) δ7.44–7.42 (1H, m), 7.12–7.07 (1H, m), 6.73–6.70 (1H, d, J 9.0 Hz), 4.71–4.60 (1H, m), 2.52–2.41 (2H, m), 2.30–2.18 (2H, m), and 1.92–1.55 (2H, m).

DESCRIPTION 30

2-(2-Hydroxyethoxy)-5-(trifluoromethoxy)bromobenzene

Prepared from the compound of Description 14 according to the method of Description 16. $^1$H NMR (360 MHz, CDCl$_3$) δ2.20 (1H, t, J 6.3 Hz), 4.0 (2H, q, J 5.6 Hz), 4.13 (2H, q, J 4.2 Hz), 6.91 (1H, d, J 9 Hz), 7.15 (1H, m), and 7.45 (1H, d, J 2.3 Hz).

DESCRIPTION 31

2-(2-Fluoroethoxy)-5-(trifluoromethoxy)bromobenzene

To a cooled (−78° C.) suspension of 2-(2-hydroxyethoxy)-5-(trifluoromethoxy)bromobenzene (Description 30; 8.9 g, 30 mmol). in dichoromethane (80 ml) was added diethylaminosulphur trifluoride (3.88 ml, 31.5 mmol). The solution was stirred at ambient temperature for 2 h., then quenched by the dropwise addition of water (100 ml). The organic layer was separated, washed with brine (100 ml), dried (MgSO$_4$), and evaporated in vacuo. Purification in silica, eluting with 15%–20% ethyl acetate in hexane gave the title compound as a clear oil (1.9 g, 15%). $^1$H NMR (360 MHz, CDCl$_3$) δ4.23 (1H, m), 4.31 (1H, m), 4.37 (1H, m), 4.86 (1H, m), 6.90 (1H, m), 7.15 (1H, m), and 7.47 (1H, t, J 0.7 Hz).

DESCRIPTION 32

2-Bromo-4-(trifluoromethoxy)phenyl Trifluoromethanesulfonate

To a cooled (0° C.) solution of 2-bromo-4-(trifluoromethoxy)phenol (Description 11, 10 g, 40 mmol) in pyridine (20 ml), was added trifluooromethanesulphonic anhydride (7.2 ml, 44 mmol), and the reaction was stirred at ambient temperature for 2 h. The reaction was diluted with saturated cooper (II) sulphate (80 ml) and extracted into ethyl acetate (3×60 ml). The combined organic fractions were washed with water (80 ml), brine (80 ml), dried (MgSO$_4$) and evaporated in vacuo. Purification on silica, eluting with hexane gave the title compound as a clear oil (13.1 g, 85%). $^1$H NMR (250 MHz, CDCl$_3$) δ7.28 (1H, m), 7.40 (1H, d, J 9.1 Hz), and 7.58 (1H, d, J 2.8 Hz).

DESCRIPTION 33

2-(Ethen-1-yl)-5-(trifluoromethoxy)bromobenzene

A mixture of 2-bromo-4-(trifluoromethoxy)phenyl trifluoromethanesulfonate (Description 32; 1.8 g, 4.6 mmol), vinyl tributylin (1.61 g, 5.1 mmol) and lithium chloride (1.18 g, 27.6 mmol) in N,N-dimethylformamide (20 ml) was degassed before addition of dichloro-bis (triphenylphosphine)palladium (II). After further degassing, the reaction mixture was heated at 110° C. for 14 h. The solution was partitioned between water (70 ml) and ethyl acetate (3×50 ml). The combined organic fractions were washed with brine (50 ml), dried (MgSO$_4$) and evaporated in vacuo. Purification on silica, eluting with hexane gave the title compound as a clear oil (780 mg, 64%). $^1$H NMR (250 MHz, CDCl$_3$) δ5.40 (1H, dd, J 9.1 Hz, J 1.8 Hz), 5.70 (1H, dd, J 10.5 Hz, J 0.5 Hz), 7.0 (1H, m), 7.16 (1H, m), 7.44 (1H, d, J 1.4 Hz), and 7.56 (1H, d, J 8.7 Hz).

DESCRIPTION 34

2-Benzyloxy-5-(trifluoromethoxy)bromobenzene 2-bromo-4-(trifluoromethoxy)phenol (Description 11; 5 g, 20 mmol) was dissolved in N,N-dimethylformamide (60 ml), and potassium carbonate (5.4 g, 40 mmol) was added, followed by benzyl bromide (3.5 ml, 30 mmol), and the reaction was stirred at ambient temperature for 15 h. The reaction was diluted with water (150 ml) and extracted into ethyl acetate (3×60 ml). The combined organic fractions were washed with water (100 ml), brine (100 ml), dried (MgSO$_4$) and evaporated in vacuo. Purification on silica, eluting with 2% and 5% ethyl acetate in hexane gave the title compound as a clear oil (6.7 g, 96%). $^1$H NMR (250 MHz, CDCl$_3$) δ5.47 (2H, s), 7.23 (1H, d, J 9 Hz), 7.43 (1H, dd, J 8.2, 2.9 Hz), and 7.75 (6H, m).

DESCRIPTION 35

2-Bromo-4-(trifluoromethyl)phenol

Prepared from 4-(trifluoromethyl)phenol according to the method of Description 11. $^1$H NMR (250 MHz, CDCl$_3$) δ7.06 (1H, dd, J 8.5, 0.5 Hz), 7.4 (1H, dd, J 6.5, 2.0 Hz), 7.7 (1H, d, J 1.7 Hz), and 8.93 (1H, s).

DESCRIPTION 36

1-Benzyloxy-2-bromo-4-(trifluoromethyl)benzene

2-Bromo-4-(trifluoromethoxy)phenol (Description 35; 3.85 g) and benzyl bromide (2.36 ml) were dissolved in dimethylformamide and potassium carbonate (6.8 g) was added. The mixture was stirred at 60° C. for 3 h. The mixture was diluted with water (200 ml) and extracted with ethyl acetate. The organic fraction was dried (MgSO$_4$) and the solvent was evaporated under reduced pressure. The residue was purified by column chromatography on silicagel, eluting with hexane/ethyl acetate (99:1 increasing to 95:5) to give the title compound. $^1$H NMR (360 MHz, CDCl$_3$) δ5.21 (2H, s), 6.98 (1H, d, J 8.65 Hz), 7.31–7.51 (6H, m), and 7.82 (1H, d, J 1.7 Hz).

DESCRIPTION 37

(3S,5R,6S)-3-(2-Methoxy-5-trifluoromethoxyphenyl)-6-phenyl-1-oxa-7-(tert-butoxycarbonyl)aza-spiro[4.5]decan-3-ol 2-Bromo-4-trifluoromethoxyanisole (Description 12, 417 mg, 1.54 mmol) was added portionwise to magnesium (41 mg, 1.7 mmol) in diethyl ether (1 ml), under a nitrogen atmosphere, and the mixture was heated briefly at reflux following each addition. Once the addition was complete, the mixture was heated at reflux for 30 min., during which most of the magnesium dissolved. The solution was cooled to room temperature and added dropwise to a cooled (0° C.) solution of (5R,6S)-3-keto-6-phenyl-1-oxa-7-(tert-butoxycarbonyl)aza-spiro[4.5]decane (Description 4, 212 mg, 0.64 mmol) in diethyl ether (10 ml). The mixture was stirred at 0° C. for 10 min. and at room temperature overnight. Saturated aqueous ammonium chloride (40 ml) was added and the mixture was extracted with ethyl acetate (2×40 ml). The combined organic fractions were washed with brine (20 ml), dried (MgSO$_4$) and the solvent was evaporated under reduced pressure. The residue was purified by column chromatography on silica gel, eluting with ethyl acetate/hexane (1:5) to give the title compound as a pale foam (240 mg, 72%). $^1$H NMR (360 MHz, CDCl$_3$) δ1.47 (9H, s), 1.52–1.71 (3H, m), 2.17–2.22 (1H, m), 2.42 (1H, d, J 13.5 Hz), 2.56 (1H, d, J 13.5 Hz), 2.77–2.84 (1H, m), 3.89 (3H, s), 3.96–4.00 (1H, m), 4.20 (1H, d, J 9.5 Hz), 4.29 (1H, d, J 9.5 Hz), 5.78 (1H, s), 6.90 (1H, d, J 8.9 Hz), 7.13–7.16 (1H, m), 7.21–7.25 (1H, m), 7.30–7.35 (1H, m), and 7.62 (2H, d, J 7.7 Hz). m/z (ES$^+$) 524 (M+1).

DESCRIPTION 38

Z-(2S,3R)-3-(1-tert-Butoxycarbonyl-3-hydroxy-2-phenylpiperidin-3-yl)-2-(2-methoxyphenyl)prop-2-en-1-ol Formic acid (138 ml, 3.77 mmol) was added to a stirred, degassed solution of (2S,3R)-1-tert-butoxycarbonyl-3-(3-hydroxypropyn-1-yl)-2-phenylpiperidin-3-ol (Description 7, 473 mg, 1.43 mmol), palladium (II) acetate (33 mg, 0.14 mmol), trio-o-tolylphosphine (85 mg, 0.28 mmol), tributylamine (1.12 ml, 4.87 mmol) and 2-iodoanisole (446 ml, 3.44 mmol) in N,N-dimethylformamide (3 ml) at room temperature and the resulting mixture was heated at 70° C. for 5 h. The mixture was cooled, filtered, diluted with ethyl acetate (50 ml), washed with water (100 ml), hydrochloric acid (2M, 50 ml) and saturated aqueous sodium chloride (50 ml), dried (MgSO$_4$) and the solvent was evaporated under reduced pressure. The residue was chromatographed on silica gel, eluting with hexane/ethyl acetate (60:40) to give the title compound as a yellow glass (220 mg, 35%). $^1$H NMR (360 MHz, CDCl$_3$) δ7.41 (2H, d, J 7.6 Hz), 7.22–7.34 (4H, m), 7.12 (1H, dd, J 1.7, 7.4 Hz), 6.94 (1H, t, J 7.5 Hz), 6.89 (1H, d, J 8.2 Hz), 5.84 (1H, s), 5.00 (1H, s), 4.40 (1H, d, J 12.7 Hz), 4.15 (1H, dd, J 6.0, 13.1 Hz), 4.05 (1H, d, J 12.5 Hz), 3.86 (3H, s), 3.44 (1H, dt, J 5.6, 12.3 Hz), 2.04–2.18 (1H, m), 1.80–1.96 (3H, m), 1.28 (9H, s), and 1.64–1.84 (3H, m). m/z (ES$^+$) 440 (M+1).

DESCRIPTION 39

(2S,3R,2'R)-3-(1-tert-Butoxycarbonyl-3-hydroxy-2-phenylpiperidin-3-yl)-2-(2-methoxyphenyl)propan-1-ol and (2S,3R,2'S)-3-(1-tert-butoxycarbonyl-3-hydroxy-2-phenylpiperidin-3-yl)-2-(2-methoxyphenyl)propan-1-ol Palladium (II) hydroxide on carbon (20%, 78 mg) was added to a solution Z-(2S,3R)-3-(1-tert-butoxycarbonyl-3-hydroxy-2-phenylpiperidin-3-yl)-2-(2-methoxyphenyl) prop-2-en-1-ol (Description 38, 78 mg, 0.18 mmol) and acetic acid (2 ml) in methanol (10 ml) and the mixture was hydrogenated at 50 psi with agitation for 5 h. The mixture was filtered and the solvent was evaporated under reduced pressure. The residue was diluted with ethyl acetate (20 ml), washed with saturated sodium carbonate solution (10 ml), dried (MgSO$_4$) and the solvent was evaporated under reduce pressure. The residue was purified by preparative layer chromatography on silica, eluting with hexane/ethyl acetate (80:20) to give the title compound as a 1:3 mixture of the 2'R and 2'S epimers (22 mg, 28 %). $^1$H NMR (360 MHz, CDCl$_3$) δ7.45–7.61 (2H, m, 3R and 3S isomers), 7.16–7.37 (5H, m, 3R and 3S isomers), 6.85–6.98 (2H, m, 3R and 3S isomers, 5.17 (1H, s, 3R isomer), 5.04 (1H, s, 3S isomer), 3.96–4.04 (1H, m, 3R and 3S isomers), 3.83 (3H, s, 3R isomer), 3.82 (3H, s, 3S isomer), 3.46–3.84 (3H, m, 3R and 3S isomers), 3.04–3.20 (1H, m, 3R and 3S isomers), 1.64–2.40 (8H, m, 3R and 3S isomers), 1.32 (9H, s, 3S isomer), and 1.27 (9H, s, 3R isomer). m/z (ES$^+$) 442 (M+1).

DESCRIPTION 40

2-Bromo-4-nitrophenol

Bromine (27 ml) was added dropwise to a stirred solution of 4-nitrophenol (50 g) in glacial acetic acid (400 ml) and the mixture was stirred at room temperature for 18 h. The solvent was evaporated under reduced pressure and the residue was crystallised from dichloromethane:hexane to give the title compound as a colorless solid (67 g). $^1$H NMR (250 MHz, CDCl$_3$) δ8.44 (1H, d, J 2.6 Hz), 8.16 (1H, dd, J 2.6, 8.9 Hz) and 7.13 (1H, d, J 9.0 Hz).

DESCRIPTION 41

2-Isopropoxy-5-nitrobromobenzene

A mixture of 2-bromo-4-nitrophenol (Description 40, 2.5 g), 2-iodopropane (2.2 g) and potassium carbonate (5 g) in acetone (30 ml) was heated under reflux for 18 h. The solvent was evaporated under reduced pressure, water was added and the mixture was extracted with ethyl acetate. The organic layer was washed with water and brine, dried (MgSO$_4$) and the solvent was evaporated under reduced pressure. The residue was purified by flash column chromatography on silica gel, eluting with hexane/EtOAc (90:10) to give the title compound (2.8 g, 94%). $^1$H NMR (250 MHz, CDCl$_3$) δ8.46 (1H, s), 8.20 (1H, m), 6.93 (1H, m), 4.75 (1H, m), and 1.42 (6H, d, J 7.5 Hz).

DESCRIPTION 42

2-(Difluoromethoxy)-5-nitrobromobenzene

Prepared from the compound of Description 40 according to the method of Description 23. $^1$H NMR (360 MHz, CDCl$_3$) δ8.54 (1H, d, J 2.6 Hz), 8.22 (1H, dd, J 9.0, 2.6 Hz), 7.38 (1H, d, J 9.0 Hz), and 6.68 (1H, t, J 71.7 Hz).

DESCRIPTION 43

3-Bromo-4-methoxyaniline

A mixture 3-bromo-4-methoxynitrobenzene (15 g, 64.6 mmol) and iron powder (27.3 g, 0.49 mol) in water (100 ml) and glacial acetic acid (25 ml) was heated under reflux for 2 h. The mixture was cooled and filtered through a pad of Hyflo™, washing with 25% acetic acid/water. The filtrate was extracted with ethyl acetate (2×250 ml) and the combined organic fractions were dried (Na$_2$SO$_4$) and the solvent was evaporated under reduced pressure. The residue was purified by flash column chromatography on silica eluting with hexane/EtOAc (60:40) to give the title compound as a brown solid (10.32 g, 79%). m/z (ES$^+$) 202 (M+1).

DESCRIPTION 44

3Bromo-4-isopropoxyaniline

Prepared from the compound of Description 41 according to the method of Description 43. $^1$H NMR (250 MHz, CDCl$_3$) δ6.91 (1H, d, J 2.7 Hz), 6.78 (1H, d, J 8.6 Hz), 6.57 (1H, dd, J 2.9, 8.8 Hz), 4.33 (1H, m), and 1.32 (3H, d, J 5.6 Hz).

DESCRIPTION 45

3Bromo-4-(difluoromethoxy)aniline

Prepared from the compound of Description 42 according to the method of Description 43.

DESCRIPTION 46

3Bromo-4-(trifluoromethoxy)aniline

4-Trifluoromethoxynitrobenzene (4.1 g) was suspended in water (16 ml) and concentrated sulfuric acid (16 ml) and warmed to 80° C. with stirring. Potassium bromate (3.7 g) was added portionwise over 3 h., and the mixture was heated at 80° C. for a further 2 h. The mixture was cooled to room temperature and poured onto ice (100 g). The mixture was extracted with ethyl acetate and the combined organic fractions were dried (MgSO$_4$) and the solvent was evaporated under reduced pressure. The residue) was dissolved in acetic acid (2.5 ml) and water (10 ml) and iron powder (2.0 g) was added. The mixture was heated under reflux for 2 h., cooled to room temperature and filtered through Celite™. The filtrate was extracted with ethyl acetate and the combined organic fractions were dried (MgSO$_4$) and the solvent was evaporated under reduced pressure. The residue was purified by column chromatography on silica gel, eluting with hexane/EtOAc (3:1) to give the title compound as a yellow oil. $^1$H NMR (CDCl$_3$) δ6.57 (1H, dd), 6.9 (1H, d), 7.06 (1H, dd).

DESCRIPTION 47

N-(3-Bromo-4-methoxyphenyl)trifluoroacetamide

Trifluoroacetic anhydride (3.5 ml, 24.7 mmol) was added slowly to a stirred, cooled (0° C.) solution of 3-bromo-4-methoxyaniline (Description 43, 5 g, 24.7 mmol) and triethylamine (3.44 ml, 24.7 mmol) in dichloromethane (50 ml). The mixture was stirred at room temperature for 2 h., diluted with dichloromethane (200 ml) and washed with waster (2×200 ml). The organic layer was dried (Na$_2$SO$_4$) and the solvent was evaporated under reduced pressure. The residue was purified by flash column chromatography on silica eluting with hexane/EtOAc (85:15 increasing to 75:25) to give the title compound as a colorless solid (4.4 g, 60%). $^1$H NMR (250 MHz, CDCl$_3$) δ7.79 (1H, d, J 2.6 Hz), 7.58 (1H, dd, J 2.6, 8.9 Hz), 6.90 (1H, d, J 8.9 Hz), and 3.90 (3H, s).

DESCRIPTION 48

N-(3-Bromo-4-isopropoxyphenyl)trifluoroacetamide

Prepared from the compound of Description 44 according to the method of Description 43. $^1$H NMR (250 MHz, CDCl$_3$) δ7.79 (1H, br, s), 7.76 (1H, d, J 2.7 Hz), 7.48 (1H, dd, J 8.9, 2.7 Hz), 6.92 (1H, d, J 8.9 Hz), 4.55 (1H, sept, J 6.1 Hz, and 1.38 (6H, d, J 6.1 Hz).

DESCRIPTION 49

N-[3-Bromo-4-(difluoromethoxy)phenyl]trifluoroacetamide

Prepared from the compound of Description 45 according to the method of Description 43. $^1$H NMR (250 MHz, CDCl$_3$) δ8.01 (1H, br, s), 7.94 (1H, d, J 2.6 Hz), 7.53 (1H, dd, J 8.9, 2.6 Hz), 7.26 (1H, d, J 8.9 Hz), and 6.53 (1H, t, J 73.1 Hz).

DESCRIPTION 50

N-[3-Bromo-4-(trifluoromethoxy)phenyl]trifluoroacetamide

Prepared from the compound of Description 46 according to the method of Description 47. $^1$H NMR (360 MHz, CDCl$_3$) δ8.24 (1H, br s), 7.97 (1H, d, J 2.6 Hz), 7.59 (1H, dd, J 8.9, 2.6 Hz), and 7.34 (1H, d, J 8.9 Hz).

DESCRIPTION 51

N-Methyl-3-bromo-4-(trifluoromethoxy)aniline

Sodium hydride (60% dispersion in mineral oil, 870 mg, 21.7 mmol) was added to a stirred, cooled (0° C.) solution of N-[3-Bromo-4-(trifluoromethoxy)phenyl]trifluoroacetamide (Description 50, 6.3 g, 18.0 mmol) in DMF (50 ml). The mixture was stirred at 0° C. for 20 min. and methyl iodide (1.35 ml, 21.7 mmol) was added over 5 min. The mixture was stirred at 0° C. for 45 min. and at room temperature for 4 h. Water (100 ml) was added and the mixture was extracted with ethyl acetate (3×100 ml). The combined organic fractions were washed with water (3×100 ml) and brine (100 ml), dried (MgSO$_4$) and the solvent was evaporated under reduced pressure. The residue was purified by column chromatography on silica gel, eluting with hexane/CH$_2$Cl$_2$ (3:1 increasing to 1:1) to give the title compound as a tan oil (1.20 g, 25%). $^1$H NMR (250 MHz, CDCl$_3$) δ7.11 (1H, dq, J 8.9, 1.2 Hz), 6.86 (1H, d, J 2.8 Hz), 6.56 (1H, dd, J 8.9, 2.8 Hz), and 2.83 (3H, s).

DESCRIPTION 52

N-(3-Bromo-4-methoxyphenyl)-N-(methyl)trifluoroacetamide

Sodium hydride (60% dispersion in mineral oil, 0.48 g, 12 mmol) was added to a stirred, cooled (0° C.) solution of N-(3-Bromo-4-methoxyphenyl)trifluoroacetamide (Description 43, 2.98 g, 10 mmol) in dimethylformamide (30 ml). The mixture was stirred at 0° C. for 30 min., then methyl iodide (0.75 ml, 1.70 g, 12 mmol) was added. The mixture was stirred at 0° C. for 30 min., then at room temperature for 3 h. Water (50 ml) was added and the mixture was extracted with ethyl acetate (3×50 ml). The combined organic fractions were washed with water (4×50 ml) and brine (50 ml), dried (MgSO$_4$) and the solvent was evaporated under reduced pressure. The residue was purified by column chromatography on silica gel, eluting with hexane/CH$_2$Cl$_2$ (50:50 increasing to 30:70) to give the title compound as a colorless solid (2.72 g, 87%). $^1$H NMR (250 MHz, CDCl$_3$) δ7.46 (1H, d, J 2.4 Hz), 7.18 (1H, dd, J 8.7, 2.4 Hz), 6.91 (1H, d, J 8.7 Hz), 3.94 (3H, s), and 3.32 (3H, s).

DESCRIPTION 53

N-(3-Bromo-4-isopropoxyphenyl)-N-(methyl)trifluoroacetamide

Prepared from the compound of Description 48 according to the method of Description 52. $^1$H NMR (250 MHz, CDCl$_3$) δ7.45 (1H, d, J 2.5 Hz), 7.13 (1H, dd, J 8.8, 2.5 Hz), 6.90 (1H, d, J 8.8 Hz), 4.59 (1H, sept, J 6.1 Hz), 3.32 (3H, s), and 1.41 (6H, d, J 6.1 Hz).

DESCRIPTION 54

N-[3-Bromo-4-(difluoromethoxy)phenyl]-N-(methyl)trifluoroacetamide

Prepared from the compound of Description 49 according to the method of Description 52. $^1$H NMR (360 MHz, CDCl$_3$) δ7.56 (1H, d, J 2.5 Hz), 7.26 (2H, m), 6.58 (1H, t, J 72.6 Hz), and 3.35 (3H, s).

DESCRIPTION 55

N-[3-Bromo-4-(trifluoromethoxy)phenyl]-N-(methyl)trifluoroacetamide

Prepared from the compound of Description 51 according to the method of Description 47. $^1$H NMR (250 MHz, CDCl$_3$) δ7.59 (1H, d, J 2.3 Hz), 7.39 (1H, br d, J 9 Hz), 7.27 (1H, br d, J 9 Hz), and 3.36 (3H, s).

DESCRIPTION 56

2-Methoxy-5-(2,2,2-trifluoroethylamino)bromobenzene

Borane-dimethylsulfide complex (2M in THF, 6.7 ml, 13.4 mmol) was added to a solution of N-(3-Bromo-4-methoxyphenyl)trifluoroacetamide (Description 52, 2.0 g, 6.7 mmol) in tetrahydrofuran (20 ml) and the mixture was heated under reflux for 18 h. The mixture was cooled and the solvent was evaporated under reduced pressure to give the title compound as a yellow oil (2.1 g). $^1$H NMR (360 MHz, CDCl$_3$) δ6.93 (1H, d, J 2.9 Hz), 6.80 (1H, d, J 8.8 Hz), 6.62 (1H, dd, J 8.8, 2.9 Hz), 3.82 (3H, s), and 3.71 (3H, m). m/z (ES$^+$) 284, 286 (M+1).

DESCRIPTION 57

N-(3-Bromo-4-methoxyphenyl)-N-(2,2,2-trifluoroethyl)acetamide

Acetic anhydride (1.26 ml, 13.4 mmol) was added to a cooled (0° C.) solution of 2-methoxy-5-(2,2,2-trifluoroethylamino)bromobenzene (Description 56, 2.1 g) and triethylamine (1.9 ml, 1.37 g, 13.4 mmol) in dichloromethane and the mixture was heated under reflux for 18 h. The mixture was cooled and the solvent was evaporated under reduced pressure. 1,2-Dichloroethane (20 ml) was added and the mixture was heated under reflux for 24 h. Further acetic anhydride (0.6 ml) and triethylamine (0.95 ml) were added and the mixture was heated under reflux for 24 h., cooled and diluted with dichloromethane (100 ml). The mixture was diluted with water (3×50 ml) and brine (50 ml), dried (MgSO$_4$) and the solvent was evaporated under reduced pressure. The residue was triturated with ethyl acetate and the solid was collected and dried in vacuo to give the title compound as an off-white solid (1.28 g, 59%). $^1$H NMR (360 MHz, CDCl$_3$) δ7.44 (1 H, d, J 2.5 Hz), 7.17 (1 H, dd, J 8.7, 2.5 Hz), 6.93 (1 H, d, J 8.7 Hz), 4.29 (2 H, q, J 8.8 Hz), 3.94 (3 H, s), and 1.90 (3 H, m), m/z (ES$^+$) 326, 328 (M+1).

DESCRIPTION 58

2-Ethoxy-5-(trifluoromethoxy)bromobenzene

2-Bromo-4-trifluoromethoxyphenol (Description 11, 1 g) was dissolved in N,N dimethylformamide (12 ml) and potassium carbonate (1.07 g) was added. Iodoethane (0.78 ml) was added and the mixture was stirred at room temperature. Water (150 ml) and ethyl acetate were added and the layers were separated. The organic layer was washed with brine, dried (MgSO$_4$) and the solvent was evaporated under reduced pressure. The residue was purified by flash column chromatography on silica gel, eluting with hexane/EtOAc (100:0 increasing to 95:5) to give the title compound as a colourless oil (1.02 g). $^1$H NMR (250 MHz, CDCl$_3$) δ1.47 (3 H, t, J 7.0 Hz), 4.09 (2 H, q, J 7.0 Hz), 6.85 (1 H, d, J 9.0 Hz), 7.11 (1 H, m), and 7.43 (1 H, m).

DESCRIPTION 59

2-(Trifluoromethylthio)bromobenzene

A solution of 2-bromothiophenol (2 g) and triethylamine (2.2 ml) in N,N-dimethylformamide was purged with nitrogen for 5 min., methylviologen dichloride was added and the mixture was saturated with trifluoromethyl iodide gas. After 40 min. the mixture was poured on to ice and extracted with diethyl ether. The organic layer was dried (MgSO$_4$) and the solvent was evaporated under reduced pressure. The residue was purified by flash column chromatography on silica gel, eluting with hexane to give the title compound as a colourless oil (0.8 g). $^1$H NMR (360 MHz, CDCl$_3$) δ7.30–7.42 (2 H, m) and 7.70–7.81 (2 H, m).

DESCRIPTION 60

2-Bromo-1-(2,2,2-trifluoroethoxy)-4-(trifluoromethyl)benzene

Prepared from the compound of Description 35 according to the method of Description 22. $^1$H NMR (250 MHz, CDCl$_3$) δ4.45 (2 H, q, J 7.9 Hz), 6.97 (1 H, d, J 8.6 Hz), 7.58 (1 H, dd, J 10.7, 1.5 Hz), and 7.85 (1 H, d, J 1.4 Hz).

DESCRIPTION 61

1-Isopropoxy-2-bromo-4-(trifluoromethyl)benzene

Prepared from the compound of Description 35 according to the method of Description 41. $^1$H NMR (360 MHz, CDCl$_3$) δ1.40 (6 H, d, J 6.1 Hz), 4.64 (1 H, septet, J 6.1 Hz), 6.94 (1 H, d, J 8.8 Hz), 7.49 (1 H, dd, J 8.9, 2.1 Hz), and 7.78 (1 H, d, J 1.9 Hz).

DESCRIPTION 62

2-Benzyloxybromobenzene

Benzyl bromide (27.5 ml) was added to a mixture of 2-bromophenol (10 g, 58 mmol) and potassium carbonate (64 g) in DMF (70 ml) and the mixture was stirred at room temperature for 72 h. The mixture was poured into water and extracted with ethyl acetate (2×). The combined organic fractions were washed with water, dried (Na$_2$SO$_4$) and the solvent was evaporated under reduced pressure. The residue was purified by flash column chromatography on silica gel, eluting with hexane/EtOAc (98:2) to give the title compound (2.9 g). $^1$H NMR (250 MHz, CDCl$_3$) δ7.58-7.20 (7 H, m), 6.94 (1 H, d 7.9 Hz), 6.84 (1 H, t, J 7.9 Hz), and 5.16 (2 H, s).

DESCRIPTION 63

3-Bromo-4-methoxybenzenecarboxamide

Oxalyl chloride (1.13 mL, 1.65 g, 13 mmol) was added slowly to a stirred, cooled (0° C.) solution of 3-bromo-4-methoxybenzoic acid (3 g, 13 mmol) and DMF (1 drop) in dichloromethane (50 mL) and the mixture was stirred at 0° C. for 10 min., then at room temperature for 2 h. Ammonia was bubbled through the mixture for 10 min., dichloromethane was added and the mixture was washed with water, dried (MgSO$_4$) and the solvent was evaporated under reduced pressure to give the title compound as a colorless solid (2.80 g, 86%). $^1$H NMR (250 MHz, DMSO-d$_6$) δ8.23 (1 H, d, J 2.2 Hz), 8.08 (1 H, br s), 8.03 (1 H, dd, J 8.6, 2.3 Hz), 7.47 (1 H, br s), 7.30 (1 H, d, J 8.6 Hz), and 4.03 (3 H, s).

DESCRIPTION 64
Methyl-3-Bromo-4-hydroxybenzoate

Sulfuric acid (conc., 10 ml) was added to a solution of 3-bromo-4-hydroxybenzoic acid (10.0 g, 46 mmol) in methanol (100 ml) and the mixture was stirred at room temperature for 72 h. The solvent was evaporated under reduced pressure and the residue was dissolved in ethyl acetate (250 ml). The mixture was washed with saturated aqueous sodium bicarbonate (2×250 ml), dried ($MgSO_4$) and the solvent was evaporated under reduced pressure to give the title compound as a colorless solid (8.83 g, 83%). $^1$H NMR (250 MHz, $CDCl_3$) δ8.19 (1 H, d, J 2.0 Hz), 7.92 (1 H, dd, J 8.5, 2.0 Hz), 7.05 (1 H, d, J 8.5 Hz), 5.91 (1 H, s), and 3.90 (3 H, s).

DESCRIPTION 65
Methyl 3-Bromo-4-(difluoromethoxy)benzoate

Ethyl chlorodifluoroacetate (1.12 ml, 8.7 mmol) was added to a mixture of methyl 3-bromo-4-hydroxybenzoate (Description 64, 2.0 g, 8.7 mmol) and potassium carbonate (1.2 g, 8.7 mmol) in N,N-dimethylformamide (20 ml) and the mixture was heated at 65° C. for 16 h. The mixture was cooled, water (100 ml) was added and the mixture was extracted with ethyl acetate (2×100 ml). The combined organic fractions were dried ($Na_2SO_4$) and the solvent was evaporated under reduced pressure. The residue was purified by column chromatography on silica gel, eluting with hexane/EtOAc (95:5) to give the title compound as a colorless solid (1.20 g, 49%). $^1$H NMR (250 MHz, $CDCl_3$) δ8.31 (1 H, d, J 2.0 Hz), 8.22 (1 H, dd, J 8.5, 2.0 Hz), 7.05 (1 H, m), 6.61 (1 H, t, J 73 Hz), and 3.93 (3 H, s).

DESCRIPTION 66
Methyl 3-Bromo-4-(2,2,2-trifluoroethoxy)benzoate

Sodium hydride (60% dispersion in mineral oil, 520 mg, 13.0 mmol) was added to a stirred, cooled (0° C.) solution of methyl 3-bromo-4-hydroxybenzoate (Description 64, 3.0 g, 13.0 mmol) in N,N'-dimethylformamide (100 ml) and the mixture was stirred at 0° C. for 15 min. 2,2,2-Trifluoroethyltosylate (6.61 g, 26.0 mmol) in N,N'-dimethylformamide (50 ml) was added and the mixture was stirred at 100° C. for 16 h. The mixture was concentrated under reduced pressure to half volume and poured into aqueous sodium hydroxide solution (1 M, 300 ml). The mixture was extracted with ethyl acetate (2×350 ml) and the combined organic fractions were dried ($Na_2SO_4$) and the solvent was evaporated under reduced pressure. The residue was purified by column chromatography on silica gel, eluting with hexane/EtOAc to give the title compound as a colorless oil (1.37 g, 34%). $^1$H NMR (250 MHz, $CDCl_3$) δ8.27 (1 H, d, J 2.1 Hz), 7.99 (1 H, dd, J 2.1, 8.6 Hz), 6.92 (1 H, d, J 8.6 Hz), 4.42–4.52 (2 H, quartet, J 7.9 Hz), and 3.91 (3 H, s).

DESCRIPTION 67
Methyl 3-Bromo-4-(cyclobutyloxy)benzoate

A mixture of methyl 3-bromo-4-hydroxybenzoate (Description 64, 2.3 g, 10 mmol), bromocyclobutane (2.0 g, 15 mmol) and potassium carbonate (2.42 g, 17.5 mmol) in DMF (25 ml) was stirred at room temperature for 3 days then at 70° C. for 6 h. The mixture was cooled, diluted with water (150 ml) and extracted with ethyl acetate (4×25 ml). The combined organic fractions were washed with aqueous sodium hydroxide (1M, 25 ml), dried ($MgSO_4$), and the solvent was evaporated under reduced pressure to give the title compound as a gum (1.15 g). $^1$H NMR ($CDCl_3$) δ 1.66–1.77 (1 H, m), 1.88–1.93 (1 H, m), 2.22–2.31 (2 H, m), 2.46–2.60 (2 H, m), 3.89 (3 H, s), 4.75 (1 H, app. pent, J 7.0 Hz), 6.74 (1 H, d, J 8.6 Hz), 7.91 (1 H, dd, J 8.6, 2.1 Hz), and 8.23 (1 H, d, J 2.1 Hz).

DESCRIPTION 68
3-Bromo-4-(cyclobutyloxy)benzenecarboxamide

Aqueous sodium hydroxide (4M; 4 ml) was added to a solution of methyl 3-bromo-4-(cyclobutyloxy)benzoate (Description 67, 1.15 g; 4 mmol) in methanol (15 ml) and the mixture was stirred at room temperature for 20 h. The solvent was evaporated, water (25 ml) was added and the mixture was washed with ethyl acetate (2×10 ml). The aqueous layer was acidified with hydrochloric acid (5M) and the resulting suspension was extracted with dichloromethane (2×25 ml). The combined organic fractions were dried ($MgSO_4$), and the solvent was evaporated under reduced pressure. The residue was suspended in dichloromethane (15 ml) containing DMF (3 drops), and oxalyl chloride (0.44 ml) was added. The mixture was stirred at room temperature for 1.5 h., then the solvent was evaporated under reduced pressure. The residue was dissolved in THF (5 ml) and added with stirring to concentrated aqueous ammonia (50 ml). The precipitate was collected, washed with water and dried to give the title compound (0.91 g). $^1$H NMR (DMSO-$d_6$) δ1.60–1.88 (2 H, m), 2.01–2.12 (2 H, m), 2.43–2.51 (1 H, m), 3.34 (3 H, s), 4.83 (1 H, app. pent, J 7.1 Hz), 7.00 (1 H, d, J 8.6 Hz), 7.33 (1 H, br s), 7.84 (1 H, dd, J 8.6, 2.1 Hz), 8.09 (1 H, br s), and 8.10 (1 H, d, J 2.1 Hz).

DESCRIPTION 69
2-Bromo-4-(trifluoromethoxy)benzonitrile

A solution of sodium nitrite (2.76 g, 40 mmol) in water (15 ml) was added dropwise to a suspension of 2-bromo-4-(trifluoromethoxy)aniline (10.2 g, 40 mmol) in a mixture of concentrated hydrochloric acid (20 ml) and water (50 ml) at 0° C. The mixture was stirred at 0° C. for 45 min., then added dropwise to a mixture of potassium cyanide (11.4 g, 176 mmol) and copper (II) sulfate (6.4 g, 40 mmol) in water (80 ml) at 65° C. The mixture was stirred at 65° C. for 30 min., cooled to room temperature and filtered through a pad of Hyflo™ washing with dichloromethane (2×200 ml). The phases were separated and the aqueous phase was extracted with dichloromethane (100 ml). The combined organic fractions were dried and the solvent was evaporated under reduced pressure. The residue was purified by flash column chromatography on silica, eluting with hexane/EtOAc (75:25), to give the title compound as an oil. $^1$H NMR (360 MHz, $CDCl_3$) δ7.12–7.15 (1 H, m), 7.56 (1 H, s), and 7.72 (1 H, d, J 8.6 Hz).

DESCRIPTION 70
(2-Bromophenyl)methylsulfoxide

Oxone (9.7 g) in water (40 ml) was added slowly to a stirred, cooled cooled (0° C.) solution of 2-bromothioanisole (5 g, 24.6 mmol) and sodium bicarbonate (16 g) in acetone (20 ml). The mixture was stirred for at room temperature 16 h., then water and dichloromethane was added. The layers were separated and the organic phase was dried ($MgSO_4$) and the solvent was evaporated under reduced pressure. The residue was purified by chromatography on silica gel, eluting with hexane/EtOAc (80:20 increasing to 40:60) to give the title compound (6.1 g). m/z ($ES^+$) 219 (M+1).

DESCRIPTION 71
(2-Bromophenyl)methylsulfone

Oxone™ (9.7 g) in water (40 ml) was added slowly to a stirred, cooled cooled (0° C.) solution of 2-(bromophenyl)methylsulfoxide (Description 70; 24 mmol) and sodium bicarbonate (16 g) in acetone (20 ml). The mixture was heated at 60° C. for 2 h. then water and dichloromethane was added. The layers were separated and the organic phase was dried (MgSO$_4$) and the solvent was evaporated under reduced pressure. The residue was purified by chromatography on silica gel, eluting with hexane/EtOAc (100:0 increasing to 70:30) to give the title compound (4.1 g) m.p. 106–107° C. m/z (ES$^+$) 235,237 (M+1).

DESCRIPTION 72
(3S,5R,6S)-3-(5-Cyano-2-methoxyphenyl)-6-phenyl-1-oxa-7-(trifluoroacetyl)aza-spiro[4,5]decane Prepared from the compound of Example 139 according to the method of Example 111. $^1$H NMR (250 MHz, CDCl$_3$) δ1.71–1.81 (3 H, m), 2.05–2.28 (3 H, m), 2.05–2.28 (3 H, m), 3.24–3.36 (1 H, m) 5.55 (1 H, s), 6.79–6.83 (1 H, d, J 12.3 Hz), 7.19–7.32 (4 H, m), and 7.42–7.49 (3 H, m), m/z (ES$^+$) 445 (M+1).

DESCRIPTION 73
Methyl 3-Bromo-4-hydroxyphenylethanoate

Bromine (16.59 g, 104 mmol) in chloroform (25 mL) was added dropwise to a stirred, cooled (0° C.) mixture of methyl 4-hydroxyphenylethanoate (17.25 g, 104 mmol) and acetic acid (10 mL) in chloroform (140 mL). The mixture was stirred at 0° C. for 1 h., diluted with dichloromethane (100 mL), washed with water (2×200 mL) and brine (200 mL), dried (MgSO$_4$) and the solvent was evaporated under reduced pressure to give the title compound as a colorless solid (25.43 g, 100%). $^1$H NMR (360 MHz, CDCl$_3$) δ7.39 (1 H, d, J 2.0 Hz), 7.12 (1 H, dd, J 8.3, 2.0 Hz), 6.96 (1 H, d, J 8.3 Hz), 5.54 (1 H, br s), 3.70 (3 H, s), and 3.54 (2 H, s).

DESCRIPTION 74
Methyl 3-Bromo-4-Methoxyphenylethanoate

Methyl iodide (2.05 mL, 4.68 g, 33 mmol) was added to a mixture of methyl 3-bromo-4-hydroxyphenylethanoate (Description 73, 7.35 g, 30 mmol) and potassium carbonate (8.29 g, 60 mmol) in dimethylformamide (30 mL) and the mixture was stirred at room temperature for 16 h. Water (100 mL) was added and the mixture was extracted with ethyl acetate (3×100 mL). The combined organic fractions were washed with aqueous sodium hydroxide (1M, 2×100 mL), water (2×100 mL) and brine (100 mL), dried (MgSO$_4$) and the solvent was evaporated under reduced pressure to give the title compound as a colorless solid (7.65 g, 100%). $^1$H NMR (360 MHz, CDCl$_3$) δ7.47 (1 H, d, J 2.1 Hz), 7.18 (1 H, dd, J 8.4, 2.1 Hz), 6.85 (1 H, d, J 8.4 Hz), 3.88 (3 H, s), 3.70 (3 H, s), and 3.49 (2 H, s).

DESCRIPTION 75
(3S,5R,6S)-7-(4-Chlorobut-2-yn-1-yl)-3-[2-isopropoxy-5-(trifluoromethyl)phenyl]-6-phenyl-1-oxa-7-aza-spiro[4,5]decane 1,4-Dichlorobutyne (0.2 ml) was added to a mixture of (3S,5R,6S)-3-(2-(2,2,2-trifluoroethoxy)-5-fluorophenyl)-6-phenyl-1-oxa-7-aza-spiro[4,5]decane (Example 19, 100 mg), and potassium carbonate (140 mg) in dimethylformamide (1 mL) and the mixture was stirred at room temperature overnight. The mixture was diluted with water (20 ml) and extracted with ether (3×5 ml). The combined organic fractions were washed with brine, dried (MgSO$_4$) and the solvent was evaporated under reduced pressure. The residue was purified by chromatography on silica gel, eluting with hexane/EtOAc (95:5 increasing to 80:20) to give the title compound as a colorless oil (100 mg). m/z (ES$^+$) m/z 506 (M+1).

DESCRIPTION 76
(3S,5R,6S)-7-(4-Azidobut-2-yn-1-yl)-3-[2-isopropoxy-5-(trifluoromethyl)phenyl]-6-phenyl-1-oxa-7-aza-spiro[4,5]-decane Sodium azide (15 mg) was added to a solution of (3S,5R,6S)-7-(4-chlorobut-2-yn-1-yl)-3-[2-isopropoxy-5-(trifluoromethyl)phenyl]-6-phenyl-1-oxa-7-aza-spiro[4,5]decane (Description 75, 100 mg) in dimethylsulfoxide (1 ml). The mixture was stirred at room temperature overnight, diluted with water (20 ml) and extracted with ether (3×5 ml). The combined organic fractions were washed with brine, dried (MgSO$_4$) and the solvent was evaporated under pressure to give the title compound as a colorless oil (98 mg). m/z (ES$^+$) m/z 513 (M+1).

DESCRIPTION 77
1-Dimethylamino-4-(trifluoromethoxy)benzene

A mixture of 1-bromo-4-(trifluoromethoxy)benzene (2.41 g), tris(dimethylamino)borane (1.43 g), sodium t-butoxide (1.34 g), tris(dibenzylideneacetone)dipallidium (18 mg), and o-tolylphosphine (12 mg) in toluene (30 ml) was heated under reflux for 4 h. The mixture was cooled, diluted with water (30 mL) and extracted with ethyl acetate (3×10 mL). The combined organic fractions were washed with brine, dried (MgSO$_4$) and the solvent was evaporated under reduced pressure. The residue was purified by chromatography on silica gel, eluting with hexane/EtOAc (99:1 increasing to (95:5) to give the title compound as an oil (600 mg). $^1$H NMR (360 MHz, CDCl$_3$) δ2.95 (6 H, s), 6.66 (2 H, d, J 9 Hz), and 7.08 (2 H, d, J 8.5 Hz). m/z (ES$^+$) m/z 206 (M+1).

DESCRIPTION 78
2-Dimethylamino-5-(trifluoromethoxy)bromobenzene

Bromine (0.15 ml) was added dropwise to a stirred, cooled (0° C.) mixture of 1-dimethylamino-4-(trifluoromethoxy)benzene (Description 77, 600 mg) and sodium carbonate (620 mg) in chloroform (15 ml). The mixture was stirred for 1 h. and diluted with water. The organic layer was washed with brine, dried (MgSO$_4$) and the solvent was evaporated under reduced pressure. The residue was purified by chromatography on silica gel, eluting with hexane/EtOAc (99:1 increasing to 95:5) to give the title compound as an oil (300 mg). $^1$H NMR (360 MHz, CDCl$_3$) δ2.79 (6 H, s), 7.06 (1 H, d, J 9 Hz), 7.14 (1 H, dd, J 6, 1.5 Hz), and 7.44 (1 H, d, J 2.0 Hz). m/z (ES$^+$) m/z 270, 272 (M+1).

DESCRIPTION 79
(2R,3R)-1-(Phenylmethoxycarbonyl)-2-phenylpiperidin-3-ol (2R,3R)-3-Hydroxy-2-phenylpiperidine dibenzoyltartrate (prepared by the method European Patent Specification number 0 528 495-A, 35.6 g, 0.1 mol) was added slowly to a mixture of benzylchloroformate (21.4 mL, 25.6 g, 0.15 mol), dichloromethane (50 mL) and aqueous sodium hydroxide (1M, 500 mL). The mixture was stirred vigorously for 1 h., then further benzylchloroformate (8.0 mL, 9.56 g, 56 mmol) in dichloromethane (50 mL) was added slowly. The mixture was stirred vigorously overnight, the layers were separated and the aqueous layer was extracted with dichloromethane (100 mL). The combined organic fractions were dried (MgSO$_4$) and the solvent was evaporated under reduced pressure. The residue was triturated with hexane and the solid was collected and dried in vacuo to give the title compound as a colorless solid (29.53 g, 95%). $^1$H NMR (250 MHz, CDCl$_3$) δ7.47-7.24 (10 H, m), 5.44 (1 H, d, J 5.7 Hz), 5.14 (1 H, d, J 12.4 Hz), 5.07 (1 H, d, J 12.4 Hz), 4.09 (2 H, m), 3.09 (1 H, m), and 1.88-1.58 (6 H, m).

DESCRIPTION 80
(±)-1-(Phenylmethoxycarbonyl)-2-phenylpiperidin-3-one

Dimethyl sulfoxide (9.1 mL, 10.0 g, 128.6 mmol) in dichloromethane (50 mL) was added slowly to a cooled (−75° C.) solution of oxalyl chloride (6.9 mL, 10.2 g, 80.4 mmol) in dichloromethane (500 mL). The mixture was stirred at −75° C. for 15 min., then (2R,3R)-1-(phenylmethoxycarbonyl)-2-phenylpiperidin-3-ol (Description 79, 20.0 g, 64.3 mmol) was added slowly. The mixture was stirred at −75° C. for 1 h., then triethylamine (27 mL, 19.5 g, 192.9 mmol) was added. The mixture was stirred at −75° C. for 1 h., then at room temperature overnight. The mixture was washed with aqueous citric acid (1M), aqueous sodium hydrogen carbonate, water, and brine, dried (MgSO$_4$) and the solvent was evaporated under reduced pressure to give the title compound as a yellow oil (19.56 g, 98%). $^1$H NMR (250 MHz, CDCl$_3$) δ7.39-7.20 (10 H, m), 5.74 (1 H, br s), 5.17 (2 H, br s), 4.13 (1 H, br s), 3.40 (1 H, br m), 2.47 (2 H, m), and 1.94 (2 H, m).

DESCRIPTION 81
(±)-(2S*,3R*)-3-(3-Hydroxypropyn-1yl)-1-(phenylmethoxycarbonyl)-2-phenylpiperidin-3-ol Prepared from the compound of Description 80 according to the method of Description 7. $^1$H NMR (250 MHz, CDCl$_3$) δ7.56 (2 H, d, J 6.0 Hz), 7.31 (8 H, m), 5.66 (1 H, s), 5.15 (1 H, d, J 12.5 Hz), 5.09 (1 H, d, J 12.5 Hz), 4.12 (2 H, s), 4.08 (1 H, m), 3.55 (2 H, br s), 3.20 (1 H, m), 2.91 (1 H, m), and 2.34-1.35 (3 H, m).

DESCRIPTION 82
(±)-(5R*,6S*)-3-Tributylstannyl-6-phenyl-1-oxa-7-(phenylmethoxycarbonyl)aza-spiro[4,5]dec-3-ene Prepared from the compound of Description 81 according to the method of Description 8. $^1$H NMR (250 MHz, CDCl$_3$) δ7.39-7.14 (10 H, m), 5.91 (1 H, t, J 2.4 Hz), 5.15 (1 H, d, J 12.5 Hz), 5.01 (1 H, d, J 12.5 Hz), 4.99 (1 H, s), 4.60 (1 H, dd, J 12.8, 2.4 Hz), 4.22 (1 H, m), 4.14 (1 H, dd, J 12.8, 2.4 Hz), 3.31 (1 H, m), 2.01-1.70 (4 H, m), and 1.54-0.82 (27 H, m).

DESCRIPTION 83
(±)-(5R*,6S*)-3-Iodo-6-phenyl-1-oxa-7-(phenylmethoxycarbonyl)aza-spiro[4,5]dec-3-ene A solution of iodine (2.08 g, 8.2 mmol) as dichloromethane (100 mL) was added to a stirred solution of (±)-(5R*,6S*)-3-tributylstannyl-6-phenyl-1-oxa-7-(phenylmethoxycarbonyl)aza-spiro[4,5]dec-3-ene (Description 82, 5.0 g, 7.8 mmol) at −78° C. The mixture was stirred for 1 h, and quenched with saturated sodium sulphite solution (10 mL). After warming to room temperature the mixture was washed with saturated sodium chloride solution (100 mL), dried (MgSO$_4$) and the solvent was evaporated under reduced pressure. The residue was taken up in acetonitrile (100 mL) and washed with hexane (3×100 mL). The hexane washes were extracted with acetonitrile (3×50 mL). The combined acetonitrile fractions were evaporated under reduced pressure to give a yellow oil, which was triturated with hexane to give the title compound as a white solid (2.27 g, 61%). $^1$H NMR (360 MHz, CDCl$_3$) δ7.40 (2 H, d, J 7.4 Hz), 7.20–7.33 (8 H, m), 6.36 (1 H, t, J 2.2 Hz), 5.16 (1 H, s), 5.12 (2 H, s), 4.49 (1 H, dd, J 2.2 and 12.6 Hz), 4.16 (1 H, dd, J 2.2 and 12.6 Hz), 4.13–4.19 (1 H, m), 3.08–3.18 (1 H, m), 2.00–2.12 (1 H, m), 1.70–1.84 (3 H, m). m/z (ES$^+$) 476 (M+1).

DESCRIPTION 84
(±)-5R*,6S*)-6-Phenyl-1-oxa-7-(phenylmethoxycarbonyl)aza-spiro[4,5]dec-3-ene A solution of (±)-(5R*,6S*)-3-iodo-6-phenyl-1-oxa-7-(phenylmethoxycarbonyl)aza-spiro[4,5]dec-3-ene (Description 83, 1.11 g, 2.34 mmol), α,α'-azoisobutyronitrile (38 mg, 0.23 mmol) and tributyltin hydride (0.75 mL, 2.80 mmol) in toluene (10 mL) was heated at 100° C. for 5 h., cooled and the solvent was evaporated under reduced pressure. The residue was taken up in acetonitrile (50 mL) and washed with hexane (3×50 mL). The hexane washes were extracted with acetonitrile (50 mL). The combined acetonitrile fractions were the solvent was evaporated under reduced pressure to give an oil, which was chromatographed with 10% ethyl acetate in hexane to give the title compound as a colourless oil (665 mg, 81%). $^1$H NMR (360 MHz, CDCl$_3$) δ7.45 (2 H, d, J 7.2 Hz), 7.20–7.31 (8 H, m), 6.00 (1 H, dt, J 6.2, 2.3 Hz), 5.87 (1 H, bd, J 6.2 Hz), 5.15 (1 H, s), 5.15 (1 H, d, J 12.5 Hz), 5.09 (1 H, d, J 12.5 Hz), 4.61 (1 H, dt, J 13.3, 1.9 Hz), 4.32 (1 H, dt, J 13.2, 2.1 Hz), 4.16 (1 H, dd, J 13.1, 5.7 Hz), 3.08–3.18 (1 H, m), 2.00–2.10 (1 H, m), and 1.70–1.90 (3 H, m). m/z (ES$^+$) 350 (M+1).

DESCRIPTION 85
Z-(2S,3R)-1-tert-Butoxycarbonyl-3-(3-hydroxyprop-1-en-1-yl)-2-phenylpiperidin-3-ol Palladium on calcium carbonate, poisoned with lead (Lindlar catalyst, 2 g) was added to a solution of (2S,3R)-1-tert-butoxycarbonyl-3-(3-hydroxypropyn-1yl)-2-phenylpiperidin-3-ol (Description 7; 32 g, 96.6 mmol) in ethyl acetate (300 mL) and the mixture was stirred under hydrogen (1 Atm.) for 4 h. The mixture was filtered and the solvent was evaporated under reduced pressure to give the title compound as an oil (32 g, 100%). $^1$H NMR (360 MHz, CDCl$_3$) δ7.42 (2 H, d, J 7.6 Hz), 7.35-7.25 (3 H, m), 5.83 (1 H, d, J 12.3 Hz), 5.68 (1 H, dt, J 12.3, 6.0 Hz), 5.06 (1 H, s), 4.27 (1 H, m), 4.12 (2 H, m), 3.32 (1 H, m), 3.13 (1 H, s), 2.28 (1 H, t, J 5.9 Hz), 2.02 (1 H, m), 1.92-1.78 (3 H, m), and 1.32 (9 H, s). m/z (ES$^+$) 334 (M+1).

DESCRIPTION 86
(5R,6S)-6-Phenyl-1-oxa-7-(tert-butoxycarbonyl)aza-spiro[4,5]dec-3-ene Diethylazodicarboxylate (18.2 mL, 115 mmol) in THF (100 mL) was added dropwise to a solution of Z-(2S,3R)-1-tert-butoxycarbonyl-3-(3-hydroxyprop-1-en-1-yl)-2-phenylpiperidin-3-ol (Description 85; 32 g, 96 mmol) and triphenylphosphine (30.2 g, 115 mmol) in THF (700 mL). The mixture was stirred at 0° C. for 30 min. then at room temperature for 1.5 h. The solvent was evaporated under reduced pressure and the residue was purified by flash column chromatography on silica gel, eluting with hexane/EtOAc (95:5 increasing to 80:20) to give the title compound as a colorless solid (23.4 g, 77%). $^1$H NMR (CDCl$_3$) δ7.45 (2 H, d, J 7.4 Hz), 7.27 (2 H, t, J 7.4 Hz), 7.20 (1 H, t, J 7.4 Hz), 6.03 (1 H, dt, J 6.1, 2.0 Hz), 5.68 (1 H, dt, J 6.1, 2.0 Hz), 5.06 (1 H, s), 4.61 (1 H, dt, J 13.1, 2.0 Hz), 4.32 (1 H, dt, J 13.1, 2.0 Hz), 4.08 (1 H, m), 3.05 (1 H, m), 2.05 (1 H, m), 1.75 (3 H, m), and 1.37 (9 H, s). m/z (ES$^+$) 316 (M+1).

DESCRIPTION 87
(2S)-1-tert-Butoxycarbonyl-2-(4-fluorophenyl)piperidin-3-one

Prepared from (2S,3S)-1-tert-butoxycarbonyl-3-hydroxy-2-(4-fluorophenyl)piperidine (prepared by the method described in Int. Patent Publication WO 94/19323) according to the method of Description 1. $^1$H NMR (360 MHz, CDCl$_3$) δ 1.43 (9 H, s), 1.99 (2 H, m), 2.48 (2 H, m) 3.31 (1 H, m), 4.05 (1 H, br s), 5.62 (1 H, br s), 7.04 (2 H, t, J 7.4 Hz), and 7.21 (2 H, dd, J 7.5, 8.9 Hz).

DESCRIPTION 88
(2S,3R)-1-tert-Butoxycarbonyl-3-(3-hydroxypropyn-1-yl)-2-(4-fluorophenyl)piperidin-3-ol Prepared from the compound of Description 87 according to the method of Description 7. $^1$H NMR (360 MHz, CDCl$_3$) δ1.40 (9 H, s), 1.64 (1 H, m), 2.04 (2 H, m), 2.1 (1 H, m), 2.75 (1 H, td, J 13.4, 3.6 Hz), 3.03 (1 H, br s), 3.47 (1 H, br s), 3.96 (1 H, dd, J 14.8, 4.7 Hz), 4.25 (2 H, s), 5.58 (1 H, s), 6.96 (2 H, t, J 6.7 Hz), and 7.53 (2 H, dd, J 8.5, 5.4 Hz).

DESCRIPTION 89
Z-(2S,3R)-1-tert-Butoxycarbonyl-3-(3-hydroxyprop-1-en-1-yl)-2-(4-fluorophenyl)piperidin-3-ol Prepared from the compound of Description 88 according to the method of Description 85. $^1$H NMR (360 MHz, CDCl$_3$) δ1.34 (9 H, s), 1.77 (1 H, m), 1.90 (1 H, m), 2.03 (1 H, m), 3.19 (2 H, dd, J 11.3, 5.9 Hz), 4.06 (1 H, dd, J 13.7, 6.04 Hz), 4.18 (1 H, dd, J 5.73, 1.2 Hz), 4.30 (1 H, dd, J 14.0, 7.4 Hz), 5.10 (1 H, s), 5.68 (1 H, m), 5.85 (1 H, dt, J 12.3, 1.3 Hz), 7.00 (2 H, t, J 8.9 Hz), and 7.41 (2 H, dd, J 8.71, 5.6 Hz).

DESCRIPTION 90
(5R,6S)-6-(4-Fluorophenyl)-1-oxa-7-(tert-butoxycarbonyl)aza-spiro[4,5]dec-3-ene Prepared from the compound of Description 89 according to the method of Description 86. $^1$H NMR (360 MHz, CDCl$_3$) δ1.37 (9 H, s), 1.75 (3 H, m), 1.99 (1 H, m), 3.04 (1 H, td, J 11.7 Hz), 4.08 (1 H, dd, J 13.2 Hz), 4.27 (1 H, dt, J 12.9 Hz), 4.60 (1 H, dt, J 13.2, 1.8 Hz), 5.00 (1 H, s), 5.87 (1 H, d, J 6.16 Hz), 5.99 (1 H, d, J 8.6 Hz), 6.95 (2 H, t, J 8.7 Hz), and 7.40 (2 H, dd, J 8.7, 5.8 Hz).

DESCRIPTION 91
(3S,5R,6S)-3-(2-Methoxy-5-(trifluoromethoxy)phenyl)-6-phenyl-1-oxa-7-(tert-butoxycarbonyl)aza-spiro[4,5]-decan-3-ol 2-Bromo-4-(trifluoromethoxy)anisole (Description 12, 417 mg, 1.54 mmol) was added portionwise to magnesium (41 mg, 1.7 mmol) in diethyl ether (1 mL), under a nitrogen atmosphere, and the mixture was heated briefly at reflux following each addition. Once the addition was complete, the mixture was heated at reflux for 30 min., during which most of the magnesium dissolved. The solution was cooled to room temperature and added dropwise to a cooled (0° C.) solution of (5R,6S)-3-keto-6-phenyl-1-oxa-7-(tert-butoxycarbonyl)aza-spiro[4.5]decane (Description 4, 212 mg, 0.64 mmol) in diethyl ether (10 mL). The mixture was stirred at 0° C. for 10 min. and at room temperature overnight. Saturated aqueous ammonium chloride (40 mL) was added and the mixture was extracted with ethyl acetate (2×40 mL). The combined organic fractions were washed with brine (20 mL), dried (MgSO$_4$) and the solvent was evaporated under reduced pressure. The residue was purified by column chromatography on silica gel, eluting with ethyl acetate/hexane (1:5) to give the title compound as a pale foam (240 mg, 72%). $^1$H NMR (360 MHz, CDCl$_3$) δ1.47 (9 H, s), 1.52–1.71 (3 H, m), 2.17–2.22 (1 H, m), 2.42 (1 H, d, J 13.5 Hz), 2.56 (1 H, d, J 13.5 Hz), 2.77–2.84 (1 H, m), 3.89 (3 H, s), 3.96–4.00 (1 H, m), 4.20 (1 H, d, J 9.5 Hz), 4.29 (1 H, d, J 9.5 Hz), 5.78 (1 H, s), 6.90 (1 H, d, J 8.9 Hz), 7.13–7.16 (1 H, m), 7.21–7.25 (1 H, m), 7.30–7.35 (1 H, m), and 7.62 (2 H, d, J 7.7 Hz), m/z (ES$^+$) 524 (M+1).

DESCRIPTION 92
(5R,6S)-3-(2-Methoxy-5-(trifluoromethoxy)phenyl)-6-phenyl-1-oxa-7-aza-spiro[4,5]-dec-2ene and (5R,6S)-3-(2-methoxy-5-(trifluoromethoxy)phenyl-6-phenyl-1-oxa-7-aza-spiro[4,5]dec-3-ene Trifluoroacetic acid (1 mL) was added to a cooled (0° C.) solution of (3S,5R,6S)-3-(2-methoxy-5-(trifluoromethoxy)phenyl)-6-phenyl-1-oxa-7-(tert-butoxycarbonyl)aza-spiro[4.5]decan-3-ol (Description 91, 240 mg, 0.46 mmol) in dichloromethane (10 mL). The solution was stirred at 0° C. for 10 min. and at room temperature for 1 h. The solvent was evaporated under reduced pressure and saturated aqueous potassium carbonate was added. The mixture was extracted with ethyl acetate (2×40 mL) and the combined organic fractions were washed with brine (20 mL), dried (MgSO$_4$) and the solvent was evaporated under reduced pressure. The residue was purified by column chromatography on silica gel, eluting with dichloromethane/methanol/ammonia (160:8:1) to give (5R,6S)-3-(2-methoxy-5-(trifluoromethoxy)phenyl)-6-phenyl-1-oxa-7-aza-spiro[4.5]dec-2-ene (29 mg, 16%), $^1$H NMR (360 MHz, CDCl$_3$) δ1.56–1.65 (2 H, m), 2.05–2.12 (1 H, m), 2.22–2.26 (1 H, m), 2.41 (1 H, dd, J 14.0, 1.6 Hz), 2.76 (1 H, dd, J 14.0, 1.9 Hz), 2.87 (1 H, dt, J 12.2, 2.7 Hz), 3.23–3.28 (1 H, m), 3.59 (1 H, s), 3.79 (3 H, s), 6.58 (1 H, d, J 2.7 Hz), 6.98 (1 H, d, J 8.9 Hz), 6.83–6.85 (1 H, m), 7.13 (1 H, s), 7.15–7.26 (3 H, m), and 7.43–7.45 (2 H, m), m/z (ES$^+$) 506 (M+1) and (5R,6S)-3-(2-methoxy-5-(trifluoromethoxy)phenyl)-6-phenyl-1-oxa-7-aza-spiro[4.5]dec-3-ene (69 mg, 37%), $^1$H NMR (250 MHz, CDCl$_3$) δ7.45 (2 H, d, J 7.2 Hz), 7.30-7.2 (3 H, m), 7.13-7.09 (1 H, dd, J 9.0 Hz), 6.89 (2 H, s+d), 6.64 (1 H, t, J 2.04 Hz), 5.16 (1 H, s), 4.96 and 4.56 (2 H, ABdd, J 12.1 and 2 Hz), 4.11 (1 H, m), 3.86 (3 H, s), 3.08 (1 H, m), 2.1 (1 H, m), 1.87-1.77 (3 H, m), and 1.37 (9 H, s), m/z (ES$^+$) 506 (M+1).

DESCRIPTION 93
3-Bromo-2-phenylprop-1-ene

A mixture of 2-phenylprop-1-ene (14.16 g, 0.12 mol), N-bromosuccinimide (13.5 g, 72 mmol) and α,α'-azoisobutyronitrile (1.5 mg) in carbon tetrachloride (7.5 mL) was placed in a pre-heated oil bath at 170° C. (the internal temperature rose to 110° C.). The slurry was stirred vigorously at this temperature for 2 h. and was then allowed to cool to ambient temperature. The mixture was filtered, washing with carbon tetrachloride, and the solvent was evaporated under reduced pressure. The residue was purified by column chromatography on silica gel, eluting with hexane to give the title compound as an oil (320 mg). $^1$H NMR (250 MHz, CDCl$_3$) δ(7.85-7.81 (2 H, m), 7.75-7.63 (3 H, m), 5.89 (1 H, s), 5.82 (1 H, s), and 4.72 (2 H, s).

DESCRIPTION 94
(2S,3R)-1-tert-Butoxycarbonyl-2-phenyl-3-(2phenylprop-1-en-3-yl)piperidin-3-ol A Grignard reagent was prepared from 3-bromo-2-phenylprop-1-ene (Description 93, 150 mg, 0.76 mmol) and magnesium metal (24 mg, 1 mmol) in THF (4 mL). The solution was cooled to −30° C. and a solution of (2S)-1-tert-butoxycarbonyl-2-phenylpiperidin-3-one (Description 1, 161 mg, 0.59 mmol) in THF (1 mL) was added. The mixture was stirred at ambient temperature for 16 h., then saturated aqueous ammonium chloride (10 mL) was added. The mixture was extracted with ethyl acetate (2×20 mL) and the combined organic fractions were dried (Na$_2$SO$_4$). The solvent was evaporated under reduced pressure and the residue was purified by column chromatography on silica gel, eluting with hexane/ethyl acetate (85:15) to give the title compound as an oil (52 mg). $^1$H NMR (360 MHz, CDCl$_3$) δ7.44-7.20 (10 H, m), 5.43 (1 H, s), 5.25 (1 H, s), 5.12 (1 H, s), 4.06-4.03 (1 H, m), 3.34-3.30 (1 H, m), 3.08-2.94 (3 H, m), 2.47-2.43 (1 H, m), 1.93-1.86 (2 H, m), 1.70-1.64 (2 H, m), and 1.38 (9 H, s). m/z (ES$^+$) 394 (M+1).

DESCRIPTION 95
(2S,3R,2'R)-3-(1-tert-Butoxycarbonyl-3-hydroxy-2-phenylpiperidin-3-yl)-2-phenylpropan-1-ol (2S,3R)-1-tert-Butoxycarbonyl-2-phenyl-3-(2-phenylprop-1en-3-yl)piperidin-3-ol (Description 94, 46 mg, 0.12 mmol) was dissolved in THF (5 mL) and cooled to 0° C. Borane-tetrahydrofuran complex (1.0M solution in THF, 0.36 mL, 0.36 mmol) was added over 5 min. and the resulting mixture was stirred at ambient temperature for 16 h. Aqueous sodium hydroxide (4M, 0.5 mL) and aqueous hydrogen peroxide (30%, 0.5 mL) were added and the mixture was stirred at ambient temperature for 1 h. The mixture was diluted with eater (10 mL) and extracted with ethyl acetate (15 mL). The organic layer was dried ($Na_2SO_4$) and the solvent was evaporated under reduced pressure. The residue was purified by preparative thin layer chromatography on silica, eluting with hexane/ethyl acetate (75:25) to give the title compound as an oil (13 mg). $^1$H NMR (250 MHz, $CDCl_3$) δ7.51-7.48 (2 H, m), 7.34-7.19 (8 H, m), 5.29 (1 H, s), 4.03-3.98 (1 H, m), 3.83-3.70 (2 H, m), 3.29-3.19 (1 H, m), 3.15-3.03 (1 H, m), 2.41-2.30 (3 H, m), 2.12-1.95 (2 H, m), 1.78-1.73 (2 H, m), 1.45-1.41 (1 H, m), and 1.31 (9 H, s). m/z ($ES^+$) 412 (M+1).

DESCRIPTION 96
(4S)-4-Benzyl-3-(2-methoxyphenyl)acetyl-1,3-oxazolidin-2-one

Thionyl chloride (6.91 mL) was added slowly to a warmed (50° C.) solution of 2-methoxyphenylacetic acid (13.77 g, 0.083 mol) and dimethylformamide (0.1 mL) in toluene (50 mL) and the mixture was stirred at 50° C. for 2 h. The solvent was evaporated under reduced pressure and the residue was dissolved in tetrahydrofuran (50 mL). To a cooled solution (−20° C.) of (4S)-4-benzyl oxazolidine-2-one (14.7 g, 83 mmol) in tetrahydrofuran (80 mL) was slowly added n-butyl lithium (1.6 M, 52 mL, 83 mmol) and the mixture was warmed to 0° C. To this solution was slowly added the solution of the acid chloride (above) in tetrahydrofuran over 20 min. The mixture was warmed to room temperature and was stirred for 72 h. Saturated aqueous ammonium chloride was added and the mixture was extracted with ethyl acetate. The combined organic fractions was washed with water and brine, dried ($MgSO_4$) and the solvent was evaporated under reduced pressure. The residue was purified by chromatography on silica gel eluting with hexane/EtOAc (90:10 increasing to 50:50) to give the title compound (12.8 g) $^1$H NMR (360 MHz, $CDCl_3$) δ7.37-7.15 (7 H, m), 6.92 (2 H, m), 4.71 (1 H, m), 4.30 (1 H, d, J 17.6 Hz), 4.26-4.17 (4 H, m), 3.82 (3 H, s), 3.29 (1 H, dd, J 13.4, 3.1 Hz), and 2.81 (1 H, dd, J 13.3 9.4 Hz).

DESCRIPTION 97
(2'R,4S)-4-Benzyl-3-[3-benzyloxy-2-(2-methoxyphenyl)]propionyl-1,3-oxazolidin-2-one Titanium tetrachloride in dichloromethane (1M, 37.2 mL) was added to a cooled (−80° C.) solution of (4S)-4-benzyl-3-(2-methoxyphenyl)acetyl-1,3-oxazolidin-2-one (Description 96, 12.1 g, 37.2 mmol) in dichloromethane (100 mL) and the mixture was warmed to room temperature. The mixture was cooled −80° C. and diisopropylethylamine (7.0 mL, 39.4 mmol) was added. The mixture was warmed to 0° C. for 1 h., benzyloxymethyl chloride (10.3 mL, 74.4 mmol) was added and the mixture was stirred at room temperature for 16 h. The mixture was poured into saturated aqueous ammonium chloride and ethyl acetate and the organic phase was washed with water and brine and dried ($MgSO_4$). The solvent was evaporated under reduced pressure and the residue was recrystallized from ethyl acetate/hexane to give the title compound (9.14 g). $^1$H NMR (360 MHz, $CDCl_3$) δ7.36-7.21 (14 H, m), 6.9-6.85 (2 H, m), 5.80 (1 H, dd J 9.33 Hz and 4.45 Hz), 4.69 (1 H, m), 4.63 (2 H, s), 4.16-4.06 (3 H, m), 3.85 (3 H, s), 3.74 (1 H, dd J 9.3 Hz and 4.5 Hz), 3.30 (1 H, dd J 13.5 Hz and 3.14 Hz), and 2.83 (1 H, dd J 13.5 Hz and 9.2 Hz).

DESCRIPTION 98
(2S)-3-Benzyloxy-2-(2-methoxyphenyl)propan-1-ol

Lithium borohydride (0.366 g, 16.8 mmol) was added to a solution of (2'R,4S)-4-benzyl-3-[3-benzyloxy-2-(2-methoxyphenyl)]propionyl-1,3-oxazolidin-2-one (Description 97, 6.8 g, 15.3 mmol) in tetrahydrofuran (100 mL) and water (0.3 mL) and the mixture was stirred at room temperature for 2 h. Aqueous sodium hydroxide (1 M, 100 mL) and ethyl acetate (200 mL) were added and the layers were separated. The organic phase was washed with water and brine, dried ($MgSO_4$) and the solvent was evaporated under reduced pressure. The residue was purified by chromatography on silica gel, eluting with hexane/EtOAc (90:10 increasing to 80:20) to give the title compound as an oil (3.4 g). $^1$H NMR (250 MHz, $CDCl_3$) δ7.38-7.13 (5 H, m), 6.94-6.85 (2 H, m), 4.56 (2 H, s), 4.06-3.98 (1 H, dd J 10.7 Hz and 7.03 Hz), and 3.90-3.52 (7 H, m).

DESCRIPTION 99
(2R)-3-Benzyloxy-1-chloro-2-(2-methoxyphenyl)propane

A solution of (2S)-3-benzyloxy-2-(2-methoxyphenyl)propan-1-ol (Description 98, 2 g, 7.4 mmol) and triphenylphosphine (2.12 g, 8.1 mmol) in carbon tetrachloride (10 mL) was heated in an oil bath at 100° C. for 5 h. Methanol (1 mL) was cautiously added and the mixture was cooled to room temperature and stirred for 16 h. The solvent was evaporated under reduced pressure and the residue was purified by chromatography on silica gel, eluting with hexane/EtOAc (100:0 increasing to 95:5) to give the title compound (1.5 g). $^1$H NMR (250 MHz, $CDCl_3$) δ7.37-7.2 (7 H, m), 6.96-6.86 (2 H, m), 4.54 (2 H, s), 3.92 (2 H, m), and 3.81-3.73 (7 H, m).

DESCRIPTION 100
(2S,3R,2'R)-1-tert-Butoxycarbonyl-3-hydroxy-3-[3-benzyloxy-2-(2-methoxyphenyl)propyl]-2-phenylpiperidine A suspension of magnesium (0.1 g, 4.2 mmol) in tetrahydrofuran (1 mL) was treated with a solution of (2R)-3-benzyloxy-1-chloro-2-(2-methoxyphenyl)propane (Description 99, 0.45 g, 1.55 mmol) in tetrahydrofuran (1 mL) at 60° C. for 3 h. The mixture was cooled and (2S)-1-tert-butoxycarbonyl-2-phenylpiperidin-2-one (Description 1) in tetrahydrofuran (1 mL) was added. The mixture was stirred at room temperature for 1 h., partitioned between ethyl acetate and saturated ammonium chloride solution and the organic phase was washed with water and saturated brine and dried ($MgSO_4$). The solvent was evaporated under reduced pressure and the residue was purified by chromatography on silica gel, eluting with hexane/EtOAc (95:5) to give the title compound (0.115 g). $^1$H NMR (360 MHz, $CDCl_3$) δ7.48 (2 H, d J 6.8 Hz), 7.36 (1 H, d J 4.5 Hz), 7.30-7.16 (9 H, m), 6.88 (1 H, t J 7.4 Hz), 6.84 (1 H, d J 8.0 Hz), 5.17 (1 H, s), 4.53 (2 H, s), 4.00 (1 H, dd), 3.83-3.68 (5 H, m), 3.67 (2 H, m), 3.27 (1 H, s), 3.02 (1 H, td J 3.0 Hz and 12.0 Hz), 2.35 (1 H, dd J 14.7 Hz and 6.12 Hz), 2.20 (1 H, dd J 14.6 Hz and 6.2 Hz), 2.04 (1 H, m), 1.76 (2 H, m), and 1.28 (9 H, s). m/z ($ES^+$) 532 (M+1).

DESCRIPTION 101
(2S,3R,2'R)-3-(1-tert-Butoxycarbonyl-3-hydroxy-2-phenylpiperidin-3-yl)-2-(2-methoxyphenyl)propan-1-ol A solution of (2S,3R,2'R)-1-tert-butoxycarbonyl-3-hydroxy-3-[3-benzyloxy-2-(2-methoxyphenyl)propyl]-2-phenylpiperidine (Description 100, 0.115 g) was hydrogenated in the presence of 10% palladium hydroxide on carbon (50 mg) in ethyl acetate (10 mL) and methanol (10 mL) at 50 psi for 1 h. The mixture was filtered and the solvent was evaporated under reduced pressure. The residue was purified by chromatography on silica gel, eluting with hexane/EtOAc (95:5 increasing to 75:25) to give the title compound (0.073 g). $^1$H NMR (360 MHz, CDCl$_3$) δ 7.48 (2H, d J 7.2 Hz), 7.30–7.16 (5H, m), 6.91 (1H, t J 7.5 Hz), 6.86 (1H, d J 7.9 Hz), 5.19 (1H, s), 4.00 (1H, dd J 13.0 Hz and 4.7 Hz), 3.82 (3H, s), 3.79–3.62 (3H, m), 3.09 (1H, m), 2.69 (2H, vbs), 2.33 (1H, dd J 14.7 Hz and 5.6 Hz), 2.08 (1H, dd J 14.9 Hz and 6.4 Hz), 1.98 (1H, m), 1.73 (3H, m), 1.27 (9H, s). m/z (ES$^+$) 442 (M+1).

DESCRIPTION 102

2-Benzyloxy-5-(trifluoromethoxy)benzene

Benzyl bromide (66.17 mL, 95.35 g, 0.56 mol) was added to a mixture of 4-(trifluoromethoxy)phenol (90.26 g, 0.51 mol) and potassium carbonate (140.97 g, 1.2 mol) in dimethylformamide (160 mL) and the mixture was stirred at room temperature for 72 h. The mixture was poured into water (1.5 l) and extracted with ethyl acetate (3×500 mL). The combined organic fractions were washed with aqueous sodium carbonate (saturated, 500 mL), dried (MgSO$_4$) and the solvent was evaporate under reduced pressure to give the title compound as a colorless solid (133.5 g, 99%). $^1$H NMR (360 MHz, CDCl$_3$) δ 7.39 (5H, m), 7.14 (2H, d, J 9.0 Hz), 6.95 (2H, d, J 9.0 Hz), and 5.05 (2H, s).

DESCRIPTION 103

2-Benzyloxy-5-(trifluoromethoxy)iodobenzene

Iodine (71.96 g, 0.28 mol) in chloroform was added dropwise to a mixture of 2-benzyloxy-5-(trifluoromethoxy) benzene (Description 102, 73.06 g, 0.27 mol) and silver trifluoroacetate (71.57 g, 0.32 mol) in dichloromethane and the mixture was stirred at room temperature for 18 h. The mixture was filtered through celite, washed with aqueous sodium thiosulfate (5%, 2×2 l), dried (MgSO$_4$) and the solvent was evaporated under reduced pressure. The residue was purified by flash column chromatography on silica gel, eluting with hexane/EtOAc, to give the title compound as a colorless oil (108.03 g), containing 11% unreacted 2-benzyloxy-5-(trifluoromethoxy)iodobenzene. $^1$H NMR (360 MHz, CDCl$_3$) δ 7.67 (1H, d, J 2.8 Hz), 7.40 (5H, m), 7.16 (1H, dd, J 8.9, 2.8 Hz), 6.82 (1H, d, J 8.9 Hz), and 5.14 (2H, s).

DESCRIPTION 104

1-Benzyloxy-4-(difluoromethoxy)benzene

Ethyl chlorodifluoroacetate (25 mL, 0.20 mol) was added to 4-(benzyloxy)phenol (20.10 g, 0.10 mol), and potassium carbonate (41.90 g, 0.30 mol) in dimethylformamide (200 mL) and the mixture was stirred at 80° C. for 18 h. Additional ethyl chlorodifluoroacetate (12.7 mL, 0.10 mol) and potassium carbonate (27.74 g, 0.20 mol) were added and the mixture was stirred at 80° C. for 6 h. Additional ethyl chlorodifluoroacetate (12.7 mL, 0.10 mol) and potassium carbonate (27.74 g, 0.20 mol) were added and the mixture was stirred at 120° C. for 15 h. The mixture was cooled, poured into water (1000 mL) and extracted with ethyl acetate (500 mL). The organic fraction was washed with aqueous sodium hydroxide (1M, 500 mL) and brine (500 mL), dried (MgSO$_4$) and the solvent was evaporated under reduced pressure. The residue was purified by column chromatography on silica gel, eluting with hexane/CH$_2$Cl$_2$ (90:10) to give the title compound as a colorless solid (6.67 g, 27%). $^1$H NMR (360 MHz, CDCl$_3$) δ 5.05 (2H, s), 6.42 (1H, t, J 74 Hz), 6.94 (2H, m) 7.06 (2H, m), and 7.31–7.44 (5H, m).

DESCRIPTION 105

2-Benzyloxy-5-(difluoromethoxy)iodobenzene

Prepared from the compound of Description 104 according to the method of Description 103. $^1$H NMR (360 MHz, CDCl$_3$) δ 5.13 (2H, s), 6.40 (1H, t, J 74 Hz), 6.80 (1H, d, J 8.9 Hz), 7.07 (1H, dd, J 8.9, 2.8 Hz), 7.33 (1H, m), 7.40 (2H, m), 7.48 (2H, m), 7.60 (1H, d, J 2.8 Hz).

DESCRIPTION 106

5-Fluoro-2-hydroxyiodobenzene

Chloramine-T trihydrate (50 g, 178 mmol) was added to a stirred, cooled (0° C.) solution of 4-fluorophenol (20 g, 178 mmol) and sodium iodide (26.7 g, 178 mmol) in dimethylformamide (250 mL). The mixture was stirred at 0° C. for 1 h., and poured into water (1000 mL). The mixture was acidified with hydrochloric acid (1M) and extracted with ether (4×200 mL). The combined organic fractions were washed with aqueous sodium thiosulfate (5%, 3×100 mL), water (2×50 mL) and brine (50 mL), dried (MgSO$_4$) and the solvent was evaporated under reduced pressure. The reside was purified by flash column chromatography on silica gel, eluting with hexane/CH$_2$Cl$_2$ to give the title compound as an off-white solid (7.8 g, 18%). $^1$H NMR (360 MHz, CDCl$_3$) δ 5.08 (1H, s), 6.90–7.01 (2H, m), and 7.37 (1H, dd, J 7.6, 2.9 Hz).

DESCRIPTION 107

2-Benzyloxy-5-fluoroiodobenzene

Prepared from the compound of Description 106 according to the method of Description 36. $^1$H NMR (360 MHz, CDCl$_3$) δ 5.10 (2H, s), 6.78 (1H, dd, J 9.0, 4.6 Hz), 6.94–7.01 (1H, m), and 7.30–7.56 (6H, m).

DESCRIPTION 108

5-Benzyloxy-2-isopropoxynitrobenzene

2-Bromopropane (4.51 mL, 5.90 g, 48 mmol) was added to a mixture of 4-benzyloxy-2-nitrophenol (J.Biol.Chem., 1985, 260, 3440, 2.94 g, 12 mmol) and potassium carbonate (9.95 g, 72 mmol) in dimethylformamide (20 mL) and the mixture was stirred at 50° C. for 22 h. The mixture was cooled, diluted with water (100 mL) and extracted with ethyl acetate (3×100 mL). The combined organic fractions were washed with aqueous sodium hydroxide (1M, 4×100 mL) and brine (100 mL), dried (MgSO$_4$) and the solvent was evaporated under reduced pressure to give the title compound as an orange oil (3.40 g, 99%). $^1$H NMR (360 MHz, CDCl$_3$) δ 7.41–7.33 (6H, m), 7.12 (1H, dd, J 9.1, 3.1 Hz), 7.02 (1H, d, J 9.1 Hz), 5.05 (2H, s), 4.52 (1H, hept, J 6.1 Hz), and 1.35 (6H, d, J 6.1 Hz).

DESCRIPTION 109

5-Benzyloxy-2-isopropoxybenzeneamine

Titanium trichloride (10% solution in 20–30% hydrochloric acid, 50 mL) was added to a solution of 5-benzyloxy-2- isopropoxynitrobenzene (Description 108, 2.78 g, 9.7 mmol) in acetic acid (50 mL) and the mixture was stirred at room temperature for 18 h. The mixture was poured into ice-cooled aqueous sodium hydroxide (4M, 400 mL) and the mixture was extracted with dichloromethane (8×100 mL). The combined organic fractions were washed with saturated aqueous sodium hydrogen carbonate (2×200 mL), dried ($MgSO_4$) and the solvent was evaporated under reduced pressure to give the title compound as a dark oil (1.74 g, 71%). $^1$H NMR (360 MHz, $CDCl_3$) δ 7.42–7.25 (5H, m), 6.71 (1H, d, J 8.7 Hz), 6.41 (1H, d, J 2.9 Hz), 6.30 (1H, dd, J 8.7, 2.9 Hz), 4.97 (2H, s), 4.38 (1H, hept, J 6.0 Hz), 3.6 (2H, br s), and 1.32 (6H, d, d 6.0 Hz).

DESCRIPTION 110

5-Benzyloxy-2-isopropoxyiodobenzene

Sodium nitrite (589 mg, 8.5 mmol) in water (2.5 mL) was added dropwise to a stirred, cooled (0° C.) suspension of 5-benzyloxy-2-isopropoxybenzeneamine (Description 109, 2.05 g, 8.4 mmol) in aqueous sulfuric acid (2M, 14 mL). The mixture was stirred at 0° C. for 30 min., then added dropwise to a stirred, cooled (0° C.) solution of potassium iodide (2.50 g, 15.1 mmol) in water (10 mL). The mixture was stirred at room temperature for 90 min., then water (50 mL) was added. The mixture was extracted with ethyl acetate (3×50 mL). The combined organic fractions were washed with aqueous sodium thiosulfate (10%, 2×50 mL), hydrochloric acid (2M, 2×50 mL), saturated aqueous sodium hydrogen carbonate (2×50 mL), and brine (50 mL), dried ($MgSO_4$) and the solvent was evaporated under reduced pressure. The residue was purified by flash column chromatography on silica gel, eluting with hexane/$CH_2Cl_2$ (80:20), to give the title compound as a cream solid (1.49 g, 48%). $^1$H NMR (360 MHz, $CDCl_3$) δ 7.42–7.30 (6H, m), 6.90 (1H, dd, J 9.0, 2.9 Hz), 6.77 (1H, d, J 9.0 Hz), 4.98 (2H, s), 4.41 (1H, hept, J 6.1 Hz), and 1.35 (6H, d, J 6.1 Hz).

DESCRIPTION 111

(3S,5R,6S)-3-[2-(1-Phenylthiocycloprop-1-yl)oxy-5-(trifluoromethoxy)phenyl]-6-phenyl-1-oxa-7-(tert-butoxycarbonyl)aza-spiro[4.5]decane (3S,5R,6S)-3-(2-Hydroxy-5-(trifluoromethoxy)phenyl)-6-phenyl-1-oxa-7-(tert-butoxycarbonyl)aza-spiro[4.5] decane (Example 212) (290 mg, 0.59 mmol) was dissolved in toluene (5 mL) and silver carbonate (179 mg, 0.65 mmol) was added in one portion. (1-Iodocycloprop-1-yl) phenylsulfide (Cohen T. and Matz J. R., *J. Am. Chem. Soc.* 1980, 102, 6902) (180 mg, 0.65 mmol) was then added over one minute at room temperature. The mixture was stirred at 55° C. for 4 h., then further portions of silver carbonate (179 mg, 0.65 mmol) and (1-iodocycloprop-1-yl)phenylsulfide (180 mg, 0.65 mmol) were added. The mixture was stirred at 55° C. for a further 3 h., cooled, filter and the solvent was evaporated under reduced pressure. The residue was purified by column chromatography on silica gel, eluting with hexane/ethyl acetate (90:10 increasing to 80:20) to give the title compound was a colourless oil (120 mg, 32%). $^1$H NMR (250 MHz, $CDCl_3$) δ 7.55–7.44 (4H, m), 7.36–7.23 (7H, m), 7.13–7.02 (2H, m), 5.16 (1H, br s), 4.09 (1H, t, J 6 Hz), 4.03–3.92 (1H, m), 3.67–3.49 (2H, m), 2.94–2.79 (1H, m), 2.26 (1H, dd, J 7.9, 12.9 Hz), 2.15–2.01 (2H, m), 1.76–1.59 (3H, m), 1.53–1.45 (4H, m), and 1.36 (9H, s). m/z ($ES^+$) 642 (M+1).

DESCRIPTION 112

(3R,5R,6S)-3-[2-(1-Phenylthiocycloprop-1-yl)oxy-5-(trifluoromethoxy)phenyl]-6-phenyl-1-oxa-7-(tert-butoxycarbonyl)aza-spiro[4.5]decane Prepared from (3R,5R,6S)-3-(2-hydroxy-5-(trifluoromethoxy)phenyl)-6-phenyl-1-oxa-7-(tert-butoxycarbonyl)aza-spiro[4.5]decane (Example 212) according to the method of Description 111. $^1$H NMR (360 MHz, $CDCl_3$) δ 7.57 (2H, app. d, J 7.6 Hz), 7.45 (2H, app. d, J 7.7 Hz), 7.36–7.19 (7H, m), 7.16–7.06 (2H, m), 5.28 (1H, br s), 4.13 (1H, app. t, J 7.8 Hz), 3.96 (1H, br. d, J 13 Hz), 3.80–3.60 (2H, m), 2.79 (1H, br. t, J 13 Hz), 2.50 (1H, dd, J 13, 7.9 Hz), 2.17 (1H, dt, J 13, 4.6 Hz), 1.80 (1H, dd, J 12, 9.8 Hz), 1.75–1.38 (7H, m), and 1.44 (9H, s). m/z ($ES^+$) 642 (M+1).

DESCRIPTION 113

(3S,5R,6S)-3-[2-(1-Phenylthiocycloprop-1-yl)oxy-5-(trifluoromethyl)phenyl]-6-phenyl-1-oxa-7-(tert-butoxycarbonyl)aza-spiro[4.5]decane Prepared from (3S,5R,6S)-3-(2-hydroxy-5-(trifluoromethyl)phenyl)-6-phenyl-1-oxa-7-(tert-butoxycarbonyl)aza-spiro[4.5]decane (Example 216) according to the method of Description 111. $^1$H NMR (360 MHz, $CDCl_3$) δ 7.53–7.22 (13H, m), 5.13 (1H, s), 4.11 (1H, m), 3.97 (1H, m), 3.59 (2H, m), 2.89 (1H, m), 2.28 (1H, dd, J 12.7, 7.6 Hz), 2.08 (2H, m), 1.68 (3H, m), 1.75–1.48 (4H, m), and 1.34 (9H, s). m/z ($ES^+$) 626 (M+1).

DESCRIPTION 114

(3R,5R,6S)-3-[2-(1-Phenylthiocycloprop-1-yl)oxy-5-(difluoromethoxy)phenyl]-6-phenyl-1-oxa-7-(tert-butoxycarbonyl)aza-spiro[4.5]decane Prepared from the compound of Example 225 according to the method of Description 111. $^1$H NMR (360 MHz, $CDCl_3$) δ 7.57 (2H, d, J 7.6 Hz), 7.46 (2H, d, J 7.2 Hz), 7.35–7.20 (7H, m), 7.03 (2H, m), 6.44 (1H, t, J 74.3 Hz), 5.27 (1H, s), 4.12 (1H, m), 3.96 (1H, m), 3.70 (2H, m), 2.80 (1H, m), 2.49 (1H, m), 2.18 (1H, m), 1.82 (1H, m), 1.75–1.26 (7H, m), and 1.44 (9H, s). m/z ($ES^+$) 624 (M+1).

DESCRIPTION 115

(3R,5R,6S)-3-[2-(1-Phenylthiocycloprop-1-yl)oxy-5-(trifluoromethoxy)phenyl]-6-(4-fluorophenyl)-1-oxa-7-(tert-butoxycarbonyl)aza-spiro[4.5]decane Prepared from the compound of Example 223 according to the method of Description 111. $^1$H NMR (360 MHz, $CDCl_3$) δ 1.42 (9H, s), 1.43–1.65 (5H, m), 1.80 (1H, dd, J 12.5, 9.6 Hz), 2.12 (1H, m), 2.47 (1H, dd, J 7.8, 12.8 Hz), 2.77 (1H, td, J 13.2, 9.5 Hz), 3.65 (1H, qn, J 8.6 Hz), 3.73 (1H, t, J 8.3 Hz), 3.95 (1H, dd, J 9.67 Hz), 4.10 (1H, m), 5.23 (1H, s), 7.00 (2H, t, J 8.76 Hz), 7.10 (2H, s), 7.29 (6H, m), 7.47 (2H, d, J 8.5 Hz), and 7.53 (2H, dd, J 8.9, 5.8 Hz).

DESCRIPTION 116

Tetracyclopropyl Tin

Cyclopropyl bromide (3.3 mL) in tetrahydrofuran (18 mL) was added dropwise to magnesium (1.1 g) in tetrahydrofuran (2 mL) and the mixture was heated until self sustaining reflux started. The mixture was stirred at 65° C. for 1 h., cooled to room temperature and tin (IV) chloride (2.4 mL) was added dropwise. The mixture was stirred at 65° C. for 16 h., cooled and diluted with aqueous ammonium chloride (saturated, 30 mL). The mixture was extracted with ether (3×20 mL) and the combined organic fractions were washed with brine, dried ($MgSO_4$) and the solvent was evaporated under reduced pressure. The residue was purified by flash column chromatography on silica gel, eluting with hexane, to give the title compound as a colourless oil. $^1$H NMR (360 MHz, CDCl$_3$) δ −0.38 (4H, m), 0.37 (8H, m), and 0.57 (8H, m).

DESCRIPTION 117

3-Iodo-4-(4-methoxybenzyloxy)benzonitrile

Iodine (21. g, 84 mmol) was added to a solution of 4-cyanophenol (10.0 g, 84 mmol) and sodium hydrogen carbonate (7.06 g, 84 mmol) in water (100 mL) and the mixture was stirred at room temperature for 24 h. The solid was collected, washed with water and dried in vacuo. The solid was dissolved in tetrahydrofuran (100 mL) and triphenylphosphine (14.4 g, 55 mmol) and 4-methoxybenzyl alcohol (8.3 g, 60 mmol) were added. Diethyl azodicarboxylate (8.5 mL, 55 mmol) was added slowly and the mixture was stirred at room temperature for 16 h. The mixture was poured into sodium hydrogen carbonate solution (saturated, 200 mL) and extracted with ethyl acetate (2×200 mL). The combined organic fractions were dried (MgSO$_4$) and the solvent was evaporated under reduced pressure. The residue was purified by flash column chromatography on silica gel to give the title compound (3.38 g). $^1$H NMR (250 MHz, CDCl$_3$) δ 8.05 (1H, d, J 2.0 Hz), 7.57 (1H, dd, J 2.0, 8.5 Hz), 7.38 (2H, d, J 6.8 Hz), 6.79–6.96 (3H, m), 5.14 (2H, s), and 3.82 (3H, s).

DESCRIPTION 118

(3R,5R,6S)-3-[5-Cyano-2-(4-methoxybenzyloxy)phenyl]-6-phenyl-1-oxa-7-(tert-butoxycarbonyl)aza-spiro[4.5]decane Prepared from the compound of Description 117 and (5R,6S)-6-phenyl-1-oxa-7-(tert-butoxycarbonyl)aza-spiro[4.5]dec-3-ene (Description 86) according to the method of Example 219. $^1$H NMR (250 MHz, CDCl$_3$) δ 7.48–7.57 (4H, m), 7.20–7.34 (5H, m), 6.89–7.01 (3H, m), 5.29 (1H, s), 5.07 (1H, s), 4.22–4.32 (1H, m), 3.90–3.99 (1H, m), 3.81 (3H, s), 2.76 (1H, dt, J 12.0, 4.3 Hz), 2.50–2.57 (1H, m), 1.91–2.23 (2H, m), 1.60–1.66 (5H, m), and 1.42 (9H, s).

DESCRIPTION 119

(3R,5R,6S)-3-[5-Cyano-2-(tert-butoxycarbonyl)oxyphenyl]-6-phenyl-1-oxa-7-(tert-butoxycarbonyl)aza-spiro[4.5]decane Di(tert-butyl)dicarbonate (698 mg, 3.2 mmol) was added to a solution of (3R,5R,6S)-3-(5-cyano-2-hydroxyphenyl)-6-phenyl-1-oxa-7-aza-spiro[4.5]decane (Example 274, 533 mg, 1.6 mmol) and diisopropylethylamine (0.556 mL, 3.2 mmol) in dichloromethane (50 mL) and the mixture was stirred at room temperature for 16 h. The mixture was washed with sodium hydrogen carbonate solution (saturated, 50 mL), dried MgSO$_4$) and the solvent was evaporated under reduced pressure. The residue was purified by flash column chromatography on silica get to give the title compound as a colorless solid (465 mg). $^1$H NMR (250 MHz, CDCl$_3$) δ 7.72 (1H, d, J 1.9 Hz), 7.54–7.60 (3H, m), 7.22–7.36 (4H, m), 5.33 (1H, s), 4.26 (1H; dd, 7.2, 8.7 Hz), 3.94–3.98 (1H, m), 3.81–3.88 (1H, m), 3.69–3.75 (1H, m), 2.77 (1H, dt, J 3.5, 12.6 Hz), 2.64 (1H, dd, J 8.3, 13.0 Hz), 2.25 (1H, dt, J 8.1, 13.1 Hz), 1.89 (1H, dd, J 8.6, 13.0 Hz), 1.71–1.77 (3H, m), 1.56 (9H, s), and 1.46 (9H, s).

DESCRIPTION 120

(3R,5R,6S)-3-[2-(1-Phenylthiocycloprop-1-yl)oxy-5-(trifluoromethyl)phenyl]-6-phenyl-1-oxa-7-(tert-butoxycarbonyl)aza-spiro[4.5]decane Prepared from (3R,5R,6S)-3-(2-hydroxy-5-(trifluoromethyl)phenyl)-6-phenyl-1-oxa-7-(tert-butoxycarbonyl)aza-spiro[4.5]decane (Example 216) according to the method of Description 111. $^1$H NMR (360 MHz, CDCl$_3$) δ 1.44 (9H, s), 1.40–1.72 (7H, m), 1.84 (1H, m), 2.16 (1H, m), 2.51 (1H, m), 2.80 (1H, m), 3.71 (2H, m), 3.97 (1H, m), 4.15 (1H, m), 5.29 (1H, s), and 7.22–7.59 (13H, m). m/z (ES$^+$) 570 (M+1-C$_4$H$_8$).

DESCRIPTION 121

6-Fluoro-2-methoxyiodobenzene n-Butyllithium (1.6 M in hexanes, 26 mL, 42 mmol) was added dropwise to a stirred, cooled (−78° C.) solution of 3-fluoroanisole (5.0 g, 40 mmol) in THF (150 mL) and the mixture was stirred at −78° C. for 2.5 h. Iodine (11.1 g, 43 mmol) in THF (50 mL) was added dropwise and the mixture was allowed to warm to room temperature. Water (200 mL), saturated aqueous sodium thiosulfate (100 mL) and ether (300 mL) were added and the layers were separated. The aqueous layer was extracted with ether (200 mL), the combined organic fractions were dried (MgSO$_4$) and the solvent was evaporated under reduced pressure. The residue was purified by column chromatography on silica gel, eluting with hexane/EtOAc (99:1) to give the title compound as a pale yellow oil (7.65 g, 77%). $^1$H NMR (360 MHz, CDCl$_3$) δ 7.27 (1H, dt, J$_d$ 6.6 Hz, J$_t$ 8.2 Hz), 6.71 (1H, t, J 8.2 Hz), 6.62 (1H, d, J 8.2 Hz), and 3.90 (3H, s).

EXAMPLE 1

(5R,6S)-3-(2-Methoxy-5-trifluoromethoxyphenyl)-6-phenyl-1-oxa-7-(tert-butoxycarbonyl)aza-spiro[4.5]dec-3-ene (5R,6S)-3-Trimethylstannyl-6-phenyl-1-oxa-7-(tert-butoxycarbonyl)aza-spiro[4.5]dec-3-ene (Description 6; 3.07 g, 6.43 mmol), lithium chloride (0.163 g), 2-bromo-4-trifluoromethoxyanisole (Description 12; 2.07 g, 7.7 mmol) in toluene (25 ml) was degassed before addition of triphenylphosphine palladium (0) (0.37 g). The solution was degassed thoroughly before heating to 110° C. for 14 h. The solution was partitioned between water and ethyl acetate and the dried organic phase was purified by chromatography on a column containing silica gel (eluting with hexane containing increasing proportions of ethyl acetate between 0% to 4%) to give the title compound. $^1$H NMR (250 MHz, CDCl$_3$) δ 7.45 (2H, d, J 7.2 Hz), 7.30–7.2 (3H, m), 7.13– 7.09 (1H, dd, J 9.0 Hz), 6.89 (2H, s+d), 6.64 (1H, t, J 2.04 Hz), 5.16 (1H, s), 4.96 and 4.56 (2H, ABdd, J 12.1, 2 Hz), 4.11 (1H, m), 3.86 (3H, s), 3.08 (1H, m), 2.1 (1H, m), 1.87–1.1.77 (3H, m), and 1.37 (9H, s). m/z (ES$^+$) 506 (M+1).

EXAMPLE 2

(5R,6S)-3-(2-Methoxy-5-trifluoromethoxyphenyl-6-phenyl-1-oxa-7-aza-spiro[4.5]dec-3-ene (5R,6S)-3-(2-Methoxy-5-trifluoromethoxyphenyl)-6-phenyl-1-oxa-7-(tert-butoxycarbonyl)aza-spiro[4.5]dec-3-ene (Example 1; 2.7 g) was dissolved in dichloromethane (25 ml) and anhydrous trifluoroacetic acid (25 ml) added for 10 min. before evaporation to dryness and purification by chromatography on a column containing silica gel (eluting with dichloromethane containing increasing proportions of methanol/aqueous ammonia (25:1) between 0% to 5% to give the title compound. $^1$H NMR (360 MHz, CDCl$_3$) δ 7.35 (2H, dd, J 8.4, 1.58 Hz), 7.20–7.10 (3H, m), 7.00 (1H, dd, J 8.89, 1.89 Hz), 6.77 (1H, d, J 8.97 Hz), 6.64 (1H, d, J 2.58 Hz), 6.12 (1H, t, J 2.11 Hz), 4.85 and 4.26 (2H, ABdd, J 11.91, 2.0 Hz), 3.75 (4H, s), 3.26 (1H, bd), 2.83 (1H, td, J 12.1, 2.75 Hz), and 2.06–1.63 (4H, m). m/z (ES⁺) 406 (M+1). A sample of this material was crystallized from diethyl ether as the hydrochloride salt m.p. 278–286° C.

EXAMPLE 3

(3S,5R,6S)-3-(2-Methoxy-5-trifluoromethoxyphenyl)-6-phenyl-1-oxa-7-aza-spiro[4.5]decane A mixture of (5R,6S)-3-(2-methoxy-5-trifluoromethoxyphenyl)-6-phenyl-1-oxa-7-aza-spiro[4.5]dec-3-ene (Example 2; 1.4 g), 10% palladium hydroxide/carbon (0.25 g) in methanol (90 ml) containing acetic acid (9 ml) was hydrogenated at 50 psi for 16 h. The solution was filtered, evaporated and the residue was crystallized twice from hexane to give the title compound. m.p. 91–104° C. ¹H NMR (250 MHz, CDCl₃) δ 7.50–7.54 (2H, m), 7.33–7.36 (3H, m),), 6.90 (1H, dd, J 8.9, 2.07 Hz), 6.68 (1H, d, J 8.9 Hz), 6.17 (1H, d, J 2.7 Hz), 4.08 (1H, t, J 7.8 Hz), 3.75 (1H, m), 3.69 (4H, s+d), 3.24 (1H, bd), 3.12 (1H, dd, J 10.3, 8.03 Hz), 2.82 (1H, td, J 12.4, 2.6 Hz), 2.16–1.80 (6H, m), and 1.55–1.64 (2H, m). m/z (ES⁺) 408 (M+1).

EXAMPLE 4

(±)-(3*S,5R*,6S*)-3-(2-Methoxy-5-trifluoromethoxyphenyl)-6-phenyl-1-oxa-7-aza-spiro[4.5]decane The title compound was prepared in a manner analogous to Examples 1, 2 and 3 using racemic (5R*,6S*)-3-trimethylstannyl-6-phenyl-1-oxa-7-(tert-butoxycarbonyl)aza-spiro[4.5]dec-3-ene (3.07 g, 0.419 mmol) as the starting material, which compound was prepared in an analogous fashion to Descriptions 2–6 using (±) -1-tert-butoxycarbonyl-2-phenylpiperidin-3-one (Description 1) as starting material. ¹H NMR (250 Mz) δ 1.55–1.64 (2H, m), 1.85 (2H, d, J 9.9 Hz), 2.10–2.14 (2H, m), 2.80 (1H, m), 3.10–3.28 (2H, m), 3.69 (1H, s), 3.76–3.86 (2H, m), 4.11 (1H, m), 6.17 (1H, d, J 2.7 Hz), 6.68 (1H, d, J 8.9 Hz), 6.89–6.94 (1H, m), 7.33–7.36 (3H, m), and 7.50–7.54 (2H, m). m/z (ES⁺) 408 (M+1).

EXAMPLE 5

(3S,5R,6S)-3-(2-Methoxy-5-trifluoromethoxyphenyl)-6-phenyl-7-(1,2,4-triazolyl-3-methylene)-1-oxa-7-aza-spiro[4.5]decane To a solution of the (3S,5R,6S)-3-(2-methoxy-5-trifluoromethoxyphenyl)-6-phenyl-1-oxa-7-aza-spiro[4.5]decane (Example 3, 0.15 g, 0.369 mmol) and K₂CO₃ (0.254 g, 1.84 mmol) in dimethylformamide (2 ml) was added a solution of N-formyl-2-chloro-amidrazone (0.055 g, 0.405 mmol) in dimethylformamide (0.5 ml). The solution was stirred at room temperature for 2 h. then was heated in an oil bath at 140° C. for 2 h. The cooled solution was poured into a mixture of ethyl acetate and water and the organic phase was washed with saturated brine and dried (MgSO₄). The solvent was removed in vacuo and the residue purified on a column containing silica gel (eluting with dichloromethane containing 1–5% of a mixture of methanol:ammonia (SG 0.88) (96:4) to give the title compound. ¹H NMR (360 MHz, CDCl₃) δ 7.91 (1H, s), 7.55 (2H, bs), 7.34–7.33 (3H, m), 6.92 (1H, d, J 8.8 Hz), 6.69 (1H, d, J 8.9 Hz), 6.13 (1H, s), 4.09 (1H, t, 7.89 Hz), 3.84 (1H, s), 3.77 (1H, t, J 9.15 Hz), 3.71 (3H, s), 3.48–3.39 (2H, m), 3.10–3.01 (2H, m), 2.36 (1H, t J 12.0 Hz), 2.17–2.06 (3H, m), 1.86 (2H, m), and 1.62 (2H, m). m/z (ES⁺) 489 (M+1).

EXAMPLE 6

(5R,6S)-3-(2-Isopropoxy-5-trifluoromethoxyphenyl-6-phenyl-1-oxa-7-aza-spiro[4.5]dec-3-ene Prepared from the compound of Description 13 and (5R,6S)-3-trimethylstannyl-6-phenyl-1-oxa-7-(tert-butoxycarbonyl)aza-spiro[4.5]dec-3-ene according to the methods of Examples 1 and 2. ¹H NMR (360 MHz, CDCl₃) δ 1.25 (3H, d, J 2.6 Hz), 1.27 (3H, d, J 2.6 Hz), 1.66 (1H, m), 1.78 (1H, dd, J 13.5, 4.5 Hz), 1.96 (1H, m), 2.08 (1H, m), 2.83 (1H, dt, J 12.6, 2.8 Hz), 3.30 (1H, d, J 10.4 Hz), 3.79 (1H, s), 4.33 (1H, dd, J 12, 2.1 Hz), 4.45 (1H, m), 4.86 (1H, dd, J 12, 2 Hz), 6.10 (1H, t, 2.1 Hz), 6.69 (1H, d, J 2.5 Hz), 6.73 (1H, d, J 9.1 Hz), 6.96 (1H, d, J 8.6 Hz), 7.17 (3H, m), and 7.37 (2H, d, 6.4 Hz). m/z (ES⁺) 434 (M+1).

EXAMPLE 7

(5R,6S)-3-(2-Allyloxy-5-trifluoromethoxyphenyl)-6-phenyl-1-oxa-7-aza-spiro-[4.5]dec-3-ene Hydrochloride Prepared from the compound of Description 14 and (5R,6S)-3-trimethylstannyl-6-phenyl-1-oxa-7-(tert-butoxycarbonyl)aza-spiro[4.5]dec-3-ene according to the methods of Examples 1 and 2. m.p. 234–245° C., ¹H NMR (360 MHz, DMSO-d₆) δ 1.73 (1H, d, J 12.4 Hz), 1.81 (1H, m), 1.92 (1H, dt, J 13, 3.9 Hz), 2.03 (1H, m), 2.43 (1H, dd, J 16.3, 5.9 Hz), 2.60 (1H, dd, J 16.6, 5.3 Hz), 3.02 (1H, m), 3.26 (1H, m), 3.89 (1H, d, J 13.4 Hz), 4.34 (1H, d, J 12.4 Hz), 4.43 (1H, m), 4.57 (1H, dd, J 17, 1.6 Hz), 4.80 (1H, d, J 10.1 Hz), 5.34 (1H, m), 5.42 (1H, s), 7.36 (5H, m), 8.99 (1H, bs), and 9.68 (1H, bs).

EXAMPLE 8

(5R,6S)-3-(5-Trifluoromethoxy-2,3-dihydrobenzofuran-7-yl)-6-phenyl-1-oxa-7-aza-spiro[4.5]dec-3-ene Prepared from the compound of Description 17 and (5R,6S)-3-trimethylstannyl-6-phenyl-1-oxa-7-(tert-butoxycarbonyl)aza-spiro[4.5]dec-3-ene according to the methods of Examples 1 and 2. ¹H NMR (250 MHz, CDCl₃) δ 1.68 (1H, m), 1.80 (1H, dd, J 13.3, 4.33 Hz), 1.95 (1H, m), 2.11 (1H, m), 2.80 (1H, td, J 12.5, 2.7 Hz), 3.17 (2H, t, J 8.8 Hz), 3.28 (1H, m), 3.80 (1H, s), 4.32 (1H, dd, J 2.2, 12 Hz), 4.63 (2H, t, J 8.8 Hz), 4.80 (1H, dd, J 12, 2.1 Hz), 6.23 (1H, t, J 2.1 Hz), 6.41 (1H, d, J 1.61 Hz), 6.88 (1H, d, 1.2 Hz), 7.17 (3H, m), and 7.37 (2H, m). m/z (ES⁺) 418 (M+1).

EXAMPLE 9

(5R,6S)-3-(2-Methoxy-5-(2,2,2-trifluoroethoxy)phenyl)-6-phenyl-1-oxa-7-aza-spiro[4.5]dec-3-ene Prepared from the compound of Description 21 and (5R,6S)-3-trimethylstannyl-6-phenyl-1-oxa-7-(tert-butoxycarbonyl)aza-spiro[4.5]dec-3-ene according to the methods of Examples 1 and 2. ¹H NMR (360 MHz, DMSO-d₆) δ 1.64 (1H, m), 1.79 (1H, dt, J 13.4, 4.2 Hz), 2.00 (2H, m), 2.82 (1H, dt, J 12.4, 2.8 Hz), 3.26 (1H, m), 3.70 (3H, s), 3.75 (1H, s), 4.21 (2H, dq, J 8.3, 2.5 Hz), 4.3 (1H, dd, J 11.9, 2.2 Hz), 4.84 (1H, dd, J 11.9, 2.1 Hz), 6.12 (1H, t, J 2.1 Hz), 6.41 (1H, t, J 1.7 Hz), 6.72 (2H, d, J 1.7 Hz), 7.15 (3H, m), and 7.35 (2H, m). m/z (ES⁺) 420 (M+1).

EXAMPLE 10

(5R,6S)-3-(2,5-Bis(2,2,2-trifluoroethoxy)phenyl)-6-phenyl-1-oxa-7-aza-spiro[4.5]dec-3-ene Prepared from the compound of Description 22 and (5R,6S)-3-trimethylstannyl-6-phenyl-1-oxa-7-(tert-butoxycarbonyl)aza-spiro-[4.5]dec-3-ene according to the methods of Examples 1 and 2. $^1$H NMR (250 MHz, CDCl$_3$) δ 1.60 (1H, m), 1.80 (1H, dt, J 13.5 and 4.3 Hz), 1.97 (1H, m), 2.02 (1H, m), 2.83 (1H, dt, J 12.4 and 2.7 Hz), 3.28 (1H, m), 3.78 (1H, s), 4.08 (2H, m), 4.22 (2H, q, J 8 Hz), 4.36 (1H, dd, J 11.9 and 2.2 Hz), 4.84 (1H, dd, J 11.9 and 1.9 Hz), 6.16 (1H, t, J 2.1 Hz), 6.45 (1H, t, 1.7 Hz), 6.72 (2H, d, J 1.7 Hz), 7.15 (3H, m), and 7.36 (2H, m). m/z (ES$^+$) 488 (M+1).

EXAMPLE 11

(5R,6S)-3-(2-Difluoromethoxy-5-trifluoromethoxyphenyl)-6-phenyl-1-oxa-7-aza-spiro[4.5]dec-3-ene Prepared from the compound of Description 23 and (5R,6S)-3-trimethylstannyl-6-phenyl-1-oxa-7-(tert-butoxycarbonyl)aza-spiro[4.5]dec-3-ene according to the methods of Examples 1 and 2. $^1$H NMR (360 MHz, DMSO-d$_6$) δ 1.8–1.9 (1H, m), 1.9–2.1 (1H, m), 3.04–3.12 (1H, m), 3.26–3.36 (1h, m), 4.33 (1H, d, J 12 Hz), 4.60 (1H, s), 4.91 (1H, d, J 12 Hz), 6.41 (1H, s), 7.08 (1H, d, J 3 Hz), 7.16 (1H, t, J 7.3 Hz), 7.25–7.4 (5H, m), and 7.45–7.47 (2H, m). m/z (ES$^+$) 442 (M+1).

EXAMPLE 12

(5R,6S)-3-(2-(2,2,2-Trifluoroethoxy)-5-trifluoromethoxyphenyl)-6-phenyl-1-oxa-7-aza-spiro[4.5]dec-3-ene Hydrochloride Prepared from the compound of Description 24 and (5R,6S)-3-trimethylstannyl-6-phenyl-1-oxa-7-(tert-butoxycarbonyl)aza-spiro[4.5]dec-3-ene according to the methods of Examples 1 and 2. m/z (ES$^+$) 474 (M+1).

EXAMPLE 13

(3S,5R,6S)-3-(2-Isopropoxy-5-trifluoromethoxyphenyl)-6-phenyl-1-oxa-7-aza-spiro[4.5]decane Hydrochloride Prepared from the compound of Example 6 according to the method of Example 3. m.p. 85–88° C. $^1$H NMR (360 MHz, DMSO-d$_6$) δ 1.23 (6H, t, J 6.4 Hz), 1.65 (1H, t, J 12.3 Hz), 1.80 (2H, d, J 11.7 Hz), 2.04 (3H, m), 3.06 (2H, q, J 9 Hz), 3.30 (1H, m), 3.79 (1H, m), 4.15 (1H, t, J 7.8 Hz), 4.49 (1H, s), 4.55 (1H, m), 6.12 (1H, s), 6.99 (1H, d, 9 Hz), 7.06 (1H, m), 7.46 (3H, m), 7.56 (2H, m), 9.0 (1H, bs), and 9.65 (1H, bs). m/z (ES$^+$) 436 (M+1).

EXAMPLE 14

(3S,5R,6S)-3-(5-Trifluoromethoxy-2,3-dihydrobenzofuran-7-yl)-6-phenyl-1-oxa-7-aza-spiro[4.5]decane Hydrochloride Prepared from the compound of Example 8 according to the method of Example 3. m.p. 303–305° C. $^1$H NMR (360 MHz, DMSO-d$_6$) δ 1.81 (3H, m), 2.0 (3H, m), 3.09 (3H, t, J 8.9 Hz), 3.22 (2H, m), 3.57 (1H, m), 4.06 (1H, t, J 7.9 Hz), 4.35 (2H, dt, J 8.9, 4 Hz), 4.46 (1H, s), 6.17 (1H, s), 7.03 (1H, s), 7.47 (3H, m), and 7.54 (2H, m). m/z (ES$^+$) 420 (M+1).

EXAMPLE 15

(3S,5R,6S)-3-(2-Methoxy-5-(2,2,2-trifluoroethoxy)phenyl)-6-phenyl-1-oxa-7-aza-spiro[4.5]decane Hydrochloride Prepared from the compound of Example 9 according to the method of Example 3. m.p. 126–128° C. $^1$H NMR (360 MHz, DMSO-d$_6$) δ 1.77 (3H, m), 1.99 (3H, m), 3.17 (1H, t, J 10.2 Hz), 3.59 (3H, s), 4.09 (1H, t, J 7.7 Hz), 4.47 (1H, q, J 8.9 Hz), 6.05 (1H, s), 6.82 (2H, s), 7.47 (3H, m), and 7.57 (2H, m). m/z (ES$^+$) 422 (M+1).

EXAMPLE 16

(3S,5R,6S)-3-(2,5-Bis(2,2,2-trifluoroethoxy)phenyl)-6-phenyl-1-oxa-7-aza-spiro-[4.5]-decane Hydrochloride Prepared from the compound of Example 10 according to the method of Example 3. m.p. 210–212° C., $^1$H NMR (250 MHz, DMSO-d$_6$) δ 1.88 (1H, t, J 11.7 Hz), 2.04 (2H, m), 2.27 (3H, m), 3.35 (2H, t, J 9.9 Hz), 3.48 (1H, m), 3.96 (1H, m), 4.37 (1H, t, J 7.9 Hz), 4.73 (3H, q, J 2.9 Hz), 7.09 (1H, dd, J 9.0, 2.9 Hz), 7.23 (1H, d, 9.1 Hz), 7.67 (3H, m), and 7.77 (2H, m). m/z (ES$^+$) 490 (M+1).

EXAMPLE 17

(3S,5R,6S)-3-(2-Difluoromethoxy-5-trifluoromethoxyphenyl)-6-phenyl-1-oxa-7-aza-spiro[4.5]decane Hydrochloride Prepared from the compound of Example 11 according to the method of Example 3. $^1$H NMR (360 MHz, DMSO-d$_6$) δ 1.67 (1H, t, J 12 Hz), 1.74–1.84 (2H, m), 2.00–2.18 (3H, m), 3.07 (1H, m), 3.14 (1H, t, J 8 Hz), 3.3 (1H, m), 3.81 (1H, qn, J 9 Hz), 4.15 (1H, t, J 8 Hz), 4.51 (1H, s), 6.10 (1H, s), 7.16 (1H, t, J 7.3 Hz), 7.23 (2H, s), 7.40–7.54 (3H, m), and 7.58–7.60 (2H, m). m/z (ES$^+$) 444 (M+1).

EXAMPLE 18

(3S,5R,6S)-3-(2-(2,2,2-Trifluoroethoxy)-5-trifluoromethoxyphenyl)-6-phenyl-1-oxa-7-aza-spiro[4.5]decane Hydrochloride Prepared from the compound of Example 12 according to the method of Example 3. m.p. 209–211° C. $^1$H NMR (360 MHz, DMSO-d$_6$) δ 1.63–1.69 (1H, m), 1.70–1.88 (2H, m), 2.0–2.14 (3H, m), 3.06–3.12 (2H, m), 3.24–3.32 (1H, m), 3.77 (1H, m), 4.16 (1H, t, J 8 Hz), 4.51 (1H, s), 4.74–4.78 (2H, m), 6.19 (1H, s), 7.11–7.20 (2H, m), 7.44–7.48 (3H, m), and 7.56–7.58 (2H, m). m/z (ES$^+$) 476 (M+1).

EXAMPLE 19

(3S,5R,6S)-3-(2-(2,2,2-Trifluoroethoxy)-5-fluorophenyl)-6-phenyl-1-oxa-7-aza-spiro[4.5]decane Prepared from the compound of Description 25 according to the methods of Examples 1, 2 and 3. $^1$H NMR (360 MHz, CDCl$_3$) δ 1.69 (1H, m), 1.81 (1H, dd, J 8.5, 8 Hz), 1.92–2.07 (2H, m), 2.74 (1H, dt, J 12, 2.7 Hz), 3.11 (1H, t), 3.15 (1H, m), 3.58 (1H, s), 3.73 (1H, qn, J 8 Hz), 4.02 (1H, t, J 8 Hz), 4.16 (2H, q, J 8 Hz), 5.95 (1H, dd, J 9.6, 3 Hz), 6.56–6.69 (2H, m), 7.18–7.27 (3H, m), and 7.39–7.41 (2H, m). m/z (ES$^+$) 410 (M+1).

EXAMPLE 20

(5R,6S)-3-(5-Methanesulfonyl-2-methoxyphenyl)-6-phenyl-1-oxa-7-(tert-butoxycarbonyl)aza-spiro[4.5]dec-3-ene Prepared from the compound of Description 28 and (5R,6S)-3-trimethylstannyl-6-phenyl-1-oxa-7-(tert-butoxycarbonyl)aza-spiro[4.5]dec-3-ene according to the method of Example 1. $^1$H NMR (250 Mz, CDCl$_3$) δ 7.86–7.83 (1H, dd, J 8.8, 2.4 Hz), 7.59–7.58 (1H, d, J 2.4 Hz), 7.49–7.43 (2H, m), 7.31–7.20 (3H, m), 7.05–7.02 (1H, d, 8.8 Hz), 6.69–6.68 (1H, m), 5.17 (1H, s), 5.00–4.94 (1H, dd, J 12.1, 2.06 Hz), 4.68–4.62 (1H, dd, J 12.1, 2.06 Hz), 4.15–4.11 (1H, m), 3.95 (3H, s), 3.18–3.01 (1H, m), 3.03 (3H, s), 2.13–2.06 (1H, m), 1.92–1.79 (3H, m), and 1.37 (9H, s). m/z (ES$^+$) 500 (M+1).

EXAMPLE 21

(5R,6S)-3-(5-Methanesulfonyl-2-methoxyphenyl)-6-phenyl-1-oxa-7-aza-spiro[4.5]dec-3-ene Prepared from the compound of Example 20 according to the method of Example 2. $^1$H NMR (250 MHz, CDCl$_3$) δ 10.33 (1H, br s), 7.78–7.73 (1H, dd, J 8.7, 2.4 Hz), 7.55–7.45 (2H, m), 7.32–7.31 (1H, d, J 2.4 Hz), 7.28–7.21 (3H, m), 6.92–6.89 (1H, d, J 8.7 Hz), 6.05–6.03 (1H, m), 5.34 (1H, s), 4.91–4.86 (1H, m), 4.46–4.41 (1H, m), 4.16–4.12 (1H, m), 3.82 (3H, s), 3.53–3.49 (1H, m), 2.97 (3H, s), 2.56–2.50 (1H, m), and 2.1–1.95 (3H, m). m/z (ES$^+$) 400 (M+1).

EXAMPLE 22

(3S,5R,6S)-3-(5-Methanesulfonyl-2-methoxyphenyl)-6-phenyl-1-oxa-7-aza-spiro[4.5]decane Prepared from the compound of Example 21 according to the method of Example 3. $^1$H NMR (250 MHz, CDCl$_3$) δ 7.72–7.67 (1H, dd, d 8.7, 2.3 Hz), 7.54–7.50 (2H, m), 7.39–7.29 (3H, m), 7.06–7.05 (1H, d, J 2.3 Hz), 6.85–6.82 (1H, d, J 8.7 Hz), 4.13–4.07 (1H, m), 3.86–3.74 (1H, m), 3.74 (3H, s), 3.70 (1H, s), 3.27–3.22 (1H, m), 3.19–3.11 (1H, m), 2.87 (3H, m), 2.88–2.78 (1H, m), and 2.14–1.56 (6H, m). m/z (ES$^+$) 402 (M+1).

EXAMPLE 23

(5R,6S)-3-[2-(Trifluoromethoxy)phenyl]-6-phenyl-1-oxa-7-(tert-butoxycarbonyl)aza-spiro[4.5]dec-3-ene Prepared from 2-(trifluoromethoxy)iodobenzene and (5R,6S)-3-trimethylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 7.56–7.43 (3H, m), 7.34–7.17 (6H, m), 6.51–6.49 (1H, m), 5.14 (1H, s), 4.95–4.89 (1H, dd, J 12.2, 2.0 Hz), 4.61–4.55 (1H, dd, J 12.2, 2.0 Hz), 4.18–4.11 (1H, m), 3.20–3.15 (1H, m), 2.12–2.08 (1H, m), 1.90–1.78 (3H, m), and 1.35 (9H). m/z (ES$^+$) 420 (M+1-C$_4$H$_8$).

EXAMPLE 24

(5R,6S)-3-[2-(Trifluoromethoxy)phenyl]-6-phenyl-1-oxa-7-aza-spiro[4.5]dec-3-ene

Prepared from the compound of Example 23 according to the method of Example 2. $^1$H NMR (250 MHz, CDCl$_3$) δ 7.39–7.35 (2H, m), 7.25–7.06 (6H, m), 6.90–6.87 (1H, m), 6.04–6.03 (1H, m), 4.87–4.82 (1H, dd, J 12.0, 2.0 Hz), 4.38–4.33 (1H, dd, J 12.0, 2.0 Hz), 3.79 (1H, s), 3.31–3.25 (1H, m), 3.05–2.95 (1H, br s), 2.85–2.75 (1H, m), 2.14–1.94 (2H, m), and 1.85–1.64 (2H, m). m/z (ES$^+$) 376 (M+1).

EXAMPLE 25

(3S,5R,6S)-3-[2-(Trifluoromethoxy)phenyl]-6-phenyl-1-oxa-7-aza-spiro-[4.5]decane Hydrochloride Prepared from the compound of Example 24 according to the method of Example 3. $^1$H NMR (360 MHz, DMSO-d$_6$) δ 9.76 (1H, br s), 9.04 (1H, br s), 7.62–7.51 (5H, m), 7.27–7.25 (2H, m), 7.12–7.07 (1H, m), 6.23–6.21 (1H, d, J 7.5 Hz), 4.52 (1H, s), 4.15–4.11 (1H, m), 3.80–3.74 (1H, m), 3.39–3.26 (1H, m), 3.22–3.17 (1H, m), 3.10–3.04 (1H, m), 2.14–2.08 (3H, m), and 1.83–1.67 (3H, m). m/z (ES$^+$) 378 (M+1).

EXAMPLE 26

(5R,6S)-3-[2-Cyclobutoxy-5-(trifluoromethoxy)phenyl]-6-phenyl-1-oxa-7-(tert-butoxycarbonyl)aza-spiro[4.5]dec-3-ene Prepared from the compound of Description 29 and (5R,6S)-3-trimethylstannyl-6-phenyl-1-oxa-7-(tert-butoxycarbonyl)aza-spiro[4.5]dec-3-ene according to the method of Example 1. $^1$H NMR (360 MHz, CDCl$_3$) δ 7.47–7.45 (2H, m), 7.28–7.20 (3H, m), 7.06–7.02 (1H, m), 6.96–6.94 (1H, m), 6.70–6.67 (1H, d, J 8.9 Hz), 6.64–6.63 (1H, m), 5.15 (1H, s), 5.00–4.94 (1H, m), 4.66–4.59 (2H, m), 4.15–4.11 (2H, m), 3.10–3.08 (1H, m), 2.48–2.44 (2H, m), 2.20–2.10 (3H, m), 1.88–1.67 (4H, m), and 1.36 (9H, s).

EXAMPLE 27

(5R,6S)-3-[2-Cyclobutoxy-5-(trifluoromethoxy)phenyl]-6-phenyl-1-oxa-7-aza-spiro[4.5]dec-3-ene Prepared from the compound of Example 26 according to the method of Example 2. $^1$H NMR (250 MHz, CDCl$_3$) δ 7.38–7.34 (2H, m), 7.23–7.10 (3H, m), 6.97–6.92 (1H, m), 6.68–6.67 (1H, d, J 2.3 Hz), 6.60–6.56 (1H, d, J 9.0 Hz), 6.16–6.14 (1H, m), 4.90–4.85 (1H, dd, J 12.0, 2.1 Hz), 4.60–4.49 (1H, m), 4.33–4.27 (1H, dd, J 12.0, 2.1 Hz), 3.76 (1H, s), 3.31–3.24 (1H, m), 2.87–2.76 (1H, m), 2.48–2.36 (2H, m), and 2.19–1.62 (8H, m). m/z (ES$^+$) 446 (M+1).

EXAMPLE 28

(3S,5R,6S)-3-[2-Cyclobutoxy-5-(trifluoromethoxy)phenyl]-6-phenyl-1-oxa-7-aza-spiro[4.5]decane Hydrochloride Prepared from the compound of Example 27 according to the method of Example 3. $^1$H NMR (360 MHz, DMSO-d$_6$) δ 9.69 (1H, br s), 9.00 (1H, br s) 7.58–7.57 (2H, m), 7.48–7.43 (3H, m) 7.07–7.05 (1H, m), 6.81–6.79 (1H, d, J 9.0 Hz), 6.13 (1H, s), 4.67–4.63 (1H, m), 4.51–4.48 (1H, m), 4.19–4.15 (1H, m), 3.82–3.78 (1H, m), 3.41–3.36 (1H, m), 3.09–3.04 (2H, m), 2.40–2.36 (2H, m), 2.12–1.96 (5H, m), and 1.80–1.60 (5H, m). m/z (ES$^+$) 448 (M+1).

EXAMPLE 29

(5R,6S)-3-(2-(2-Fluoroethoxy)-5-(trifluoromethoxy)phenyl)-6-phenyl-1-oxa-7-(tert-butoxycarbonyl)aza-spiro[4.5]dec-3-ene Prepared from the compound of Description 31 and (5R,6S)-3-trimethylstannyl-6-phenyl-1-oxa-7-(tert-butoxycarbonyl)aza-spiro[4.5]dec-3-ene according to the method of Example 1. $^1$H NMR (360 MHz, CDCl$_3$) δ 1.36 (9H, s), 1.84 (3H, m), 2.09 (1H, m), 3.12 (1H, dt, J 12 Hz, J 5.1 Hz), 4.11 (1H, m), 4.18 (1H, q, J 4.6 Hz), 4.27 (1H, q, J 4.7 Hz), 4.60 (1H, dd, J 12.2 Hz, J 2.1 Hz), 4.69 (1H, m), 4.82 (1H, m), 4.95 (1H, dd, J 12.3 Hz, J 2.1 Hz), 5.14 (1H, s), 6.65 (1H, t, J 2.1 Hz), 6.85 (1H, d, J 9 Hz), 6.95 (1H, d, J 2.4 Hz), 7.09 (1H, d, J 8.1 Hz), 7.24 (3H, m), and 7.45 (2H, d, J 7.5 Hz).

EXAMPLE 30

(5R,6S)-3-(2-(2-Fluoroethoxy)-5-(trifluoromethoxy)phenyl)-6-phenyl-1-oxa-7-aza-spiro-[4.5]dec-3-ene Hydrochloride The compound of Example 29 was stirred in 1N methanolic HCl at ambient temperature for 15 h. The solvent was evaporated in vacuo and the residue partitioned between aqueous saturated potassium carbonate (50 ml) and ethyl acetate (3×50 ml). The combined organic fractions were washed with brine (50 ml), dried (MgSO$_4$) and evaporated in vacuo. Purification on silica, eluting with 10% methanol in dichloromethane gave the title compound as a white solid (180 mg, 68%). $^1$H NMR (360 MHz, CDCl$_3$) δ 1.86 (2H, m), 2.02 (2H, m), 3.14 (1H, m), 3.40 (1H, m), 4.21 (1H, m), 4.28 (1H, m), 4.33 (1H, d, J 12.5 Hz), 4.58 (1H, d, J 11.7 Hz), 4.71 (1H, m), 4.84 (1H, m), 4.94 (1H, d, J 12.4 Hz), 6.44 (1H, s), 6.94 (1H, d, J 2.5 Hz), 7.08 (1H, d, J 9.1 Hz), 7.30 (3H, m), 7.45 (2H, d, J 6.6 Hz), 9.07 (1H, broad s), and 9.70 (1H, broad s). m/z (ES$^+$) 438 (M+1).

EXAMPLE 31

(3S,5R,6S)-3-(2-(2-Fluoroethoxy)-5-(trifluoromethoxy)-6-phenyl-1-oxa-7-aza-spiro[4.5]decane Hydrochloride Prepared from the compound of Example 30 according to the method of Example 3. $^1$H NMR (500 Hz, DMSO-d$_6$ 300K) δ 1.70 (1H, m), 1.80 (2H, m), 1.95 (1H, m), 2.09 (2H, m), 3.07 (2H, m), 3.73 (1H, d, J 12.8 Hz), 3.82 (1H, m), 4.17 (1H, m), 4.22 (1H, m), 4.33 (1H, d, J 11.3 Hz), 4.51 (1H, d, J 11.6 Hz), 4.65 (1H, m), 4.75 (1H, m), 7.01 (1H, d, J 9 Hz), 7.12 (1H, d, J 10.8 Hz), 7.18 (2H, m), 7.39 (1H, m), 7.46 (2H, m), 7.55 (1H, d, J 7.4 Hz), 8.93 (1H, m), and 9.53 (1H, m). m/z (ES$^+$) 440 (M+1).

EXAMPLE 32

(5R,6S)-3-(2-Ethen-1-yl)-5-(trifluoromethoxy)phenyl)-6-phenyl-1-oxa-7-(tert-butoxycarbonyl)aza-spiro[4.5]dec-3-ene Prepared from the compound of Description 33 and (5R,6S)-3-trimethylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 1.36 (9H, s), 1.86 (2H, m), 2.12 (1H, m), 3.22 (1H, m), 4.12 (1H, q, J 7.1 Hz), 4.18 (1H, m), 4.37 (1H, dd, J 12.6 Hz, J 2.2 Hz), 4.7 (1H, dd, J 12.6 Hz, J 2.0 Hz), 5.1 (1H, s), 5.28 (1H, d, J 11.1 Hz), 5.61 (1H, d, J 17.4 Hz), 6.03 (1H, t, J 2.1 Hz), 6.66 (1H, m), 6.85 (1H, m), 7.11 (1H, m), 7.28 (3H, m), 7.46 (2H, m), and 7.50 (1H, d, J 8.6 Hz).

EXAMPLE 33

(5R,6S)-3-(2-(Ethen-1-yl)-5-(trifluoromethoxy)phenyl)-6-phenyl-1-oxa-7-aza-spiro[4.5]dec-3-ene Prepared from the compound of Example 32 according to the method of Example 30. $^1$H NMR (360 MHz, CDCl$_3$) δ 1.67 (1H, m), 1.81 (2H, m), 2.83 (1H, dt, J 3 Hz, J 12.3 Hz), 3.26 (1H, m), 3.74 (1H, s), 4.28 (1H, dd, J 2.4 Hz, J 12.6 Hz), 4.68 (1H, dd, J 2.2 Hz, J 12.4 Hz), 5.06 (1H, dd, J 1.2 Hz, J 11 Hz), 5.47 (1H, dd, J 1.1 Hz, J 17.3 Hz), 5.57 (1H, t, J 2.2 Hz), 5.92 (1H, m), 6.60 (1H, s), 7.01 (1H, d, J 8.6 Hz), 7.28 (4H, m), and 7.40 (2H, m).

EXAMPLE 34

(3S,5R,6S)-3-(2-Ethyl-5-(trifluoromethoxy)phenyl)-6-phenyl-1-oxa-7-aza-spiro[4.5]decane Prepared from the compound of Example 33 according to the method of Example 3. $^1$H NMR (250 MHz, CDCl$_3$) δ 1.12 (3H, t, J 7.5 Hz), 1.61 (2H, m), 1.90 (2H, m), 2.12 (2H, m), 2.58 (2H, q, J 7.6 Hz), 2.77 (1H, dt, J 2.5 Hz, J 12.2 Hz), 3.16 (1H, m), 3.27 (1H, m); 3.61 (1H, m), 3.73 (1H, s), 4.05 (1H, t, J 8.1 Hz), 4.56 (1H, broad s), 5.88 (1H, d, J 1.63 Hz), 6.85 (1H, dd, J 1.2 Hz, J 8.3 Hz), 7.03 (1H, d, J 8.4 Hz), 7.36 (3H, m), and 7.54 (2H, m). m/z (ES$^+$) 406 (M+1).

EXAMPLE 35

(5R,6S)-3-(2-Benzyloxy-5-(trifluoromethoxy)phenyl)-6-phenyl-1-oxa-7-(tert-butoxycarbonyl)aza-spiro[4.5]dec-3-ene Prepared from the compound of Description 34 and (5R,6S)-3-trimethylstannyl-6-phenyl-1-oxa-7-(tert-butoxycarbonyl)aza-spiro[4.5]dec-3-ene according to the method of Example 1. $^1$H NMR (360 MHz, CDCl$_3$) δ 1.33 (9H, s), 1.65 (1H, m), 1.76 (2H, m), 2.08 (1H, m), 3.11 (1H, m), 4.08 (1H, m), 4.60 (1H, dd, J 12.2 Hz, J 2 Hz), 4.92 (1H, dd, J 12.1 Hz, J 1.8 Hz), 5.08 (1H, s), 5.1 (2H, q, J 11.5 Hz), 6.65 (1H, s), 6.94 (2H, d, J 8.9 Hz), 7.08 (1H, d, J 9 Hz), 7.18 (2H, t, J 8.1 Hz), 7.25 (3H, m), 7.38 (5H, m).

EXAMPLE 36

(5R,6S)-3-(2-Benzyloxy-5-(trifluoromethoxy)phenyl)-6-phenyl-1-oxa-7-aza-spiro[4.5]dec-3-ene Prepared from the compound of Example 35 according to the method of Example 30. $^1$H NMR (250 MHz, CDCl$_3$) δ 1.70 (2H, m), 1.94 (1H, m), 2.05 (1H, m), 2.77 (1H, td, J 12.5 Hz, J 2.8 Hz), 2.93 (1H, broad s), 3.25 (1H, m), 3.70 (1H, s), 4.34 (1H, dd, J 14.5 Hz, J 2 Hz), 4.99 (1H, s), 6.14 (1H, t, J 2 Hz), 6.67 (1H, d, J 2.7 Hz), 6.80 (1H, d, J 9 Hz), 6.98 (1H, dd, J 9 Hz, J 2 Hz), 7.17 (3H, m), and 7.26–7.47 (7H, m). m/z (ES$^+$) 482 (M+1).

EXAMPLE 37

(3S,5R,6S)-3-(2-Hydroxy-5-(trifluoromethoxy)phenyl)-6-phenyl-1-oxa-7-aza-spiro[4.5]decane Hydrochloride Prepared from the compound of Example 36 according to the method of Example 3. $^1$H NMR (360 MHz, DMSO-d$_6$) δ 1.67 (1H, t, J 12.1 Hz), 1.80 (2H, d, J 11.5 Hz), 2.05 (3H, m), 3.06 (2H, t, J 8.1 Hz), 3.30 (1H, m), 3.77 (1H, m), 4.13 (1H, t, J 7.8 Hz), 4.48 (1H, m), 6.03 (1H, d), 6.80 (1H, d, J 8.8 Hz), 6.92 (1H, dd, J 8.9 Hz), 7.45 (3H, m), and 7.56 (2H, m). m/z (ES$^+$) 394 (M+1).

EXAMPLE 38

(3S,5R,6S)-3-(2-Hydroxy-5-(trifluoromethoxy)phenyl)-6-phenyl-1-oxa-7-(tert-butoxycarbonyl)aza-spiro[4.5]decane To a solution of (3S,5R,6S)-3-(2-hydroxy-5-(trifluoromethoxy)phenyl)-6-phenyl-1-oxa-7-aza-spiro[4.5]decane hydrochloride (Example 37, 290 mg, 0.7 mmol) in water (3 ml) was added sodium carbonate solid until pH 10. To this was added dichloromethane (2 ml) followed by di-tert-butyl dicarbonate (170 mg, 0.8 mmol) and the reaction was stirred at ambient temperature for 16 h. The reaction was diluted with water (40 ml) and the organic layer separated. The organic layer was washed with brine (50 ml), dried (MgSO$_4$), and evaporated in vacuo, to give the title compound as a white solid, (320 mg, 96%). $^1$H NMR (360 MHz, CDCl$_3$) δ 1.38 (9H, s), 1.73 (2H, m), 1.81 (1H, m), 2.18 (2H, m), 2.50 (1H, m), 2.81 (1H, m), 3.62 (1H, t, J 7.2 Hz), 3.92 (1H, m), 3.98 (1H, d, J 13.2 Hz), 4.23 (1H, m), 5.33 (1H, s), 6.75 (1H, d, J 8.5 Hz), 6.94 (2H, m), 7.25 (1H, m), 7.31 (2H, m), and 7.55 (2H, d, J 7.8 Hz).

EXAMPLE 39

(3S,5R,6S)-3-(2-(Ethen-1-yl)-5-(trifluoromethoxy) phenyl)-6-phenyl-1-oxa-7-(tert-butoxycarbonyl)aza-spiro[4.5]decane Prepared from the compound of Example 144 and vinyl tributyl tin according to the method of Description 33. $^1$H NMR (250 MHz, CDCl$_3$) δ 1.76 (2H, m), 2.10 (2H, m), 2.43 (1H, m), 2.90 (1H, m), 3.69 (2H, m), 4.0 (1H, d, J 13.5 Hz), 4.12 (1H, d, J 7.1 Hz), 4.22 (1H, m), 5.18 (1H, s), 5.38 (1H, dd, J 10.9 Hz, J 1.2 Hz), 5.59 (1H, dd, J 17.2 Hz, J 1.2 Hz), 6.96 (1H, m), 7.04 (1H, m), 7.15 (1H, m), 7.32 (3H, m), 7.45 (1H, d, J 8.2 Hz), and 7.56 (2H, m).

EXAMPLE 40

(3S,5R,6S)-3-(2-(Ethen-1-yl)-5-(trifluoromethoxy) phenyl)-6-phenyl-1-oxa-7-aza-spiro[4.5]decane Prepared from the compound of Example 39 according to the method of Example 2. $^1$H NMR (250 MHz, CDCl$_3$) δ 1.62 (2H, d, J 11.1 Hz), 1.88 (2H, d, J 9.5 Hz), 2.10 (2H, m), 2.78 (1H, dt, J 12.2 Hz, J 2.5 Hz), 3.17 (1H, m), 3.25 (1H, dt, J 9.9 Hz, J 2.1 Hz), 3.66 (1H, m), 3.72 (1H, s), 4.06 (1H, d, J 8 Hz), 5.29 (1H, dd, J 10.9 Hz, J 1.3 Hz), 5.49 (1H, dd, J 17.2 Hz, J 1.3 Hz), 6.04 (1H, d, J 1.5 Hz), 6.83 (1H, m), 6.92 (1H, d, J 7.6 Hz), 7.36 (4H, m), and 7.50 (2H, m). m/z (ES$^+$) 404 (M+1).

EXAMPLE 41

(5R,6S)-3-(2-Methoxyphenyl)-6-phenyl-1-oxa-7-(tert-butoxycarbonyl)aza-spiro[4.5]dec-3-ene Prepared from 2-methoxychlorobenzene and (5R,6S)-3-trimethylstannyl-6-phenyl-1-oxa-7-(tert-butoxycarbonyl) aza-spiro[4.5]dec-3-ene according to the method of Example 1. $^1$H NMR (360 MHz, CDCl$_3$) δ 1.27 (9H, s), 1.75–1.90 (3H, m), 2.09–2.12 (1H, m), 3.07–3.14 (1H, m), 3.86 (3H, s), 4.11–4.15 (1H, m), 4.61 (1H, dd, J 12.0 and 2.1 Hz), 4.97 (1H, dd, J 12.0 and 2.1 Hz), 5.16 (1H, s), 6.19 (1H, s), 6.88–6.92 (2H, m), 7.04 (1H, d, J 8.1 Hz), 7.16–7.27 (4H, m), and 7.46 (2H, d, J 7.4 Hz).

EXAMPLE 42

(5R,6S)-3-(2-Methoxyphenyl)-6-phenyl-1-oxa-7-aza-spiro[4.5]dec-3-ene

Prepared from the compound of Example 41 according to the method of Example 2. $^1$H NMR (360 MHz, CDCl$_3$) δ 2.02–2.23 (4H, m), 3.27 (1H, t, J 12.7 Hz), 3.57–3.60 (1H, m), 3.77 (3H, s), 4.49 (1H, s), 4.51 (1H, d, J 12.3 Hz), 4.93 (1H, d, J 12.3 Hz), 6.31 (1 H, s), 6.89 (2H, d, J 4.4 Hz), 6.99 (1H, d, J 8.3 Hz), 7.26–7.38 (4H, m), and 7.46 (2H, d, 7.4 Hz).

EXAMPLE 43

(3S,5R,6S)-3-(2-Methoxyphenyl)-6-phenyl-1-oxa-7-aza-spiro[4.5]decane Hydrochloride Prepared from the compound of Example 42 according to the method of Example 3. $^1$H NMR (360 MHz, D$_2$O) δ 1.87–1.95 (3H, m), 2.07–2.20 (3H, m), 3.23 (1H, t, J 12.6 Hz), 3.33–3.38 (1H, m), 3.49–3.53 (1H. m), 3.67 (3H, s), 4.14 (1H, t, J 7.8 Hz), 4.42 (1H, s), 6.49 (1H, d, J 7.7 Hz), 6.79 (1H, t, J 7.4 Hz), 6.95 (1H, d, J 7.4 Hz), 7.19 (1H, t, J 8.7 Hz), and 7.48–7.54 (5H, m).

EXAMPLE 44

(3S,5R,6S)-3-(2-Hydroxy-5-(trifluoromethoxy) phenyl)-6-phenyl-1-oxa-7-(tert-butoxycarbonyl)aza-spiro[4.5]decane (5R,6S)-3-(2-Benzyloxy-5-(trifluoromethoxy)phenyl)-6-phenyl-1-oxa-7-(tert-butoxycarbonyl)aza-spiro[4.5]dec-3-ene (Example 35) (3.88 g) was dissolved in ethyl acetate (15 ml) and methanol (15 ml). Palladium hydroxide on carbon (1.00 g) was added and the suspension was shaken under a hydrogen atmosphere (50 psi) for 72 h. The mixture was filtered and the solvent was evaporated under reduced pressure. The residue was purified by medium pressure chromatography on silica gel, eluting with hexane/ethyl acetate (75:25) to give (3R,5R,6S)-3-(2-hydroxy-5-(trifluoromethoxy)phenyl)-6-phenyl-1-oxa-7-(tert-butoxycarbonyl)aza-spiro[4.5]decane (191 mg), $^1$H NMR (250 MHz, CDCl$_3$) δ 7.70 (2H, d, J 7.3 Hz), 7.33 (2H, t, J 7.3 Hz), 7.26 (1H, d, J 7.3 Hz), 7.05 (1H, br s), 6.96 (2H, m), 6.82 (1H, d, J 9.4 Hz), 5.43 (1H, s), 4.27 (1H, m), 4.01 (1H, m), 3.95 (1H, m), 3.73 (1H, m), 2.73 (2H, m), 2.33 (1H, m), 1.87–1.58 (4H, m); and 1.50 (9H, s) and (3S,5R,6S)-3-(2-hydroxy-5-(trifluoromethoxy)phenyl)-6-phenyl-1-oxa-7-(tert-butoxycarbonyl)aza-spiro[4.5]decane (2.3 g), $^1$H NMR (360 MHz, CDCl$_3$) δ 1.38 (9H, s), 1.73 (2H, m), 1.81 (1H, m), 2.18 (2H, m), 2.50 (1H, m), 2.81 (1H, m), 3.62 (1H, t, J 7.2 Hz), 3.92 (1H, m), 3.98 (1H, d, J 13.2 Hz), 4.23 (1H, m), 5.33 (1H, s), 6.75 (1H, d, J 8.5 Hz), 6.94 (2H, m), 7.25 (1H, m), 7.31 (2H, m), and 7.55 (2H, d, J 7.8 Hz).

EXAMPLE 45

(5R,6S)-3-(2-Benzyloxy-5-(trifluoromethyl)phenyl)-7-(tert-butoxycarbonyl)-6-phenyl-1-oxa-7-aza-spiro [4.5]dec-3-ene Prepared from the compound of Description 36 and (5R,6S)-3-tributylstannyl-6-phenyl-1-oxa-7-(tert-butoxycarbonyl)aza-spiro[4.5]dec-3-ene according to the method of Example 1. $^1$H NMR (360 MHz, CDCl$_3$) δ 1.33 (9H, s), 1.72–1.83 (3H, m), 2.03–2.11 (1H, m), 3.06–3.15 (1H, m), 4.07–4.11 (1H, m), 4.64 (1H, dd, J 11.5, 15.5 Hz), 4.96 (1H, dd, J 2, 12 Hz), 5.09 (1H, s), 5.16 (2H, dd, J 11.5, 15.5 Hz), 6.66 (1H, t, J 2 Hz), 7.02 (1H, d, 8.5 Hz), 7.16–7.27 (3H, m), 7.32 (1H, d, J 2 Hz), and 7.34–7.49 (8H, m). m/z (ES$^+$) 566 (M+1).

EXAMPLE 46

(3S,5R,6S)-3-(2-Hydroxy-5-(trifluoromethyl) phenyl)-6-phenyl-1-oxa-7-(tert-butoxycarbonyl)aza-spiro[4.5]decane Prepared from the compound of Example 45 according to the method of Example 44. (3R,5R,6S)-3-(2-Hydroxy-5-(trifluoromethyl)phenyl)-6-phenyl-1-oxa-7-(tert-butoxycarbonyl)aza-spiro[4.5]decane, $^1$H NMR (250 MHz, CDCl$_3$) δ 1.51 (9H, s), 1.58–1.75 (2H, m), 1.82–1.88 (2H, m), 2.33 (1H, dt, J 4, 13 Hz), 2.70 (1H, dd, J 8.6, 13 Hz), 2.79 (1H, dt, J 3, 13 Hz), 3.84 (1H, qn), 3.93–3.97 (2H, m), 4.31 (1H, t, J 9 Hz), 5.44 (1H, s,), 6.89 (1H, d, J 9 Hz), 7.23–7.35 (5H, m), and 7.58–7.60 (2H, m). m/z (ES$^+$) 478 (M+1). (3S,5R,6S)-3-(2-Hydroxy-5-(trifluoromethyl) phenyl)-6-phenyl-1-oxa-7-(tert-butoxycarbonyl)aza-spiro [4.5]decane, $^1$H NMR (360 MHz, CDCl$_3$) δ 1.34 (9H, s), 1.72–182 (3H, m), 2.10–2.21 (2H, m), 2.53 (1H, dd, J 9, 13 Hz), 2.79–2.88 (1H, m), 3.65 (1H, qn, J 8.6 Hz), 3.94–3.98 (2H, m), 4.24 (1H, dd, J 7, 9 Hz), 5.33 (1H, s,), 6.83 (1H,

EXAMPLE 47

(5R,6S)-3-(2-methoxy-5-trifluoromethoxyphenyl)-6-phenyl-1-oxa-7-aza-spiro[4.5]dec-3-ene Trifluoroacetic acid (1 ml) was added to a cooled (0° C.) solution of (3S,5R,6S)-3-(2-methoxy-5-trifluoromethoxyphenyl)-6-phenyl-1-oxa-7-(tert-butoxycarbonyl)aza-spiro[4.5]decan-3-ol (Description 37, 240 mg, 0.46 mmol) in dichloromethane (10 ml). The solution was stired at 0° C. for 10 min. and at room temperature for 1 h. The solvent was evaporated under reduced pressure and saturated aqueous potassium carbonate was added. The mixture was extracted with ethyl acetate (2×40 ml) and the combined organic fractions were washed with brine (20 ml), dried (MgSO$_4$) and the solvent was evaporated under reduced pressure. The residue was purified by column chromatography on silica gel, eluting with dichloromethane/methanol/ammonia (160:8:1) to give (5R,6S)-3-(2-methoxy-5-trifluoromethoxyphenyl)-6-phenyl-1-oxa-7-aza-spiro[4.5]dec-2-ene (29 mg, 16%), $^1$H NMR (360 MHz, CDCl$_3$) δ 1.56–1.65 (2H, m), 2.05–2.12 (1H, m), 2.22–2.26 (1H, m), 2.41 (1H, dd, J 14.0, 1.6 Hz), 2.76 (1H, dd, J 14.0, 1.9 Hz), 2.87 (1H, dt, J 12.2, 2.7 Hz), 3.23–3.28 (1H, m), 3.59 (1H, s), 3.79 (3H, s), 6.58 (1H, d, J 2.7 Hz), 6.98 (1H, d, J 8.9 Hz), 6.83–6.85 (1H, m), 7.13 (1H, s), 7.15–7.26 (3H, m), and 7.43–7.45 (2H, m), m/z (ES$^+$) 506 (M+1) and (5R,6S)-3-(2-methoxy-5-trifluoromethoxyphenyl)-6-phenyl-1-oxa-7-aza-spiro[4.5]dec-3-ene (69 mg, 37%), $^1$H NMR (250 MHz, CDCl$_3$) δ 7.45 (2H, d, J 7.2 Hz), 7.30–7.2 (3H, m), 7.13–7.09 (1H, dd, J 9.0 Hz), 6.89 (2H, s+d), 6.64 (1H, t, J 2.04 Hz), 5.16 (1H, s), 4.96 and 4.56 (2H, ABdd, J 12.1 and 2 Hz), 4.11 (1H, m), 3.86 (3H, s), 3.08 (1H, m), 2.1 (1H, m), 1.87–1.77 (3H, m), and 1.37 (9H, s), m/z (ES$^+$) 506 (M+1).

EXAMPLE 48

(5R,6S)-3-(2-Methoxy-5-trifluoromethoxyphenyl)-6-phenyl-1-oxa-7-aza-spiro[4.5]dec-3-ene and (3S,5R,6S)-3-(2-methoxy-5-trifluoromethoxyphenyl)-6-phenyl-1-oxa-7-aza-spiro[4.5]decane Triethylsilane (100 (1, 0.6 mmol) was added to a solution of (5R,6S)-3-(2-methoxy-5-trifluoromethoxyphenyl)-6-phenyl-1-oxa-7-aza-spiro[4.5]dec-2-ene (Example 47, 14 mg, 0.03 mmol) in trifluoroacetic acid (1 ml) and the mixture was stirred at room temperature for 2 h. Additional triethylsilane (100 (1, 0.6 mmol) was added and the mixture was stirred at room temperature for 15 h. The solvent was evaporated under reduced pressure and the residue was azeotroped with toluene (2×10 ml). Saturated aqueous sodium carbonate was added and the mixture was extracted with dichloromethane (3×10 ml). The combined organic fractions were washed with brine (20 ml), dried (MgSO$_4$) and the solvent was evaporated under reduced pressure. The residue was purified by preparative thin layer chromatography on silica gel, eluting with dichloromethane/methanol/ammonia (120:8:1) to give a gum (6 mg). HPLC analysis of the gum [HIPRB column (250×4.6 mm); 40% MeCN in 25 mM KH$_2$PO$_4$, 0.2% triethylamine. pH 3.1, 210 nm] showed that it consisted of a mixture of (5R,6S)-3-(2-methoxy-5-trifluoromethoxyphenyl)-6-phenyl-1-oxa-7-aza-spiro[4.5]dec-3-ene, (3S,5R,6S)-3-(2-methoxy-5-trifluoromethoxyphenyl)-6-phenyl-1-oxa-7-aza-spiro[4.5]decane and (3R,5R,6S)-3-(2-methoxy-5-trifluoromethoxyphenyl)-6-phenyl-1-oxa-7-spiro[4.5]decane (ratio; 1.5:2.5:1).

EXAMPLE 49

(3S,5R,6S)-3-(2-Methoxy-5-trifluoromethoxyphenyl)-6-phenyl-1-oxa-7-aza-spiro[4.5]decane Triethylsilane (252 (1, 1.6 mmol) was added to a solution of (5R,6S)-3-(2-methoxy-5-trifluoromethoxyphenyl)-6-phenyl-1-oxa-7-aza-spiro[4.5]dec-3-ene (Example 47, 32 mg, 0.08 mmol) in trifluoroacetic acid (2 ml) and the solution was stirred at 50° C. for 16 h. The solvent was evaporated under reduced pressure and the residue was azeotroped with toluene (2×10 ml). Saturated aqueous sodium carbonate was added and the mixture was extracted with dichloromethane (4×20 ml). The combined organic fractions were washed with brine (20 ml), dried (MgSO$_4$) and the solvent was evaporated under reduced pressure. The residue was purified by preparative thin layer chromatography on silica gel, eluting with dichloromethane/methanol/ammonia (120:8:1) to give a gum (6 mg). HPLC analysis of the gum [HIPRB column (250×4.6 mm); 40% MeCN in 25 mM KH$_2$PO$_4$, 0.2% triethylamine. pH 3.1, 210 nm] showed that it consisted of a mixture of (3S,5R,6S)-3-(2-methoxy-5-trifluoromethoxyphenyl)-6-phenyl-1-oxa-7-aza-spiro[4.5]decane and (3R,5R,6S)-3-(2-methoxy-5-trifluoromethoxyphenyl)-6-phenyl-1-oxa-7-aza-spiro[4.5]decane (ratio; 2:1).

EXAMPLE 50

(3S,5R,6S)-3-(2-Methoxyphenyl)-6-phenyl-1-oxa-7-(tert-butoxycarbonyl)aza-spiro[4.5]decane Methanesulfonyl chloride (10 ml, 0.14 mmol) was added to a stirred solution of triethylamine (42 ml, 0.3 mmol) and the product of Description 39 (19 mg, 0.043 mmol) in dichloromethane (2 ml) at 0° C. The mixture was allowed to warm to room temperature, stirred for 18 h., diluted with dichloromethane (20 ml), washed with hydrochloric acid (2M, 10 ml) and saturated aqueous sodium carbonate (10 ml), dried (MgSO$_4$) and the solvent was evaporated under reduced pressure. The residue was taken up in tetrahydrofuran (3 ml) and heated with sodium hydride (60% dispersion in oil, 100 mg) at reflux for 18 h., cooled, poured into hydrochloric acid solution (2M, 20 ml) and extracted with ethyl acetate (2×20 ml). The combined organic fractions were washed with saturated aqueous sodium chloride (10 ml), dried (MgSO$_4$) and the solvent was evaporated under reduced pressure. The residue was chromatographed on silica gel, eluting with hexane/ethyl acetate(80:20) to give the title compound as a 1:3 mixture with of the 3R and 3S epimers (8 mg, 44%). $^1$H NMR (360 MHz, CDCl$_3$) δ 7.61 (2H, d, J 7.6 Hz, 3R isomer), 7.57 (2H, d, J 7.5 Hz, 3S isomer), 7.05–7.34 (5H, m, 3R and 3S isomers), 6.80–6.98 (2H, m, 3R and 3S isomers), 5.37 (1H, s, 3R isomer), 5.25 (1H, s, 3S isomer), 4.31 (1H, t, J 7.4 Hz, 3R isomer), 4.21 (1H, t, J 7.2 Hz, 3S isomer), 3.95–4.04 (1H, m, 3R and 3S isomers), 3.82 (3H, s, 3R isomer), 3.81 (3H, s, 3S isomer), 3.64–3.81 (2H, m, 3R and 3S isomers), 2.85 (1H, dt, J 5.9 and 12.1 Hz, 3S isomer), 2.67 (1H, dt, J 4.9, 12.7 Hz, 3R isomer), 2.59 (1H, dd, J 7.3 and 12.7 Hz, 3R isomer), 2.37 (1H, dd, J 8.0 and 12.6 Hz, 3S isomer), 2.21 (1H, dd, J 9.1, 12.6 Hz, 3S isomer), 2.08–2.23 (1H, m, 3R and 3S isomers), 1.93 (1H, dd, J 10.4, 12.4 Hz, 3R isomer), 1.64–1.78 (3H, m, 3R and 3S isomers), 1.47 (9H, s, 3R isomer), and 1.38 (9H, s, 3S isomer). m/z (ES$^+$) 424 (M+1).

EXAMPLE 51

(3S,5R,6S)-3-(2-Methoxyphenyl)-6-phenyl-1-oxa-7-aza-spiro[4.5]decane

Prepared from the compound of Example 50 according to the method of Example 2 as a mixture of (3S,5R,6S)-3-(2-methoxyphenyl)-6-phenyl-1-oxa-7-aza-spiro[4.5]decane and (3R,5R,6S)-3-(2-methoxyphenyl)-6-phenyl-1-oxa-7-aza-spiro[4.5]decane. $^1$H NMR (360 MHz, CDCl$_3$) δ 7.51–7.59 (2H, m, 3R and 3S isomers), 7.32–7.45 (3H, m, 3R and 3S isomers), 7.05–7.13 (1H, m, 3R and 3S isomers), 6.97 (1H, d, J 7.6 Hz, 3R isomer), 6.81 (1H, t, J 7.5 Hz, 3R isomer), 6.71–6.82 (1H, m, 3R and 3S isomers), 6.69 (1H, t, J 7.5 Hz, 3S isomer), 6.43 (1H, d, J 7.6 Hz, 3S isomer), 4.09 (1H, t, J 7.8 Hz, 3S isomer), 3.94 (1H, t, J 7.6 Hz, 3R isomer), 3.67–3.87 (1H, m, 3R and 3S isomers), 3.68 (4H, s, 3S isomer), 3.63 (3H, s, 3R isomer), 3.53 (1H, s, 3R isomer), 3.17–3.25 (1H, m, 3R and 3S isomers), 2.75–2.84 (1H, m, 3R and 3S isomer), and 1.55–2.37 (8H, m, 3R and 3S isomers). m/z (ES$^+$) 324 (M+1).

EXAMPLE 52

(5R,6S)-3-(2-Methoxy-5-trifluoromethoxyphenyl)-6-phenyl-1-oxa-7-(tert-butoxycarbonyl)aza-spiro[4.5]dec-3-en-2-one A mixture of (5R,6S)-7-tert-butoxycarbonyl-6-phenyl-3-tributylstannyl-1-oxa-7-aza-spiro[4.5]dec-3-en-2-one (Description 10, 538 mg, 0.87 mmol), 2-bromo-4-trifluoromethoxyanisole (Description 12, 244 mg, 0.90 mmol) and lithium chloride (230 mg, 5.4 mmol) in toluene (10 ml) was degassed with nitrogen at 60° C. for 30 min. Tetrakis(triphenylphosphine)palladium (0) (100 mg) was added and the mixture was heated under reflux under nitrogen for 16 h. The mixture was cooled, filtered and the solvent was evaporated under reduced pressure. The residue was dissolved in acetonitrile (50 ml), washed with hexane (4×20 ml), then treated with 10% methanolic potassium fluoride solution. The mixture was stirred for 30 min., filtered and the solvent was evaporated under reduced pressure. The residue was then partitioned between saturated aqueous sodium hydrogen carbonate (50 ml) and ethyl acetate (50 ml). The organic phase was dried (Na$_2$SO$_4$) and the solvent was evaporated under reduced pressure. The residue was purified by chromatography on silica gel to give the title compound as a gum (200 mg, 0.39 mmol, 44%). $^1$H NMR (250 MHz, CDCl$_3$) δ 8.60 (1H, s), 8.02 (1H, d), 7.40 (2H, m), 7.26 (4H, m), 6.93 (1H, d, J 9.11 Hz), 5.28 (1H, s), 4.20 (1H, m), 3.91 (3H, s), 3.18 (1H, m), 2.32 (1H, m), 1.89 (3H, m), and 1.39 (9H, s).

EXAMPLE 53

(3S,5R,6S)-3-(2-Methoxy-5-trifluoromethoxyphenyl)-6-phenyl-1-oxa-7-(tert-butoxycarbonyl)aza-spiro[4.5]decan-2-one A mixture of (5R,6S)-3-(2-methoxy-5-trifluoromethoxyphenyl)-6-phenyl-1-oxa-7-(tert-butoxycarbonyl)aza-spiro[4.5]dec-3-en-2-one (Example 52, 100 mg, 0.19 mmol) and palladium acetate (10 mg) in N,N'-dimethylformamide (1 ml) was degassed with nitrogen for 30 min. Potassium formate (42 mg, 0.50 mmol) was added and the mixture was heated at 80° C. for 16 h. The mixture was poured into water (10 ml) and extracted with ethyl acetate (2×10 ml). The combined organic fractions were dried (Na$_2$SO$_4$) and the solvent was evaporated under reduced pressure. The residue was purified by chromatography on silica gel to give the title compound as a colorless solid (44 mg, 0.08 mmol, 44%). $^1$H NMR showed this to be a 1:1 mixture of (3S,5R,6S)- and (3R,5R,6S)-diastereoisomers which were separated by preparative liquid chromatography using a KR60 column, eluting with 5% ethanol/hexane containing 0.1% DEA to give (3R,5R,6S)-3-(2-Methoxy-5-trifluoromethoxyphenyl)-6-phenyl-1-oxa-7-(tert-butoxycarbonyl)aza-spiro[4.5]decan-2-one, $^1$H NMR (250 MHz, CDCl$_3$) δ 7.50–7.53 (2H, m), 7.26–7.39 (3H, m), 7.14 (1H, dd, J 2.59, 8.96 Hz), 7.02 (1H, d, J 2.59 Hz), 6.88 (1H, d, J 8.96 Hz), 5.35 (1H, s), 4.00–4.05 (1H, m), 3.85 (3H, s), 3.70 (1H, t, J 11.02 Hz), 2.70–2.97 (2H, m), 2.38–2.50 (1H, m), 2.22 (1H, dd, J 11.32, 12.97 Hz), 1.72–1.92 (3H, m), and 1.46 (9H, s); and the title compound (3S,5R,6S)-3-(2-Methoxy-5-trifluoromethoxyphenyl)-6-phenyl-1-oxa-7-(tert-butoxycarbonyl)aza-spiro[4.5]decan-2-one, $^1$H NMR (250 MHz, CDCl$_3$) δ 7.50–7.53 (2H, m), 7.26–7.39 (3H, m), 7.13 (1H, dd, J 2.91, 8.97 Hz), 6.90 (1H, d, J 2.91 Hz), 6.83 (1H, d, J 8.97 Hz), 5.31 (1H, br s), 4.02–4.10 (1H, m), 3.92 (1H, t, J 10.56 Hz), 3.64 (3H, s), 2.91–3.02 (1H, m), 2.67 (1H, dd, J 10.04, 12.98 Hz), 2.29–2.52 (2H, m), 1.80–1.87 (3H, m), and 1.36 (9H, s).

EXAMPLE 54

(3S,5R,6S)-3-(2-Methoxy-5-(trifluoromethoxy)phenyl)-6-phenyl-1-oxa-7-aza-spiro[4.5]decan-2-one Hydrochloride Prepared from the compound of Example 53 according to the method of Example 2. m.p. 248–250° C. $^1$H NMR (360 MHz, DMSO-d$_6$) δ 9.90 (1H, br s), 9.30 (1H, br s), 7.42–7.60 (5H, m), 7.19 (1H, d, J 7.17 Hz), 6.93 (1H, d, J 7.17 Hz), 4.70 (1H, br s), 4.42–4.48 (1H, m), 3.30–3.33 (1H, m), 3.11–3.15 (1H, m), 2.29–2.36 (1H, m), and 1.94–2.03 (5H, m). m/z (ES$^+$) 422 (M+1). Found: C, 55.94; H, 5.06; N, 3.06. C$_{22}$H$_{22}$F$_3$NO$_4$.HCl.H$_2$O requires: C, 55.53; H, 5.30; N, 2.94%.

EXAMPLE 55

(5R,6S)-N-{4-Methoxy-3-[6-phenyl-1-oxa-7-(tert-butoxycarbonyl)aza-spiro[4.5]dec-3-en-3-yl]phenyl}trifluoroacetamide Prepared from the compound of Description 47 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 7.83 (1H, br s), 7.53 (1H, dd, J 8.9, 2.7 Hz), 7.47 (2H, m), 7.23 (3H, m), 7.13 (1H, d, J 2.7 Hz), 6.97 (1H, d, J 8.9 Hz), 6.67 (1H, t, J 2.1 Hz), 5.15 (1H, s), 4.94 (1H, dd, J 12, 2.1 Hz), 4.58 (1H, dd, J 12, 2.1 Hz), 4.12 (1H, m), 3.87 (3H, s), 3.11 (1H, m), 2.11 (1H, m), 1.88–1.82 (3H, m), and 1.36 (9H, s). m/z (ES$^+$) 533 (M+1).

EXAMPLE 56

(5R,6S)-N-[4-Methoxy-3-(6-phenyl-1-oxa-7-aza-spiro[4.5]dec-3-en-3-yl)phenyl]trifluoroacetamide Prepared from the compound of Example 55 according to the method of Example 2. $^1$H NMR (250 MHz, CDCl$_3$) δ 7.94 (1H, br s), 7.41 (1H, dd, J 8.9, 2.7 Hz), 7.36 (2H, m), 6.91 (1H, d, J 2.7 Hz), 6.80 (1H, d, J 8.9 Hz), 6.18 (1H, t, J 2.0 Hz), 4.83 (1H, dd, J 11.8, 2.0 Hz), 4.32 (1H, dd, J 11.8, 2.0 Hz), 3.78 (3H, s), 3.77 (1H, m), 3.27 (1H, m), 2.81 (1H, m), 2.20–1.95 (2H, m), 1.88–1.79 (2H, m), and 1.69 (1H, m). m/z (ES$^+$) 433 (M+1).

EXAMPLE 57

(3S,5R,6S)-N-[4-Methoxy-3-(6-phenyl-1-oxa-7-aza-spiro[4.5]decan-3-yl)phenyl]trifluoroacetamide Prepared from the compound of Example 56 according to the method of Example 3. $^1$H NMR (360 MHz, DMSO-d$_6$) δ 7.44 (2H, m), 7.32 (1H, dd, J 8.8, 2.5 Hz), 7.27–7.16 (5H, m), 6.87 (1H, d, J 8.8 Hz), 6.78 (1H, d, J 2.5 Hz), 3.97 (1H, t, J 7.5 Hz), 3.64 (3H, s), 3.63 (1H, m), 3.01 (1H, m), 2.93 (1H, m), 1.89–1.73 (3H, m), and 1.59–1.48 (2H, m). m/z (ES$^+$) 435 (M+1).

EXAMPLE 58

(5R,6S)-3-(5-Amino-2-methoxyphenyl)-6-phenyl-1-oxa-7-(tert-butoxycarbonyl)aza-spiro[4.5]dec-3-ene Prepared from the compound of Description 43 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 7.46 (2H, m), 7.23 (3H, m), 6.79 (1H, d, J 8.7 Hz), 6.64 (2H, m), 6.43 (1H, d, J 2.8 Hz), 5.13 (1H, s), 4.92 (1H, dd, J 12.0, 2.0 Hz), 4.56 (1H, dd, J 12.0, 2.0 Hz), 4.12 (1H, m), 3.78 (3H, s), 3.12 (1H, m), 1.87–1.81 (4H, m), and 1.36 (9H, s). m/z (ES$^+$) 437 (M+1).

EXAMPLE 59

(3S,5R,6S)-3-(5-Amino-2-methoxyphenyl)-6-phenyl-1-oxa-7-(tert-butoxycarbonyl)aza-spiro[4.5]decane Prepared from the compound of Example 58 according to the method of Example 3. $^1$H NMR (360 MHz, CDCl$_3$) δ 7.52 (2H, m), 7.27 (3H, m), 6.68 (1H, d, J 8.4 Hz), 6.55 (1H, d, J 2.7 Hz), 6.52 (1H, dd, J 8.4, 2.7), 5.25 (1H, s), 4.18 (1H, m), 4.00 (1H, m), 3.77 (1H, m), 3.74 (3H, s), 3.67 (1H, m), 2.91 (1H, m), 2.35 (1H, m), 2.38–2.32 (2H, m), 2.20–2.09 (3H, m), and 1.38 (9H, s). m/z (ES$^+$) 439 (M+1).

EXAMPLE 60

(3S,5R,6S)-Methyl N-{4-Methoxy-3-[6-phenyl-1-oxa-7-(tert-butoxycarbonyl)aza-spiro[4.5]decan-3-yl]phenyl}carbamate Potassium carbonate (200 mg, 1.4 mmol) and methyl chloroformate (70 μL, 86 mg, 0.9 mmol) were added to a solution of (3R,5R,6S)-3-(5-amino-2-methoxyphenyl)-6-phenyl-1-oxa-7-(tert-butoxycarbonyl)aza-spiro[4.5]decane (Example 59, 100 mg, 0.23 mmol) in acetone (4 ml) and the mixture was stirred at room temperature overnight. The solvent was evaporated under reduced pressure and water (50 ml) was added. The mixture was extracted with ethyl acetate, dried (MgSO$_4$), and the solvent was evaporated under reduced pressure. The residue was purified by flash column chromatography on silica gel, eluting with hexane/EtOAc (80:20) to give the title compound as a solid (80 mg, 70%). $^1$H NMR (250 MHz, CDCl$_3$) δ 7.56 (2H, m), 7.35–7.21 (4H, m), 7.01 (1H, d, J 2.5 Hz), 6.79 (1H, d, J 8.8 Hz), 6.60 (1H, br s), 5.27 (1H, s), 4.22 (1H, m), 4.00 (1H, m), 3.79 (3H, s), 3.74 (3H, s), 3.81–3.66 (2H, m), 2.89 (1H, m), 2.39–2.06 (3H, m), 1,37 (3H, m), and 1.38 (9H, s). m/z (ES$^+$) 497 (M+1).

EXAMPLE 61

(3S,5R,6S)-Methyl-N-{4-Methoxy-3-[6-phenyl-1-oxa-7-(tert-butoxycarbonyl)aza-spiro[4.5]decan-3-yl]phenyl}-N-(methyl)carbamate Sodium hydride (60% dispersion in mineral oil, 16 mg, 0.4 mmol) was added to a solution of (3S,5R,6S)-methyl N-{4-methoxy-3-[6-phenyl-1-oxa-7-(tert-butoxycarbonyl) aza-spiro[4.5]decan-3-yl]phenyl}carbamate (Example 60, 80 mg, 0.16 mmol) in DMF (8 ml) and the mixture was stirred at room temperature for 30 min. Iodomethane (50 μL, 114 mg, 0.8 mmol) was added and the mixture was stirred for 3 h. Water (100 ml) was added and the mixture was extracted with ethyl acetate. The combined organic fractions were washed with water, dried (MgSO$_4$), and the solvent was evaporated under reduced pressure. The residue was purified by flash column chromatography on silica gel, eluting with hexane/EtOAc (70:30) to give the title compound as a colorless foam (67 mg, 83%). $^1$H NMR (360 MHz, CDCl$_3$) δ 7.56 (2H, m), 7.32–7.21 (4H, m), 7.02 (1H, br s), 6.81 (1H, d, J 9.2 Hz), 5.02 (1H, s), 4.20 (1H, m), 4.00 (1H, m), 3.81 (3H, s), 3.77–3.67 (2H, m), 3.62 (3H, br s), 3.2 (3H, s), 2.87 (1H, m), 2.35 (1H, m), 2.22–2.08 (2H, m), 1.74 (3H, m), and 1.36 (9H, s). m/z (ES$^+$) 511 (M+1).

EXAMPLE 62

(3S,5R,6S)-Methyl N-[4-Methoxy-3-(6-phenyl-1-oxa-7-aza-spiro[4.5]decan-3-yl)phenyl]-N-(methyl)carbamate Prepared from the compound of Example 61 according to the method of Example 2. $^1$H NMR (360 MHz, CDCl$_3$) δ 7.49 (2H, m), 7.33–7.26 (3H, m), 6.91 (1H, br s), 6.69 (1H, d, J 8.7 Hz), 6.15 (1H, m), 4.09 (1H, m), 3.79 (1H, m), 3.69 (3H, s), 3.68 (1H, s), 3.64 (3H, brs), 3.25–3.15 (2H, m), 3.08 (3H, s), 2.28 (1H, m), 2.15–2.02 (2H, m), 1.90–1.83 (2H, m), 1.62–1.55 (2H, m), 1.26 (1H, m).). m/z (ES$^+$) 411 (M+1).

EXAMPLE 63

(5R,6S)-N-{4-Methoxy-3-[6-phenyl-1-oxa-7-(tert-butoxycarbonyl)aza-spiro[4.5]dec-3-en-3-yl] phenyl}-N-(methyl)trifluoroacetamide Prepared from the compound of Description 52 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 7.49–7.20 (5H, m), 7.12 (1H, dd, J 8.7, 2.0 Hz), 6.91 (1H, d, J 8.7 Hz), 6.89 (1H, d, J 2.0 Hz), 6.63 (1H, s), 5.16 (1H, s), 4.93 (1H, d, J 12.0 Hz), 4.57 (1H, d, J 12.0 Hz), 4.12 (1H, m), 3.89 (3H, s), 3.31 (3H, s), 3.11 (1H, m), 2.13 (1H, m), 1.82 (3H, m), and 1.36 (9H, s). m/z (ES$^+$) 547 (M+1).

EXAMPLE 64

(5R,6S)-N-[4-Methoxy-3-(6-phenyl-1-oxa-7-aza-spiro[4.5]dec-3-en-3-yl)phenyl]-N-(methyl-trifluoroacetamide Hydrochloride Prepared from the compound of Example 63 according to the method of Example 2. $^1$H NMR (250 MHz, CD$_3$OD) δ 7.47 (2H, d, J 7.5 Hz), 7.34 (3H, m), 7.19 (1H, dd, J 8.9, 2.0 Hz), 6.99 (1H, d, J 8.9 Hz), 6.85 (1H, d, J 2.0 Hz), 6.26 (1H, t, J 1.9 Hz), 4.95 (1H, dd, J 12.3, 1.9 Hz), 4.51 (1H, dd, J 12.3, 1.9 Hz), 4.47 (1H, s), 3.82 (3H, s), 3.44 (1H, m), 3.24 (3H, s), 3.23 (1H, m), and 2.34–1.95 (4H, m). m/z (ES$^+$) 447 (M+1). Found: C, 59.47; H, 5.43; N, 5.80. C$_{24}$H$_{25}$F$_3$N$_2$O$_3$.HCl requires: C,59.69; H, 5.43; N, 5.80%.

EXAMPLE 65

(3S,5R,6S)-N-[4-Methoxy-3-(6-phenyl-1-oxa-7-aza-spiro[4.5]decan-3-yl)phenyl]-N-(methyl) trifluoroacetamide Hydrochloride Prepared from the compound of Example 64 according to the method of Example 3. $^1$H NMR (360 MHz, D$_2$O) δ

1.80–2.00 (3H, m), 2.10–2.20 (3H, m), 3.17 (3H, s), 3.22–3.33 (2H, m), 3.48–3.60 (1H, m), 3.75 (3H, s), 3.97 (1H, t, J 9.2 Hz), 4.15 (1H, t, J 8.3 Hz), 4.41 (1H, s), 5.79 (1H, m), 6.96 (1H, d, J 8.8 Hz), 7.15 (1H, dd, J 8.8, 2.4 Hz), and 7.50–7.56 (5H, m). m/z (ES$^+$) 449 (M+1).

EXAMPLE 66

(5R,6S)-N-{4-Isopropoxy-3-[6-phenyl-1-oxa-7-(tert-butoxycarbonyl)aza-spiro[4.5]dec-3-en-3-yl]phenyl}-N-(methyl)trifluoroacetamide Prepared from the compound of Description 53 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 7.46 (2H, d, J 7.4 Hz), 7.24 (3H, m), 7.08 (1H, dd, J 8.8, 2.5 Hz), 6.95 (1H, d, J 2.5 Hz), 6.88 (1H, d, J 8.8 Hz), 6.60 (1H, s), 5.15 (1H, s), 4.94 (1H, d, J 12.3 Hz), 4.61 (2H, m), 4.12 (1H, m), 3.31 (3H, s), 3.12 (1H, m), 2.10 (1H, m), 1.84 (3H, m), and 1.36 (15H, m). m/z (ES$^+$) 575 (M+1).

EXAMPLE 67

(5R,6S)-N-[4-Isopropoxy-3-(6-phenyl-1-oxa-7-aza-spiro[4.5]dec-3-en-3-yl)phenyl]-N-(methyl)trifluoroacetamide Prepared from the compound of Example 66 according to the method of Example 2. $^1$H NMR (360 MHz, CDCl$_3$) δ 7.36 (2H, d, J 6.6 Hz), 7.17 (3H, m), 6.97 (1H, dd, J 8.8, 2.6 Hz), 6.77 (1H, d, J 8.8 Hz), 6.66 (1H, d, J 2.6 Hz), 6.11 (1H, t, J 2.1 Hz), 4.86 (1H, dd, J 12.0, 2.1 Hz), 4.51 (1H, sept, J 6.0 Hz), 4.30 (1H, dd, J 12.0, 2.1 Hz), 3.77 (1H, s), 3.31 (1H, m), 3.25 (3H, s), 2.83 (1H, m), 2.14–1.64 (5H, m), and 1.31 (6H, d, J 6.0 Hz). m/z (ES$^+$) 475 (M+1).

EXAMPLE 68

3S,5R,6S)-N-[4-Isopropoxy-3-(6-phenyl-1-oxa-7-aza-spiro[4.5]decan-3-yl)phenyl]-N-(methyl)trifluoroacetamide Hydrochloride Prepared from the compound of Example 67 according to the method of Example 3. $^1$H NMR (360 MHz, CD$_3$OD) δ 7.63–7.44 (5H, m), 7.05 (1H, dd, J 8.8, 2.5 Hz), 6.93 (1H, d, J 8.8 Hz), 5.98 (1H, d, J 2.5 Hz), 4.89 (2H, br s), 4.59 (1H, sept, J 5.8 Hz), 4.43 (1H, s), 4.23 (1H, m), 3.98 (1H, m), 3.44 (1H, m), 3.21 (2H, m), 3.15 (3H, s), 2.32–1.76 (6H, m), 1.30 (3H, d, J 5.8 Hz) and 1.29 (3H, d, J 5.8 Hz). m/z (ES$^+$) 477 (M+1). Found: C, 60.61; H, 6.14; N, 5.46. C$_{26}$H$_{31}$F$_3$N$_2$O$_3$.HCl requires: C, 60.87; H, 6.29; N, 5.46%.

EXAMPLE 69

(5R,6S)-N-{4-(Difluoromethoxy)-3-[6-phenyl-1-oxa-7-(tert-butoxycarbonyl)aza-spiro[4.5]dec-3-en-3-yl]phenyl}-N-(methyl)trifluoroacetamide Prepared from the compound of Description 54 and (5R,6S)-3-tributylstannyl-6-phenyl-1-oxa-7-(tert-butoxycarbonyl)aza-spiro[4.5]dec-3-ene according to the method of Example 1. $^1$H NMR (360 MHz, CDCl$_3$) δ 7.45 (2H, d, J 7.4 Hz), 7.29–7.17 (5H, m), 7.03 (1H, s), 6.59 (1H, s), 6.52 (1H, t, J 73.0 Hz), 5.15 (1H, s), 4.91 (1H, d, J 12.2 Hz), 4.56 (1H, d, J 12.2 Hz), 4.12 (1H, m), 3.33 (3H, s), 2.12 (1H, m), 1.84 (3H, m), and 1.36 (9H, s). m/z (ES$^+$) 583 (M+1).

EXAMPLE 70

(5R,6S)-N-[4-(Difluoromethoxy)-3-(6-phenyl-1-oxa-7-aza-spiro[4.5]dec-3-en-3-yl)phenyl]-N-(methyl)trifluoroacetamide Prepared from the compound of Example 69 according to the method of Example 2. $^1$H NMR (360 MHz, CDCl$_3$) δ 1.65–1.69 (1H, m), 1.80–2.05 (4H, m), 2.80–2.87 (1H, m), 3.27 (3H, s), 3.41 (1H, s), 4.29–4.32 (1H, m), 4.81–4.85 (1H, m), 6.14 (1H, s), 6.23 (1H, t, J 73 Hz), 6.74 (1H, s), 7.08 (2H, s), 7.15–7.22 (3H, m), and 7.37 (2H, d, J 6.5 Hz). m/z (ES$^+$) 483 (M+1).

EXAMPLE 71

(3S,5R,6S)-N-[4-(Difluoromethoxy)-3-(6-phenyl-1-oxa-7-aza-spiro[4.5]decan-3-yl)phenyl]-N-(methyl)trifluoroacetamide Hydrochloride Prepared from the compound of Example 70 according to the method of Example 3. $^1$H NMR (360 MHz, D$_2$O) δδ 1.83–1.96 (3H, m), 2.14–2.30 (3H, m), 3.18 (3H, s), 3.23–3.35 (2H, m), 3.50–3.54 (1H, m), 4.00 (1H, quin, J 9.3 Hz), 4.19 (1H, t, J 8.5 Hz), 4.42 (1H, s), 5.70 (1H, s), 6.75 (1H, t, J 73 Hz), 7.19 (2H, s), and 7.50–7.57 (5H, m). m/z (ES$^+$) 485 (M+1).

EXAMPLE 72

(5R,6S)-N-[4-Methoxy-3-(6-phenyl-1-oxa-7-(tert-butoxycarbonyl)aza-spiro[4.5]dec-3-en-3-yl)phenyl]-N-(2,2,2-trifluoroethyl)acetamide Prepared from the compound of Description 57 and (5R,6S)-3-tributylstannyl-6-phenyl-1-oxa-7-(tert-butoxycarbonyl)aza-spiro[4.5]dec-3-ene according to the method of Example 1. $^1$H NMR (360 MHz, CDCl$_3$) δ 7.47 (2H, d, J 7.5 Hz), 7.24 (3H, m), 7.12 (1H, dd, J 8.7, 2.6 Hz), 6.93 (1H, d, J 8.7 Hz), 6.87 (1H, d, J 2.6 Hz), 6.64 (1H, t, J 2.0 Hz), 5.17 (1H, s), 4.94 (1H, dd, J 12.0, 2.0 Hz), 4.58 (1H, d, J 12.0, 2.0 Hz), 4.29 (2H, m), 4.13 (1H, m), 3.90 (3H, s), 3.10 (1H, m), 2.12 (1H, m), 1.87 (3H, s), 1.82 (3H, m), and 1.37 (9H, s). m/z (ES$^+$) 561 (M+1).

EXAMPLE 73

(5R,6S)-N-[4-Methoxy-3-(6-phenyl-1-oxa-7-aza-spiro[4.5]dec-3-en-3-yl)phenyl]-N-(2,2,2-trifluoroethyl)acetamide Prepared from the compound of Example 72 according to the method of Example 2. $^1$H NMR (360 MHz, CDCl$_3$) δ 7.37 (2H, d, J 6.8 Hz), 7.16 (3H, m), 7.01 (1H, dd, J 8.7, 2.6 Hz), 6.81 (1H, d, J 8.7 Hz), 6.60 (1H, d, J 2.6 Hz), 6.08 (1H, t, J 2.1 Hz), 4.85 (1H, dd, J 12.0, 2.1 Hz), 4.23 (3H, m), 4.29 (2H, m), 3.80 (3H, s), 3.77 (1H, s), 3.29 (1H, m), 2.83 (1H, m), 2.06–1.65 (5H, m), and 1.79 (3H, s). m/z (ES$^+$) 461 (M+1).

EXAMPLE 74

(3S,5R,6S)-N-[4-Methoxy-3-(6-phenyl-1-oxa-7-aza-spiro[4.5]decan-3-yl)phenyl]-N-(2,2,2-trifluoroethyl)acetamide Prepared from the compound of Example 73 according to the method of Example 3. $^1$H NMR (360 MHz, CD$_3$OD) δ 7.64 (2H, m), 7.52 (3H, m), 7.12 (1H, dd, J 8.8, 2.5 Hz), 6.98 (1H, d, J 8.8 Hz), 6.24 (1H, d, J 2.5 Hz), 4.88 (2H, br s), 4.47 (1H, s), 4.36–4.22 (3H, m), 4.02 (1H, m), 3.78 (3H, s), 3.47 (1H, m), 3.39 (1H, m), 3.23 (1H, m), 2.35–1.86 (6H, m) and 1.70 (3H, s). m/z (ES$^+$) 463 (M+1). Found: C, 60.39; H, 5.99; N, 5.63. C$_{25}$H$_{29}$F$_3$N$_2$O$_3$.HCl requires: C, 60.18; H, 6.06; N, 5.61%.

EXAMPLE 75

(3S,5R,6S)-N-[4-Methoxy-3-(6-phenyl-1-oxa-7-(tert-butoxycarbonyl)aza-spiro[4.5]decan-3-yl)phenyl]benzamide Benzoyl chloride (40 μl, 0.34 mmol) was added to a stirred, cooled (0° C.) solution of (3S,5R,6S)-3-(5-amino- 2-methoxyphenyl)-6-phenyl-1-oxa-7-(tert-butoxycarbonyl) aza-spiro[4.5]decane (Example 59, 98 mg, 0.22 mmol) and pyridine (200 μl, 2.47 mmol) in dichloromethane (3 ml). The mixture was stirred for 15 min., then water (20 ml) and ether (30 ml) were added. The layers were separated and the aqueous layer was extracted with ether (10 ml). The combined organic fractions were washed with aqueous copper (II) sulfate (0.5M, 2×20 ml) and saturated aqueous sodium hydrogen carbonate solution (20 ml), dried (MgSO$_4$) and the solvent was evaporated under reduced pressure. The residue was purified by column chromatography on silica gel, eluting with hexane/EtOAc (75:25) to give the title compound as a colourless glass (102 mg, 84%). $^1$H NMR (250 MHz, CDCl$_3$) δ 8.07 (1H, br s), 8.0–7.85 (2H, m), 7.65–7.18 (10H, m), 6.84 (1H, d, J 8.8 Hz), 5.43 (1H, br s), 4.28 (1H, t, J 7.8 Hz), 4.03–3.68 (3H, m), 3.82 (3H, s), 2.94–2.79 (1H, m), 2.30–2.05 (2H, m), 1.80–1.60 (4H, m), and 1.38 (9H, s). m/z (ES$^+$) 543 M+1).

EXAMPLE 76

(3S,5R,6S)-N-[4-Methoxy-3-(6-phenyl-1-oxa-7-(tert-butoxycarbonyl)aza-spiro[4.5]decan-3-yl) phenyl]-N-(methyl)benzamide (3S,5R,6S)-N-[4-Methoxy-3-(6-phenyl-1-oxa-7-(tert-butoxycarbonyl)aza-spiro[4.5]decan-3-yl)phenyl] benzamide (Example 75, 100 mg, 0.18 mmol) was added to a cooled (0° C.) suspension of sodium hydride (60% dispersion in mineral oil, 22 mg, 0.55 mmol) in DMF (3 ml). Methyl iodide (79 mg, 0.55 mmol) was then added and the mixture was stirred at room temperature for 1 h. Water (10 ml) was added and the mixture was extracted with ethyl acetate (3×10 ml). The combined organic fractions were washed with water (3×10 ml) and brine (10 ml), dried (MgSO$_4$) and the solvent was evaporated under reduced pressure. The residue was purified by column chromatography on silica gel, eluting with hexane/EtOAc (2:1) to give the title compound as a colourless glass (95 mg, 93%). $^1$H NMR (250 MHz, CDCl$_3$) δ 7.59–7.50 (2H, m), 7.38–7.05 (8H, m), 6.90–6.75 (2H, m), 6.64 (1H, d, J 9.6 Hz), 5.15 (1H, br s), 4.07–3.92 (2H, m), 3.75 (3H, s), 3.75–3.60 (1H, m), 3.41 (3H, s), 3.40–3.25 (1H, m), 2.98–2.82 (1H, m), 2.27 (1H, dd, J 13, 9 Hz), 2.11–1.96 (1H, m), 1.78–1.60 (4H, m), and 1.38 (9H, s). m/z (ES$^+$) 557 (M+1).

EXAMPLE 77

(3S,5R,6S)-N-[4-Methoxy-3-(6-phenyl-1-oxa-7-aza-spiro[4.5]decan-3-yl)phenyl]-N-(methyl)benzamide Hydrochloride Prepared from the compound of Example 76 according to the method of Example 2. m.p. 275–280° C. $^1$H NMR (360 MHz, CD$_3$OD) δ 7.62–7.52 (5H, m), 7.28–7.02 (5H, m), 6.91 (1H, br d, J 8.6 Hz), 6.74 (1H, d, J 8.6 Hz), 5.98 (1H, br s), 4.40 (1H, s), 4.01 (1H, t, J 8.0 Hz), 3.82 (1H, app. quin, J 9.8 Hz), 3.64 (3H, s), 3.41 (1H, dd, J 12, 4.2 Hz), 3.28 (3H, s), 3.19 (1H, dt, J 13, 3.2 Hz), 3.13–3.05 (1H, m), 2.30–2.08 (2H, m), and 1.96–1.65 (4H, m). m/z (ES$^+$) 457 (M+1). Found: C, 69.80; H, 6.75; N, 5.45. C$_{29}$H$_{32}$N$_2$O$_3$.HCl requires: C,70.60; H, 6.75; N, 5.68%.

EXAMPLE 78

(5R,6S)-3-[5-Methylamino-2-(trifluoromethoxy) phenyl]-6-phenyl-1-oxa-7-(tert-butoxycarbonyl)aza-spiro[4.5]dec-3-ene Prepared from the compound of Description 51 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 7.50-7.40 (2H, m), 7.31-7.20 (3H, m), 7.09 (1H, dq, J 8.8, 1.5 Hz), 6.55 (1H, dd, J 8.8, 2.9 Hz), 6.44 (1H, t, J 2.1 Hz), 6.38 (1H, d, J 2.9 Hz), 5.13 (1H, br s), 4.88 (1H, dd, J 12, 2.1 Hz), 4.55 (1H, dd, J 12, 2.2 Hz), 4.17-4.08 (1H, m), 3.20-3.05 (1H, m), 2.83 (3H, s), 1.90-1.50 (5H, m), and 1.35 (9H, s).

EXAMPLE 79

(5R,6S)-3-[5-Methylamino-2-(trifluoromethoxy) phenyl]-6-phenyl-1-oxa-7-aza-spiro[4.5]dec-3-ene Prepared from the compound of Example 78 according to the method of Example 2. $^1$H NMR (250 MHz, CDCl$_3$) δ 7.42-7.30 (2H, m), 7.25-7.13 (3H, m), 6.98 (1H, dq, J 8.8, 1.4 Hz), 6.38 (1H, dd, J 8.8, 2.9 Hz), 5.99-5.97 (2H, m), 4.80 (1H, dd, J 13, 2.1 Hz), 4.31 (1H, dd, j 13, 2.3 Hz), 3.78 (1H, s), 3.68 (1H, br.s), 3.33-3.20 (1H, m), 2.82 (1H, dd, J 12, 3.0 Hz), 2.75 (3H, s), 2.15-1.60 and (5H, m). m/z (ES$^+$) 405 (M+1).

EXAMPLE 80

(5R,6S)-3-[5-Methylamino-2-(trifluoromethoxy) phenyl]-6-phenyl-1-oxa-7-aza-spiro[4.5]decane Prepared from the compound of Example 79 according to the method of Example 3. $^1$H NMR (250 MHz, CDCl$_3$) δ 7.60-7.50 (2H, m), 7.40-7.35 (3H, m), 6.91 (1H, br d, J 7.5 Hz), 6.30 (1H, dd, J 8.8, 2.8 Hz), 5.28 (1H, d, J 2.9 Hz), 4.10 (1H, t, J 8.0 Hz), 3.98 (1H, s), 3.82-3.72 (1H, m), 3.40-2.85 (5H, m), 2.57 (3H, s), and 2.30-1.55 (6H, m). m/z (ES$^+$) 407 (M+1).

EXAMPLE 81

(5R,6S)-N-Methyl-N-{3-[6-phenyl-1-oxa-7-(tert-butoxycarbonyl)aza-spiro[4.5]dec-3-en-3-yl]-4-(trifluoromethoxy)phenyl}trifluoroacetamide Prepared from the compound of Description 55 and (5R,6S)-3-tributylstannyl-6-phenyl-1-oxa-7-(tert-butoxycarbonyl)-aza-spiro[4.5]dec-3-ene according to the method of Example 1. $^1$H NMR (250 MHz, CDCl$_3$) δ 7.50-7.40 (2H, m), 7.35-7.15 (5H, m), 7.06 (1H, br s), 6.54 (1H, t, J 2 Hz), 5.16 (1H, br s), 4.90 (1H, br. d, J 12 Hz), 4.55 (1H, br d, J 12 Hz), 4.18-4.08 (1H, m), 3.35 (3H, s), 3.20-3.04 (1H, m), 2.20-2.05 (1H, m), 1.95-1.70 (3H, m), and 1.35 (9H, s).

EXAMPLE 82

(5R,6S)-N-Methyl-N-[3-(6-phenyl-1-oxa-7-aza-spiro [4.5]dec-3-en-3-yl)-4-(trifluoromethoxy)phenyl] trifluoroacetamide Prepared from the compound of Example 81 according to the method of Example 2. $^1$H NMR (250 MHz, CDCl$_3$) δ 7.40-7.30 (2H, m), 7.25-7.05 (5H, m), 6.73 (1H, br s), 6.08 (1H, t, J 2.1 Hz), 4.81 (1H, dd, J 2.0, 12 Hz), 4.30 (1H, dd, J 12, 2.0 Hz), 3.80 (1H, s), 3.28 (3H, s), 2.83 (1H, dt, J 12, 2.9 Hz), and 2.25-1.60 (6H, m). m/z (ES$^+$) 501 (M+1).

EXAMPLE 83

(3S,5R,6S)-N-Methyl-N-[3-(6-phenyl-1-oxa-7-aza-spiro[4.5]decan-3-yl)-4-(trifluoromethoxy)phenyl] trifluoroacetamide Hydrochloride Prepared from the compound of Example 82 according to the method of Example 3. $^1$H NMR (250 MHz, CD$_3$OD) δ

7.65-7.40 (5H, m), 7.28 (1H, dd, J 6.1, 1.0 Hz), 7.22 (1H, br d, J 6.1 Hz), 5.89 (1H, br s), 4.44 (1H, s), 4.22 (1H, t, J 5.8 Hz), 3.93 (1H, app. quin, J 6.5 Hz), 3.42 (1H, dd, J 8.8, 2.7 Hz), 3.35 (1H, t, J 6.2 Hz), 3.22 (1H, dd, j 9.0, 2.2 Hz), 3.16 (3H, s), 2.26-2.15 (3H, m) and 1.95-1.75 (3H, m). m/z (ES$^+$) 503 (M+1). Found: C, 53.10; H, 4.69; N, 5.06. $C_{24}H_{24}F_6N_2O_3$.HCl requires: C, 53.50; H, 4.68; N, 5.20%.

EXAMPLE 84

(5R,6S)-3-[2-Ethoxy-5-(trifluoromethoxy)phenyl]-6-phenyl-1-oxa-7-(tert-butoxycarbonyl)aza-spiro[4.5]dec-3-ene Prepared from the compound of Description 58 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 1.36 (9H, s), 1.45 (3H, t, J 7.0 Hz), 1.73-1.93 (3H, m), 2.06-2.16 (1H, m), 3.05-3.18 (1H, m), 3.98-4.19 (3H, m), 4.61 (1H, dd, J 12.2, 2.2 Hz), 4.97 (1H, dd, J 12.2, 2.2 Hz), 5.15 (1H, s), 6.64 (1H, t, J 2.1 Hz), 6.84 (1H, d, J 9.0 Hz), 6.93 (1H, d, J 2.7 Hz), 7.07 (1H, bd, J 8.15 Hz), 7.18-7.32 (3H, m), and 7.44-7.51 (2H, m). m/z (ES$^+$) 520 (M+1).

EXAMPLE 85

(5R,6S)-3-[2-Ethoxy-5-(trifluoromethoxy)phenyl]-6-phenyl-1-oxa-7-aza-spiro[4.5]dec-3-ene Prepared from the compound of Example 84 according to the method of Example 2. $^1$H NMR (360 MHz, CDCl$_3$) δ 1.39 (3H, t, J 7.0 Hz), 1.67 (1H, bd, J 15.3 Hz), 1.78 (1H, td, J 13.4,4.3 Hz), 1.93-2.16 (2H, m), 2.83 (1H, td, J 12.6, 2.9 Hz), 3.27 (1H, bd, J 12.4 Hz), 3.83 (1H, s), 3.94 (2H, q, J 7.0 Hz), 4.34 (1H, dd, J 12.0, 2.2 Hz), 4.89 (1H, dd, J 12.0, 2.2 Hz), 6.12 (1H, t, J 2.1 Hz), 6.67 (1H, d, J 3.0 Hz), 6.73 (1H, d, J 9.0 Hz), 6.98 (1H, d, J 8.8 Hz), 7.10-7.23 (3H, m), and 7.32-7.39 (2H, m). m/z (ES$^+$) 420 (M+1).

EXAMPLE 86

(3S,5R,6S)-3-[2-Ethoxy-5-(trifluoromethoxy) phenyl]-6-phenyl-1-oxa-7-aza-spiro[4.5]decan Hydrochloride Prepared from the compound of Example 85 according to the method of Example 3. $^1$H NMR (360 MHz, DMSO-d$_6$) δ 1.27 (3H, t J 7.0 Hz), 1.66-1.84 (3H, m), 2.01-2.10 (3H, m), 3.03-3.12 (2H, m), 3.24-3.32 (1H, m), 3.79 (1H, q), 3.96 (2H, q, J 7.0 Hz), 4.14 (1H, t, J 8.0 Hz), 4.48 (1H, br s), 6.17 (1H, br s), 6.95 (1H, d, J 9.0 Hz), 7.08 (1H, br d, J 9.0 Hz), 7.41-7.49 (3H, m), and 7.54-7.59 (2H, m). m/z (ES$^+$) 422 (M+1).

EXAMPLE 87

(5R,6S)-3-[2-(Trifluoromethylthio)phenyl]-6-phenyl-1-oxa-7-(tert-butoxycarbonyl)aza-spiro[4.5]dec-3-ene Prepared from the compound of Description 59 and (5R,6S)-3-tributylstannyl-6-phenyl-1-oxa-7-(tert-butoxycarbonyl)aza-spiro[4.5]dec-3-ene according to the method of Example 1. m/z (ES$^+$) 492 (M+1).

EXAMPLE 88

(5R,6S)-3-[2-(Trifluoromethylthio)phenyl]-6-phenyl-1-oxa-7-aza-spiro[4.5]dec-3-ene Prepared from the compound of Example 87 according to the method of Example 2. $^1$H NMR (360 MHz, CDCl$_3$) δ 1.66 (1H, m), 1.76-1.86 (1H, m), 1.96-2.11 (2H, m), 2.82 (1H, td, J 12, 3 Hz), 3.26 (1H, br d, J 10.3 Hz), 3.75 (1H, s), 4.30 (1H, dd, J 12.3, 2.2 Hz), 4.81 (1H, dd, J 12.3, 2.2 Hz), 5.66 (1H, t, J 2.0 Hz), 6.70 (1H, dd, J 7.13, 1.8 Hz), 7.18-7.32 (4H, m), 7.39 (1H, dd, J 5.8, 1.5 Hz), and 7.58 (1H, d, J 7.4 Hz). m/z (ES$^+$) 392 (M+1).

EXAMPLE 89

(3S,5R,6S)-3-[2-(Trifluoromethylthio)phenyl]-6-phenyl-1-oxa-7-aza-spiro[4.5]decane Prepared from the compound of Example 88 according to the method of Example 3. $^1$H NMR (360 MHz, CDCl$_3$) δ 1.54-1.64 (2H, m), 1.81-2.21 (5H, m), 2.81 (1H, td, J 12.2, 2.5 Hz), 3.21-3.32 (2H, m), 3.66 (1H, s), 4.07 (1H, t, J 8.2 Hz), 4.20-4.32 (1H, m), 6.20 (1H, dd, J 7.6, 2.0 Hz), 7.08-7.18 (2H, m), 7.30-7.43 (3H, m), and 7.48-7.62 (3H, m). m/z (ES$^+$) 394 (M+1).

EXAMPLE 90

(5R,6S)-3-[2-(2,2,2-Trifluoroethyl)-5-(trifluoromethyl)phenyl)-6-phenyl-1-oxa-7-(tert-butoxycarbonyl)aza-spiro[4.5]dec-3-ene Prepared from the compound of Description 60 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 1.36 (9H, s), 1.86 (3H, m), 2.10 (1H, m), 3.18 (1H, m), 4.11 (1H, m), 4.43 (2H, dq J 7.8, 3.9 Hz), 4.64 (1H, dd, J 12.2 2.2 Hz), 4.96 (1H, dd, J 12.2, 2.0 Hz), 5.15 (1H, s), 6.67 (1H, t, J 2.1 Hz), 6.90 (1H, d, J 8.6 Hz), 7.27 (4H, m), 7.36 (1H, d, J 2.1 Hz), 7.45 (1H, d, J 7.3 Hz), and 7.55 (1H, d, J 8.8 Hz).

EXAMPLE 91

(5R,6S)-3-[2-(2,2,2-Trifluoroethoxy)-5-(trifluoromethyl)phenyl)-6-phenyl-1-oxa-7-aza-spiro[4.5]dec-3-ene Prepared from the compound of Example 90 according to the method of Example 2. $^1$H NMR (250 MHz, CDCl$_3$) δ 1.79 (2H, m), 1.90 (1H, m), 2.24 (1H, m), 2.83 (1H, td, J 12.6, 2.6 Hz), 3.47 (1H, d, J 10.7 Hz), 3.93 (1H, s), 4.33 (2H, q, J 7.9 Hz), 4.40 (1H, dd, J 12.2, 2.2 Hz), 4.90 (1H, dd, J 12.2, 2.0 Hz), 6.16 (1H, t, J 2.0 Hz), 6.81 (1H, d, J 8.6 Hz), 7.01 (1H, d, J 2.0 Hz), 7.18 (3H, m), and 7.74 (3H, m). m/z (ES$^+$) 458 (M+1).

EXAMPLE 92

(3S,5R,6S)-3-[2-(2,2,2-Trifluoroethoxy)-5-(trifluoromethyl)phenyl)-6-phenyl-1-oxa-7-aza-spiro[4.5]decane Hydrochloride Prepared from the compound of Example 91 according to the method of Example 3. $^1$H NMR (250 MHz, DMSO-d$_6$) δ 1.72 (3H, m), 2.10 (3H, m), 3.11 (1H, t, J 8.4 Hz), 3.80 (1H, m), 4.15 (1H, t, J 8.0 Hz), 4.49 (1H, s), 4.83 (2H, dq, J 8.8, 4.9 Hz), 6.58 (1H, s), 7.21 (1H, d, J 8.7 Hz), 7.44 (7.44 (3H, m), and 7.56 (4H, m). m/z (ES$^+$) 460 (M+1).

EXAMPLE 93

(5R,6S)-3-[2-Isopropoxy-5-(trifluoromethyl) phenyl]-6-phenyl-1-oxa-7-(tert-butoxycarbonyl)aza-spiro[4.5]dec-3-ene Prepared from the compound of Description 61 and (5R,6S)-3-tributylstannyl-6-phenyl-1-oxa-7-(tert-butoxycarbonyl)aza-spiro[4.5]dec-3-ene according to the method of Example 1. ¹H NMR (250 MHz, CDCl₃) δ 0.93 (2H, m), 1.31 (15H, m), 1.83 (2H, m), 2.30 (1H, m), 3.14 (1H, m), 4.61 (2H, m), 4.98 (1H, dd, J 12.3, 2.0 Hz), 5.15 (1H, s), 6.78 (1H, d, J 2.1 Hz), 7.22 (1H, d, J 8.4 Hz), 7.44 (2H, m), and 7.55 (5H, m).

EXAMPLE 94

(5R,6S)-3-[2-Isopropoxy-5-(trifluoromethyl) phenyl]-6-phenyl-1-oxa-7-aza-spiro[4.5]dec-3-ene Hydrochloride Prepared from the compound of Example 93 according to the method of Example 2. ¹H NMR (360 MHz, DMSO-d₆) δ 1.25 (6H, dd, J 8.8 Hz), 1.85 (2H, m), 2.01 (2H, m), 3.12 (1H, m), 3.33 (1H, m), 4.37 (1H, d, J 14.2 Hz), 4.60 (1H, s), 4.72 (1H, septet, J 6.0 Hz), 4.94 (1H, d, J 12.3 Hz), 6.41 (1H, t), 7.17 (2H, m), 7.30 (3H, m), 7.47 (2H, d, J 6.4 Hz), and 7.53 (1H, d, J 8.5 Hz).

EXAMPLE 95

(5R,6S)-3-[2-Isopropoxy-5-(trifluoromethyl) phenyl]-6-phenyl-1-oxa-7-aza-spiro[4.5]decane Hydrochloride Prepared from the compound of Example 94 according to the method of Example 3. ¹H NMR (360 MHz, DMSO-d₆) δ 1.23 (6H, dd, J 8.8, 5.9 Hz), 1.79 (2H, m), 2.06 (2H, m), 3.07 (2H, t, J 10.2 Hz), 3.81 (1H, qn), 4.14 (1H, t, J 7.9 Hz), 4.46 (1H, s), 4.66 (1H, septet, J 6.0 Hz), 6.52 (1H, s), 7.09 (1H, d, J 8.6 Hz), 7.44 (5H, m), and 7.56 (2H, d, J 6.5 Hz).

EXAMPLE 96

(3S,5R,6S)-3-[2-Cyclopropyl-5-(trifluoromethoxy) phenyl]-6-phenyl-1-oxa-7-(tert-butoxycarbonyl)aza-spiro[4,5]decane Magnesium turnings (128 mg) were placed in a dry flask and covered with a minimum of tetrahydrofuran. Dibromoethane (0.1 ml) was added and the reaction heated. On observation of effervescence a solution of cyclopropylbromide (0.4 ml) in tetrahydrofuran (10 ml) was added dropwise to maintain a steady reflux. The reaction was then heated at 65° C. for 1 h. The mixture was allowed to cool to room temperature and a solution of zinc bromide (1.6 g) in tetrahydrofuran (5 ml) was added causing a white precipitate to form. The reaction was stirred at room temperature for 2 h. [1,1-Bis(diphenylphosphino)ferrocene]dichloropalladium (11) (50 mg) was added and the reaction stirred for 5 min. (3S,5R,6S)-3-(5-(Trifluoromethoxy)-2-(trifluoromethylsulfonyloxy)phenyl)-6-phenyl-1-oxa-7-(tert-butoxycarbonyl)aza-spiro[4.5]decane (Example 144, 300 mg) was added and the solution was stirred at room temperature for 16 h., then at at 65° C. for 1 h. The mixture was cooled, diluted with saturated aqueous ammonium chloride (20 ml) and extracted with dichloromethane (3×20 ml). The combined organic fractions were washed with brine, dried (MgSO₄) and the solvent was evaporated under reduced pressure. The residue was purified by medium pressure liquid chromatography on silica gel, eluting with hexane/EtOAc (80:20) to give the title compound as an oil (121 mg). ¹H NMR (250 MHz, CDCl₃) δ 0.64 (2H, m), 0.97 (2H, dt, J 8.1, 1.4 Hz), 1.36 (9H, s), 1.78 (1H, m), 1.92 (1H, m), 2.16 (1H, m), 2.48 (1H, m), 3.66 (1H, t, J 8.6 Hz), 4.07 (3H, m), 4.22 (1H, t, J 6.9 Hz), 5.22 (1H, s), 6.99 (3H, m), 7.30 (3H, m), and 7.56 (2H, d, J 7.5 Hz).

EXAMPLE 97

(3S,5R,6S)-3-[2-Cyclopropyl-5-(trifluoromethoxy) phenyl]-6-phenyl-1-oxa-7-aza-spiro[4.5]decane Hydrochloride Prepared from the compound of Example 96 according to the method of Example 2. ¹H NMR (360 MHz, DMSO-d₆) δ 0.56 (2H, m), 0.88 (2H, d, J 8.1 Hz), 1.72 (1H, m), 1.80 (2H, m), 1.94 (1H, m), 2.14 (3H, m), 3.15 (2H, t, J 8.2 Hz), 4.18 (2H, m), 4.51 (1H, s), 5.92 (1H, s), 7.02 (2H, m), 7.51 (3H, m), and 7.60 (2H, d, J 6.3 Hz).

EXAMPLE 98

(5R,6S)-3-(2-Benzyloxyphenyl)-6-phenyl-1-oxa-7-(tert-butoxycarbonyl)aza-spiro[4.5]dec-3-ene Prepared from the compound of Description 62 and (5R,6S)-3-tributylstannyl-6-phenyl-1-oxa-7-(tert-butoxycarbonyl)aza-spiro[4.5]dec-3-ene according to the method of Example 1. ¹H NMR (250 MHz, CDCl₃) δ 7.43-6.90 (14H, m), 6.65 (1H, t, J 2.1 Hz), 5.15 (1H, d, J 11.5 Hz), 5.09 (1H, d, J 11.5 Hz), 5.07 (1H, s), 4.95 (1H, dd, J 12.0, 2.1 Hz), 4.648 (1H, dd, J 12.0, 2.1 Hz), 4.10 (1H, m), 3.13 (1H, m), 2.04 (1H, m), 1.76 (3H, m), and 1.32 (9H, s). m/z (ES⁺) 498 (M+1).

EXAMPLE 99

(5R,6S)-3-(2-Benzyloxyphenyl)-6-phenyl-1-oxa-7-(tert-butoxycarbonyl)aza-spiro[4.5]decane Prepared from the compound of Example 98 according to the method of Example 3. ¹H NMR (360 MHz, CDCl₃) δ 7.58 (2H, d, J 7.5 Hz), 7.32 (2H, t, J 7.5 Hz), 7.24 (1H, t, J 7.5 Hz), 7.13 (1H, d, J 7.7 Hz), 7.08 (1H, t, J 7.7 Hz), 6.85 (1H, t, J 7.7 Hz), 6.76 (1H, d, J 7.7 Hz), 5.79 (1H, s), 4.24 (1H, dd, J 8.9, 7.1 Hz), 3.96 (1H, m), 3.92 (1H, dd, J 8.9, 7.2 Hz), 3.68 (1H, m), 2.83 (1H, m), 2.47 (1H, m), 2.22 (1H, m), 2.09 (1H, m), 1.75 (3H, m), and 1.36 (9H, s). m/z (ES⁺) 410 (M+1).

EXAMPLE 100

(3S,5R,6S)-3-(5-Bromo-2-hydroxyphenyl)-6-phenyl-1-oxa-7-(tert-butoxycarbonyl)aza-spiro[4.5]decane Tetrabutylammonium perbromide (118 mg) was added over 10 min. to a solution of (3S,5R,6S)-3-(2-hydroxyphenyl)-6-phenyl-1-oxa-7-(tert-butoxycarbonyl) aza-spiro[4.5]decane (Example 99, 100 mg, 0.24 mmol) in dichloromethane (3 ml)/methanol (2 ml) and the mixture was stirred at room temperature for 10 min. The residue was poured into water and extracted with ethyl acetate. The combined organic fractions were dried (Na₂SO₄) and the solvent was evaporated under reduced pressure. The residue was purified by flash column chromatography on silica gel, eluting with hexane/EtOAc (80:20) to give the title compound as a foam (76 mg, 64%). ¹H NMR (360 MHz, CDCl₃) δ 7.56 (2H, d, J 7.5 Hz), 7.33 (2H, t, J 7.5 Hz), 7.26 (1H, t, J 7.5 Hz), 7.21 (1H, d, J 2.4 Hz), 7.17 (1H, dd, J 8.4, 2.4 Hz), 6.66 (1H, d, J 8.4 Hz), 6.20 (1H, br s), 5.33 (1H, s), 4.21 (1H, dd, J 9.1, 7.1 Hz), 3.98 (1H, m), 3.91 (1H, dd, J 9.1, 6.6 Hz), 3.59 (1H, m), 2.84 (1H, m), 2.48 (1H, m), 2.14 (2H, m), 1.74 (3H, m), and 1.36 (9H, s). m/z (ES⁺) 488, 490 (M+1).

EXAMPLE 101

(3S,5R,6S)-3-(5-Bromo-2-isopropoxyphenyl)-6-phenyl-1-oxa-7-(tert-butoxycarbonyl)aza-spiro[4.5]decane 2-Bromopropane (0.053 ml) was added to a mixture of (3S,5R,6S)-3-(5-bromo-2-hydroxyphenyl)-6-phenyl-1-oxa- 7-(tert-butoxycarbonyl)aza-spiro[4.5]decane (Example 100, 69 mg, 0.14 mmol) and potassium carbonate (157 mg) in DMF (5 ml) and the mixture was stirred at 50° C. for 3 days. The mixture was cooled, poured into water and extracted with ethyl acetate (2×). The combined organic fractions were washed with water, dried (Na$_2$SO$_4$) and the solvent was evaporated under reduced pressure. The residue was purified by flash column chromatography on silica gel, eluting with hexane/EtOAc (85:15) to give the title compound as an oil (68 mg, 91%). $^1$H NMR (360 MHz, CDCl$_3$) δ 7.56 (2H, d, J 7.4 Hz), 7.34-7.23 (5H, m), 6.72 (1H, d, J 8.5 Hz), 5.20 (1H, s), 4.50 (1H, hept, J 6.2 Hz), 4.23 (1H, t, J 8.2 Hz), 4.00 (1H, m), 3.73 (1H, m), 3.63 (1H, t, J 8.2 Hz), 2.89 (1H, m), 2.38 (1H, m), 2.15 (2H, m), 1.74 (3H, m), 1.40 (9H, s), 1.34 (3H, d, J 6.2 Hz), and 1.32 (3H, d, J 6.2 Hz). m/z (ES$^+$) 530, 532 (M+1).

EXAMPLE 102

(3S,5R,6S)-3-(5-Bromo-2-isopropoxyphenyl)-6-phenyl-1-oxa-7-aza-spiro[4.5]decane

Prepared from the compound of Example 101 according to the method of Example 2. $^1$H NMR (360 MHz, CDCl$_3$) δ 7.49-7.47 (2H, m), 7.37-7.31 (3H, m), 7.12-7.09 (1H, dd, J 8.6, 2.4 Hz), 6.62-6.60 (1H, d, J 8.6 Hz), 6.35-6.34 (1H, d, J 2.4 Hz), 4.42-4.36 (1H, m), 4.09-4.04 (1H, t, J 7.9 Hz), 3.84-3.73 (1H, m), 3.65 (1H, s), 3.24-3.21 (1H, m), 3.10-3.06 (1H, m), 2.85-2.78 (1H, m), 2.14-1.96 (2H, m), 1.87-1.76 (3H, m), 1.63-1.55 (2H, m), and 1.28-1.24 (6H, m). m/z (ES$^+$) 430, 432 (M+1).

EXAMPLE 103

(3S,5R,6S)-3-(5-Cyano-2-isopropoxyphenyl)-6-phenyl-1-oxa-7-(tert-butoxycarbonyl)aza-spiro[4.5]decane A solution of (3S,5R,6S)-3-(5-bromo-2-isopropoxyphenyl)-6-phenyl-1-oxa-7-(tert-butoxycarbonyl)aza-spiro[4.5]decane (Example 101; 226 mg, 0.43 mmol) and copper(I) cyanide (227 mg, 2.54 mmol) in DMF (4 ml) was heated under reflux for 17. The mixture was allowed to cool, poured into aqueous ethylenediamine (10%, 50 ml) and extracted with ethyl acetate (2×50 ml). The organic fractions were washed with aqueous ethylenediamine (10%, 50 ml) and brine (50 ml), combined, dried (MgSO$_2$) and the solvent was evaporated under reduced pressure. The residue was dissolved in dichloromethane (4 ml), treated with di-tert-butyl dicarbonate (110 mg, 0.50 mmol) and the mixture was stirred at room temperature overnight. The solvent was evaporated under reduced pressure and the residue was purified by flash chromatography on silica gel, eluting with hexane/EtOAc (80:20 increasing to 70:30), to give the title compound (92 mg, 45%). m/z (ES$^+$) 477 (M+1).

EXAMPLE 104

(3S,5R,6S)-3-(5-Cyano-2-isopropoxyphenyl)-6-phenyl-1-oxa-7-aza-spiro[4.5]decane Hydrochloride Prepared from the compound of Example 103 according to the method of Example 3. m.p. 230–234° C. (dec.). $^1$H NMR (360 MHz, D$_2$O) δ 1.27 (6H, m), 1.73-1.97 (3H, m), 2.19 (3H, m), 3.23 (1H, m), 3.39 (1H, m), 3.53 (1H, m), 3.76 (1H, m), 4.17 (1H, t, J 8.1 Hz), 4.39 (1H, s), 4.61 (1H, p, J 6.0 Hz), 6.49 (1H, s), 6.88 (1H, d, J 8.7 Hz), 7.32 (1H, m), and 7.47 (5H, m); m/z (ES$^+$) 377 (M+1). Found: C, 66.59; H, 6.80; N, 6.51. C$_{24}$H$_{28}$N$_2$O$_2$.HCl.H$_2$O requires: C, 66.89; H, 7.25; N, 6.50%.

EXAMPLE 105

(5R,6S)-Methyl 4-(Difluoromethoxy)-3-(6-phenyl-1-oxa-7-(tert-butoxycarbonyl)aza-spiro[4.5]dec-3-en-3-yl]benzoate Prepared from the compound of Description 65 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 7.98 (1H, dd, J 2.1, 8.6 Hz), 7.85 (1H, d, J 2.1 Hz), 7.47 (2H, m), 7.25 (4H, m), 6.62 (1H, t, J 2.1 Hz), 6.55 (1H, t, J 73 Hz), 5.16 (1H, s), 4.97 (1H, dd, J 2., 12.3 Hz), 4.62 (1H, dd, J 2.1, 12.3 Hz), 4.13 (1H, m), 3.92 (3H, s), 3.18 (1H, m), 2.12 (1H, m), 1.85 (3H, m), and 1.37 (9H, s).

EXAMPLE 106

(5R,6S)-Methyl 3-[6-Phenyl-1-oxa-7-(tert-butoxycarbonyl)aza-spiro[4.5]dec-3-en-3-yl]-4-(2,2,2-trifluoroethoxy)benzoate Prepared from the compound of Description 66 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 7.97 (1H, dd, J 8.67, 2.14 Hz), 7.80 (1H, d, J 2.1 Hz), 7.44 (2H, m), 7.17-7.30 (3H, m), 6.85 (1H, d, J 8.7 Hz), 6.67 (1H, t, J 2.1 Hz), 5.15 (1H, s), 4.98 (1H, dd, J 2.0, 12.2 Hz), 4.67 (1H, dd, J 2., 12.2 Hz), 4.36-4.51 (2H, m), 4.13 (1H, m), 3.90 (3H, s), 3.14 (1H, m), 2.08 (1H, m), 1.79-1.89 (3H, m), and 1.36 (9H, s).

EXAMPLE 107

(3S,5R,6S)-Methyl 4-(Difluoromethoxy)-3-[6-phenyl-1-oxa-7-(tert-butoxycarbonyl)aza-spiro[4.5]decan-3-yl]benzoate Prepared from the compound of Example 105 according to the method of Example 3. $^1$H NMR (250 MHz, CDCl$_3$) δ 7.96 (2H, m), 7.56 (2H, m), 7.30 (3H, m), 7.13 (1H, d, J 5.9 Hz), 6.59 (1H, t, J73 Hz), 5.22 (1H, s), 4.23 (1H, m), 3.98 (1H, m), 3.89 (3H, s), 3.77 (2H, m), 2.89 (1H, m), 2.19 (2H, m), 1.75 (3H, m), and 1.37 (9H, s).

EXAMPLE 108

(3S,5R,6S)-Methyl 3-[6-Phenyl-1-oxa-7-(tert-butoxycarbonyl)aza-spiro[4.5]decan-3-yl]-4-(2,2,2-trifluoroethoxy)benzoate Prepared from the compound of Example 106 according to the method of Example 3. $^1$H NMR (250 MHz, CDCl$_3$) δ 7.96 (1H, m), 7.83 (2H, m), 7.22-7.36 (4H, m), 6.82 (1H, d, J 8.4 Hz), 5.22 (1H, s), 4.38-4.52 (2H, m), 3.94 (1H, m), 3.88 (3H, s), 3.74 (1H, m), 2.85-2.93 (1H, m), 2.46-2.54 (1H, m) 2.10-2.22 (1H, m), 1.76-1.81 (3H, m), and 1.38 (9H, s).

EXAMPLE 109

(3S,5R,6S)-{4-(Difluoromethoxy)-3-[6-phenyl-1-oxa-7-(tert-butoxycarbonyl)aza-spiro[4.5]decan-3-yl]phenyl}carboxamide A cooled (0° C.) solution of (3S,5R,6S)-methyl 4-(Difluoromethoxy)-3-(6-phenyl-1-oxa-7-(tert-butoxycarbonyl)aza-spiro[4.5]decan-3-yl]benzoate (Example 107, 730 mg, 1.41 mmol) in methanol (100 ml) was saturated with ammonia gas, then heated at 80° C. in a sealed tube for 16 h. The mixture was cooled and the solvent was evaporated under reduced pressure. The residue was purified by column chromatography on silica gel, eluting with hexane/EtOAc (50:50) to give the title compound as a colorless solid (410 mg, 58%). $^1$H NMR (250 MHz, CDCl$_3$) δ 8.25 (1H, br s), 8.00 (1H, dd, J 2.1, 8.6 Hz), 7.64 (2H, m), 7.30 (3H, m), 7.15 (1H, d, J 8.6 Hz), 6.57 (1H, t, J 73 Hz), 5.78 1H, br s), 5.53 (1H, br s), 4.34 (1H, t, J 8.8 Hz), 4.10 (2H, m), 3.68 (1H, t, J 8.8 Hz), 2.75 (1H, m), 1.65 (3H, m), and 1.47 (9H, s).

EXAMPLE 110

(3S,5R,6S)-{3-[6-Phenyl-1-oxa-7-(tert-butoxycarbonyl)aza-spiro[4.5]decan-3-yl]-4-(2,2,2-trifluoroethoxy)phenyl}carboxamide Prepared from the compound of Example 108, according to the method of Example 109. m/z (ES$^+$) 535 (M+1).

EXAMPLE 111

(3S,5R,6S)-3-[5-Cyano-2-(difluoromethoxy)phenyl]-6-phenyl-1-oxa-7-(tert-butoxycarbonyl)aza-spiro[4.5]decane Trifluoroacetic anhydride (252 μl, 1.8 mmol) was added dropwise to a solution of (3S,5R,6S)-{4-difluoromethoxy)-3-[6-phenyl-1-oxa-7-(tert-butoxycarbonyl)aza-spiro[4.5] decan-3-yl]phenyl}carboxamide (Example 109, 410 mg, 0.82 mmol) and pyridine (332 μl, 4.1 mmol) in 1,4-dioxane (20 ml) and the mixture was stirred at room temperature for 1 h. The mixture was poured into saturated aqueous sodium bicarbonate (50 ml) and extracted with ethyl acetate (2×50 ml). The combined organic fractions were dried (Na$_2$SO$_4$) and the solvent was evaporated under reduced pressure. The residue was purified by column chromatography on silica gel, eluting with hexane/EtOAc (75:25) to give the title compound as a gum (347 mg, 87%). $^1$H NMR (250 MHz, CDCl$_3$) δ 7.50 (4H, m), 7.25 (4H, m), 7.15 (1H, d, J 8.6 Hz), 6.60 (1H, t, J 73 Hz), 5.13 (1H, br s), 4.16 (1H, m), 4.03 (1H, m), 3.67 (2H, m), 2.94 (1H, m), 2.42 (1H, m), 2.13 (2H, m), 1.75 (3H, m), and 1.47 (9H, s).

EXAMPLE 112

(3S,5R,6S)-3-[5-Cyano-2-(2,2,2-trifluoroethoxy)phenol]-6-phenyl-1-oxa-7-(tert-butoxycarbonyl)aza-spiro[4.5]decane Prepared from the compound of Example 110 according to the method of Example 111. $^1$H NMR (250 MHz, CDCl$_3$) δ 7.48-7.56 (4H, m), 7.22-7.36 (3H, m), 6.84 (1H, d, J 8.5 Hz), 5.14 (1H, s), 4.42 (2H, q, J 7.8 Hz), 4.25 (1H, m), 4.00 (1H, m), 3.67-3.84 (2H, m), 2.84-3.00 (1H, m), 2.40-2.56 (1H, m), 2.02-2.18 (2H, m), 1.64-1.75 (3H, m), and 1.37 (9H, s).

EXAMPLE 113

(3S,5R,6S)-3-[5-Cyano-2-(difluoromethoxy)phenyl]-6-phenyl-1-oxa-7-aza-spiro[4.5]decane Hydrochloride Prepared from the compound of Example 111 according to the method of Example 2. $^1$H NMR (360 MHz, DMSO-d$_6$) δ 9.78 (1H, br s), 9.05 (1H, br s), 7.70 (1H, dd, J 2.0, 8.5 Hz), 7.50 (5H, m), 7.31 (1H, t, J 73Hz), 7.20 (1H, d, J 8.5 Hz), 6.58 (1H, d, J 2.0 Hz), 4.51 (1H, br s), 4.14 (1H, t J 8.1 Hz), 3.78 (1H, m), 3.28 (1H, m), 3.07 (1H, m), 2.09 (3H, m), and 1.70 (3H, m). m/z (ES$^+$) 385 (M+1).

EXAMPLE 114

(3S,5R,6S)-3-[5-Cyano-2-(2,2,2-trifluoroethoxy)phenyl]-6-phenyl-1-oxa-7-aza-spiro[4.5]decane Prepared from the compound of Example 112 according to the method of Example 2. $^1$H NMR (360 MHz, DMSO-d$_6$) δ 9.60 (1H, br s), 8.96 (1H, br s), 7.66 (1H, dd, J 6.7, 1.9 Hz), 7.44-7.54 (5H, m), 7.18 (1H, d, J 8.7 Hz), 6.66 (1H, d, J 1.9 Hz), 4.81-4.88 (2H, m), 4.50 (1H, m), 4.16 (1H, t, J 8.0 Hz), 3.72 (1H, m), 3.26 (2H, m), 3.06 (1H, br m), 1.99-2.17 (3H, m), and 1.60-1.81 (3H, m). m/z (ES$^+$) 417 (M+1).

EXAMPLE 115

(5R,6S)-{4-(Cyclobutyloxy)-3-[6-phenyl-1-oxa-7-(tert-butoxycarbonyl)aza-spiro[4.5]dec-3-en-3-yl]-phenyl}carboxamide Prepared from the compound of Description 68 and (5R,6S)-3-tributylstannyl-6-phenyl-1-oxa-7-(tert-butoxycarbonyl)aza-spiro[4.5]dec-3-ene according to the method of Example 1. $^1$H NMR (CDCl$_3$) δ 1.37 (9H, s), 1.70-1.93 (4H, m), 2.14-2.21 (3H, m), 2.42-2.34 (3H, m), 3.07-3.20 (1H, m), 4.09-4.18 (1H, m), 4.66-4.75 (2H, m), 5.00 (1H, dd, J 12.3, 2.0 Hz), 5.16 (1H, br. s), 6.20 (2H, br. s), 6.67 (1H, br. s), 6.74 (2H, d, J 8.5 Hz), 7.20-7.29 (3H, m), 7.47 (2H, d, J 8.0 Hz), 7.60 (1H, d, J 2.2 Hz), and 7.64 (1H, dd, J 8.5, 2.2 Hz).

EXAMPLE 116

(3S,5R,6S)-{4-(Cyclobutyloxy)-3-[6-phenyl-1-oxa-7-(tert-butoxycarbonyl)aza-spiro[4.5]decan-3-yl]phenyl}carboxamide Trifluoroacetic acid (0.5 ml) was added to a solution of (5R,6S)-{4-(cyclobutyloxy)-3-[6-phenyl-1-oxa-7-(tert-butoxycarbonyl)aza-spiro[4.5]dec-3-en-3-yl]phenyl}carboxamide (Example 115, 0.5 g) in dichloromethane (15 ml) and the mixture was stirred at room temperature overnight. The solvent was evaporated under reduced pressure and the residue was purified by column chromatography on silica gel, eluting with dichloromethane/methanol/ammonia (90:10:1). The residue was dissolved in a mixture of methanol (25 ml) and acetic acid )0.5 ml), palladium hydroxide on carbon (50 mg) was added and the mixture was shaken for two days under an atmosphere of hydrogen at 50 psi.. The mixture was filtered and the solvent was evaporated under reduced pressure. The residue was dissolved in dichloromethane (15 ml) and triethylamine (0.14 ml) and di-tert-butyl dicarbonate (130 mg) were added and the mixture was stirred at room temperature overnight. The solvent was evaporated under reduced pressure and the the residue was purified by column chromatography on silica gel, eluting with ethyl acetate/hexane to give the title compound as a gum (210 mg). $^1$H NMR (CDCl$_3$) δ (CDCl$_3$) δ 1.46 (9H, s), 1.64-1.93 (5H, m), 2.08-2.27 (4H, m), 2.39-2.48 (3H, m), 2.74-2.80 (1H, m), 3.64 (1H, app. t, J 9.0 Hz), 3.93 (1H, br d, J 12.7 Hz), 3.98-4.09 (1H, m), 4.35 (1H, app. t, J 8.6 Hz), 4.69 (1H, app. pent, J 7.0 Hz), 5.68 (1H, br s), 6.73 (1H, d, J 8.6 Hz), 7.21-7.25 (1H, m), 7.30-7.34 (2H, m), 7.62 (2H, d, J 7.7 Hz), 7.90 (1H, d, J 8.5 Hz), and 8.06 (1H, br s).

EXAMPLE 117

(3S,5R,6S)-3-[5-Cyano-2-(cyclobutyloxy)phenyl]-6-phenyl-1-oxa-7-(tert-butoxycarbonyl)aza-spiro[4.5]decane Prepared from the compound of Example 116 according to the method of Example 111. ¹H NMR (CDCl₃) δ 1.38 (9H, s), 1.67-1.81 (4H, m), 1.86-1.95 (1H, m), 2.09-2.22 (4H, m), 2.41 (1H, dd, J 12.9, 8.3 Hz), 2.44-2.54 (2H, m), 2.87-2.95 (1H, m), 3.65 (1H, app. t, J 8.4 Hz), 3.68-3.76 (1H, m), 4.01 (1H, br. d, J 13.1 Hz), 4.26 (1H, app. t, J 8.4 Hz), 4.68 (1H, app. pent, J 7.1 Hz), 5.16 (1H, br s), 6.71 (2H, d, J 8.5 Hz), 7.23-7.27 (1H, m), 7.33 (2H, app. t, J 7.1 Hz), 7.42 (1H, d, J 1.9 Hz), 7.45 (1H, dd, J 8.4, 1.9 Hz), and 7.54 (2H, d, J 7.7 Hz). m/z (ES⁺) 489 (M+1).

EXAMPLE 118

(3S,5R,6S)-3-[5-Cyano-2-(cyclobutyloxy)phenyl]-6-phenyl-1-oxa-7-aza-spiro[4.5]decane Hydrochloride Prepared from the compound of Example 117 according to the method of Example 2. m.p. (MeOH/tert-butyl methyl ether) 252–254° C. ¹H NMR (D₂O) δ 1.59-1.82 (3H, m), 1.87-1.96 (3H, m), 2.04-2.23 (3H, m), 2.26-2.41 (2H, m), 3.11-3.24 (1H, m), 3.24-3.37 (2H, m), 3.47 (1H, br d, J 10.3 Hz), 3.74 (1H, app. pent, J 8.6 Hz), 4.14 (1H, app. t, J 8.2 Hz), 4.34 (1H, s), 4.60 (1H, app. pent, J 7.1 Hz), 6.40 (1H, d, J 1.9 Hz), 6.66 (1H, d, J 8.7 Hz), 7.27 (1H, dd, J 8.6, 1.9 Hz), and 7.35-7.52 (5H, m). m/z (ES⁺) 389 (M+1). Found: C, 66.82; H, 7.01; N, 6.38. C₂₅H₂₅N₂O₂.HCl.1.25H₂O requires: C, 67.10; H, 7.10; N, 6.26%.

EXAMPLE 119

(5R,6S)-3-[2-Cyano-5-(trifluoromethoxy)phenyl]-6-phenyl-1-oxa-7-(tert-butoxycarbonyl)aza-spiro[4.5]dec-3-ene Prepared from the compound of Description 69 and (5R,6S)-3-tributylstannyl-6-phenyl-1-oxa-7-(tert-butoxycarbonyl)aza-spiro[4.5]dec-3-ene according to the method of Example 2. ¹H NMR (360 MHz, CDCl₃) δ 1.34 (9H, s), 1.82-1.94 (3H, m), 2.12-2.16 (1H, m), 3.18-3.24 (1H, m), 4.13-4.16 (1H, m), 4.48 (1H, d, J 11.7 Hz), 4.91 (1H, d, J 11.7 Hz), 5.13 (1H, s), 6.85 (1H, s), 7.20-7.29 (4H, m), 7.43 (2H, d, J 7.2 Hz), and 7.74 (1H, d, J 8.6 Hz).

EXAMPLE 120

(5R,6S)-3-[2-Cyano-5-(trifluoromethoxy)phenyl]-6-phenyl-1-oxa-7-aza-spiro[4.5]dec-3-ene Hydrochloride Prepared from the compound of Example 119 according to the method of Example 2. ¹H NMR (360 MHz, D₂O) δ 1.96-2.18 (3H, m), 3.19-3.29 (1H, m), 3.49-3.56 (1H, m), 4.49 (1H, d, J 12.5 Hz), 4.91 (1H, d, J 12.5 Hz), 6.44 1H, s), 6.81 (1H, s), 7.17-7.19 (1H, m), 7.33-7.38 (4H, m), 7.42-7.45 (2H, m), and 7.61 (1H, d, J 8.7 Hz).

EXAMPLE 121

(3S,5R,6S)-3-[2-(Cyclopropylmethoxy)-5-(trifluoromethoxy)phenyl]-6-phenyl-1-oxa-7-(tert-butoxycarbonyl)aza-spiro[4.5]decane Cyclopropylmethyl bromide (0.078 ml, 0.8 mmol) was added to a mixture (3R,5R,6S)-3-[2-hydroxy-5-(trifluoromethoxy)phenyl]-6-phenyl-1-oxa-7-(tert-butoxycarbonyl)aza-spiro[4.5]decane (Example 44, 330 mg, 0.67 mmol) and potassium carbonate (103 mg, 0.75 mmol) in DMF (5 ml) and the mixture was stirred at room temperature for 48 h. Water (20 ml) was added and the mixture was extracted with ethyl acatate (2×20 ml). The combined organic fractions were dried and the solvent was evaporated under reduced pressure. The residue was purified by flash column chromatography on silica, eluting with hexane/EtOAc (90:10), to give the title compound (150 mg). ¹H NMR (360 MHz, CDCl₃) δ 0.31-0.35 (2H, m), 0.61-0.65 (2H, m), 1.20-1.29 (1H, m), 1.37 (9H, s), 1.72-1.84 (3H, m), 2.09-2.18 (2H, m), 2.41-2.47 (1H, m), 2.83-2.91 (1H, m), 3.39 (1H, br s), 3.62-3.68 (1H, m), 3.77-3.84 (2H, m), 3.98-4.02 (1H, m), 4.27-4.32 (1H, m), 5.21 (1H, s), 6.74-6.77 (1H, m), 6.99-7.04 (2H, m), 7.21-7.33 (3H, m), and 7.56 (1H, d, J 7.5 Hz).

EXAMPLE 122

(3S,5R,6S)-3-[2-(Cyclopropylmethyloxy)-5-(trifluoromethoxy)phenyl]-6-phenyl-1-oxa-7-aza-spiro[4.5]decane Hydrochloride Prepared from the compound of Example 121 according to the method of Example 2. ¹H NMR (360 MHz, D₂O) δ 0.29-0.28 (2H, m), 0.56-0.58 (2H, m), 1.14-1.18 (1H, m), 1.78-2.02 (2H, m), 2.16-2.26 (3H, m), 3.18-3.28 (2H, m), 3.48-3.55 (1H, m), 3.74-3.79 (2H, m), 4.18-4.22 (1H, m), 4.40 (1H, s), 6.20 (1H, s), 6.92 (1H, d, J 9.0 Hz), 7.02-7.06 (1H, m), and 7.45-7.53 (6H, m).

EXAMPLE 123

(3S,5R,6S)-3-[2-Methoxy-5-(trifluoromethyl)phenyl]-6-phenyl-1-oxa-7-(tert-butoxycarbonyl)aza-spiro[4.5]decane Sodium hydride (60% dispersion in mineral oil, 10 mg) was added to a solution of (3S,5R,6S)-3-(2-hydroxy-5-(trifluoromethyl)phenyl)-6-phenyl-1-oxa-7-(tert-butoxycarbonyl)aza-spiro[4.5]decane (Example 46, 100 mg) in dimethylformamide (2 ml). The mixture was stirred at room temperature until effervescence had subsided, methyl iodide (0.4 ml) was added and the mixture was stirred at room temperature for 1 h. Water (10 ml) was added and the mixture was extracted with ethyl acetate (3×10 ml). The combined organic fractions were washed with brine, dried (MgSO₄) and the solvent was evaporated under reduced pressure to give the title compound as a yellow oil (102 mg). m/z (ES⁺) 492 (M+1).

EXAMPLE 124

(3S,5R,6S)-3-[2-Methoxy-5-(trifluoromethyl)phenyl]-6-phenyl-1-oxa-7-aza-spiro[4.5]decane Prepared from the compound of Example 123 according to the method of Example 2. ¹H NMR (250 MHz, CDCl₃)δ 1.18 (2H, d, J 11.1 Hz), 1.87 (1H, d, J 12.2 Hz), 2.04 (2H, d, J 12.0 Hz), 2.73 (1H, t, J 12.4 Hz), 3.10 (1H, dd, J 8.0, 10.4 Hz), 3.18 (1H, d, J 11.7 Hz), 3.65 (3H, s), 4.02 (1H, t, J 7.6 Hz), 6.52 (1H, d, J 2.1 Hz), 6.69 (1H, d, J 8.6 Hz), 7.24 (4H, m), and 7.43 (3H, m).

EXAMPLE 125

(3S,5R,6S)-3-[2-Methoxy-5-(trifluoromethyl)phenyl]-6-phenyl-1-oxa-7-(1,2,4-triazolyl-3-methyl)-7-aza-spiro[4.5]decane Prepared from the compound of Example 124 according to the method of Example 5. ¹H NMR (500 MHz, CDCl₃)δ

0.9 (2H, s), 1.35 (1H, q, J 7.35 Hz), 1.54 (1H, dt, J 9.8, 4 Hz), 1.62 (2H, m), 2.00 (2H, m), 2.15 (1H, d, J 12.3 Hz), 3.11 (1H, m), 3.74 (3H, s), 3.82 (1H, m), 4.08 (1H, t, J 8.0 Hz), 6.52 (1H, s), 6.77 (1H, d, J 8.6 Hz), 7.25 (1H), s), 7.35 (4H, m), 7.58 (1H, m), and 8.13 (1H, s).

EXAMPLE 126

(5R,6S)-3(2-Methanesulfonylphenyl)-6-phenyl-1-oxa-7-(tert-butoxycarbonyl)aza-spiro[4.5]dec-3-ene Prepared from the compound of Description 71 and (5R,6S)-3-tributylstannyl-6-phenyl-1-oxa-7-(tert-butoxycarbonyl)aza-spiro[4.5]dec-3-ene according to the method of Example 1. $^1$H NMR (360 MHz, CDCl$_3$)δ 8.14 (1H, dd, J 7.7, 1.34 Hz), 7.61-7.47 (4H, m), 7.36-7.26 (3H, m), 7.10 (1H, dd, J 7.33, 1.51 Hz), 6.16 (1H, t, J 2.15 Hz), 5.19 (1H, s), 4.90 (1H, dd, J 12.5,2.1 Hz), 4.56 (1H, dd, J 12.5, 2.2 Hz), 4.11 (1H, dt, J 12.3 Hz), 3.20 (1H, m), 3.07 (3H, s), 2.17 (1H, m), 1.90 (3H, m), and 1.35 (9H, s). m/z (ES$^+$)470 (M+1).

EXAMPLE 127

(5R,6S)-3(2-Methanesulfonylphenyl)-6-phenyl-1-oxa-7-aza-spiro[4.5]dec-3-ene

Prepared from the compound of Example 126 according to the method of Example 2. $^1$H NMR (250 MHz, CD$_3$OD)δ 7.89 (1H, m), 7.50-7.22 (8H, m), 6.33 (1H, m), 5.71 (1H, t, J 2.1 Hz), 4.87 (1H, dd, J 12.5, 2.2 Hz), 4.76 (5H, br s), 4.39 (1H, dd, J 12.5, 2.2 Hz), 4.28 (1H, s), 3.38 (1H, broad d, J 11.7 Hz), 3.13 (1H, td, J 10.2, 2.5 Hz), 2.71 (3H, s), and 2.27-1.87 (4H, m). m/z (ES$^+$) 370 (M+1).

EXAMPLE 128

(3S,5R,6S)-3-(2-Methanesulfonylphenyl)-6-phenyl-1-oxa-7-aza-spiro[4.5]decane

Prepared from the compound of Example 127 according to the method of Example 3. $^1$H NMR (360 MHz, CDCl$_3$) δ 7.9 (1H, dd, J 7.7, 1.99 Hz), 7.55 (2H, br d), 7.38 (3H, m), 7.21 (2H, m), 6.16 (1H, d, J 7.3 Hz), 5.01 (2H, br s), 4.39 (1H, q, J 8.9 Hz), 4.17 (1H, t, J 8.3 Hz), 3.88 (1H, s), 3.47 (1H, m), 3.33 (1H, dm, J 13.2 Hz), 3.04 (3H, s), 2.88 (1H, td, J 12.61 Hz), 2.17 (3H, m), 1.86 (1H, dd, J 12.7, 10.3 Hz), and 1.06 (2H, m). m/z (ES$^+$) 372 (M+1).

EXAMPLE 129

(5R,6S)-Methyl{4-Hydroxy-3-[6-phenyl-1-oxa-7-(tert-butoxycarbonyl)aza-spiro[4.5]dec-3-en-3-yl]phenyl}ethanoate Prepared from the compound of Description 73 and (5R,6S)-3-tributylstannyl-6-phenyl-1-oxa-7-(tert-butoxycarbonyl)aza-spiro[4,5]dec-3-ene according to the method of Example 1. $^1$H NMR (250 MHz, CDCl$_3$) δ 7.50–7.53 (2H, m), 7.18–7.32 (3H, m), 7.05 (1H, dd, J 2.27, 8.31 Hz), 6.86 (1H, d, J 2.27 Hz), 6.82 (1H, d, J 8.31 Hz), 6.51 (1H, t, J 2.06 Hz), 6.33 (1H, br s), 5.24 (1H, br s), 4.98 (1H, dd, J 2.01, 12.44 Hz), 4.62 (1H, dd, J 2.01, 12.44 Hz), 4.03–4.10 (1H, m), 3.68 (3H, s), 3.51 (2H, s), 3.02–3.10 (1H, m), 2.11–2.18 (1H, m), 1.75–1.88 (3H, m), and 1.42 (9H, s).

EXAMPLE 130

(5R,6S)-Methyl [4-Hydroxy-3-(6-phenyl-1-oxa-7-aza-spiro[4.5]dec-3-en-3-yl)phenyl]ethanoate Prepared from the compound of Example 129 according to the method of Example 2. $^1$H NMR (250 MHz, CDCl$_3$) δ 7.37–7.42 (2H, m), 7.16–7.30 (3H, m), 6.96 (1H, dd, J 2.18, 8.40 Hz), 6.70 (1H, d, J 2.18 Hz),6.68 (1H, d, J 8.40 Hz), 5.87 (1H, t, J 2.18 Hz), 4.82 (1H, dd, J 2.06, 12.54 Hz), 4.30 (1H, dd, J 2.06, 12.54 Hz), 3.78 (1H, s), 3.65 (3H, s), 3.44 (2H, s), 3.25–3.36 (1H, dt, J 2.83, 12.39 Hz), 1.97–2.09 (2H, m), and 1.65–1.84 (2H, m).

EXAMPLE 131

(3S,5R,6S)-Methyl [4-Hydroxy-3-(6-phenyl-1-oxa-7-aza-spiro[4.5]decan-3-yl)phenyl]ethanoate Prepared from the compound of Example 130 according to the method of Example 3. $^1$H NMR (250 MHz, DMSO-d$_6$), δ 9.33 (1H, br s), 7.50–7.54 (2H, m), 7.35–7.44 (3H, m), 6.80 (1H, dd, J 2.11, 8.18 Hz), 6.65 (1H, d, J 8.18 Hz), 5.99 (1H, d, J 2.11 Hz), 3.89–4.04 (2H, m), 3.64–3.72 (1H, m), 3.60 (3H, s), 3.30 (2H, s), 3.11–3.16 (1H, m), 2.94 (1H, dd, J 7.84, 10.36 Hz), 2.78–2.87 (1H, m), and 1.62–2.06 (6H, m)

EXAMPLE 132

(3S,5R,6S)-Methyl {4-Hydroxy-3-[6-phenyl-1-oxa-7-(tert-butoxycarbonyl)aza-spiro[4.5]-decan-3-yl]phenyl}ethanoate N-Ethyl diisopropylamine (0.324 ml, 1.9 mmol) was added to a mixture of (3S,5R,6s)-methyl [4-hydroxy-3-(6-phenyl-1-oxa-7-aza-spiro[4.5]decan-3-yl)phenyl]ethanoate (Example 131, 309 mg, 0.81 mmol) and di-tert-butyl dicarbonate (400 mg, 1.83 mmol) in tetrahydrofuran (100 ml) and the mixture was stirred at room temperature for 4 h. Further N-ethyl diisopropylamine (0.324 ml, 1.9 mmol) was added and the mixture was stirred at room temperature for 16 h., poured into saturated aqueous sodium hydrogen carbonate (100 ml) and extracted with ethyl acetate (2×100 ml). The combined organic fractions were dried (MgSO$_4$) and the solvent was evaporated under reduced pressure. The residue was purified by chromatography on silica gel to give the title compound as a colorless solid (259 mg, 66%). $^1$H NMR (250 MHz, CDCl$_3$), δ7.55–7.58 (2H, m) 7.24–7.35 (3H, m), 6.98–7.01 (2H, m), 6.71 (1H, d, J 8.75 Hz), 5.99 (1H, br s), 5.35 (1H, br s), 4.22 (1H, dd, J 7.13, 8.95 Hz), 3.90–3.98 (2H, m), 3.66 (3H, s), 3.51 (2H, s), 2.84–2.88 (1H, m), 2.48 (1H, dd, J 8.84, 12.87 Hz), 2.05–2.24 (3H, m), 1.72–1.82 (3H, m), and 1.35 (9H, s).

EXAMPLE 133

(3S,5R,6S)-Methyl {4-Hydroxy-3-[6-phenyl-1-oxa-7-(tert-butoxycarbonyl)aza-spiro[4.5]-decan-3-yl]phenyl}ethanoate Iodomethane (0.051 ml, 0.81 mmol) was added to a mixture of (3S,5R,6S)-methyl {4-hydroxy-3-[6-phenyl-1-oxa-7-(tert-butoxycarbonyl)aza-spiro[4.5]decan-3-yl]phenyl}ethanoate (Example 132, 259 mg, 0.54 mmol) and potassium carbonate (149 mg, 1.08 mmol) in acetone (10 ml) and the mixture was heated under reflux for 16 h. The mixture was cooled, filtered and the solvent was evaporated under reducde pressure. Saturated aqueous sodium bicarbonate solution (20 ml) was added and the mixture was extracted with ethyl acetate (2×20 ml The combined organic fractions were dried (Na$_2$SO$_4$) and the solvent was evaporated under reduced pressure. The residue was purified by chromatography on silica gel to give the title compound as a gum (179 mg, 67%). $^1$H NMR (250 MHz, CDCl$_3$) δ 7.55–7.58 (2H, m), 7.20–7.35 (3H, m), 7.10 (1H, dd, J 2.25, 8.28 Hz), 7.04 (1H, d, J 2.25 Hz), 6.80 (1H, d, J 8.28 Hz), 5.21 (1H, br s), 4.16–4.20 (1H, m), 3.96–4.02 (1H, m), 3.80 (3H, s), 3.69–3.72 (2H, m), 3.64 (3H, s), 3.52 (2H, s), 2.82–2.94 (1H, m), 2.34–2.42 (1H, m), 2.08–2.24 (2H, m), 1.72–1.78 (3H, m), and 1.37 (9H, s).

EXAMPLE 134

(3S,5R,6S)-{4-Methoxy-3-[6-phenyl-1-oxa-7-(tert-butoxycarbonyl)aza-spiro[4.5]-decan-3-yl]phenyl}ethanamide Prepared from the compound of Example 133 according to the method of Example 109. $^1$H NMR (250 MHz, CDCl$_3$) δ 7.54–7.57 (2H, m), 7.23–7.34 (4H, m), 7.13 (1H, dd, J 8.27, 2.24 Hz), 6.81 (1H, d J 8.27 Hz), 5.31 (1H, br s), 5.17 (1H, br s), 4.25 (1H, dd, J 6.84, 14.75 Hz), 3.93–4.00 (1H, m), 3.81 (3H, s), 3.47 (2H, s), 3.00 (1H, t, J 7.04 Hz), 2.80–2.84 (1H, m), 2.27–2.31 (2H, m), 2.12–2.16 (1H, m), 1.66–1.73 (3H, m), and 1.39 (9H, s).

EXAMPLE 135

(3S,5R,6S)-3-[5-(Cyanomethyl)-2-methoxyphenyl]-6-phenyl-1-oxa-7-(tert-butoxycarbonyl)aza-spiro[4.5]decane Prepared from the compound of Example 134 according to the method of Example 111. $^1$H NMR (250 MHz, CDCl$_3$) δ 7.54–7.57 (2H, m), 7.24–7.36 (3H, m), 7.17 (1H, dd, J 2.34, 8.36 Hz), 7.05 (1H, d, J 2.34 Hz), 6.83 (1H, d, J 8.36 Hz), 5.21 (1H, br s), 4.20 (1H, t, J 6.84 Hz), 3.96–4.02 (1H, m), 3.82 (3H, s), 3.68–3.79 (2H, m), 3.63 (2H, s), 2.84–2.96 (1H, m), 2.32–2.41 (1H, m), 2.06–2.23 (2H, m), 1.73–1.78 (3H, m), and 1.37 (9H, s)

EXAMPLE 136

(3S,5R,6S)-3-[5-(Cyanomethyl)-2-methoxyphenyl]-6-phenyl-1-oxa-7-aza-spiro[4.5]decane Hydrochloride Prepared from the compound of Example 135 according to the method of Example 111. $^1$H NMR (360 MHz, DMSO-d$_6$) δ 9.56 (1H, br d), 8.84 (1H, br d), 7.55–7.58 (2H, m), 7.48–7.51 (3H, m), 7.09 (1H, d, J 8.52 Hz), 6.87 (1H, d, J 8.52 Hz), 6.34 (1H, s), 4.47–4.50 (1H, m), 4.09 (1H, t, J 7.63 Hz), 3.72 (2H, s), 3.59 (3H, s), 3.08–3.30 (4H, m), 1.96–2.07 (3H, m), and 1.77–1.85 (3H, m). m/z (ES+) 363 (M+1).

EXAMPLE 137

(5R,6S)-(4-Methoxy-3-[6-phenyl-1-oxa-7-(tert-butoxycarbonyl)aza-spiro[4.5]dec-3-en-3-yl]phenyl)carboxamide Prepared from the compound of Description 63 and (5R,6S)-3-tributylstannyl-6-phenyl-1-oxa-7-(tert-butoxycarbonyl)aza-spiro[4.5]dec-3-ene according to the method of Example 1. $^1$H NMR (250 MHz, CDCl$_3$) δ 1.36 (9H, s), 1.81–2.11 (4H, m), 3.02–3.16 (1H, m), 3.86 (3H, s), 4.10–4.16 (1H, m), 4.62–4.67 (1H, dd, J 2, 12 Hz), 4.95–5.01 (1H, dd, J 2, 12 Hz), 5.16 (1H, s), 6.66 (1H, m), 6.91–6.95 (2H, m), 7.19–7.58 (5H, m), and 7.59 (1H, d, J 2.2 Hz). m/z (ES$^+$) 465 (M+1).

EXAMPLE 138

(5R,6S)-(4-Methoxy-3-[6-phenyl-1-oxa-7-aza-spiro[4.5]dec-3-en-3-yl)phenyl]carboxamide Prepared from the compound of Example 137 according to the method of Example 2. $^1$H NMR (250 MHz, DMSO-d$_6$) δ 1.51–1.63 (1H, m), 1.86–1.96 (3H, m), 2.58–2.72 (1H, m), 3.10–3.15 (1H, m), 3.81 (1H, s), 3.87 (3H, s), 4.20–4.25 (1H, dd, J 2, 12 Hz), 4.77–4.83 (1H, dd, J 2, 12 Hz), 6.43 (1H, s), 7.04–7.39 (7H, m), and 7.77–7.81 (1H, dd, J 2, 8.6 Hz).

EXAMPLE 139

(5R,6S)-(4-Methoxy-3-[6-phenyl-1-oxa-7-aza-spiro[4.5]decan-3-yl)phenyl]carboxamide Prepared from the compound of Example 138 according to the method of Example 3. $^1$H NMR (360 MHz, DMSO-d$_6$) δ 1.78–1.85 (3H, m), 1.97–2.08 (3H, m), 3.00–3.08 (1H, m), 3.21–3.31 (2H, m), 3.61 (3H, s), 3.63–3.88 (1H, m), 4.11–4.15 (1H, m), 4.47–4.51 (1H, m), 6.90 (1H, d, J 8.60 Hz), 7.08 (1H, s), 7.21 (1H, d, J 2.04 Hz), 7.41–7.48 (3H, m), 7.54–7.56 (2H, m), 7.66–7.69 (2H, m), 8.93 (1H, br s), and 9.55 (1H, br s). m/z (ES$^+$) 367 (M+1).

EXAMPLE 140

(5R,6S)-3-(5-Cyano-2-methoxyphenyl)-6-phenyl-1-oxa-7-aza-spiro[4.5]decane

Potassium carbonate (250 mg) was added to a solution of (3S,5R,6S)-3-(5-cyano-2-methoxyphenyl)-6-phenyl-1-oxa-7-(trifluoroacetyl)aza-spiro[4.5]decane (Description 72, 160 mg) in methano (10 ml) and water (1 ml) and the mixture was heated under reflux for 2 h. The mixture was cooled and diluted with water. The mixture was extracted with ethyl acetate and the combined organic fractions were dried (MgSO$_4$) and the solvent was evaporated under reduced pressure. The residue was purified by flash column chromatography on silica gel, eluting with CH$_2$Cl$_2$/MeOH (97.5:2.5 increasing to 92.5:7.5), to give the title compound. $^1$H NMR (250 MHz, DMSO-d$_6$) δ 1.72–1.79 (3H, m), 2.01–2.09 (3H, m), 3.06–3.12 (1H, m), 3.23–3.28 (2H, m), 3.66, (3H, s), 3.71–3.76 (1H, m), 4.08–4.12 (1H, m), 4.47–4.50 (1H, m), 6.67 (1H, d, J 2.0 Hz), 6.99 (1H, J 8.7 Hz), Nd 7.47–7.63 (5H, m). m/z (ES$^+$) 349 (M+1).

EXAMPLE 141

(5R,6S)-Methyl {4-Methoxy-3-[6-phenyl-1-oxa-7-(tert-butoxycarbonyl)aza-spiro[4.5]dec-3-en-3-yl]phenyl}ethanoate Prepared from the compound of Description 74 and (5R,6S)-3-tributylstannyl-6-phenyl-1-oxa-7-(tert-butoxycarbonyl)aza-spiro[4.5]dec-3-ene according to the method of Example 1. $^1$H NMR (360 MHz, CDCl$_3$) δ 7.47 (2H, d, J 7.3 Hz), 7.26 (2H, t, J 7.3 Hz), 7.19 (1H, t, J 7.3 Hz), 7.16 (1H, dd, J 8.4, 2.3 Hz), 6.94 (1H, d, J 2.3 Hz), 6.86 (1H, d, J 8.4 Hz), 6.61 (1h, t, J 2.1 Hz), 5.15 (1H, s), 4.96 (1H, dd, J 12.0, 2.1 Hz), 4.63 (1H, dd, J 12.0, 2.1 Hz), 4.14 (1H, m), 3.84 (3H, s), 3.68 (3H, s), 3.54 (2H, s), 3.11 (1H, m), 2.10 (1H, m), 1.95–1.74 (3H, m), and 1.37 (9H, s).

EXAMPLE 142

(5R,6S)-Methyl [4-Methoxy-3-(6-phenyl-1-oxa-7-aza-spiro[4.5]dec-3-en-3-yl)phenyl]ethanoate Prepared from the compound of Example 141 according to the method of Example 2. $^1$H NMR (360 MHz, CDCl$_3$) δ 7.37 (2H, d, J 6.9 Hz), 7.16 (3H, m), 7.07 (1H, dd, J 8.4, 2.2 Hz), 6.76 (1H, d, J 8.4 Hz), 6.70 (1H, d, J 2.2 Hz), 6.10 (1H, t, J 2.1 Hz), 4.86 (1H, dd, J 11.9, 2.1 Hz), 4.33 (1H, dd, J 11.9, 2.1 Hz), 3.76 (1H, s), 3.74 (3H, s), 3.66 (3H, s), 3.46

EXAMPLE 143

(3S,5R,6S)-Methyl [4-Methoxy-3-(6-phenyl-1-oxa-7-aza-spiro[4.5decan-3-yl)phenyl]ethanoate Prepared from the compound of Example 142 according to the method of Example 3. $^1$H NMR (360 MHz, D$_2$O) δ 7.52 (5H, m), 7.01 (1H, dd, J 8.4, 2.1 Hz), 6.87 (1H, d, J 8.4 Hz), 6.03 (1H, d, J 2.1 Hz), 4.74 (2H, br s), 4.39 (1H, s), 4.10 (1H, m), 3.87 (1H, m), 3.69 (3H, s), 3.68 (3H, s), 3.51 (1H, m), 3.42 (2H, s), 3.34-3.18 (2H, m), and 2.21-1.80 (6H, m). m/z (ES$^+$) 396 (M+1).

EXAMPLE 144

(3S,5R,6S)-3-(5-(Trifluoromethoxy)-2-(trifluoromethysulfonyloxy)phenyl)-6-phenyl-1-oxa-7-(tert-butoxycarbonyl)aza-spiro[4.5]decane To a cooled (0° C.) solution of (3S,5R,6S)-3-(2-hydroxy-5-(trifluoromethoxy)phenyl)-6-phenyl-1-oxa-7-(tert-butoxycarbonyl)aza-spiro[4.5]decane (Example 38, 320 mg, 0.65 mmol) in pyridine (2 ml), was added trifluoromethanesulphonic anhydride (0.12 ml, 0.71 mmol), and the reaction was stirred at ambient temperature for 2 h. The reaction was diluted with saturated copper (II) sulphate (80 ml) and extracted into ethyl acetate (3×60 ml). The combined organic fractions were washed with water (80 ml), brine (80 ml), dried (MgSO$_4$) and evaporated in vacuo. Purification on silica, eluting with 25% ethyl acetate in hexane gave the title compound as a yellow oil (160 mg). $^1$H NMR (250 MHz, CDCl$_3$) δ 1.36 (9H, s), 1.75 (3H, m), 2.11 (2H, m), 2.53 (1H, m), 2.95 (1H, m), 3.66 (1H, , J 7.9 Hz), 3.72 (1H, m), 4.0 (1H, m), 4.23 (1H, t, J 6.5 Hz), 5.18 (1H, s), 7.16 (2H, m), 7.30 (4H, m), and 7.53 (2H, d, J 7.1 Hz).

EXAMPLE 145

(3S,5R,6S)-3-(5-(Trifluoromethoxy)-2-(trifluoromethysulfonyloxy)phenyl)-6-phenyl-1-oxa-7-aza-spiro[4.5-]decane Hydrochloride Prepared from the compound of Example 144 according to the method of Example 2. $^1$H NMR (360 MHz, D$_2$O) δ 1.78-2.00 (3H, m), 2.07–2.36 (3H, m), 3.42–3.50 (2H, m), 3.77–3.89 (1H, m), 4.16–4.24 (1H, m), 4.44 1H, s), 6.09 (1H, s), 7.16–7.20 (1H, m), 7.36 (1H, d, J 9.2 Hz), and 7.50–7.55 (6H, m).

EXAMPLE 146

(3S,5R,6S)-7-{[5-Dimethylaminomethyl)-1H-[1,2,3]triazol-4-yl]methyl}-3-[2-isopropoxy-5-(trifluoromethyl)phenyl]-6-phenyl-1-oxa-7-aza-spiro[4.5]decane Dihydrochloride Dimethylamine was bubbled through a solution of (3S, 5R,6S)-7-(4-azidobut-2-yn-1-yl)-3-[2-isopropoxy-5-(trifluoromethyl)phenyl]-6-phenyl-1-oxa-7-aza-spiro[4.5]decane (description 76, 98 mg) in dioxane (3 mL) for 10 min. The mixture was heated at 80° C. overnight in a sealed tube. The mixture was cooled and the solvent was evaporated under reduced pressure. The mixture was diluted with water (20 ml) and extracted with ethyl acetate (3×5 ml). The combined organic fractions were washed with brine, dried (MgSO$_4$) and the solvent was evaporated under reduced pressure. The residue was purified by chromatography on silica gel, eluting with CH$_2$Cl$_2$/MeOH/NH$_3$(Aq.) (98:2:0 increasing to 90:10:1). The residue was dissolved in ether and treated with excess ethereal hydrogen chloride. The solvent was evaporated under reduced pressure and the residue recrystallised from ethanol/ethyl acetate. The solid was collected and dried in vacuo to give the title compound as a colorless solid. $^1$H NMR (360 MHz, DMSO-d$_6$) δ 1.24 (6H, t, J 6.2 Hz), 1.62 (1H, m), 1.68–1.92 (2H, m), 2.04–2.26 (3H, m), 2.68 (6H, s), 3.07 (1H, m), 3.36 (1H, m), 3.58–3.72 (1H, m), 3.74–3.96 (2H, m), 4.10–4.39 (4H, m), 4.66 (1H, q, J 6.0 Hz), 4.6 (1H, br s), 6.45 (1H, s), 7.09 (1H, d, J 8.6 Hz), 7.36–7.68 (5H, m), and 8.00–8.10 (1H, m). m/z (ES$^+$) m/z 558 (M+1).

EXAMPLE 147

(3S,5R,6S)-3-[5-Fluoro-2-(2,2,2-trifluoroethoxy)phenyl)-6-phenyl-1-oxa-7-(1,2,4-triazolyl-3-methyl)-7-aza-spiro[4.5]decane Prepared from the compound of Example 19 according to the method of Example 5. $^1$H NMR (360 MHz, CDCl$_3$) δ 1.54 (1H, dt, J 13, 4 Hz), 1.58–1.64 (1H, m), 1.77 (1H, t, J 12 Hz), 1.94 (1H, dd, J 12, 12 Hz), 2.00–2.22 (2H, m), 2.37 (1H, m), 3.00–3.10 (1H, m), 3.13 (1H, t, J 8 Hz), 3.38–3.52 (2H, m), 3.74–3.92 (2H, m), 4.11 (1H, t, J 8 Hz), 4.22 (2H, q, J 8 Hz), 5.95 (1H, dd, J 9, 3 Hz), 6.66 (1H, dd, J 9, 4.5 Hz), 6.76 (1H, dt, J 9, 3 Hz), 7.30–7.37 (3H, m), 7.56 (2H, br s, ArH), and 7.92 (1H, s). m/z (ES$^+$) m/z 491 (M+1). Found C, 60.76; H, 5.28; N, 11.15 C$_{25}$H$_{26}$F$_4$N$_4$O$_2$ requires: C, 61.22; H, 5.34; N, 11.42%.

EXAMPLE 148

(5R,6S)-3-[2-Dimethylamino-5-(trifluoromethoxy)phenyl]-6-phenyl-1-oxa-7-(tert-butoxycarbonyl)aza-spiro[4.5]dec-3-ene Prepared from the compound of Description 78 and (5R,6S)-3-tributylstannyl-6-phenyl-1-oxa-7-(tert-butoxycarbonyl)aza-spiro[4.5]dec-3-ene according to the method of Example 1. $^1$H NMR (360 MHz, CDCl$_3$) δ 7.47 (2H, d, J 7.4 Hz), 7.29-6.94 (6H, m), 6.36 (1H, t, J 2.1 Hz), 5.12 (1H, s), 4.92 (1H, dd, J 12.6, 2.1 Hz), 4.61 (1H, dd, J 12.6, 2.1 Hz), 4.13 (1H, m), 3.14 (1H, m), 2.57 (6H, s), 2.05 (1H, m), 1.85 (3H, m), and 1.35 (9H, s).

EXAMPLE 149

(5R,6S)-3-[2-Dimethylamino-5-(trifluoromethoxy)phenyl]-6-phenyl-1-oxa-7-aza-spiro[4.5]dec-3-ene Prepared from the compound of Example 148 according to the method of Example 2.

EXAMPLE 150

(5R,6S)-3-[2-Dimethylamino-5-(trifluoromethoxy)phenyl]-6-phenyl-1-oxa-7-aza-spiro[4.5]decane Prepared from the compound of Example 149 according to the method of Example 3. m/z (ES$^+$) m/z 421 (M+1).

EXAMPLE 151

(±)-(3R*, 5R*,6S*)-3-(2-Methoxyphenyl)-6-phenyl-1-oxa-7-(phenylmethoxycarbonyl)aza-spiro[4.5]decane Formic acid (35 mL, 0.95 mmol) was added to a stirred degassed solution of (±)-(5R*,6S*)-6-phenyl-1-oxa-7-

(phenylmethoxycarbonyl)aza-spiro[4.5]dec-3-ene (Description 84, 125 mg, 0.36 mmol), palladium (II) acetate (8.3 mg, 0.036 mmol), tri-o-tolyphosphine (21 mg. 0.071 mmol), tributylamine (282 mL, 1.23 mmol) and 2-iodoanisole (112 mL, 0.87 mmol) in N,N-dimethylformamide (2 mL) at room temperature and the resulting mixture was heated at 100° C. for 2 h. A second equivalent of palladium (II) acetate, tri-o-tolyphosphine, tributylamine and 2-iodoanisole were added and the mixture stirred at 90° C. for 18 h. The mixture was cooled, filtered, diluted with diethyl ether (15 mL), washed with water (5 mL), hydrochloric acid (2M, 10 mL) and saturated aqueous sodium chloride (10 mL), dried ($MgSO_4$) and the solvent was evaporated under reduced pressure. The residue was chromatographed on silica gel, eluting with hexane/ethyl acetate(80:20) to give the title compound as a yellow oil (28 mg, 17%). $^1$H NMR (360 MHz, $CDCl_3$) δ 7.60 (2H, d, J 7.8 Hz), 7.18–7.32 (10 H, m), 6.92 (1H, t, J 7.5 Hz), 6.85 (1H, d, J 8.7 Hz), 5.42 (1H, s), 5.19 (1H, d, J 12.4 Hz), 5.16 (1H, d, J 12.6 Hz), 4.31 (1H, t, J 6.6 Hz), 4.02–4.10 (1H, m), 3.80–3.90 (2H, m), 3.79 (3H, s), 2.87 (1H, dt, J 4.4, 12.7 Hz), 2.54 (1H, dd, J 7.2, 12.7 Hz), 2.23 (1H, dt, J 5.5, 12.5 Hz), 1.95 (1H, dd, J 10.4, 12.6 Hz), and 1.64–1.84 (3H, m). m/z ($ES^+$) 458 (M+1).

EXAMPLE 152

(±)-(3R*,5R*,6S*, )-3-(2-Methoxyphenyl)-6-phenyl-1-oxa-7-aza-spiro[4.5]decane

Palladium on carbon (10%, 10 mg) was added to a stirred solution of (±)-(3R*,5R*,6S*)-3-(2-methoxyphenyl)-6-phenyl-1-oxa-7-(phenylmethoxycarbonyl)aza-spiro]4.5] decane (Example 151, 17 mg, 0.037 mmol) and cyclohexene (2 mL) in ethanol (10 mL) and the resulting suspension was heated at reflux for 5 h. The mixture was cooled, filtered and the solvent was evaporated under reduced pressure. The residue was purified by preparative layer chromatography on silica gel, eluting with dichloromethane/methanol/ammonia (95:5:1) to give the title compound as an orange oil (4 mg, 33%). $^1$H NMR (360 MHz, $CDCl_3$) δ 7.47 (2H, dd, J 1.9, 7.9 Hz), 7.27–7.35 (3 H, m), 7.10 (1H, dt, J 1.7, 7.8 Hz), 6.97 (1H, d, J 7.6 Hz), 6.81 (1H, t, J 7.5 Hz), 6.72 (1H, d, J 8.2 Hz), 3.94 (1H, t, J 7.6 Hz), 3.68 (1H, dd, J 7.9, 10.6 Hz), 3.63 (3H, s), 3.53 (3H, s), 3.16–3.26 (1H, m), 2.78 (1H, dt, J 2.7, 12.3 Hz), 2.28–2.38 (1H, m), 2.15 (1H, dd, J 8.0, 12.4 Hz), 1.92–2.10 (2H, m), and 1.56–1.70 (4H, m). m/z ($ES^+$) 324 (M+1).

EXAMPLE 153

(3R,5R,6S)-3-(2-Methoxy-5-(trifluoromethoxy) phenyl)-6-phenyl-1-oxa-7-aza-spiro[4.5]decane Triethylsilane (0.1 mL, 0.6 mmol) was added to a solution of (5R,6S)-3-(2-methoxy-5-(trifluoromethoxy)phenyl)-6-phenyl-1-oxa-7-aza-spiro[4.5]dec-2-ene (Description 92, 14 mg, 0.03 mmol) in trifluoroacetic acid (1 mL) and the mixture was stirred at room temperature for 2 h. Additional triethylsilane (0.1 mL, 0.6 mmol) was added and the mixture was stirred at room temperature for 15 h. The solvent was evaporated under reduced pressure and the residue was azeotroped with toluene (2× 10 mL). Saturated aqueous sodium carbonate was added and the mixture was extracted with dichloromethane (3×10 mL). The combined organic fractions were washed with brine (20 mL), dried ($MgSO_4$) and the solvent was evaporated under reduced pressure. The residue was purified by preparative thin layer chromatography on silica gel, eluting with dichloromethane/methanol/ ammonia (120:8:1) to give a gum (6 mg). HPLC analysis of the gum [HIPRB column (250×4.6 mm); 40% MeCN in 25 mM $KH_2PO_4$, 0.2% triethylamine. pH 3.1, 210 nm] showed that it consisted of a mixture of (5R,6)-3-(2-methoxy-5-(trifluoromethoxy)phenyl)-6-phenyl-1-oxa-7-aza-spiro[4.5] dec-3-ene, (3S,5R,6S)-3-(2-methoxy-5-(trifluoromethoxy) phenyl)-6-phenyl-1-oxa-7-aza-spiro[4.5]decane and (3R, 5R,6S)-3-(2-methoxy-5-(trifluoromethoxy)phenyl)-6-phenyl-1-oxa-7-aza-spiro[4.5]decane (ratio; 1.5:2.5:1).

EXAMPLE 154

(3R,5R,6S)-3-(2-Methoxy-5-(trifluoromethoxy) phenyl)-6-phenyl-1-oxa-7-aza-spiro[4.5]decane Triethylsilane (0.25 mL, 1.6 mmol) was added to a solution of (5R,6S)-3-(2-methoxy-5-(trifluoromethoxy) phenyl)-6-phenyl-1-oxa-7-aza-spiro[4.5]dec-3-ene (Description 92, 32 mg, 0.08 mmol) in trifluoroacetic acid (2 mL) and the solution was stirred at 50° C. for 16 h. The solvent was evaporated under reduced pressure and the residue was azeotroped with tolune (2×10 mL). Saturated aqueous sodium carbonate was added and the mixture was extracted with dichloromethane (4×20 mL). The combined organic fractions were washed with brine (20 mL), dried ($MgSO_4$) and the solvent was evaporated under reduced pressure. The residue was purified by preparative thin layer chromatography on silica gel, eluting with dichloromethane/ methanol/ammonia (12:8:1) to give a gum (6 mg). HPLC analysis of the gum [HIPRB column (250×4.6 mm); 40% MeCN in 25 mM $KH_2PO_4$, 0.2% triethylamine. pH 3.1, 210 nm] showed that it consisted of a mixture of (3S,5R,6S)-3-(2-methoxy-5-(trifluoromethoxy)phenyl)-6-phenyl-1-oxa-7-aza-spiro[4.5]decane and (3R,5R,6S)-3(2-methoxy-5-(trifluoromethoxy)phenyl)-6-phenyl-1-oxa-7-aza-spiro[4.5] decane (ratio; 2:1).

EXAMPLE 155

(3R,5R,6S)-3,6-Bis(phenyl)-1-oxa-7-(tert-butoxycarbonyl)aza-spiro[4.5]decane (2S,3R,2'R)-3-(1-tert-Butoxycarbonyl-3-hydroxy-2-phenylpiperidin-3-yl)-2-phenylpropan-1-ol (Description 95, 13 mg, 0.03 mmol) was dissolved in dichloromethane (1 mL). Pyridine (0.038 mL, 0.045 mmol) was added, followed by methanesulfonyl chloride (3.2 mL, 0.039 mmol) and the mixture was stirred at ambient temperature for 72 h. Dichloromethane (10 mL) was added and the mixture was washed with water (10 mL), dried ($Na_2SO_4$) and the solvent was evaporated under reduced pressure. The residue was purified by preparative thin layer chromatography on silica, eluting with ethyl acetate/hexane (25:75) to give the title compound as an oil (6.4 mg). $^1$H NMR (360 MHz, $CDCl_3$) δ 7.61-7.59 (2H, m), 7.35-7.30 (7.30 (4H, m), 7.27-7.22 (4H, m), 5.34 (1H, s), 4.31 (1H, t, J 8.1 Hz), 4.00-3.96 (1H, m), 3.89 (1H, t, J 8.9 Hz), 3.62-3.54 (1H, m), 2.80-2.72 (1H, m), 2.70-2.65 (1H, m), 2.29-2.21 (1H, m), 1.92-1.85 (1H, m), 1.81-1.78 (1H, m), 1.70-1.54 (3H, m), and 1.47 (9H, s). m/z ($ES^+$) 394 (M+1).

EXAMPLE 156

(3R,5R,6S)-3,6-Bis(phenyl)-1-oxa-7-aza-spiro[4.5] decane

Prepared from the compound of Example 155 according to the method of Example 181. $^1$H NMR (360 MHz, $CDCl_3$) δ 7.51-7.48 (2H, m), 7.35-7.33 (3H, m), 7.21-7.13 (3H, m), 6.91-6.88 (2H, m), 4.04-3.99 (1H, t, J 7.9 Hz), 3.66 (1H, s), 3.66-3.60 (1H, m), 3.26-3.22 (1H, m), 2.75 (1H, br s), 2.24-2.11 (2H, m), 2.03-1.94 (2H, m), and 1.73-1.61 (3H, m). m/z (ES$^+$) 294 (M+1).

EXAMPLE 157

(3R,5R,6S)-3-(2-Methoxyphenyl)-6-phenyl-1-oxa-7-(tert-butoxycarbonyl)aza-spiro[4.5]decane Methanesulfonyl chloride (10 mL, 0.14 mmol) was added to a stirred solution of triethylamine (42 mL, 0.3 mmol) and the product of Description 39 (19 mg, 0.043 mmol) in dichloromethane (2 mL) at 0° C. The mixture was allowed to warn to room temperature, stirred for 18 h., diluted with dichloromethane (20 mL), washed with hydrochloric acid (2M, 10 mL) and saturated aqueous sodium carbonate (10 mL), dried (MgSO$_4$) and the solvent was evaporated under reduced pressure. The residue was taken up in tetrahydrofuran (3 mL) and heated with sodium hydride (60% dispersion in oil, 100 mg) at reflux for 18 h., cooled, poured into hydrochloric acid solution (2M, 20 mL) and extracted with ethyl acetate (2×20 mL). The combined organic fractions were washed with saturated aqueous sodium chloride (10 mL), dried (MgSO$_4$) and the solvent was evaporated under reduced pressure. The residue was chromatographed on silica gel, eluting with hexane/ethyl acetate (80:20) to give (3R,5R,6S)-3-(2-methoxyphenyl)-6-phenyl-1-oxa-7-(tert-butoxycarbonyl)aza-spiro[4.5]decane and (3S,5R,6S)-3-(2-methoxyphenyl)-6-phenyl-1-oxa-7-(tert-butoxycarbonyl)aza-spiro[4.5]decane as a 1:3 mixture (8 mg, 44%). $^1$H NMR (360 MHz, CDCl$_3$) δ 7.61 (2H, d, J 7.6 Hz, 3R isomer), 7.57 (2H, d, J 7.5 Hz, 3S isomer), 7.05-7.34 (5H, m, 3Rand 3S isomers), 6.80–6.98 (2H, m, 3R and 3S isomers), 5.37 (1H, s, 3R isomer), 5.25 (1H, s, 3S isomer), 4.31 (1H, t, J 7.4 Hz 3R isomer), 4.21 (1H, t, J 7.2 Hz, 3S isomer), 3.95–4.04 (1H, m, 3R and 3S isomers), 3.82 (3H, s, 3R isomer), 3.81 (3H, s, 3S isomer), 3.64–3.81 (2H, m, 3R and 3R isomers), 2.85 (1H, dt, J 5.9 and 12.1 Hz, 3S isomer), 2.67 (1H, dt, J 4.9, 12.7 Hz, 3R isomer), 2.59 (1H, dd, J 7.3 and 12.7 Hz, 3R isomer), 2.37 (1H, dd, J 8.0 and 12.6 Hz, 3S isomer), 2.21 (1H, dd, J 9.1, 12.6 Hz, 3S isomer), 2.08–2.23 (1H, m, 3R and 3S isomers), 1.93 (1H, dd, J 10.4, 12.4 Hz, 3R isomer), 1.64–1.78 (3H, m, 3R and 3S isomers), 1.47 (9H, s, 3R isomer), and 1.38 (9H, s, 3S isomer). m/z (ES$^+$) 424 (M+1).

EXAMPLE 158

(3R,5R,6S)-3-(2-Methoxyphenyl)-6-phenyl-1-oxa-7-aza-spiro[4.5]decane

Prepared as a mixture of (3R,5R,6S)-3-(2-methoxyphenyl)-6-phenyl-1-oxa-7-aza-spiro[4.5]decane and (3S,5R,6S)-3-(2-methoxyphenyl)-6-phenyl-1-oxa-7-aza-spiro[4.5]decane from the compound of Example 157 according to the method of Example 181. $^1$H NMR (360 MHz, CDCl$_3$) δ 7.51–7.59 (2H, m, 3R and 3S isomers), 7.32–7.45 (3H, m, 3R and 3S isomers), 7.05–7.13 (1H, m, 3R and isomers), 6.97 (1H, d, J 7.6 Hz, 3R isomer), 6.81 (1H, t, J 7.5 Hz, 3R isomer), 6.71–6.82 (1H, m, 3R and 3S isomers), 6.69 (1H, t, J 7.5 Hz, 3S isomer), 6.43 (1H, d, J 7.6 Hz, 3S isomer), 4.09 (1H, t, J 7.8 Hz, 3S isomer), 3.94 (1H, t, J 7.6 Hz, 3R isomer), 3.67–3.87 (1H, m, 3R and 3S isomers), 3.68 (4H, s, 3S isomer), 3.63 (3H, s, 3R isomer), 3.53 (1H, s, 3R isomer), 3.17–3.25 (1H, m, 3R and 3S isomers), 2.75–2.84 (1H, m, 3R and 3S isomer), and 1.55–2.37 (8H, m, 3R and 3S isomers). m/z (ES$^+$) 324 (M+1).

EXAMPLE 159

(3R,5R,6S)-3-(2-Methoxyphenyl)-6-phenyl-1-oxa-7-(tert-butoxycarbonyl)-aza-spiro[4.5]decane To a solution of (2S,3R,2'R)-3-(1-tert-butoxycarbonyl-3-hydroxy-2-phenylpiperidin-3-yl)-2-(2-methoxyphenyl) propane-1-ol (Description 101, 0.0073 g, 0.166 mmol) in dichloromethane (1 mL) and anhydrous pyridine (0.067 mL) was added methanesulfonyl chloride (0.015 mL, 0.2 mmol). The solution was stirred at room temperature for 16 h., then pyridine (1 mL) was added and the solution was heated in an oil bath at 80° C. for a further 2 h. The solvent was evaporated under reduced pressure and the residue was dissolved in dilute aqueous copper sulphate solution and ethyl acetate. The organic phase was washed with water and saturated brine, dried (MgSO$_4$) and the solvent was evaporated under reduced pressure. The residue was purified by chromatography on silica gel, eluting with hexane/EtOAc (95:5) to give the title compound (0.55 mg). $^1$H NMR (360 MHz, CDCl$_3$) δ 7.56 (2H, d J 7.9 Hz), 7.25 (2H, t J 7.2 Hz), 7.20-7.14 (1H, m), 6.88 (1H, td J 7.5 Hz and 1 Hz), 6.79 (1H, d J 7.8 Hz), 5.30 (1H, s), 4.24 91H, t J 7.4 Hz), 3.90-3.79 (3H, m), 3.75 (3H, s), 2.67 (1H, td J 12.0 Hz and 4.5 Hz), 2.53 (1H, dd J 12.6 Hz and 7.2 Hz), 2.14 (1H, td, J 12.5 Hz and 5.7 Hz), 1.85 (1H, dd J 12.4 Hz and 10.4 Hz), 1.65 (1H, broad d J 12.3 Hz), 1.63-1.47 (2H, m), and 1.40 (9H, s). m/z (ES$^+$) 424 (M+1).

EXAMPLE 160

(3R,5R,6S)-3-(2-Methoxyphenyl)-6-phenyl-1-oxa-7-aza-spiro[4.5]decane Hydrochloride Prepared from the compound of Example 159 according to the method of Example 188, mp 243–253° C. $^1$H NMR (360 MHz, CD$_3$OD) δ 7.57 (2H, m), 7.53 (3H, m), 7.11 (1h, t J 8.1 Hz), 6.95 (1H, d H 7.7 Hz), 6.80 (2H, m), 4.27 (1H, s), 4.02 (1H, t J 7.64), 3.77 (1H, dd J 10.5 Hz and 8.3 Hz), 3.63 (3H, s), 3.40 (1H, broad d), 3.18 (1H, broad t), 2.34-2.21 (3H, m), 2.07 (1H, m), and 1.96-1.83 (3H, m).

EXAMPLE 161

(3R,5R,6S)-3-(2-Methoxy-5-(trifluoromethoxy)phenyl)-6-phenyl-1-oxa-7-(tert-butoxycarbonyl)aza-spiro[4.5]decan-2-one A mixture of (5R,6S)-3-(2-methoxy-5-(trifluoromethoxy)phenyl)-6-phenyl-1-oxa-7-(tert-butoxycarbonyl)aza-spiro[4.5]dec-3-en-2-one (Example 52, 100 mg, 0.19 mmol) and palladium acetate (10 mg) in N,N'-dimethylformamide (1 mL) was degassed with nitrogen for 30 min. Potassium formate (42 mg, 0.50 mmol) was added and the mixture was heated at 80° C. for 16 h. The mixture was poured into water (10 mL) and extracted with ethyl acetate (2×10 mL). The combined organic fractions were dried (Na$_2$SO$_4$) and the solvent was evaporated under reduced pressure. The residue was purified by chromatography on silica gel to give the title compound as a colorless solid (44 mg, 0.08 mmol, 44%). $^1$H NMR showed this to be a 1:1 mixture of (3S,5R,6S)-and (3R,5R,6S)-diastereoisomers which were separated by preparative liquid chromatography using a KR60 column, eluting with 5% ethanol/hexane containing 0.1% DEA to give (3R,5R,6S)-3-(2-methoxy-5-(trifluoromethoxy)phenyl)-6-phenyl-1-oxa-7-(tert-butoxycarbonyl)aza-spiro[4.5]decan-2-one. $^1$H NMR (250 MHz, CDCl$_3$) δ 7.50–7.53 (2H, m), 7.26–7.39 (3H, m), 7.14 (1H, dd, J 2.59, 8.96 Hz), 7.02 (1H, d, J 2.59 Hz), 6.88 (1H, d, J 8.96 Hz), 5.35 (1H, s), 4.00–4.05 (1H, m), 3.85 (3H, s), 3.70 (1H, t, J 11.02 Hz), 2.70–2.97 (2H, m), 2.38–2.50 (1H, m), 2.22 (1H, dd, J 11.32, 12.97 Hz), 1.72–1.92 (3H, m), and 1.46 (9H, s); and (3S,5R,6S)-3-(2-methoxy-5-(trifluoromethoxy)phenyl)-6-phenyl-1-oxa-7-(tert-butoxycarbonyl)aza-spiro[4.5]decan-2-one, $^1$H NMR (250 MHz, CDCl$_3$) δ 7.50-7.53 (2H, m), 7.26-7.39 (3H, m), 7.13 (1H, dd, J 2.91, 8.97 Hz), 6.90 (1H, d, J 2.91

Hz), 6.83 (1H, d, J 8.97 Hz), 5.31 (1H, br s), 4.02–4.10 (1H, m), 3.92 (1H, t, J 10.56 Hz), 3.64 (3H, s), 2.91–3.02 (1H, m), 2.67 (1H, dd, J 10.04, 12.98 Hz), 2.29–2.52 (2H, m), 1.80–1.87 (3H, m), and 1.36 (9H, s).

EXAMPLE 162

(3R,5R,6S)-3-(2-Methoxy-5-(trifluoromethoxy) phenyl)-6-phenyl-1-oxa-7-aza-spiro[4.5]decan-2-one Hydrochloride Prepared from the compound of Example 161 according to the method of Example 181. m.p. 244–245° C. $^1$H NMR (360 MHz, DMSO-d$_6$) δ 10.20 (1H, br s), 9.40 (1H, br s), 7.60–7.62 (2H, m), 7.52–7.54 (3H, m), 7.23 (1H, dd, J 2.61, 9.03 Hz), 7.04 (1H, d, J 9.03 Hz), 6.88 (1H, d, J 2.61 Hz), 4.67 (1H, br s), 3.34–3.38 (1H, m), 3.10–3.12 (1H, m), 2.61 (1H, dd, J 9.78, 12.65 Hz), and 1.93–2.20 (6H, m). m/z (ES$^+$) 422 (M+1).

EXAMPLE 163

(3R,5R,6S)- and (3S,5R,6S)-3-(2-Hydroxy-5-(trifluoromethoxy)phenyl)-6-phenyl-1-oxa-7-(tert-butoxycarbonyl)aza-spiro[4.5]decane (5R,6S)-3-(2-Benzyloxy-5-(trifluoromethoxy)phenyl)-6-phenyl-1-oxa-7-(tert-butoxycarbonyl)aza-spiro[4.5]dec-3-ene (Example 35, 3.88 g) was dissolved in ethyl acetate (15 mL) and methanol (15 mL). Palladium hydroxide on carbon (1.00 g) was added and the suspension was shaken under a hydrogen atmosphere (50 psi) for 72 h. The mixture was filtered and the solvent was evaporated under reduced pressure. The residue was purified by medium pressure chromatography on silica gel, eluting with hexane/ethyl acetate (75:25) to give (3R,5R,6S)-3-(2-hydroxy-5-(trifluoromethoxy)phenyl)-6-phenyl-1-oxa-7-(tert-butoxycarbonyl)aza-spiro[4.5]decane (191 mg), $^1$H NMR (250 MHz, CDCl$_3$) δ 7.70 (2H, d, J 7.3 Hz), 7.33 (2H, t, J 7.3 Hz), 7.26 (1H, d, J 7.3 Hz), 7.05 (1H, br s), 6.96 (2H, m), 6.82 (1H, d, J 9.4 Hz), 5.43 (1H, s), 4.27 (1H, m), 4.01 (1H, m), 3.95 (1H, m), 3.73 (1H, m), 2.73 (2H, m), 2.33 (1H, m), 1.87-1.58 (4H, m);and 1.50 (9H, s). and (3S,5R,6S)-3-(2-hydroxy-5-(trifluoromethoxy)phenyl)-6-phenyl-1-oxa-7-(tert-butoxycarbonyl)aza-spiro[4.5]decane (2.3 g), $^1$H NMR (360 MHz, CDCl$_3$) δ 1.38 (9H, s), 1.73 (2H, m), 1.81 (1H, m), 2.18 (2H, m), 2.50 (1H, m), 2.81 (1H, m), 3.62 (1H, t, J 7.2 Hz), 3.92 (1H, m), 3.98 (1H, d, J 13.2 Hz), 4.23 (1H, m), 5.33 (1H, s), 6.75 (1H, d, J 8.5 Hz), 6.94 (2H, m), 7.25 (1H, m), 7.31 (2H, m), and 7.55 (2H, d, J 7.8 Hz).

EXAMPLE 164

(3R,5R,6S)-3-(2-Methoxy-5-(trifluoromethoxy) phenyl)-6-phenyl-1-oxa-7-(tert-butoxycarbonyl)aza-spiro[4.5]decane (3R,5R,6S)-3-(2-Methoxy-5-(trifluoromethoxy)phenyl)-6-phenyl-1-oxa-7-(tert-butoxycarbonyl)aza-spiro[4.5]decane (Example 163, 180 mg) was dissolved in dimethylformamide (2 mL) and sodium hydride (60% dispersion in minimal oil, 23 mg) was added. After the effervescence had ceased, methyl iodidie (0.1 mL) was added and the mixture was stirred at room temperature for 3 h. Water (5 mL) was added dropwise to the reaction solution. The mixture was diluted with water (20 mL) and extracted with ethyl acetate (3×10 mL). The combined organic fractions were washed with brine, dried (MgSO$_4$) and the solvent was evaporated under reduced pressure to give the title compound as an oil (235 mg). $^1$H NMR (250 MHz, CDCl$_3$) δ 7.61 (2H, d, J 7.9 Hz), 7.36-7.24 (3H, m), 7.09 (2H, m), 6.82 (1H, d, j 8.7 Hz), 5.35 (1H, s), 4.30 (1H, m), 3.98 (1H, m), 3.89-3.78 (2H, m), 3.83 (3H, s), 2.77 (1H, m), 2.59 (1H, m), 2.22 (1H, m), 1.90, 1.66 (4H, m), 1.47 (9H, s).

EXAMPLE 165

(3R,5R,6S)-3-(2-Methoxy-5-(trifluoromethoxy) phenyl)-6-phenyl-1-oxa-7-aza-spiro[4.5]decan Hydrochloride Prepared from the compound of Example 164 according to the method of Example 181. $^1$H NMR (500 MHz, CD$_3$OD) δ 1.88 (1H, dd, J 12.6, 10.9 Hz), 1.99 (2H, m), 2.13 (1H, d, J 15.4 Hz), 2.34 (2H, m), 2.39 (1H, m), 3.25 (1H, dt, J 15.8, 3.3 Hz), 3.45 (1H, m), 3.72 (3H, s), 3.79 (1H, dd, J 8.3, 1.2 Hz), 4.09 (1H, t, J 7.5 Hz), 4.48 (1H, s), 6.94 (2H, m), 7.10 (1H, d, J 8.9 Hz), 7.58 (3H, t, J 2.6 Hz), and 7.64 (2H, t, J 3.6 Hz).

EXAMPLE 166

(3R, 5R,6S)-7-Benzyl-3-(2-methoxy-5-(trifluoromethoxy)phenyl)-6-phenyl-1-oxa-7-aza-spiro[4,5]decane Hydrochloride (3R,5R,6S)-3-(2-Methoxy-5-(trifluoromethoxy)phenyl)-6-phenyl-1-oxa-7-aza-spiro[4,5]decane hydrochloride (Example 165, 100 mg, 0.2 mmol) and potassium carbonate (38 mg) were dissolved in dimethyl formamide (0.5 mL). Benzyl bromide (0.3 mL) was added and the mixture was stirred at room temperature overnight, then at 60° C. for 3 h. The mixture was cooled, diluted with water (10 mL) and extracted into ether (3×10 mL). The combined organic fractions were washed with brine, dried (MgSO$_4$) and the solvent was evaporated under reduced pressure. The residue was dissolved in ethyl acetate (5 mL) and ethereal hydrogen chloride (1 M, 1 mL) was added. The solid was collected and dried in vacuo to give the title compound as a crystalline solid (19 mg). $^1$H NMR (360 MHz, d$_6$-DMSO) δ 1.75 (3H, m), 2.01 (2H, m), 2.22 (2H, m), 2.96 (1H, m) 3.63 (3H, s), 3.67 (1H, m), 3.92 (1H, m), 4.01 (1H, m), 4.41 (1H, d, J 9.74 Hz), 6.92 (1H, d, J 8.9 Hz), 7.05 (1H, s), 7.13 (1H, d, J 8.65 Hz), 7.31 (2H, d, J 6.53 Hz), 7.42 (3H, m), 7.60 (4H, m), and 7.91 (1H, m).

EXAMPLE 167

(3R, 5R,6S)- and (3S,5R,6S)-3-(2-Hydroxy-5-(trifluoromethoxy)phenyl)-6-phenyl-1-oxa-7-(tert-butoxycarbonyl)aza-spiro[4,5]decane Prepared from the compound of Example 45 according to the method of Example 163, (3R,5R,6S)-3-(2-Hydroxy-5-(trifluoromethyl)phenyl)-6-phenyl-1-oxa-7-(tert-butoxycarbonyl)aza-spiro[4,5]decane, $^1$H NMR (250 MHz, CDCl$_3$) δ 1.51 (9H, s), 1.58–1.75 (2H, m), 1.82–1.88 (2H, m), 2.33 (1H, dt, J 4, 13 Hz), 2.70 (1H, dd, J 8.6, 13 Hz), 2.79 (1H, dt, J 3, 13 Hz), 3.84 (1H, qn), 3.93–3.97 (2H, m), 4.31 (1H, t, J 9 Hz), 5.44 (1H, s,), 6.89 (1H, d, J 9 Hz), 7.23–7.35 (5H, m), and 7.58–7.60 (2H, m). m/z (ES$^+$) 478 (M+1). (3S,5R,6S)-3-(2-Hydroxy-5-(trifluoromethyl) phenyl)-6-phenyl-1-oxa-7-(tert-butoxycarbonyl)aza-spiro [4.5]decane, $^1$H NMR (360 MHz, CDCl$_3$) δ 1.34 (9H, s), 1.72–1.82 (3H, m), 2.10–2.21 (2H, m), 2.53 (1H, dd, J 9, 13 Hz), 2.79–2.88 (1H, m), 3.65 (1H, qn, J 8.6 Hz), 3.94–3.98 (2H, m), 4.24 (1H, dd, J 7, 9 Hz), 5.33 (1H, s,), 6.83 (1H, d, J 9 Hz), 7.01 (1H, s), 7.23–7.34 (5H, m), and 7.55 (2H, d, J 7.5 Hz). m/z (ES$^+$) 478 (M+1).

EXAMPLE 168

(3R,5R,6S)-3-(2-Methoxy-5-(trifluoromethyl)
phenyl)-6-phenyl-1-oxa-7-(tert-butoxycarbonyl)aza-
spiro[4,5]decane Prepared from (3R,5R,6S)-3-(2-hydroxy-5-(trifluoromethyl)phenyl)-6-phenyl-1-oxa-7-(tert-butoxycarbonyl)aza-spiro[4,5]decane (Example 167) according to the method of Example 164. m/z (ES$^+$) 492 (M+1).

EXAMPLE 169

(3R,5R,6S)-3-(2-Methoxy-5-(trifluoromethoxy)
phenyl)-6-phenyl-1-oxa-7-aza-spiro[4,5]decane
Hydrochloride Prepared from the compound of Example 168 according to the method of Example 181. $^1$H NMR (500 MHz, CDCl$_3$+CD$_3$OD)δ1.71–1.78 (3H, m), 1.94–1.98 (1H, m), 2.13–2.24 (3H, m), 3.00 (1H, dt, J 3, 12 Hz), 3.42 (1H, dd, J 4, 12 Hz), 3.61 (3H, s), 3.67 (1H, dd, J 8, 14 Hz), 3.96–4.01 (2H, m), 6.71 (1H, d, J 8 Hz), 7.04 (1H, d, J 2 Hz), 7.32 (1H, dd, J 2, 8 Hz), 7.38–7.36 (3H, m), and 7.42–7.44 (2H, m). m/s (ES$^+$) 392 (M+1).

EXAMPLE 170

(3R,5R,6S)-3-(2-Benzyloxy-5-(trifluoromethoxy)
phenyl)-6-phenyl-1-oxa-7-(tert-butoxycarbonyl)aza-
spiro[4,5]decane A mixture of 2-benzyloxy-5-(trifluoromethoxy) iodobenzene (Description 103, 21.8 g, 55.2 mmol), (5R,6S)-6-phenyl-1-oxa-7-(tert-butoxycarbonyl)aza-spiro[4,5]dec-3-ene (Description 86, 7.0 g, 22.1 mmol), tetra-n-butylammonium chloride (6.18 g, 22.2 mmol), lithium chloride (9.35 g, 0.22 mol) and potassium formate (5.64 g, 67.0 mmol) in dimethylformamide (100 mL) was degassed with a firestone valve (5 x). Palladium acetate (491 mg, 2.2 mmol) was added and the mixture was degassed with a firestone valve (5 x). The mixture was stirred at 60° C. for 15 h., then further 2-benzyloxy-5-(trifluoromethoxy) iodobenzene (Description 103, 4.32 g, 11.0 mmol), potassium formate (2.78 g, 33.5 mmol) and palladium acetate (260 mg, 1.1 mmol), were added. The mixture was stirred at 60° C. for 22 h., cooled and filtered. The solvent was evaporated under reduced pressure, water (600 mL) was added and the mixture was extracted with ethyl acetate (2×300 mL). The combined organic fractions were washed with brine (300 mL), dried (MgSO$_4$) and the solvent was evaporated under reduced pressure. The residue was purified by flash column chromatography on silica gel, eluting with hexane/CH$_2$Cl$_2$ (75:25 increasing to 0:100) then CH$_2$Cl$_2$/EtOAc (95.5), to give the title compound (9.42 g, 73%). $^1$H NMR (360 MHz, CDCl$_3$) δ7.56 (2H, d, J 7.7 Hz), 7.40–7.20 (8H, m), 7.14 (1H, d, J 2.0 Hz), 7.00 (1H, dd, J 8.9, 2.0 Hz), 6.88 (1H, d, J 8.9 Hz), 5.30 (1H, s), 5.08 (2H, s), 4.27 (1H, m), 3.97 (1H, m), 3.87 (2H, m), 2.78 (1H, m), 2.56 (1H, m), 2.15 (1H, m), 1.96 (1H, m), 1.67 (3H, m), and 1.42 (9H, s).

EXAMPLE 171

(3R,5R,6S)-3-(2-Hydroxy-5-(trifluoromethoxy)
phenyl)-6-phenyl-1-oxa-7-(tert-butoxycarbonyl)aza-
spiro[4,5]decane Palladium on carbon (10%, 0.59 g) was added to a solution of (3R,5R,6S)-3-(2-benzyloxy-5-(trifluoromethoxy)phenyl-6-phenyl-1-oxa-7-(tert-butoxycarbonyl)aza-spiro[4,5]decane (Example 170, 6.10 g, 10.5 mmol) in methanol-water (99:1, 200 mL) and the mixture was stirred under hydrogen (50 psi.) for 72 h. The mixture was filtered, washing with ethanol, and the solvent was evaporated under reduced pressure. The residue was purified by flash column chromatography on silica gel, eluting with CH$_2$Cl$_2$/EtOAc (99:1 increasing to 90:10) to give the title compound. $^1$H NMR (360 MHz, CDCl$_3$) δ7.70 (2H, d, J 7.3 Hz), 7.33 (2H, t, J 7.3 Hz), 7.26 (1H, d, J 7.3 Hz), 7.05 (1H, br s), 6.96 (2H, m), 6.82 (1H, d, J 9.4 Hz), 5.43 (1H, s), 4.27 (1H, m), 4.01 (1H, m), 3.95 (1H, m), 3.73 (1H, m), 2.73 (2H, m), 2.33 (1H, m), 1.87–1.58 (4H, m) and 1.50 (9H, s).

EXAMPLE 172

(3R,5R,6S)-3-[2-Hydroxy-5-(trifluoromethoxy)
phenyl]-6-phenyl-1-oxa-7-aza-spiro[4,5]decane
Hydrochloride Prepared from the compound of Example 171 according to the method of Example 181. $^1$H NMR (360 MHz, D$_2$O) δ1.83–2.35 (7H, m), 3.20 (1H, m), 3.50 (1H, m), 3.73 (1H, m), 4.05 (1H, t, J 8.0 Hz), 4.29 (1H, s), 6.79 (1H, d, J 9.4 Hz), 7.02 (2H, m), and 7.54 (5H, br s). m/s (ES$^+$) 394 (M+1).

EXAMPLE 173

(3R,5R,6S)-3-(2-Benzyloxy-5-(trifluoromethoxy)
phenyl)-6-(4-fluorophenyl)-1-oxa-7-(tert-
butoxycarbonyl)aza-spiro[4,5]decane Prepared from the compound of Description 103 and (5R,6S)-6-(4-fluorophenyl)-1-oxa-7-(tert-butoxycarbonyl) aza-spiro[4,5]dec-3-ene (Description 90) according to the method of Example 170. $^1$H NMR (360 MHz, CDCl$_3$) δ7.54–6.80 (12H, m), 5.25 (1H, s), 5.08 (2H, s), 4.26 (1H, m) 3.97 (1H, m), 3.86 (2H, m), 2.76 (1H, m), 2.53 (1H, m), 2.10 (1H, m), 1.97 (1H, m), 1.66 (3H, m), and 1.42 (9H, s). m/z (ES$^+$) 546 (M+1—C$_4$H$_8$).

EXAMPLE 174

(3R,5R,6S)-3-(2-Hydroxy-5-(trifluoromethoxy)
phenyl)-6-(4-fluorophenyl)-1-oxa-7-(tert-
butoxycarbonyl)aza-spiro[4,5]decane Prepared from the compound of Example 173 according to the method of Example 171. $^1$H NMR (360 MHz, CDCl$_3$) δ1.49 (9H, s), 1.72 (1H, m), 1.83 (3H, m), 2.25 (1H, td, J 12.5, 4.8 Hz), 2.69 (2H, m), 3.72 (1H, qn), 3.98 (1H, m), 4.01 (1H, dd, J 9.4, 5.4 Hz), 4.25 (1H, dd, J 9.3, 7.4 Hz), 5.39 (1H, s), 6.81 (1H, d, J 9.4 Hz), 6.98 (4H, m), and 7.57 (2H, dd, J 8.7, 5.6 Hz).

EXAMPLE 175

(3R,5R,6S)-3-[2-Benzyloxy-5-(difluoromethoxy)
phenyl]-6-phenyl-1-oxa-7-(tert-butoxycarbonyl)aza-
spiro[4,5]decane Prepared from the compound of Description 105 and (5R,6S)-6-phenyl-1-oxa-7-(tert-butoxycarbonyl)aza-spiro [4,5]dec-3-ene (Description 86) according to the method of Example 170. $^1$H NMR (360 MHz, CDCl$_3$) δ1.42 (9H, s), 1.65 (3H, m), 1.98 (1H, m), 2.15 (1H, m), 3.85 (2H, m), 3.97 (1H, m), 4.28 (1H, m), 5.07 (2H, m), 5.30 (1H, s), 6.42 (1H, t, J 74 Hz), 6.85 (1H, d, J 8.8 Hz), 6.95 (1H, dd, J 8.8, 2.8 Hz), 7.07 (1H, d, J 2.8 Hz), 7.22–7.39 (8H, m), and 7.56 (2H, m). m/z (ES$^+$) 566 (M+1).

EXAMPLE 176

(3R, 5R,6S)-3-[5-Difluoromethoxy)-2-hydroxyphenyl]-6-phenyl-1-oxa-7-(tert-butoxycarbonyl)aza-spiro[4,5]decane Prepared from the compound of Example 175 according to the method of Example 171. $^1$H NMR (360 MHz, CDCl$_3$) δ1.50 (9H, s), 1.64 (1H, m), 1.70 (1H, m), 1.83 (2H, m), 2.33 (1H, dt, J 4.8, 13.0 Hz), 2.72 (2H, m), 3.71 (1H, m), 3.94 (1H, m), 4.02 (1H, dd, J 9.4, 5.3 Hz), 4.27 (1H, dd, J 9.4, 7.4 Hz), 5.43 (1H, s), 6.40 (1H, t, J 74 Hz), 6.80 (1H, m), 6.89 (2H, m), 7.27 (1H, m), 7.33 (2H, m), and 7.60 (2H, m). m/z (ES$^+$) 476 (M+1).

EXAMPLE 177

(3R,5R,6S)-3-(2-Benzyloxy-5-fluorophenyl)-6-phenyl-1-oxa-7-(tert-butoxycarbonyl)aza-spiro[4,5]decane Prepared from the compound of Description 107 and (5R,6S)-6-phenyl-1-oxa-7-(tert-butoxycarbonyl)aza-spiro[4,5]dec-3-ene (Description 86) according to the method of Example 170. 7.56 (2H, d, J 7.4 Hz), 7.39–7.21 (8H, m), 7.01 (1H, dd J 9.4, 2.7 Hz), 6.84 (2H, m), 5.30 (1H, s), 5.05 (2H, s), 4.27 (1H, m), 3.97 (1H, m), 3.84 (2H, m), 2.78 (1H, m), 2.56 (1H, m), 1.95 (1H, m), 1.66 (3H, m), and 1.42 (9H, s), m/z (ES$^+$) 518 (M+1).

EXAMPLE 178

(3R,5R,6S)-3-(5-Fluoro-2-hydroxyphenyl)-6-phenyl-1-oxa-7-(tert-butoxycarbonyl)aza-spiro[4,5]decane Prepared from the compound of Example 177 according to the method of Example 171. $^1$H NMR (360 MHz, CDCl$_3$) δ1.49 (9H, s), 1.59–1.69 (2H, m), 1.80–1.86 (2H, m), 2.31 (1H, dt, J 13.0, 4.9 Hz), 2.67–2.79 (2H, m), 3.70–3.74 (1H, m), 3.93–4.01 (2H, m), 4.24–4.29 (1H, m), 5.42 (1H, s), 6.73–6.85 (3H, m), 7.23–7.35 (3H, m), and 7.60 (2H, d, J 7.5 Hz), m/z (ES$^+$) 428 (M+1).

EXAMPLE 179

(3R,5R,6S)-3-(5-Benzyloxy-2-isopropoxyphenyl)-6-phenyl-1-oxa-7-(tert-butoxycarbonyl)aza-spiro[4,5]decane Prepared from the compound of Description 110 and (5R,6S)-6-phenyl-1-oxa-7-(tert-butoxycarbonyl)aza-spiro[4,5]dec-3-ene (Description 86) according to the method of Example 170. $^1$H NMR (360 MHz, CDCl$_3$) δ7.60 (2H, d, J 7.9 Hz), 7.53–7.21 (8H, m), 6.91 (1H, d, J 1.9 Hz), 6.78 (2H, m), 5.32 (1H, s), 5.01 (2H, s), 4.43 (1H, hept, J 6.0 Hz), 4.29 (1H, m), 3.97 (1H, m), 3.82 (2H, m), 2.78 (1H, m), 2.54 (1H, m), 2.20 (1H, m), 1.90 (1H, m), 1.77–1.65 (3H, m), 1.45 (9H, s), and 1.31 (6H, d, J 6.0 Hz). m/z (ES$^+$) 558 (M+1).

EXAMPLE 180

(3R,5R,6S)-3-(5-Hydroxy-2-isopropoxyphenyl)-6-phenyl-1-oxa-7-(tert-butoxycarbonyl)aza-spiro[4,5]decane Prepared from the compound of Example 179 according to the method of Example 171. $^1$H NMR (360 MHz, CDCl$_3$) δ7.60 (2H, d, J 7.5 Hz), 7.32 (2H, t, J 7.5 Hz), 7.24 (1H, t, J 7.5 Hz), 6.76 (1H, d, J 3.0 Hz), 6.73 (1H, d, J 8.7 Hz), 6.63 (1H, dd, J 8.7, 3.0 Hz), 5.32 (1H, s), 4.77 (1H, s), 4.41 (1H, hept, J 6.0 Hz), 4.28 (1H, m), 3.98 (1H, m), 3.82 (2H, m), 2.78 (1H, m), 2.55 (1H, m), 2.21 (1H, m), 1.91 (1H, m), 1.79–1.62 (3H, m), 1.45 (9H, s), and 1.36 (6H, d, J 6.0 Hz). m/z (ES$^+$) 468 (M+1).

EXAMPLE 181

(3R,5R,6S)-3-(5-Hydroxy-2-isopropoxyphenyl)-6-phenyl-1-oxa-7-aza-spiro[4,5]decane Hydrochloride Ethanolic hydrogen chloride (5 M, 4 mL) was added to a stirred, cooled (0° C.) solution of (3R,5R,6S)-3-(5-hydroxy-2-isopropoxyphenyl)-6-phenyl-1-oxa-7-(tert-butoxycarbonyl)aza-spiro[4.5]decane (Example 180, 43 mg, 0.09 mmol) in ethanol (2 mL) and the mixture was stirred at room temperature for 3 h. The solvent was evaporated under reduced pressure and the residue was crystallized from ether-ethanol. The solid was collected and dried in vacuo to give the title compound as a colorless solid (34 mg, 92%). m.p. 175–178° C. $^1$H NMR (360 MHz, CD$_3$OD) δ7.63 (2H, m), 7.56 (3H, m), 6.70 (1H, d, J 8.6 Hz), 6.57 (1H, dd, J 8.6, 2.9 Hz), 6.52 (1H, d, J 2.9 Hz), 4.88 (2H, br s), 4.60 (1H, s), 4.32 (1H, s), 4.27 (1H, hept, J 6.0 Hz), 4.11 (1H, m), 3.71 (1H, m), 3.44 (1H, m), 3.22 (1H, m), 2.50 (1H, m), 2.29 (2H, m), 2.14 (1H, m), 2.02–1.84 (3H, m), 1.14 (3H, d, J 6.0 Hz), and 1.36 (3H, d, J 6.0 Hz). m/z (ES$^+$) 368 (M+1). Found: C, 67.24; H, 7.59; N, 3.43. C$_{23}$H$_{29}$NO$_3$.HCl.0.4H$_2$O requires: C, 67.19; H, 7.55; N, 3.41%.

EXAMPLE 182

(3R,5R,6S)-3-[2,4-Bis(methoxy)phenyl]-6-phenyl-1-oxa-7-(tert-butoxycarbonyl)aza-spiro[4,5]decane Prepared from 2,4-(dimethoxy)iodobenzene and (5R,6S)-6-phenyl-1-oxa-7-(tert-butoxycarbonyl)aza-spiro[2,4]dec-3-ene (Description 86) according to the method of Example 170. $^1$H NMR (360 MHz, CDCl$_3$) δ7.60 (2H, d, J 8 Hz), 7.36–7.20 (3H, m), 7.14 (1H, d, J 9 Hz), 6.50–6.42 (2H, m), 5.35 (1H, s), 4.32–4.24 (1H, m), 3.97 (1H, br d, J 12 Hz), 3.85–3.75 (2H, m), 3.80 (6H, s), 2.73 (1H, dt, J 12.45 Hz), 2.55 (1H, dd, J 12, 6.5 Hz), 2.20 (1H, dt, J 12, 5.6 Hz), 1.94–1.84 (1H, m), 1.80–1.60 (3H, m), and 1.47 (9H, s). m/z (ES$^+$) 454 (M+1).

EXAMPLE 183

(3R,5R,6S)-3-[2,4-Bis(methoxy)phenyl]-6-phenyl-1-oxa-7-aza-spiro[4,5]decane Hydrochloride Prepared from the compound of Example 182 according to the method of Example 181. $^1$H NMR (360 MHz, CD$_3$OD)δ7.60–7.40 (5H, m),6.84 (1H, br d, J 9 Hz), 6.40–6.32 (2H, m), 4.26 (1H, s), 3.98 (1H, t, J 7.7 Hz), 3.78–3.70 (1H, m), 3.70 (3H, s), 3.61 (3H, s), 3.40 (1H, dd, J 12, 4 Hz), 3.17 (1H, dt, J 11, 3 Hz), 2.40–2.15 (3H, m), 2.07 (1H, br d, J 13 Hz), and 1.96–1.78 (3H, m). m/z (ES$^+$) 354 (M+1).

EXAMPLE 184

(3R,5R,6S)-3-[2-Difluoromethoxy-5-(trifluoromethoxy)phenyl]-6-phenyl-1-oxa-7-(tert-butoxycarbonyl)aza-spiro[4,5]decane Ethyl chlorodifluoroacetate (0.86 mL) was added dropwise to stirred, heated (110° C.) mixture of (3R,5R,6S)-3-(2-hydroxy-5-(trifluoromethoxy)phenyl)-6-phenyl-1-oxa-7-(tert-butoxycarbonyl)aza-spiro[4.5]decane (Example 171, 1.5 g) and potassium carbonate (1.4 g) in dimethylformamide (10 mL). Slow gas evolution was observed and the mixture was heated at 110° C. for 2 h. until all gas evolution ceased. The mixture was cooled and diluted with water (150 mL). The mixture was extracted with ether (3×20 mL), and the combined organic fractions were washed with brine, dried (MgSO$_4$) and the solvent was evaporated under reduced pressure. The residue was purified by MPLC on silica gel, eluting with hexane/EtOAc (90:10) to give the title compound as a colourless oil (800 mg). $^1$H NMR (250 MHz, CDCl$_3$)δ1.46 (9H, s), 1.63–1.72 (4H, m), 2.26 (1H, dt, J 12.5, 5.0 Hz), 2.63–2.82 (2H, m), 3.81–4.04 (3H, m), 4.23–4.36 (1H, m), 5.34 (1H, s), 6.53 (1H, t, J 73 Hz), 7.12–7.36 (6H, m), and 7.58–7.61 (2H, m). m/z (ES$^+$) 544 (M+1).

EXAMPLE 185

(3R,5R,6S)-3-[2-Difluoromethoxy-5-(trifluoromethoxy)phenyl]-6-phenyl-1-oxa-7-aza-spiro[4,5]decane Prepared from the compound of Example 184 according to the method of Example 181. $^1$H NMR (500 MHz, CDCl$_3$)δ1.58–1.71 (3H, m), 1.93–2.00 (1H, m), 2.12–2.19 (2H, m), 2.35–2.43 (1H, m), 2.80 (1H, m), 3.34–3.37 (1H, m), 3.55 (1H, t, J 9 Hz), 3.82 (1H, t, J 10 Hz), 3.96 (1H, t, J 7.5 Hz), 6.10 (1H, t, J 7.3 Hz), 6.83 (1H, s), 6.90–6.95 (2H, m), 7.25–7.35 (3H, m), 7.53 (2H, br s), 9.18 (1H, br s) and 10.16 (1H, br s). m/z (ES$^+$) 444 (M+1).

EXAMPLE 186

(3R,5R,6S)-3-[2-Isopropoxy-5-(trifluoromethoxy)phenyl]-6-phenyl-1-oxa-7-(tert-butoxycarbonyl)aza-spiro[4,5]decane Prepared from the compound of Example 171 according to the method of Description 108. $^1$H NMR (360 MHz, CDCl$_3$)δ1.33–1.35 (6H, m), 1.45 (9H, s), 1.87–1.93 (1H, m), 2.17–2.33 (4H, m), 2.5–2.59 (1H, m), 2.74–2.82 (1H, m), 3.80–3.83 (2H, m), 3.96–4.00 (1H, m), 4.30 (1H, m), 4.50–4.57 (1H, m), 5.35 (5.33 (1H, s), 6.81 (1H, d, J 8.9 Hz), 6.95–7.02 (1H, m), 7.09 (1H, m), 7.22–7.26 (1H, m), 7.30–7.34 (2H, m), and 7.60 (2H, d, J 7.9 Hz). m/z (ES$^+$) 434 (M+1—CO$_2^t$Bu).

EXAMPLE 187

(3R,5R,6S)-3-[2-Isopropoxy-5-(trifluoromethoxy)phenyl]-6-phenyl-1-oxa-7-aza-spiro[4,5]decane Hydrochloride Prepared from the compound of Example 186 according to the method of Example 181. $^1$H NMR (360 MHz, D$_2$O)δ1.01 (3H, d, J 6.0 Hz), 1.07 (3H, d, J 6.0 Hz), 1.78 (1H, m), 2.00–2.10 (3H, m), 2.20–2.40 (3H, m), 3.30–3.40 (1H, m), 3.50–3.58 (1H, m), 3.62–3.68 (1H, m), 4.02–4.10 (1H, m), 4.10–4.18 (1H, m), 4.39 (1H, s), 6.61 (1H, d, J 9.2 Hz), 6.86–6.89 (1H, m), 6.93 (1H, s), 7.56–7.58 (3H, m), and 7.66 (2H, m). m/z (ES$^+$) 436 (M+1).

EXAMPLE 188

(3R,5R,6S)-3-[5-(Trifluoromethoxy)-2-(trifluoromethylsulfonyloxy)phenyl]-6-phenyl-1-oxa-7-(tert-butoxycarbonyl)aza-spiro[4,5]decane Trifluoromethanesulphonic anhydride (0.68 mL) was added dropwise to a stirred, cooled (0° C.) solution of (3R,5R,6S)-3-(2-hydroxy-5-(trifluoromethoxy)phenyl)-6-phenyl-1-oxa-7-(tert-butoxycarbonyl)aza-spiro[4,5]decane (Example 171, 1 g) in pyridine (4 mL). The mixture was allowed to warm to room temperature and stirred for 16 h. Further trifluoromethanesulphonic anhydride (0.34 mL) was added and the mixture was stirred at room temperature for 2 h. Aqueous copper (II) sulphate was added and the mixture was extracted with ethyl acetate (3×50 mL). The combined organic fractions were washed with brine, dried (MgSO$_4$) and the solvent was evaporated under reduced pressure. The residue was purified by MPLC on silica gel, eluting with hexane/EtOAc (80:20) to give the title compound as a colourless oil. $^1$H NMR (360 MHz, CDCl$_3$)δ1.43 (9H, s), 1.78 (3H, m), 2.25 (2H, m), 2.78 (2H, m), 3.85 (2H, m), 4.02 (1H, dd, J 13.7 Hz), 4.27 (1H, dd, J 8.7, 6.9 Hz), 5.30 (1H, s), 7.27 (1H, m), 7.31 (5H, m), and 7.57 (2H, d, J 7.6 Hz).

EXAMPLE 189

(3R,5R,6S)-3-[2-(Ethen-1-yl)-5-(trifluoromethoxy)phenyl]-6-phenyl-1-oxa-7-(tert-butoxycarbonyl)aza-spiro[4,5]decane A mixture of (3R,5R,6S)-3-[5-(trifluoromethoxy)-2-(trifluoromethylsulfonyloxy)phenyl]-6-phenyl-1-oxa-7-(tert-butoxycarbonyl)aza-spiro[4.5]decane (Example 188, 200 mg), vinyltributyltin (0.11 mL), lithium chloride (80 mg) and tetrakis(triphenylphosphine)palladium (0) (50 mg) in dioxane (5 mL) was degassed using a firestone valve (x 5 ). The mixture was heated at 110° C. for 2 h., cooled and filtered. The solvent was evaporated under reduced pressure and the residue was dissolved in acetonitrile. The mixture was washed with hexane (30 mL). The mixture was extracted with ethyl acetate (3×30 mL) and the combined organic fractions were washed with brine, dried (MgSO$_4$) and the solvent was evaporated under reduced pressure. The residue was purified by MPLC on silica gel, eluting with hexane/EtOAc (85:15) to give the title compound as an oil. $^1$H NMR (360 MHz, CDCl$_3$)δ1.47 (9H, s), 1.62 (3H, m), 1.83 (1H, m), 2.25 (1H, td), 2.63 (1H, dd, J 7.5 Hz), 2.76 (1H, td), 3.82 (1H, qn), 3.90 (1H, t, J 8.3 Hz), 3.98 (1H, dd), 4.24 (1H, t, J 7.3 Hz), 5.36 (2H, m), 5.57 (1H, d, J 16.7 Hz), 6.97 (1H, dd, J 11.0, 16.9 Hz), 7.15 (1H, d), 7.25 (1H, s), 7.33 (1H, m), 7.35 (2H, m), 7.76 (1H, d, J 8.5 Hz), and 7.60 (2H, d, J 7.6 Hz).

EXAMPLE 190

(3R,5R,6S)-3-[2-(Ethen-1-yl)-5-(trifluoromethoxy)phenyl]-6-phenyl-1-oxa-7-aza-spiro[4,5]decane Hydrochloride Prepared from the compound of Example 189 according to the method of Example 181. $^1$H NMR (360 MHz, CD$_3$OD)δ0.53 (1H, t, J 15.1 Hz), 0.72 (1H, t, J 11.9 Hz), 0.90 (1H, m), 1.09 (3H, m), 1.95 (1H, td, J 12.4 Hz), 2.16 (1H, dd, J 12.8 Hz), 2.52 (1H, t, J 9.7 Hz), 2.78 (1H, t, J 7.9 Hz), 3.08 (1H, s), 3.92 (1H, d, J 11.04 Hz), 4.18 (1H, d, J 17.2 Hz), 4.83 (1H, dd, J 17.2, 10.9 Hz), 5.83 (2H, m), 6.16 (1H, d, J 8.5 Hz), and 6.37 (5H, m).

EXAMPLE 191

(3R,5R,6S)-3-[2-(2,2,2-Trifluoroethoxy)-5-(trifluoromethyl)phenyl)-6-phenyl-1-oxa-7-(tert-butoxycarbonyl)aza-spiro[4,5]decane Prepared from the compound of Example 167 according to the method of Example 201. $^1$H NMR (360 MHz, CDCl$_3$)δ1.44 (9H, s), 1.64–1.80 (3H, m), 1.96 (1H, dd, J 13.0, 8.3 Hz), 2.21 (1H, dt, J 13.0, 5.4 Hz), 2.62 (1H, dd, J 12.2, 7.0 Hz), 2.88 (1H, dt, J 13.3, 4.0 Hz), 3.82–3.90 (2H, m), 3.98–4.05 (1H, m), 4.29–4.31 (1H, m), 4.42 (2H, q, J 7.9 Hz), 5.32 (1H, s), 6.88 (1H, d, J 8.6 Hz), 7.22–7.36 (3H, m), 7.51 (1H, d, J 8.6 Hz), and 7.54–7.63 (3H, m). m/z (ES$^+$) 560 (M+1)

EXAMPLE 192

(3R,5R,6S)-3-[2-(2,2,2-Trifluoroethoxy)-5-(trifluoromethyl)phenyl]-6-phenyl-1-oxa-7-aza-spiro [4,5]decane Prepared from the compound of Example 191 according to the method of Example 181. $^1$H NMR (360 MHz, CDCl$_3$)δ1.60–1.74 (3H, m), 1.96–2.02 (1H, m), 2.12 (1H, dt, J 13.0, 4.3 Hz), 2.20–2.38 (3H, m), 2.77 (1H, dt, J 12.4, 3.0 Hz), 3.24 (1H, dt, J 12.4, 4.0 Hz), 3.62 (1H, dd, J 9.7, 8.3 Hz), 4.07 (1H, t, J 7.2 Hz), 1H, t, J 7.2 Hz), 6.72 (1H, t, J 7.3 Hz), 7.24–7.34 (4H, m), 7.39 (1H, d, J 8.6 Hz), and 7.42–7.48 (2H, m). m/z (ES$^+$) 460 (M+1).

EXAMPLE 193

(3R,5R,6S)-3-[2,5-Bis(difluoromethoxy)phenyl]-6-phenyl-1-oxa-7-(tert-butoxycarbonyl)aza-spiro[4,5] decane Prepared from the compound of Example 176 according to the method of Example 184. $^1$H NMR (360 MHz, CDCl$_3$)δ7.60 (2H, d, J 7.5 Hz), 7.33 (2H, t, J 7.5 Hz), 7.25 (1H, t, J 7.5 Hz), 7.15 (1H, d, J 2.8 Hz), 7.12 (1H, d, J 8.8 Hz), 7.00 (1H, dd, J 8.8, 2.8 Hz), 6.50 (1H, t, J 73.3 Hz), 6.48 (1H, t, J 73.5 Hz), 5.34 (1H, s), 4.28 (1H, m), 3.97 (1H, m), 3.84 (2H, m), 2.77 (1H, m), 2.66 (1H, m), 2.26 (1H, m), 1.84–1.65 (4H, m), and 1.46 (9H, s). m/z (ES$^+$) 526 (M+1).

EXAMPLE 194

(3R,5R,6S)-3-[2,5-Bis(difluoromethoxy)phenyl]-6-phenyl-1-oxa-7-aza-spiro[4,5]decane Hydrochloride Prepared from the compound of Example 193 according to the method of Example 181. $^1$H NMR (360 MHz, D$_2$O)δ1.83 (1H, m), 1.98 (2H, m), 2.08–2.36 (4H, m), 3.20 (1H, m), 3.52 (1H, m), 3.70 (1H, m), 4.05 (1H, m), 4.30 (1H, s), 6.46 (1H, t, J 73 Hz), 6.73 (1H, t, J 74 Hz), 7.05 (3H, m, ArH), and 7.55 (5H, br s). m/s (ES$^+$) 426 (M+1). Found: C, 56.8; H, 5.0; N, 3.3. C$_{22}$H$_{23}$F$_4$NO$_3$.HCl requires: C, 57.2; H, 5.2; N, 3.0%.

EXAMPLE 195

(3R,5R,6S)-3-[5-Fluoro-2-(difluoromethoxy) phenyl]-6-phenyl-1-oxa-7-(tert-butoxycarbonyl)aza-spiro[4,5]decane Prepared from the compound of Example 178 according to the method of Example 184. $^1$H NMR (360 MHz, CDCl$_3$)δ1.45 (9H, s), 1.64–1.83 (4H, m), 2.26 (1H, dd, J 12.8, 7.6 Hz), 2.63–2.80 (2H, m), 3.81–3.89 (2H, m), 3.96–4.00 (1H, m), 4.26–4.29 (1H, m), 5.33 (1H, s), 6.47 (1H, t, 73.4 Hz), 6.89–6.94 (1H, m), 7.07–7.11 (1H, m), 7.22–7.27 (1H, m), 7.32 (2H, m), 7.59 (2H, d, J 7.9 Hz). m/z (ES$^+$) 478 (M+1).

EXAMPLE 196

(3R,5R,6S)-3-[5-Fluoro-2-(difluoromethoxy) phenyl]-6-phenyl-1-oxa-7-aza-spiro[4,5]decane Hydrochloride Prepared from the compound of Example 195 according to the method of Example 181. $^1$H NMR (360 MHz, D$_2$O)δ1.42–2.00 (7H, m), 2.82–2.93 (1H, m), 3.16–3.26 (1H, m), 3.32–3.39 (1H, m), 3.68–3.75 (1H, m), 3.97 (1H, s), 6.11 (1H, t, J 73.3 Hz), 6.58–6.74 (3H, m), and 7.58–7.61 (5H, s). m/z (ES$^+$) 378 (M+1).

EXAMPLE 197

(3R,5R,6S)-3-[5-Fluoro-2-(2,2,2-trifluoroethoxy) phenyl]-6-phenyl-1-oxa-7-(tert-butoxycarbonyl)aza-spiro[4,5]decane Prepared from the compound of Example 178 according to the method of Example 201. $^1$H NMR (360 MHz, CDCl$_3$)δ1.45 (9H, s), 1.57–1.76 (4H, m), 1.86–1.95 (1H, m), 2.18–2.23 (1H, m), 2.56–2.65 (1H, m), 2.72–2.85 (1H, m), 3.81–3.88 (1H, m), 3.94–4.03 (1H, m), 4.24–4.38 (3H, m), 5.30 (1H, s), 6.74–6.79 (1H, m), 6.89 (1H, dt, J 12.9, 4.4 Hz), 7.05 (1H, dd, J 13.6, 7 4.3 Hz), 7.25–7.35 (3H, m), and 7.59 (2H, d, J 10.9 Hz). m/z (ES$^+$) 454 (M+1—C$_4$H$_8$).

EXAMPLE 198

(3R,5R,6S)-3-[5-Fluoro-2-(2,2,2-trifluoromethoxy) phenyl]-6-phenyl-1-oxa-7-aza-spiro[4,5]decane Hydrochloride Prepared from the compound of Example 197 according to the method of Example 181. $^1$H NMR (360 MHz, D$_2$O)δ1.88–1.97 (3H, m), 2.08–2.13 (1H, m), 2.26–2.37 (3H, m), 3.15–3.21 (1H, m), 3.38–3.41 (1H, m), 3.70 (1H, dd, J 10.3, 8.3 Hz), 4.13 (1H, t, J 7.5 Hz), 4.29–4.47 (3H, m), 6.83–6.89 (3H, m), 7.48–7.50 (3H, m), and 6.29 (2H, m). m/z (ES$^+$) 410 (M+1).

EXAMPLE 199

(3R,5R,6S)-3-(5-Fluoro-2-isopropoxyphenyl)-6-phenyl-1-oxa-7-(tert-butoxycarbonyl)aza-spiro[4,5] decane Prepared from the compound of Example 178 according to the method of Description 108. $^1$H NMR (360 MHz, CDCl$_3$)δ1.30–1.33 (6H, m), 1.45 (9H, s), 1.63–1.78 (2H, m), 1.86–1.89 (1H, m), 2.18–2.27 (1H, m), 2.54–2.60 (1H, m), 2.77 (1H, dt, J 12.5, 4.0 Hz), 3.77–3.87 (2H, m), 3.96–4.01 (1H, m), 4.29 (1H, t, J 7.2 Hz), 4.43–4.51 (1H, m), 5.33 (1H, s), 6.76–6.80 (1H, m), 6.82–6.88 (1H, m), 6.96 (1H, dd, J 9.6, 3.0 Hz), 7.22–7.25 (1H, m), 7.32 (2H, m), and 7.60 (2H, d, J 7.9 Hz). m/z (ES$^+$) 470 (M+1).

EXAMPLE 200

(3R,5R,6S)-3-(5-Fluoro-2-isopropoxyphenyl)-6-phenyl-1-oxa-7-aza-spiro[4,5]decane Hydrochloride Prepared from the compound of Example 199 according to the method of Example 181. $^1$H NMR (360 MHz, D$_2$O)δ1.00 (3H, d, J 6.0 Hz), 1.04 (3H, d, J 6.0 Hz), 1.81 (1H, t, J 12.6 Hz), 1.96–2.00 (2H, m), 2.10–2.14 (2H, m), 2.26–2.32 (1H, m), 2.40–2.43 (1H, m), 3.18–3.23 (1H, m), 3.47–3.53 (1H, m), 3.64 (1H, dd, J 10.8, 8.3 Hz), 4.09 (1H, t, J 8.0 Hz), 4.24–4.28 (2H, m), 6.90–6.99 (3H, m), and 7.56 (1H, s). m/z (ES$^+$) 370 (M+1).

EXAMPLE 201

(3R,5R,6S)-3-[2-Isopropoxy-5-(2,2,2-trifluoroethoxy)phenyl]-6-phenyl-1-oxa-7-(tert-butoxycarbonyl)aza-spiro[4,5]decane 2,2,2-Trifluoroethyl trichloromethanesulfonate (127 mg, 0.45 mmol) was added to a mixture of (3R,5R,6S)-3-(5- hydroxy-2-isopropoxyphenyl)-6-phenyl-1-oxa-7-(tert-butoxycarbonyl)aza-spiro[4,5]decane (Example 180, 140 mg, 0.3 mmol) and potassium carbonate (104 mg, 0.75 mmol) in DMF (3 mL) and the mixture was heated at 60° C., adding additional 2,2,2-trifluoroethyl trichloromethanesulfonate (338 mg, 1.2 mmol) and potassium carbonate (166 mg, 1.2 mmol) after 4 h. and 22 h. After 46 h., the mixture was cooled, poured into aqueous citric acid (10%, 20 mL) and extracted with ethyl acetate (3×20 mL). The combined organic fractions were washed with aqueous citric acid (10%, 2×20 mL) and brine (20 mL), dried (MgSO$_4$) and the solvent was evaporated under reduced pressure. The residue was purified by flash column chromatography on silica gel, eluting with CH$_2$Cl$_2$/EtOAc (85:15 increasing to 80:30) to give the title compound (138 mg, 84%). $^1$H NMR (250 MHz, CDCl$_3$)δ1.31 (6H, d, J 6.0 Hz), 1.45 (9H, s), 1.60–1.80 (3H, m), 1.87–1.92 (1H, m), 2.18–2.24 (1H, m), 2.52–2.59 (1H, m), 2.71–2.81 (1H, m), 3.77–4.00 (3H, m), 4.25–4.35 (3H, m), 4.42–4.49 (1H, m), 5.38 (1H, s), 6.70–6.82 (2H, m), 6.90 (1H, d, J 2.9 Hz), 7.24–7.35 (3H, m), and 7.61 (2H, d, J 7.6 Hz). m/z (ES$^+$) 550 (M+1).

EXAMPLE 202

(3R,5R,6S)-3-[2-Isopropoxy-5-(2,2,2-trifluoroethoxy)phenyl]-6-phenyl-1-oxa-7-aza-spiro[4,5]decane Hydrochloride Prepared from the compound of Example 201 according to the method of Example 181. $^1$H NMR (360 MHz, D$_2$O)δ0.99 (3H, d, J 6.0 Hz), 1.04 (3H, d, J 6.0 Hz), 1.77–1.84 (1H, m), 1.98–2.05 (3H, m), 2.20–2.32 (2H, m), 2.38–2.48 (1H, m), 3.20–3.32 (1H, m), 3.50–3.63 (2H, m), 4.02–4.10 (1H, m), 4.12–4.20 (1H, m), 4.32 (1H, s), 4.43 (2H, dd, J 16.8, 8.4 Hz), 6.74–6.80 (3H, m), and 7.58–7.61 (5H, m). m/z (ES$^+$) 450 (M+1).

EXAMPLE 203

(3R,5R,6S)-3-[2,5-Bis(isopropoxy)phenyl)]-6-phenyl-1-oxa-7-(tert-butoxycarbonyl)aza-spiro[4,5]decane Prepared from the compound of Example 180 according to the method of Description 108. $^1$H NMR (360 MHz, CDCl$_3$)δ7.60 (2H, d, J 7.7 Hz), 7.32 (2H, t, J 7.7 Hz), 7.23 (1H, t, J 7.7 Hz), 6.82 (1H, d, J 2.9 Hz), 6.77 (1H, d, J 8.9 Hz), 6.69 (1H, dd, J 8.9, 2.9 Hz), 5.32 (1H, s), 4.43 (1H, hept, J 6.0 Hz), 4.29 (1H, m), 3.98 (1H, m), 3.83 (2H, m), 2.78 (1H, m), 2.55 (1H, m), 2.21 (1H, m), 1.93 (1H, m), 1.79–1.63 (3H, m), 1.45 (9H, s), and 1.30 (12H, d, J 6.0 Hz). m/s (ES$^+$) 510 (M+1).

EXAMPLE 204

(3R,5R,6S)-3-[2,5-Bis(isopropoxy)phenyl]-6-phenyl-1-oxa-7-aza-spiro[4,5]decane Hydrochloride Prepared from the compound of Example 203 according to the method of Example 181. m.p. 233–236° C. $^1$H NMR (360 MHz, CD$_3$OD)δ7.68 (2H, m), 7.62 (3H, m), 6.82 (1H, d, J 8.9 Hz), 6.75 (1H, dd, J 8.9, 2.7 Hz), 6.65 (1H, d, J 2.7 Hz), 4.88 (2H, br s), 4.49 (1H, hept, J 6.0 Hz), 4.38 (1H, hept, J 6.0 Hz), 4.37 (1H, s), 4.16 (1H, m), 3.77 (1H, m), 3.49 (1H, m), 3.27 (1H, m), 2.53 (1H, m), 2.34 (2H, m), 2.20 (1H, m), 2.09–1.90 (3H, m), 1.32 (6H, d, J 6.0 Hz), 1.21 (3H, d, J 6.0 Hz), and 1.15 (3H, d, J 6.0 Hz). m/s (ES$^+$) 410 (M+1).

EXAMPLE 205

(3R,5R,6S)-3-5-Chloro-2-methoxyphenyl)-6-phenyl-1-oxa-7-(tert-butoxycarbonyl)aza-spiro[4,5]decane Prepared from 5chloro-2-methoxyiodobenzene and (5R,6S)-6-phenyl-1-oxa-7-(tert-butoxycarbonyl)aza-spiro[4,5]dec-3-ene (Description 86) according to the method of Example 170. $^1$H NMR (360 MHz, CDCl$_3$)δ1.40 (9H, s), 1.59–1.83 (3H, s), 2.12–2.22 (1H, m), 2.48–2.53 (1H, m), 2.64–2.72 (1H, m), 3.71–3.83 (2H, m), 3.73 (3H, s), 4.20–4.24 (1H, m), 5.28 (1H, s), 6.69–6.71 (1H, d, J 8.6 Hz), 7.07–7.27 (5H, m), and 7.53–7.55 (2H, m). m/z (ES$^+$) 458 (M+1).

EXAMPLE 206

(3R,5R,6S)-3-(5-Chloro-2-methoxyphenyl)-6-phenyl-1-oxa-7-aza-spiro[4,5]decane Hydrochloride Prepared from the compound of Example 205 according to the method of Example 181. $^1$H NMR (360 MHz, D$_2$O)δ1.78–2.29 (7H, m), 3.22 (1H, m), 3.51–3.57 (1H, m), 3.61 (3H, s), 3.68–3.74 (1H, m), 3.99–4.03 (1H, m), 4.29 (1H, s), 6.85–6.88 (1H, d, J 8.8 Hz), 7.13–7.14 (1H, d, J 2.5 Hz), 7.17–7.21 (1H, dd, J 2.5, 8.8 Hz), and 7.56–7.59 (5H, m). m/z (ES$^+$) 358 (M+1).

EXAMPLE 207

(3R,5R,6S)-3-[2-(2,2,2-Trifluoroethoxy)-5-(trifluoromethyl)phenyl]-6-phenyl-1-oxa-7-(tert-butoxycarbonyl)aza-spiro[4,5]decane Prepared from the compound of Example 171 according to the method of Example 201. $^1$H NMR (360 MHz, CDCl$_3$)δ1.37 (9H, s), 1.61–1.67 (1H, s), 1.80–1.87 (1H, m), 2.09–2.13 (1H, m), 2.52–2.57 (1H, m), 2.71–2.77 (1H, m), 3.72–3.80 (2H, m), 3.89–4.00 (1H, m), 4.21 (1H, m), 4.26–4.33 (2H, q, J 8 Hz), 5.23 (1H, s), 6.73–6.75 (1H, d, J 8.9 Hz), 7.01–7.03 (1H, m), 7.11 (1H, m), 7.17–7.27 (3H, m), and 7.50–7.52 (2H, m). m/z (ES$^+$) 576 (M+1).

EXAMPLE 208

(3R,5R,6S)-3-[2-(2,2,2-Trifluoroethoxy)-5-(trifluoromethyl)phenyl]-6-phenyl-1-oxa-7-aza-spiro[4,5]decane Hydrochloride Prepared from the compound of Example 207 according to the method of Example 181. $^1$H NMR (360 MHz, D$_2$O)δ1.83–1.89 (1H, m), 1.90–2.04 (3H, m), 2.25–2.33 (3H, m), 3.21–3.35 (1H, m), 3.58–3.68 (2H, m), 4.07–4.12 (1H, m), 4.27–4.31 (2H, q, J 8.5 Hz), 4.35 (1H, s), 6.81–6.84 (1H, d, J 8.9 Hz), 6.99–7.05 (2H, m), and 7.54–7.61 (5H, m). m/z (ES$^+$) 476 (M+1).

EXAMPLE 209

(3R,5R,6S)-3-[2-(Cyclopropylmethoxy)-5-(trifluoromethyl)phenyl]-6-phenyl-1-oxa-7-(tert-butoxycarbonyl)aza-spiro[4,5]decane Cyclopropylmethyl bromide (112 mg) was added to a mixture of (3R,5R,6S)-3-(2-hydroxy-5-(trifluoromethoxy)phenyl)-6-phenyl-1-oxa-7-(tert-butoxycarbonyl)aza-spiro[4,5]decane (Example 171, 274 mg) and potassium carbonate (192 mg) in dimethylformamide (5 mL). The mixture was stirred at 60° C. for 18 h., poured into water (100 mL) and extracted with ethyl acetate (2×25 mL). The combined organic fractions were washed with brine (2×) and water, dried (MgSO$_4$), and the solvent was evaporated under reduced pressure. The residue was purified by chromatography on silica gel, eluting with hexane/EtOAc (95:5 increasing to 90:10), to give the title compound as an oil (178 mg). $^1$H NMR (360 MHz, CDCl$_3$)δ0.23–0.28 (2H, m), 0.54–0.59 (2H, m), 0.81 (1H, m), 1.18 (2H, m), 1.38 (9H, s), 1.63–1.72 (3H, m), 1.89–1.95 (1H, m), 2.12–2.16 (1H, m), 2.48–2.53 (1H, m), 2.69–2.75 (1H, m), 3.68–3.79 (3H, m), 3.89–3.93 (1H, m), 4.27 (1H, m), 5.27 (1H, s), 6.68–6.71 (1H, d, J 8.89 Hz), 6.95–6.97 (1H, m), 7.03 (1H, m), and 7.52–7.54 (2H, m). m/z (ES$^+$) 548 (M+1).

EXAMPLE 210

(3R,5R,6S)-3-[2-(Cyclopropylmethoxy)-5-(trifluoromethyl)phenyl]-6-phenyl-1-oxa-7-aza-spiro[4,5]decane Hydrochloride Prepared from the compound of Example 209 according to the method of Example 181. $^1$H NMR (360 MHz, D$_2$O)δ0.01–0.00 (2H, m), 0.57–0.59 (2H, m), 0.94 (1H, m), 1.76 (1H, m), 1.95 (2H, m), 2.21 (2H, m), 3.19–3.23 (2H, m), 3.53 (1H, m), 3.61 (1H, m), 3.99 (1H, m), 4.35 (1H, m), 6.28–6.30 (1H, d, J 9.0 Hz), 6.67–6.68 (1H, m), 6.75 (1H, m), 7.46–7.52 (3H, m), and 7.61–7.63 (2H, m). m/z (ES$^+$) 448 (M+1).

EXAMPLE 211

(3R,5R,6S)-3-[2-Benzyloxy-5-(trifluoromethyl)phenyl]-6-phenyl-1-oxa-7-aza-spiro[4,5]decane Hydrochloride Prepared from the compound of Example 170 according to the method of Example 181. $^1$H NMR (360 MHz, D$_2$O)δ1.83–1.91 (4H, m), 2.08–2.24 (2H, m), 3.10–3.22 (1H, m), 3.31 (3H, m), 3.42–3.48 (1H, m), 3.58–3.64 (1H, m), 4.01 (1H, m), 4.21 (1H, s), 6.86–6.89 (1H, m), 6.93 (1H, m), 7.00–7.04 (1H, m), 7.24–7.25 (2H, m), 7.32–7.34 (3H, m), and 7.44–7.46 (5H, m). m/z (ES$^+$) 484 (M+1).

EXAMPLE 212

(3R,5R,6S)-3-[5-(Difluoromethoxy)-2-(2,2,2-trifluoromethyl)phenyl]-6-phenyl-1-oxa-7-(tert-butoxycarbonyl)aza-spiro[4,5]decane Prepared from the compound of Example 176 according to the method of Example 201. $^1$H NMR (360 MHz, CDCl$_3$)δ1.37 (9H, s), 1.55–1.68 (3H, m), 1.82–1.88 (1H, m), 2.09–2.16 (1H, m), 2.50–2.56 (1H, m), 2.69–2.78 (1H, m), 3.73–3.81 (2H, m), 3.89–3.93 (1H, m), 4.17–4.20 (1H, m), 4.24–4.31 (2H, q, J 8.0 Hz), 5.22 (1H, s), 6.38 (1H, t, J 74 Hz), 6.72 (1H, d, J 8.8 Hz), 6.91–6.93 (1H, dd, J 2.8, 8.8 Hz), 7.03 (1H, d, J 2.8 Hz), 7.15–7.27 (3H, m), and 7.50–7.52 (2H, m). m/z (ES$^+$) 558 (M+1).

EXAMPLE 213

(3R,5R,6S)-3-[5-(Difluoromethoxy)-2-(2,2,2-trifluoromethyl)phenyl]-6-phenyl-1-oxa-7-aza-spiro[4,5]decane Hydrochloride Prepared from the compound of Example 212 according to the method of Example 181. $^1$H NMR (360 MHz, D$_2$O)δ1.89–2.32 (7H, m), 3.20 (1H, m), 3.49 (1H, m), 3.65–3.71 (1H, m), 4.08–4.12 (1H, m), 4.29 (1H, s), 4.29–4.37 (2H, q, J 8.5 Hz), 6.67 (1H, t, J 74 Hz), 6.87–7.02 (3H, m), and 7.54 (5H, s). m/z (ES$^+$) 458 (M+1).

EXAMPLE 214

(3R,5R,6S)-3-[2-(2,2,-Difluoroethoxy)-5-(difluoromethoxy)phenyl]-6-phenyl-1-oxa-7-(tert-butoxycarbonyl)aza-spiro[4,5]decane 2,2-Difluoroethyl bromide (120 mg) was added to a mixture of (3R,5R,6S)-3-[5-(difluoromethoxy)-2-hydroxyphenyl]-6-phenyl-1-oxa-7-(tert-butoxycarbonyl)aza-spiro[4,5]decane (Example 176, 200 mg) and potassium carbonate (145 mg) in dimethylformamide (4 mL). The mixture was stirred at 50° C. for 2 h., poured into brine and extracted with ethyl acetate. The combined organic fractions were washed with water (3 x), dried (MgSO$_4$), and the solvent was evaporated under reduced pressure. The residue was purified by chromatography on silica gel, eluting with hexane/EtOAc (90:10 increasing to 80:20), to give the title compound as an oil (178 mg). $^1$H NMR (360 MHz, CDCl$_3$) δ1.45 (9H, s), 1.62–1.76 (3H, m), 1.86–1.93 (1H, m), 2.18–2.23 (1H, m), 2.57–2.62 (1H, m), 2.74–2.82 (1H, m), 3.83–3.84 (1H, m), 3.96–3.99 (1H, m), 4.11–4.24 (2H, td, J 8.9, 12.9 Hz), 4.27 (1H, m), 5.33 (1H, s), 6.12 (1H, tt, J 55 Hz, 4 Hz), 6.43 (1H, t, J 74 Hz), 6.77–6.80 (1H, d, J 8.8 Hz), 6.97–6.98 (1H, m), 7.07 (1H, m), 7.22–7.34 (3H, m), and 7.58–7.60 (2H, m). m/z (ES$^+$) 484 (M+1—C$_4$H$_8$).

EXAMPLE 215

(3R,5R,6S)-3-[2-(2,2,2-Difluoroethoxy)-5-(difluoromethoxy)phenyl]-6-phenyl-1-oxa-7-aza-spiro[4,5]decane Hydrochloride Prepared from the compound of Example 214 according to the method of Example 181. $^1$H NMR (360 MHz, D$_2$O)δ1.88–2.33 (7H, m), 3.18–3.22 (1H, m), 3.47–3.55 (1H, m), 3.68–3.73 (1H, m), 4.04–4.13 (3H, m), 4.29 (1H, s), 6.06 (1H, tt, J 55, 4 Hz), 6.66 (1H, t, J 74 Hz), 6.67–7.03 (3H, m), and 7.55 (5H, s). m/z (ES$^+$) 440 (M+1).

EXAMPLE 216

(3R,5R,6S)-3-[2-(Cyclobutoxy)-5-(trifluoromethoxy)phenyl]-6-phenyl-1-oxa-7-(tert-butoxycarbonyl)aza-spiro[4,5]decane Cyclobutylbromide (143 mg) was added to a mixture of (3R,5R,6S)-3-(2-hydroxy-5-(trifluoromethoxy)phenyl)-6-phenyl-1-oxa-7-(tert-butoxycarbonyl)aza-spiro[4,5]decane (Example 171, 181 mg) and potassium carbonate (126 mg) in dimethylformamide (10 mL). The mixture was stirred at 60° C. for 18 h., poured into brine and extracted with ethyl acetate (2×). The combined organic fractions were washed with water (3×), dried (MgSO$_4$), and the solvent was evaporated under reduced pressure. The residue was purified by chromatography on silica gel, eluting with hexane/EtOAc (95:5), to give the title compound (96 mg). $^1$H NMR (360 MHz, CDCl$_3$)δ1.39 (9H, s), 1.58–1.87 (6H, m), 2.07–2.16 (3H, m), 2.34–2.40 (2H, m), 2.48–2.53 (1H, m), 2.66–2.75 (1H, m), 3.73–3.76 (2H, m), 3.89–3.93 (1H, m), 4.24 (1H, m), 4.52–4.56 (1H, m), 5.27 (1H, s), 6.56–6.59 (1H, d, J 8.9 Hz), 6.92–6.95 (1H, m), 7.01 (1H, m), 7.15–7.17 (1H, m), 7.23–7.27 (2H, m), and 7.52–7.55 (2H, m). m/z (ES$^+$) 548 (M+1).

EXAMPLE 217

(3R,5R,6S)-3-[2-(Cyclobutoxy)-5-(trifluoromethoxy)phenyl]-6-phenyl-1-oxa-7-aza-spiro[4,5]decane Prepared from the compound of Example 216 according to the method of Example 181. $^1$H NMR (360 MHz, CDCl$_3$) δ 1.50–1.77 (5H, m), 1.90–1.99 (4H, m), 2.08–2.14 (1H, m), 2.24–2.36 (3H, m), 2.68–2.74 (1H, m), 3.13–3.16 (1H, m), 3.46 (1H, s), 3.51–3.56 (1H, m), 3.91–3.95 (1H, m), 4.35–4.39 (1H, m), 6.42–6.45 (1H, d, J 8.8 Hz), 6.75 (1H, m), 6.81–6.83 (1H, m), and 7.22–7.43 (5H, m). m/z (ES$^+$) 448 (M+1).

EXAMPLE 218

(3R, 5R, 6S)-3-[2-(2-Methoxyethoxy)-5-(trifluoromethoxy)phenyl]-6-phenyl]-6-phenyl-1-oxa-7-(tert-butoxycarbonyl)aza-spiro[4.5]decane 2-Bromoethyl methyl ether (52 mg) was added to a mixture of (3R,5R,6S)-3-(2-hydroxy-5-(trifluoromethoxy)phenyl)-6-phenyl-1-oxa-7-(tert-butoxycarbonyl)aza-spiro[4.5]decane (Example 171, 150 mg) and potassium carbonate (92 mg) in dimethylformamide (2 mL). The mixture was stirred at 60° C. for 20 h., poured into water and extracted with ethyl acetate. The combined organic fractions were washed with brine and water, dried ($MgSO_4$), and the solvent was evaporated under reduced pressure. The residue was purified by chromatography on silica gel, eluting with hexane/EtOAc (80:20), to give the title compound (105 mg). $^1$H NMR (360 MHz, $CDCl_3$) δ 1.45 (9H, s), 1.71–1.77 (3H, m), 1.94–2.00 (1H, m), 2.18–2.21 (1H, m), 2.54–2.59 (1H, m), 2.77–2.83 (1H, m), 3.42 (3H, s), 3.48–3.87 (4H, m), 3.95–3.99 (1H, m), 4.10–4.13 (2H, t, J 4.90 Hz), 4.29 (1H, m), 5.32 (1H, s), 6.82–6.84 (1H, d, J 8.9 Hz), 7.03–7.06 (1H, m), 7.11 (1H, m), 7.24–7.34 (3H, m), and 7.58–7.60 (2H, m). m/z ($ES^+$) 552 (M+1).

EXAMPLE 219

(3R,5R,6S)-3-[2-(2-Methoxyethoxy)-5-(trifluoromethoxy)phenyl]-6-phenyl-1-oxa-7-aza-spiro[4.5]decane Hydrochloride Prepared from the compound of Example 218 according to the method of Example 181. $^1$H NMR (360 MHz, $D_2O$) δ 1.91–2.31 (7H, m), 3.21 (1H, m), 3.43 (3H, s), 3.49–3.53 (1H, m), 3.66–3.72 (3H, m), 3.93–3.95 (2H, m), 4.11 (1H, m), 4.29 (1H, m), 6.88–6.91 (1H, d, J 8.9 Hz), 7.04 (1H, m), 7.11 (1H, m), and 7.56 (5H, s). m/z ($ES^+$) 452 (M+1).

EXAMPLE 200

(3R,5R,6S)-3-[5-(Trifluoromethoxy)-2-(trifluoromethylsulfonyloxy)phenyl]-6-phenyl-1-oxa-7-aza-spiro[4.5]decane Hydrochloride Prepared from the compound of Example 188 according to the method of Example 181. m.p.>250° C. (EtOAc). $^1$H NMR (400 MHz, $D_2O$) δ 7.56 (5H, br s), 7.38 (2H, d, J 10.4 Hz), 7.30 (1H, d, J 8.8 Hz), 4.34 (1H, s), 4.22 (1H, t, J 7.9 Hz), 3.74 (1H, t, J 9.4 Hz), 3.52 (1H, br d, J 9.8 Hz), 3.23 (1H, br t, J 11.4 Hz), 2.43–2.53 (2H, m), 2.17–2.28 (2H, m), and 1.95–2.02 (3H, m). m/z ($ES^+$) 526 (M+1). Found: C, 47.19; H, 3.58; N, 2.69. $C_{22}H_{21}F_6NO_5S \cdot HCl$ requires: C, 47.02; H, 3.95; N, 2.49%.

EXAMPLE 221

(3R,5R,6S)-3-[2-(2,2-Difluoroethoxy)-5-(trifluoromethoxy)phenyl]-6-phenyl-1-oxa-7-(tert-butoxycarbonyl)aza-spiro[4.5]decane 2-Bromo-1,1-difluoroethane (100 mg, 0.69 mmol) was added to a mixture of (3R,5R,6S)-3-(2-hydroxy-5-(trifluoromethoxy)phenyl)-6-phenyl-1-oxa-7-(tert-butoxycarbonyl)aza-spiro[4.5]decane (Example 171, 159 mg, 0.32 mmol) and potassium carbonate (110 mg, 0.8 mmol) in DMF (5 mL) and the mixture was stirred at 40° C. for 72 h. Water (100 mL) was added and the mixture was extracted with ethyl acetate (2×100 mL). The combined organic fractions were dried ($MgSO_4$) and the solvent was evaporated under reduced pressure. The residue was purified by flash column chromatography on silica gel, eluting with hexane/EtOAc (75:25), to give the title compound (148 mg, 82%). $^1$H NMR (360 MHz, $CDCl_3$) δ 1.42 (9H, s), 1.58–1.76 (1H, m), 1.84–1.94 (2H, m), 2.10–2.26 (1H, m), 2.56–2.62 (1H, m), 2.74–2.82 (1H, m), 3.60–3.72 (2H, m), 3.78–3.92 (2H, m), 3.92–4.00 (1H, m), 4.06–4.32 (2H, m), 5.34 (1H, s), 6.14 (1H, m), 6.80 (1H, d, J 8.9 Hz), 7.06–7.10 (1H, m), 7.16 (1H, m), 7.20–7.36 (3H, m), and 7.56–7.62 (2H, m). m/z $ES^+$) 558 (M+1).

EXAMPLE 222

(3R,5R,6S)-3-[2-(2,2-Difluoroethoxy)-5-(trifluoromethoxy)phenyl]-6-phenyl-1-oxa-7-aza-spiro[4.5]decane Hydrochloride Prepared from the compound of Example 221 according to the method of Example 181. $^1$H NMR (360 MHz, $D_2O$) δ 1.89–2.42 (7H, m), 3.18–3.26 (1H, m), 3.46–3.58 (1H, m), 3.72–3.78(1H, m), 4.10–4.20 (4H, m), 6.10 (1H, d, J 9.05 Hz), 7.06–7.10 (2H, m), and 7.58 (5H, s). m/z ($ES^+$) 458 (M+1).

EXAMPLE 223

(3R,5R,6S)-3-[2-Cyclopropyl-5-(trifluoromethoxy)phenyl]-6-phenyl-1-oxa-7-(tert-butoxycarbonyl)aza-spiro[4.5]decane A mixture of (3R,5R,6S)-3-[5-(trifluoromethoxy-2-(trifluoromethylsulfonyloxy)phenyl]-6-phenyl-1-oxa-7-(tert-butoxycarbonyl)aza-spiro[4.5]decane (Example 188, 200 mg), tetracyclopropyl tin (Description 116, 108 mg), lithium chloride (80 mg) and tetrakis(triphenylphosphine) palladium (0) (50 mg) in dioxane (5 mL) was degassed with a firestone valve (3×) and stirred at 110° C. for 16 h. The mixture was cooled, filtered and the solvent was evaporated under reduced pressure. The residue was dissolved in acetonitrile (20 mL) and washed with hexane (20 mL). The hexane fraction was extracted with acetonitrile (2×20 mL) and the combined acetonitrile fraction were treated with methanolic potassium fluoride (5%, 5 mL). The mixture was filtered and the solvent was evaporated under reduced pressure. The residue was purified by flash column chromatography on silica gel, eluting with hexane/EtOAc (85:15), to give the title compound as a yellow oil. $^1$H NMR (360 MHz, $CDCl_3$) δ 0.63 (2H, dm, J 12.5 Hz), 0.98 (2H, d, J 8.5 Hz), 1.45 (9H, s), 1.67 (4H, m), 1.81 (1H, dd, J 12.8, 9.7 Hz), 2.04 (1H, m), 2.26 (1H, td, J 8.4, 5.1 Hz), 2.70 (1H, dd, J 12.7, 7.8 Hz), 2.78 (1H, td, J 12.5 Hz), 3.91 (1H, t J 8.3 Hz), 3.96 (1H, dd), 4.14 (1H, qn), 4.29 (1H, t, J 7.6 Hz), 5.37 (1H, s), 6.99 (1H, m), 7.04 (1H, d, J 8.5 Hz), 7.25 (1H, d, J 3.6 Hz), 7.3 (1H, m), 7.33 (1H, t, J 7.1 Hz), and 7.61 (2H, d, J 7.7 Hz). m/z ($ES^+$) 462 (M+1-$C_4H_8$).

EXAMPLE 224

(3R,5R,6S)-3-[2-Cyclopropyl-5-(trifluoromethoxy)phenyl]-6-phenyl-1-oxa-7-aza-spiro[4.5]decane Hydrochloride Prepared from the compound of Example 223 according to the method of Example 181. $^1$H NMR (360 MHz, $CDCl_3$) δ 0.3 (2H, dm, J 16.8 Hz), 0.57 (2H, dd, J 6.6 Hz), 1.10 (1H, m), 1.69 (3H, m), 2.06 (1H, m), 2.24 (1H, dd, J 13.0, 7.9 Hz), 2.46 (1H, m), 2.62 (1H, qn), 2.87 (1H, t), 3.45 (1H, d, J 7.1 Hz), 3.59 (1H, t, J 8.8 Hz), 3.90 (1H, s), 4.09 (1H, t, J 7.7 Hz), 6.88 (3H, s), 7.33 (3H, m), and 7.63 (2H, br s). m/z ($ES^+$) 418 (M+1).

EXAMPLE 225

(3R,5R,6S)-3-(5-Cyano-2-hydroxyphenyl)-6-phenyl-1-oxa-7-aza-spiro[4.5]decane

Prepared from the compound of Description 118 according to the method of Example 181. ¹H NMR (250 MHz, DMSO-d₆) δ 7.15–7.45 (7H, m), 6.71 (1H, d, J 8.4 Hz), 3.83 (1H, t, J 7.2 Hz), 3.62 (1H, s), 3.46 (1H, t, J 8.8 Hz), 3.00–3.05 (1H, m), 2.62–2.71 (1H, m), 2.07–2.16 (2H, m), 1.83–1.96 (2H, m), and 1.49–1.68 (3H, m).

EXAMPLE 226

(3R,5R,6S)-3-(5-Cyano-2-hydroxyphenyl)-6-phenyl-1-oxa-7-(tert-butoxycarbonyl)aza-spiro[4.5]decane Water (50 mL) was added to a solution of (3R,5R,6S)-3-[5-cyano-2-(tert-butoxycarbonyl)oxyphenyl]-6-phenyl-1-oxa-7-(tert-butoxycarbonyl)aza-spiro[4.5]decane (Description 119, 427 mg) in tetrahydrofuran (50 mL) and the mixture was heated under reflux for 16 h. The mixture was cooled, ammonium chloride solution (saturated, 50 mL) was added and the mixture was extracted with ethyl acetate (2×100 mL). The combined organic fractions were dried (MgSO₄) and the solvent was evaporated under reduced pressure to give the title compound as a gum (337 mg). ¹H NMR (250 MHz, CDCl₃) δ 7.56–7.59 (2H, m), 7.26–7.42 (5H, m), 6.90 (1H, d, J 9.0 Hz), 5.43 (1H, s), 4.29 (1H, dd, J 9.5, 7.4 Hz), 3.92–3.98 (2H, m), 3.80–3.82 (1H, m), 2.67–2.81 (2H, m), 2.31–2.37 (1H, m), 1.59–1.88 (4H, m), and 1.51 (9H, s).

EXAMPLE 227

(3R,5R,6S)-3-[5-Cyano-2-(2,2,2-trifluoroethoxy)phenyl]-6-phenyl-1-oxa-7-(tert-butoxycarbonyl)aza-spiro[4.5]decane Prepared from the compound of Example 226 according to the method of Example 201. ¹H NMR (250 MHz, CDCl₃) δ 7.55–7.63 (4H, m), 7.25–7.36 (3H, m), 6.87 (1H, d, J 8.5 Hz), 5.32 (1H, s), 4.43 (2H, q, J 7.8 Hz), 4.28–4.30 (1H, m), 3.95–3.96 (1H, m), 3.83–3.85 (2H, m), 2.79–2.81 (1H, m), 2.58–2.66 (1H, m), 2.19–2.24 (1H, m), 1.88–1.97 (1H, m), 1.70–1.69 (3H, m), and 1.45 (9H, s).

EXAMPLE 228

(3R,5R,6S)-3-[5-Cyano-2-(2,2,2-trifluoroethoxy)phenyl]-6-phenyl-1-oxa-7-aza-spiro[4.5]decane Hydrochloride Prepared from the compound of Example 227 according to the method of Example 181. m.p. 258–260° C. ¹H NMR (360 MHz, DMSO-d₆) δ 9.50 (1H, br s), 8.90 (1H, br s), 7.73 (1H, dd, J 2.0, 8.7 Hz), 7.64 (1H, d, J 2.0 Hz), 7.54–7.55 (2H, m), 7.4–7.46 (3H, m), 7.13 (1H, d J 8.7 Hz), 4.74 (2H, q, J 8.7 Hz), 4.40 (1H, s), 4.01 (1H, t, J 7.6 Hz), 3.61 (1H, dd, J 8.3, 10.3 Hz), 3.24–3.26 (1H, m), 3.06–3.08 (1H, m), 2.21–2.27 (1H, m), and 1.86–2.14 (6H, m). m/z (ES⁺) 417 (M+1).

EXAMPLE 229

(3R,5R,6S)-3-(5-Cyano-2-isopropoxyphenyl)-6-phenyl-1-oxa-7-(tert-butoxycarbonyl)aza-spiro[4.5]decane Prepared from the compound of Example 226 according to the method of Description 108. ¹H NMR (250 MHz, CDCl₃) δ 7.48–7.62 (4H, m), 7.26–7.33 (3H, m), 6.87 (1H, d, J 8.4 Hz), 5.35 (1H, s), 4.64 (1H, sept, J 6.1 Hz), 3.95–4.00 (1H, m), 3.75–3.79 (2H, m), 2.64–2.68 (1H, m), 2.56–2.60 (1H, m), 2.23–2.27 (1H, m), 1.90–1.94 (1H, m), 1.70–1.74 (4H, m), 1.46 (9H, s), and 1.37 (6H, d, J 6.0 Hz).

EXAMPLE 230

(3R,5R,6S)-3-(5-Cyano-2-isopropoxyphenyl)-6-phenyl-1-oxa-7-aza-spiro[4.5]decane Hydrochloride Prepared from the compound of Example 229 according to the method of Example 181. m.p. 256–258° C. ¹H NMR (360 MHz, DMSO-d₆) δ 7.76–7.82 (4H, m), 7.68–7.69 (3H, m), 7.24 (1H, d, J 8.7 Hz), 4.82 (1H, sept, J 6.0 Hz), 4.58 (1H, br s), 4.16 (1H, t, J 7.5 Hz), 3.79 (1H, dd, J 8.0, 10.7 Hz), 3.45–3.47 (1H, m), 3.23–3.27 (1H, m), 2.41–2.46 (1H, m), 2.24–2.33 (3H, m), 1.99–2.09 (3H, m), and 1.34 (6H, dd, J 6.0, 10.5 Hz). m/z ES⁺) 377 (M+1).

EXAMPLE 231

(3R,5R,6S)-3-[2-(Ethen-1-yl)-5-(trifluoromethoxy)phenyl]-6-phenyl-1-oxa-7-(tert-butoxycarbonyl)aza-spiro [4.5]decane A mixture of (3R,5R,6S)-3-[5-trifluoromethoxy-2-(trifluoromethylsulfonyloxy)phenyl]-6-phenyl-1-oxa-7-(tert-butoxycarbonyl)aza-spiro[4.5]decane (Example 188, 700 mg), vinyltributyl tin (0.4 mL), lithium chloride (290 mg) and tetrakis(triphenylphosphine) palladium (0) (50 mg) in dioxane (10 mL) was degassed with a firestone valve (3×) and stirred at 110° C. for 16 h. The mixture was cooled, filtered and the solvent was evaporated under reduced pressure. The residue was dissolved in acetonitrile (10 mL) and washed with hexane (15 mL). The hexane fraction was extracted with acetonitrile (3×10 mL) and the combined acetonitrile fractions were treated with methanolic potassium fluoride (5%, 2 mL). The mixture was filtered and the solvent was evaporated under reduced pressure. The residue was purified by flash column chromatography on silica gel, eluting with hexane/EtOAc (90:10), to give the title compound as an oil. ¹H NMR (360 MHz, CDCl₃) δ 1.47 (9H, s), 1.77 (3H, m), 1.84 (1H, m), 2.25 (1H, td), 2.64 (1H, dd, J 12.8, 7.7 Hz), 2.76 (1H, td), 3.79 (1H, qn), 3.90 (1H, t, J 8.5 Hz), 3.96 (1H, dd), 4.24 (1H, t, J 8.0 Hz), 5.34 (1H, s), 5.37 (1H, d, J 11.1 Hz), 5.59 (1H, d, J 17.2 Hz), 6.98 (1H, dd, J 17.2, 10.9 Hz), 7.08 (1H, d), 7.15 (1H, s), 7.25 (1H, m), 7.33 (2H, t, J 7.4 Hz), 7.45 (1H, d, J 8.6 Hz), and 7.60 (2H, d, J 7.5 Hz).

EXAMPLE 232

(3R,5R,6S)-3-[2-(Ethen-1-yl)-5-(trifluoromethoxy)phenyl]-6-phenyl-1-oxa-7-aza-spiro[4.5]decane Hydrochloride Prepared from the compound of Example 231 according to the method of Example 181. ¹H NMR (360 MHz, CD₃OD) δ 0.53 (1H, t, J 15.1 Hz), 0.73 (2H, m), 0.89 (1H, m), 1.09 (3H, m), 1.96 (1H, td, J 12.4 Hz), 2.16 (1H, dd, J 12.8 Hz), 2.52 (1H, t, J 9.7 Hz), 2.78 (1H, t, J 7.1 Hz), 3.08 (1H, s), 3.90 (1H, d, J 11.0 Hz), 4.18 (1H, d, J 17.2 Hz), 4.83 (1H, dd, J 17.2, 10.9 Hz), 5.83 (2H, m), 6.17 (1H, d, J 8.5 Hz), and 6.34 (5H, m). m/z (ES⁺) 404 (M+1).

EXAMPLE 233

(3R,5R,6S)-3-[2-Acetyl-5-(trifluoromethoxy)phenyl]-6-phenyl-1-oxa-7-(tert-butoxycarbonyl)aza-spiro[4.5]decane A mixture of (3R,5R,6S)-3-[5-(trifluoromethoxy-2-(trifluoromethylsulfonyloxy)phenyl]-6-phenyl-1-oxa-7-

(tert-butoxycarbonyl)aza-spiro[4.5]decane (Example 188, 270 mg), (1-ethoxyvinyl)tributyl tin (0.15 mL), lithium chloride (108 mg) and tetrakis(triphenylphosphine) palladium (0) (50 mg) in dioxane (2 mL) was degassed with a firestone valve (3×) and stirred at 110° C. at 110° C. for 16 h. The mixture was cooled, filtered and the solvent was evaporated under reduced pressure. The residue was dissolved in acetonitrile (10 mL) and washed with hexane (15 mL). The hexane fraction was extracted with acetonitrile (3×10 mL) and the combined acetonitrile fractions were treated with methanolic potassium fluoride (5%, 2 mL). The mixture was filtered and the solvent was evaporated under reduced pressure. The residue was dissolved in tetrahydrofuran (3 mL) and aqueous hydrochloric acid (6M, 2 mL) was added. The mixture was stirred at room temperature for 4 h., basified with aqueous sodium hydrogen carbonate (saturated), and extracted with dichloromethane (3×10 mL). The combined organic fractions were washed with brine, dried (MgSO$_4$) and the solvent was evaporated under reduced pressure. The residue was purified by medium pressure liquid chromatography on silica gel, eluting with hexane/EtOAc (85:15), to give the title compound as an oil. $^1$H NMR (360 MHz, CDCl$_3$) δ 1.47 (9H, s), 1.72 (3H, m), 1.81 (1H, dd, J 12.9, 8.3 Hz), 2.22 (1H, td), 2.58 (3H, s), 2.72 (1H, dd, J 12.9, 8.3 Hz), 2.76 (1H, td, 12.6 Hz), 3.86 (1H, dd, J 8.8, 6.6 Hz), 4.00 (1H, dd), 4.09 (1H, qn), 4.24 (1H, dd, J 8.8, 7.3 Hz), 5.29 (1H, s), 7.14 (1H, d, J 8.6 Hz), 7.25 (1H, m), 7.34 (3H, m), 7.58 (2H, d, J 7.8 Hz), and 7.61 (1H, d, J 8.6 Hz).

EXAMPLE 234

(3R,5R,6S)-3-[2-Acetyl-5-(trifluoromethoxy) phenyl]-6-phenyl-1-oxa-7-aza-spiro[4.5]decane Hydrochloride Prepared from the compound of Example 233 according to the method of Example 181. $^1$H NMR (360 MHz, CDCl$_3$) δ 1.69 (3H, m), 1.99 (1H, m), 2.24 (3H, s), 2.29 (1H, dd, J 13.1, 8.3 Hz), 2.45 (2H, m), 2.84 (1H, t), 3.39 (1H, d), 3.67 (1H, t, J 8.9 Hz), 3.87 (1H, s), 3.99 (1H, t, J 7.6 Hz), 7.05 (1H, d, J 8.4 Hz), 7.08 (1H, s), 7.37 (4H, m), and 7.56 (2H, d, J 7.1 Hz). m/z (ES$^+$) 420 (M+1).

EXAMPLE 235

(3R,5R,6S)-3-[2-Formyl-5-(trifluoromethoxy) phenyl]-6-phenyl-1-oxa-7-(tert-butoxycarbonyl)aza-spiro[4.5]decane A stirred, cooled (−78° C.) mixture of (3R,5R,6S)-3-[2-(ethen-1-yl)-5-(trifluoromethoxy)phenyl]-6-phenyl-1-oxa-7-(tert-butoxycarbonyl)aza-spiro[4.5]decane (Example 231, 420 mg) and the methanol (4 mL) in dichloromethane (10 mL) was purged with nitrogen, then a steady stream of ozone was bubbled through the mixture for 1 h. The mixture was purged with oxygen for 15 min., then with nitrogen for 15 min. Dimethyl sulfide (0.3 mL) was added and the mixture was stirred at room temperature overnight. The solvent was evaporated under reduced pressure and the residue was purified by column chromatography on silica gel, eluting with hexane/EtOAc (85:15), to give the title compound as an oil. $^1$H NMR (360 MHz, CDCl$_3$) δ 1.48 (9H, s), 1.55 (2H, m), 1.72 (1H, d, J 9.5 Hz), 1.85 (1H, dd, J 13.0, 8.4 Hz), 2.25 (1H, m), 2.77 (2H, m), 3.97 (2H, m), 4.27 (1H, dd, J 9.0, 7.2 Hz), 4.53 (1H, qn, J 7.2 Hz), 5.36 (1H, s), 7.26 (2H, m), 7.34 (2H, m), 7.59 (1H, d, J 7.6 Hz), 7.87 (1H, d, J 8.5 Hz), and 10.26 (1H, s). m/z (ES$^+$) 450 (M+1-C$_4$H$_8$).

EXAMPLE 236

(3R,5R,6S)-3-[2-Formyl-5-(trifluoromethoxy) phenyl]-6-phenyl-1-oxa-7-aza-spiro[4.5]decane Prepared from the compound of Example 235 according to the method of Example 181. $^1$H NMR (360 MHz, CDCl$_3$) δ 1.59 (3H, m), 2.20 (3H, m), 2.25 (1H, dd, J 12.7 Hz), 2.80 (2H, m), 3.56 (1H, s), 3.72 (1H, t, J 9.8 Hz), 3.97 (1H, t, J 7.8 Hz), 7.10 (2H, s), 7.38 (3H, m), 7.50 (2H, dd, J 7.7, 3.0 Hz), 7.78 (1H, d, J 9.3 Hz), and 9.53 (1H, s). m/z (ES$^+$) 406 (M+1).

EXAMPLE 237

(3R,5R,6S)-3-(3-Fluoro-2-methoxy-5-(trifluoromethoxy)phenyl)-6-phenyl-1-oxa-7aza-spiro[4.5]decane Selectfluor™ (630 mg) was added to a solution of (3R, 5R,6S)-3-(2-methoxy-5-(trifluoromethoxy)phenyl)-6-phenyl-1-oxa-7-(tert-butoxycarbonyl)aza-spiro[4.5]decane (Example 164, 208 mg) in acetonitrile (15 mL) and the mixture was heated under reflux for 36 h. The mixture was cooled and the solvent was evaporated under reduced pressure. The residue was purified by medium pressure liquid chromatography on silica gel, eluting with CH$_2$Cl$_2$/MeOH (92:8), to give the title compound as a pale brown oil (15 mg). $^1$H NMR (360 MHz, CDCl$_3$) δ 1.46–1.56 (1H, m), 1.0–1.75 (3H, m), 1.98–2.02 (1H, m), 2.16–2.37 (3H, m), 2.86 (1H, t, J 12.6 Hz), 3.20–3.24 (1H, m), 3.49 (3H, s), 3.56 (1H, s), 3.98 (1H, t, J 7.6 Hz), 6.64 (1H, s), 6.28 (1H, d J 11 Hz), and 7.25–7.60 (5H, m). m/z (ES$^+$) 426 (M+1).

EXAMPLE 238

(3R,5R,6S)-3-[2-Cyano-5-(trifluoromethoxy) phenyl]-6-phenyl-1-oxa-7-(tert-butoxycarbonyl)aza-spiro[4.5]decane A mixture of (3R,5R,6S)-3-[5-(trifluoromethoxy)-2-(trifluoromethylsulfonyloxy)phenyl]-6-phenyl-1-oxa-7-(tert-butoxycarbonyl)aza-spiro[4.5]decane (Example 188, 230 mg), zinc cyanide (26 mg), tris(dibenzylideneacetone) dipalladium(0) (10 mg), and 1,1'-bis(diphenylphospino) ferrocene (16 mg) in DMF (1 mL) was degassed with a firestone valve (×5) and stirred at 110° C. for 4 h. The mixture was cooled, diluted with water and extracted with ethyl acetate (3×5 mL). The combined organic fractions were washed with brine, dried (MgSO$_4$) and the solvent was evaporated under reduced pressure. The residue was purified by medium pressure liquid chromatography on silica gel, eluting with hexane/EtOAc (90:10), to give the title compound as a colorless oil (60 mg). $^1$H NMR (360 MHz, CDCl$_3$) δ 1.48 (9H, s), 1.56–1.68 (1H, m), 1.70–1.80 (2H, m), 1.88 (1H, dd, J 13.2, 8.0 Hz), 2.26 (1H, dt, J 13.0, 5.0 Hz), 2.76–2.85 (2H, m), 3.93–4.01 (3H, m), 4.28–4.35 (1H, m), 5.34 (1H, s), 7.10–7.20 (1H, m), 7.24–7.3 (1H, m), 7.31–7.36 (3H, m), 7.57–7.60 (2H, m), and 7.68 (1H, d, J 8.6 Hz). m/z (ES$^+$) 447 (M+1-C$_4$H$_8$).

EXAMPLE 239

(3R,5R,6S)-3-[2-Cyano-5-(trifluoromethoxy) phenyl]-6-phenyl-1-oxa-7-aza-spiro[4.5]decane Prepared from the compound of Example 238 according to the method of Example 181. $^1$H NMR (360 MHz, CDCl$_3$) δ 1.60–1.73 (2H, m), 1.86 (2H, mc), 1.98–2.07 (1H, m), 2.36–2.54 (2H, m), 2.79 (1H, t, J 12 Hz), 3.19–3.25 (1H, m), 3.56 (1H, s), 3.71 (1H, t, J 9.0 Hz), 4.03 (1H, t, J 8.0 Hz), 7.00–7.1 (2H, m), 7.30–7.40 (3H, m), 7.46–7.51 (2H, m), and 7.55 (1H, d, J 8.5 Hz).m/z (ES$^+$) 403 (M+1).

EXAMPLE 240

(3R,5R,6S)-3-[2-Ethyl-5-(trifluoromethoxy)phenyl]-6-phenyl-1-oxa-7-(tert-butoxycarbonyl)aza-spiro [4.5]decane A slurry of palladium hydroxide on carbon (100 mg) in methanol (2 mL) was added to a solution of (3R,5R,6S)-3-

[2-(ethen-1-yl)-5-(trifluoromethoxy)phenyl]-6-phenyl-1-oxa-7-(tert-butoxycarbonyl)aza-spiro[4.5]decane (Example 231, 200 mg) in ethyl acetate (10 mL) and the mixture was shaken under hydrogen (50 psi) overnight. The mixture was filtered and the solvent was evaporated under reduced pressure to give the title compound as an oil. $^1$H NMR (CDCl$_3$, 360 MHz), δ 1.20 (3H, t, J 7.6 Hz), 1.46 (9H, s), 1.63 (2H, m), 1.79 (2H, m), 2.27 (1H, td, J 7.6, 5.1 Hz), 2.67 (3H, m), 2.76 (1H, td, J 9.3, 3.9 Hz), 3.72 (1H, qn, J 8.0 Hz), 3.89 (1H, t, J 8.6 Hz), 3.97 (1H, dd, J 13.1 Hz), 4.24 (1H, t, J 7.8 Hz), 5.35 (1H, s), 7.01 (1H, d, J 8.7 Hz), 7.17 (2H, m), 7.25 (1H, m), 7.33 (2H, t, J 7.1 Hz), 7.60 (2H, d, J 7.7 Hz). m/z (ES$^+$) 450 (M+1-C$_4$H$_8$).

EXAMPLE 241

(3R,5R,6S)-3-[2-Ethyl-5-(trifluoromethoxy)phenyl]-6-phenyl-1-oxa-7-aza-spiro[4.5]decane Prepared from the compound of Example 240 according to the method of Example 181. $^1$H NMR (360 MHz, CDCl$_3$) δ 0.78 (3H, t, J 7.6 Hz), 1.53 (1H, m), 1.34 (3H, m), 1.71 (1H, td, J 12.2, 4.5 Hz), 2.02 (2H, q, J 7.6 Hz), 2.18 (2H, m), 2.80 (1H, t, J 12.3 Hz), 3.22 (1H, d), 3.53 (1H, s), 3.60 (1H, t, J 10.3 Hz), 3.91 (1H, t, J 7.7 Hz), 6.89 (2H, m), 6.99 (1H, d, J 8.4 Hz), 7.30 (3H, m), and 7.47 (2H, m). m/z (ES$^+$) 406 (M+1).

EXAMPLE 242

(3R,5R,6S)-3-(6-Fluoro-2-methoxyphenyl)-6-phenyl-1-oxa-7-(tert-butoxycarbonyl)aza-spiro[4.5]decane Prepared from the compound of Description 121 and (5R,6S)-6-phenyl-1-oxa-7-(tert-butoxycarbonyl)aza-spiro[4.5]dec-3-ene (Description 86) according to the method of Example 170. $^1$H NMR (360 MHz, CDCl$_3$) δ 7.63 (2H, d, J 7.8 Hz), 7.32–7.11 (6H, m), 5.36 (1H, s), 4.18–3.96 (4H, m), 3.83 (3H, s), 2.80 (1H, m), 2.42 (1H, m), 2.23 (2H, m), 1.88–1.64 (3H, m), and 1.48 (9H, s). m/z (ES$^+$) 442 (M+1).

EXAMPLE 243

(3R,5R,6S)-3-(6-Fluoro-2-methoxyphenyl)-6-phenyl-1-oxa-7-aza-spiro[4.5]decane

Prepared from the compound of Example 242 according to the method of Example 181. $^1$H NMR (360 MHz, CDCl$_3$) δ 7.47 (2H, m), 7.34 (3H, m), 7.02 (1H, dt, J$_d$ 6.4 Hz, J$_t$ 8.3 Hz), 6.52 (2H, m), 3.99 (1H, m), 3.77 (1H, m), 3.63 (3H, s), 3.55 (1H, s), 3.22 (1H, m), 2.78 (1H, m), 2.70 (1H, br s), 2.06 (1H, m), and 2.12 (6H, m). m/z (ES$^+$) 342 (M+1).

EXAMPLE 244

(3S,5R,6S)-3-[2-Cyclopropoxy-5-(trifluoromethoxy)-phenyl]-6-phenyl-1-oxa-7-(tert-butoxycarbonyl)aza-spiro[4.5]decane Naphthalene (120 mg, 0.936 mmol) was dissolved in THF (1.5 mL) under nitrogen and freshly cut lithium metal (7.0 mg, 0.94 mmol) was added. The mixture was then sonicated at room temperature for 20 min. to produce a dark green solution of lithium naphthalenide. This solution was cooled to −78° C., then (3S,5R,6S)-3-[2-(1-phenylthiocycloprop-1-yl)oxy-5-(trifluoromethoxy)phenyl]-6-phenyl-1-oxa-7-(tert-butoxycarbonyl)aza-spiro[4.5]decane (Description 111) (120 mg, 0.187 mmol) in THF (0.5 mL) was added over 1 minute. The reaction mixture was stirred for 30 min., then water (5 mL) and ether (10 mL) were added. The layers were separated and the aqueous layer was extracted with ether (10 mL). The combined organic fractions were dried (MgSO$_4$) and the solvent was evaporated under reduced pressure. The residue was purified by column chromatography on silica gel, eluting with hexane/ethyl acetate (90:10 increasing to 80:20) to give the title compound as a colourless oil (58.6 mg, 59%). $^1$H NMR (250 MHz, CDCl$_3$) δ 7.58–7.52 (2H, m), 7.36–7.17 (4H, m), 7.10–7.01 (2H, m), 5.18 (1H, br s), 4.20 (1H, t, J 6.7 Hz), 4.05–3.95 (1H, m), 3.76–3.55 (3H, m), 2.92–2.79 (1H, m), 2.37 (1H, dd, J 12.9, 7.8 Hz), 2.18–2.06 (2H, m), 1.80–1.67 (3H, m), 1.38 (9H, s), and 0.86–0.73 (4H, m). m/z (ES$^+$) 534 (M+1).

EXAMPLE 245

(3S,5R,6S)-3-[2-Cyclopropoxy-5-(trifluoromethoxy)phenyl]-6-phenyl-1-oxa-7-aza-spiro[4.5]decane Hydrochloride Trifluoroacetic acid (2.5 mL) was added dropwise to a stirred, cooled 0° C.) solution of (3S,5R,6S)-3-[2-cyclopropoxy-5-(trifluoromethoxy)phenyl]-6-phenyl-1-oxa-7-(tert-butoxycarbonyl)aza-spiro[4.5]decane (Example 244; 492 mg, 0.92 mmol) in dichloromethane (25 mL) and the mixture was stirred at room temperature for 3 h. The mixture was poured into water (50 mL), the pH was adjusted to 10.0 with aqueous sodium hydroxide (4M) and the mixture was extracted with dichloromethane (3×50 mL). The combined organic fractions were dried MgSO$_4$) and the solvent was evaporated under reduced pressure. The residue was purified by flash column chromatography on silica gel, eluting with CH$_2$Cl$_2$/MeOH/NH$_3$ (Aq.) (96:4:0.4 increasing to 94:6:0.6). The residue was dissolved in ethanol (20 mL), cooled in ice and ethereal hydrogen chloride (1M, 1.8 mL, 1.8 mmol) was added dropwise. The mixture was stirred at 0° C. for 5 min., then the solvent was evaporated under reduced pressure. The residue was crystallized from ether (20 mL)/ethanol (0.5 mL) and the solid was collected and dried in vacuo to give the title compound as a colorless solid (354 mg, 89%). m.p. 214–216° C., $^1$H NMR (500 MHz, CD$_3$OD) δ 7.59 (2H, m), 7.52 (3H, m), 7.26 (1H, d, J 8.9 Hz), 7.03 (1H, dd, J 8.9, 2.2 Hz), 6.20 (1H, d, J 2.2 Hz), 4.85 (2H, br s), 4.43 (1H, s), 4.19 (1H, t, J 8.0 Hz), 3.87 (1H, quin, J 8.0 Hz), 3.76 (1H, m), 3.44 (1H, m), 3.25 (2H, m) 2.29–1.78 (6H, m), 0.80 (2H, m), and 0.66 (2H, m). m/z (ES$^+$) 434 (M+1). Found: C, 61.41; H, 5.51; N, 3.08. C$_{24}$H$_{26}$F$_3$NO$_3$.HCl requires: C, 61.34; H, 5.79; N, 2.98%.

EXAMPLE 246

(3R,5R,6S)-3-[2-Cyclopropoxy-5-(trifluoromethoxy)phenyl]-6-phenyl-1-oxa-7-(tert-butoxycarbonyl)aza-spiro[4.5]decane Naphthalene (120 mg, 0.936 mmol) was dissolved in THF (1.5 mL) under nitrogen and freshly cut lithium metal (7.0 mg, 0.94 mmol) was added. The mixture was then sonicated at room temperature for 20 min. to produce a dark green solution of lithium naphthalenide. A solution of (3R,5R,6S)-3-[2-(1-phenylthiocycloprop-1-yl)oxy-5-(trifluoromethoxy)phenyl]-6-phenyl-1-oxa-7-(tert-butoxycarbonyl)aza-spiro [4.5]decane (Description 112, 135 mg, 0.21 mmol) in THF (2 mL) under nitrogen was cooled to −78° C. and the solution of lithium naphthalenide in THF was added dropwise until the intense green colour persisted. The reaction was then stirred for one minute, water (5 mL) was added and the mixture was warmed to room temperature. Ether (10 mL) was added and the layers were separated. The aqueous phase was extracted with a further portion of ether (10 mL) and the combined organic phases were dried (MgSO₄) and the solvent was evaporated under reduced pressure. The residue was purified by column chromatography on silica gel, eluting with hexane/ethyl acetate (50:50) to give the title compound as a colourless oil (87 mg, 78%). ¹H NMR (360 MHz, CDCl₃) δ 7.59 (2H, app. d, J 7.6 Hz), 7.32 (2H, app. t, J 7.6 Hz), 7.27–7.18 (2H, m), 7.11–7.03 (2H, m), 5.32 (1H, br s), 4.29–4.21 (1H, m), 3.97 (1H, br. d, J 13 Hz), 3.83–3.68 (3H, m), 2.76 (1H, dt, J 13, 4.1 Hz), 2.55 (1H, dd, J 13, 7.2 Hz), 2.22 (1H, dt, J 12, 5.2 Hz), 1.85 (1H, dd, J 13, 9.9 Hz), 1.80–1.63 (3H, m), 1.46 (9H, s), and 0.82–0.76 (4H, m). m/z (ES⁺) 534 (M+1).

EXAMPLE 247

(3R,5R,6S)-3-[2-Cyclopropoxy-5-(trifluoromethoxy) phenyl]-6-phenyl-1-oxa-7-aza-spiro[4.5]decane Prepared from the compound of Example 246 according to the method of Example 245. ¹H NMR (360 MHz, CDCl₃) δ 7.50–7.42 (2H, m), 7.36–7.26 (3H, m), 7.03 (1H, d, J 8.9 Hz), 6.95 (1H, br. d, J 8.9 Hz), 6.81 (1H, br s), 3.92 (1H, t, J 7.4 Hz), 3.62–3.53 (2H, m), 3.50 (1H, s), 3.20 (1H, dd, J 12, 4.2 Hz), 2.77 (1H, dt, J 12, 2.8 Hz), 2.30–1.93 (4H, m), 1.87 (1H, br s), 1.71–1.49 (3H, m), 0.76–0.65 (2H, m), and 0.65–0.54 (2H, m). m/z (ES⁺) 434 (M+1).

EXAMPLE 248

(3S,5R,6S)-3-[2-Cyclopropoxy-5-(trifluoromethyl) phenyl]-6-phenyl-1-oxa-7-(tert-butoxycarbonyl)aza-spiro[4.5]decane Prepared from the compound of Description 113 according to the method of Example 246. ¹H NMR (360 MHz, CDCl₃) δ 7.54 (2H, d, J 7.7 Hz), 7.46 (1H, d, J 8.2 Hz), 7.40 (H, s), 7.33–7.24 (4H, m), 5.17 (1H, s), 4.20 (1H, t, J 7.2 Hz), 4.00 (1H, m), 3.78–3.60 (3H, m), 2.88 (1H, m), 2.39 (1H, dd, J 12.9, 7.8 Hz), 2.16 (2H, m), 1.73 (3H, m), 1.36 (9H, s), and 0.82 (4H, m).

EXAMPLE 249

(3S,5R,6S)-3-[2-Cyclopropoxy-5-(trifluromethyl) phenyl]-6-phenyl-1-oxa-7-aza-spiro[4,5]decane Prepared from the compound of Example 248 according to the method of Example 245. ¹H NMR (360 MHz, CDCl₃) δ 7.48–7.30 (6H, m), 7.16 (1H, d, J 8.5 Hz), 6.53 (1H, s), 4.05 (1H, t, J 7.9 Hz), 3.78–3.66 (3H, m), 3.24 (1H, m), 3.06 (1H, dd, J 10.4, 8.2 Hz), 2.83 (1H, m), 2.6 (1H, br s), 2.08 (2H, m), 1.84 (2H, m), 1.61 (2H, m), and 0.74 (4H, m). m/z (ES⁺) 418 (M+1).

EXAMPLE 250

(3R,5R,6S)-3-[2-Cyclopropoxy-5-(difluoromethoxy) phenyl]-6-phenyl-1-oxa-7-(tert-butoxycarbonyl)aza-spiro[4.5]decane Prepared from the compound of Description 114 according to the method of Example 246. ¹H NMR (360 MHz, CDCl₃) δ 7.60 (2H, d, J 7.5 Hz), 7.32 (2H, t, J 7.5 Hz), 7.24 (1H, t, J 7.5 Hz), 7.18 (1H, d, J 8.7 Hz), 7.02 (1H, d, J 2.8 Hz), 6.98 (1H, dd, J 8.7, 2.8 Hz), 6.43 (1H, t, J 74.4 Hz), 5.32 (1H, s), 4.25 (1H, m), 3.97 (1H, m), 3.81–3.69 (3H, m), 2.75 (1H, m), 2.54 (1H, m), 2.22 (1H, m), 1.89–1.62 (4H, m), 1.46 (9H, s), and 0.77 (4H, m). m/z (ES⁺) 516 (M+1).

EXAMPLE 251

(3R,5R,6S)-3-[2-Cyclopropoxy-5-(difluoromethoxy)-phenyl]-6-phenyl-1-oxa-7-aza-spiro[4.5]decane Hydrochloride Prepared from the compound of Example 250 according to the method of Example 245. (360 MHz, D₂O) δ 0.51 (2H, m), 0.72 (2H, m), 1.79 (1H, m), 1.90–2.28 (6H, m), 3.21 (1H, m), 3.50 (1H, m), 3.65 (2H, m), 4.00 (1H, m), 4.26 (1H, s), 6.66 (1H, t, J 74 Hz), 6.93 (1H, d, J 2.7 Hz), 7.01 (1H, dd, J 8.9, 2.7 Hz), 7.18 (1H, d, J 8.9 Hz), and 7.55 (5H, m). m/z (ES⁺) 416 (M+1). Found: C, 62.2; H, 6.2; N, 3.1. C₂₄H₂₇F₂NO₃.HCl.0.5H₂O requires C, 62.5; H, 6.3; N, 3.0%.

EXAMPLE 252

(3R,5R,6S)-3-[2-Cyclopropoxy-5-(trifluoromethoxy) phenyl]-6-(4-fluorophenyl)-1-oxa-7-tert-butoxycarbonyl)aza-spiro[4.5]decane Prepared from the compound of Description 115 according to the method of Example 246. ¹H NMR (360 MHz, CDCl₃) δ 0.79 (2H, m), 0.86 (2H, m), 1.46 (9H, s), 1.68 (3H, m), 1.87 (1H, dd, J 9.9 Hz), 2.14 (1H, td), 2.53 (1H, dd, J 12.6 Hz), 3.77 (3H, m), 3.98 (1H, dd), 4.24 (1H, s), 5.20 (1H, s), 7.00 (2H, t, J 8.8 Hz), 7.08 (2H, s), 7.23 (2H, d, J 9.5 Hz), and 7.55 (2H, dd, J 8.7, 5.6 Hz).

EXAMPLE 253

(3R,5R,6S)-3-[2-Cyclopropoxy-5-(trifluoromethoxy) phenyl]-6-(4-fluorophenyl)-1-oxa-7-aza-spiro[4.5] decane Hydrochloride Prepared from the compound of Example 252 according to the method of Example 245. ¹H NMR (400 MHz, CDCl₃) δ 0.59 (2H, s), 0.74 (2H, d, J 6.28 Hz), 1.68 (3H, m), 2.05 (2H, m), 2.21 (1H, m), 2.42 (1H, dd, J 13.4 Hz), 2.87 (1H, dd, J 9.2 Hz), 3.39 (1H, d, J 10.2 Hz), 3.59 (2H, m), 3.87 (1H, d, J 10.4 Hz), 4.00 (1H, t, J 7.7 Hz), 6.77 (1H, s), 7.03 (4H, m), 7.61 (2H, s), 9.21 (1H, s), and 10.24 (1H, s).

EXAMPLE 254

(3R,5R,6S)-3-[2-Cyclopropoxy-5-(trifluoromethyl) phenyl]-6-phenyl-1-oxa-7-(tert-butoxycarbonyl)aza-spiro[4.5]decane Prepared from the compound of Description 120 according to the method of Example 246. ¹H NMR (360 MHz, CDCl₃) δ 0.83–0.91 (4H, m), 1.46 (9H, s), 1.55–1.8 (3H, m), 1.86–1.92 (1H, m), 2.22 (1H, dt, J 13.0, 5.0 Hz), 2.56 (1H, dd, J 12.0, 6.5 Hz), 2.76 (1H, mc), 3.77–3.80 (3H, m), 3.97 (1H, mc), 4.27 (1H, mc), 5.33 (1H, s), 7.24–7.34 (4H, m), 7.45–7.50 (2H, m), and 7.58–7.62 (2H, m). m/z (ES⁺) 462 (M+1-C₄H₈).

EXAMPLE 255

(3R,5R,6S)-3-[2-Cyclopropoxy-5-(trifluoromethyl) phenyl]-6-phenyl-oxa-7-aza-spiro[4.5]decane Prepared from the compound of Example 254 according to the method of Example 245. ¹H NMR (360 MHz, CDCl₃) δ 0.56–0.70 (2H, m), 0.70–0.80 (2H, m), 1.62–1.72 (3H, m), 1.96–2.04 (1H, m), 2.08–2.28 (3H, m), 2.81 (1H, t, J 12.0 Hz), 3.14–3.22 (1H, m), 3.58–3.68 (2H, m), 3.76 (1H, s), 4.00 (1H, t, J 7.5 Hz), 7.10–7.20 (2H, m), 7.26–7.42 (4H, m), and 7.42–7.54 (2H, m). m/z (ES⁺) 418 (M+1).

We claim:
1. A compound of the formula (I):

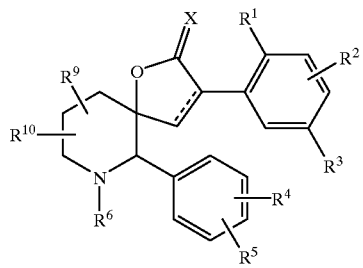

wherein
R$^1$ represents hydrogen, hydroxy, C$_{1-6}$alkyl, C$_{2-6}$alkenyl, C$_{3-7}$cycloalkyl, C$_{3-7}$cycloalkylC$_{1-4}$alkyl, C$_{1-6}$alkoxy, fluoroC$_{1-6}$alkoxy, C$_{1-6}$alkoxyC$_{1-4}$alkyl, C$_{1-6}$alkoxyC$_{1-4}$alkoxy, fluoroC$_{1-6}$alkoxyC$_{1-4}$alkyl, C$_{1-6}$alkenyloxy, C$_{3-7}$cycloalkoxy, C$_{3-7}$cycloalkylC$_{1-4}$alkoxy, phenoxy, benzyloxy, cyano, halogen, NR$^a$R$^b$, SR$^a$, SOR$^a$, SO$_2$R$^a$, OSO$_2$R$^a$, NR$^a$COR$^{14}$, COR$^a$, CO$_2$R$^a$ or CONR$^a$R$^b$ where R$^a$ and R$^b$ each independently represent hydrogen, C$_{1-4}$alkyl or fluoroC$_{1-4}$alkyl;

R$^2$ represents hydrogen, halogen, C$_{1-6}$alkyl or C$_{1-6}$alkoxy;
or when R$^2$ is adjacent to R$^1$, they may be joined together such that there is formed a 5- or 6-membered saturated or unsaturated ring containing one or two atoms selected from nitrogen, oxygen and sulphur, which ring is optionally substituted by a group selected from C$_{1-4}$alkyl, CF$_3$, =O or =S;

R$^3$ represents hydrogen, halogen, C$_{1-6}$alkyl, fluoroC$_{1-6}$alkyl, C$_{1-6}$alkoxy, fluoroC$_{1-6}$alkoxy, C$_{3-7}$cycloalkyl, C$_{3-7}$cycloalkylC$_{1-4}$alkyl, cyano, SR$^a$, SOR$^a$, SO$_2$R$^a$, NR$^a$R$^b$, NR$^a$COR$^{14}$, COR$^a$, CO$_2$R$^a$, CONR$^a$R$^b$ or C$_{1-4}$alkyl substituted by cyano, CO$_2$R$^a$ or CONR$^a$R$^b$ where R$^a$ and R$^b$ are as previously defined;

R$^4$ represents hydrogen, halogen, C$_{1-6}$alkyl, C$_{1-6}$alkoxy, CF$_3$, OCF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ are as previously defined;

R$^5$ represents hydrogen, halogen, C$_{1-6}$alkyl, CF$_3$ or C$_{1-6}$alkoxy substituted by C$_{1-4}$alkoxy;

R$^6$ represents hydrogen, COR$^a$, CO$_2$R$^a$, COCONR$^a$R$^b$, COCO$_2$R$^a$, C$_{1-6}$alkyl optionally substituted by a group selected from (CO$_2$R$^a$, CONR$^a$R$^b$, hydroxy, CN, COR$^a$, NR$^a$R$^b$, C(NOH)NR$^a$R$^b$, CONHphenyl(C$_{1-4}$alkyl), COCO$_2$R$^a$, CONHNR$^a$R$^b$, C(S)NR$^a$R$^b$, CONR$^a$C$_{1-6}$alkylR$^{12}$, CONR$^{13}$C$_{2-6}$alkenyl, CONR$^{13}$C$_{2-6}$alkynyl, COCONR$^a$R$^b$, CONR$^a$C(NR$^b$)NR$^a$R$^b$, CONR$^a$heteroaryl, and phenyl optionally substituted by one, two or three substituents selected from C$_{1-6}$alkyl, C$_{1-6}$alkoxy, halogen and trifluoromethyl);

or R$^6$ represents a group of the formula —CH$_2$C≡CCH$_2$NR$^7$R$^8$ where R$^7$ and R$^8$ are as defined below;

or R$^6$ represents C$_{1-6}$alkyl, optionally substituted by oxo, substituted by a 5-membered or 6-membered heterocyclic ring containing 1, 2 or 3 nitrogen atoms optionally substituted by =O or =S and optionally substituted by a group of the formula ZNR$^7$R$^8$ where Z is C$_{1-6}$alkylene or C$_{3-6}$cycloalkyl;

R$^7$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy or hydroxyl;

R$^8$ is hydrogen or C$_{1-4}$alkyl, C$_{3-7}$cycloalkyl, C$_{3-7}$cycloalkylC$_{1-4}$alkyl, or C$_{2-4}$alkyl substituted by C$_{1-4}$alkoxy, hydroxyl or a 4, 5 or 6 membered heteroaliphatic ring containing one or two heteroatoms selected from N, O and S;

or R$^7$, R$^8$ and the nitrogen atom to which they are attached form a heteroaliphatic ring of 4 to 7 ring atoms, optionally substituted by one or two groups selected from hydroxy or C$_{1-4}$alkoxy optionally substituted by a C$_{1-4}$alkoxy or hydroxyl group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is C$_{1-4}$alkyl optionally substituted by hydroxy or C$_{1-4}$alkoxy;

or R$^7$, R$^8$ and the nitrogen atom to which they are attached form a non-aromatic azabicyclic ring system of 6 to 12 ring atoms;

or Z, R$^7$ and the nitrogen atom to which they are attached form a heteroaliphatic ring of 4 to 7 atoms which may optionally contain an oxygen ring atom;

R$^9$ and R$^{10}$ each independently represent hydrogen, halogen, C$_{1-6}$alkyl, CH$_2$OR$^e$, oxo, CO$_2$R$^a$ or CONR$^a$R$^b$ where R$^a$ and R$^b$ are as previously defined and R$^e$ represents hydrogen, C$_{1-6}$alkyl or phenyl;

R$^{12}$ represents OR$^a$, CONR$^a$R$^b$ or heteroaryl;

R$^{13}$ represents hydrogen or C$_{1-6}$alkyl;

R$^{14}$ represents C$_{1-6}$alkyl, C$_{1-6}$alkoxy, fluoroC$_{1-6}$alkyl or phenyl;

X is an oxygen atom or two hydrogen atoms; and the broken line represents an optional double bond;

or a pharmaceutically acceptable salt thereof.

2. A compound as claimed in claim 1 wherein R$^1$ is hydroxy, C$_{1-6}$alkyl, C$_{2-6}$alkenyl, C$_{1-6}$alkoxy, fluoroC$_{1-6}$alkoxy, C$_{2-6}$alkenyloxy, C$_{3-7}$cycloalkoxy, C$_{3-7}$cycloalkylC$_{1-4}$alkoxy, cyano, NR$^a$R$^b$, SR$^a$, OSO$_2$R$^a$, or R$^1$ together with the group R$^2$ form a 5-membered saturated ring containing one oxygen atom.

3. A compound as claimed in claim 1 wherein R$^2$ is a hydrogen, fluorine or chlorine atom.

4. A compound as claimed in claim 1 wherein R$^3$ is hydrogen, halogen, fluoroC$_{1-6}$alkyl, fluoroC$_{1-6}$alkoxy, cyano, NR$^a$R$^b$, or NR$^a$COR$^{14}$.

5. A compound as claimed in claim 1 wherein R$^4$ is a hydrogen atom or a fluorine atom.

6. A compound as claimed in claim 1 wherein R$^5$ is a hydrogen atom.

7. A compound as claimed in claim 1 wherein R$^6$ is a hydrogen atom or a C$_{1-6}$alkyl group substituted by a 5-membered heterocyclic ring containing 2 or 3 nitrogen atoms as defined in claim 1.

8. A compound as claimed in claim 1 wherein one of R$^9$ and R$^{10}$ is hydrogen.

9. A compound as claimed in claim 1 wherein X represents two hydrogen atoms.

10. A compound as claimed in claim 1 wherein the double bond represented by the broken line is absent.

11. A compound of the formula (Ia) or a pharmaceutically acceptable salt thereof:

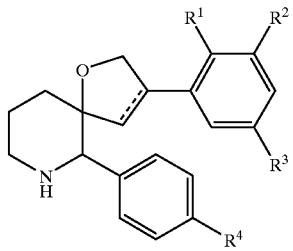

(Ia)

wherein $R^1$, $R^2$, $R^3$, $R^4$ and the broken line are as defined in claim 1.

12. A compound as claimed in claim 1 wherein $R^1$ represents hydrogen, hydroxy, $C_{1-6}$alkyl, $C_{2-6}$alkenyl, $C_{3-7}$cycloalkyl, $C_{3-7}$cycloalkyl$C_{1-4}$alkyl, $C_{1-6}$alkoxy, fluoro$C_{1-6}$alkoxy, $C_{1-6}$alkoxy$C_{1-4}$alkyl, $C_{1-6}$alkoxy$C_{1-4}$alkoxy, fluoro$C_{1-6}$alkoxy$C_{1-4}$alkyl, $C_{2-6}$alkenyloxy, $C_{3-7}$cycloalkoxy, $C_{3-7}$cycloalkyl$C_{1-4}$alkoxy, phenoxy, benzyloxy, cyano, halogen, $NR^aR^b$, $SR^a$, $SOR^a$, $SO_2R^a$, $OSO_2R^a$, $NR^aCOR^{14}$, $COR^a$, $CO_2R^a$ or $CONR^aR^b$ where $R^a$ and $R^b$ each independently represent hydrogen, $C_{1-4}$alkyl or fluoro$C_{1-4}$alkyl;

$R^2$ represents hydrogen or halogen;

or when $R^2$ is adjacent to $R^1$, they may be joined together such that there is formed a 5-membered unsaturated ring containing an oxygen atom;

$R^3$ represents hydrogen, halogen, $C_{1-6}$alkyl, fluoro$C_{1-6}$alkyl, $C_{1-6}$alkoxy, fluoro$C_{1-6}$alkoxy, $C_{3-7}$cycloalkyl, $C_{3-7}$cycloalkyl$C_{1-4}$alkyl, cyano, $SR^a$, $SOR^a$, $SO_2R^a$, $NR^aR^b$, $NR^aCOR^{14}$, $COR^a$, $CO_2R^a$, $CONR^aR^b$ or $C_{1-4}$alkyl substituted by cyano, $CO_2R^a$ or $CONR^aR^b$ where $R^a$ and $R^b$ are as previously defined;

$R^4$ represents hydrogen or halogen;

$R^5$ represents hydrogen;

$R^6$ represents hydrogen, or $R^6$ represents $C_{1-6}$alkyl, substituted by a 5-membered heterocyclic ring containing 1, 2 or 3 nitrogen atoms and optionally substituted by a group of the formula $ZNR^7R^8$;

$R^7$ is hydrogen or $C_{1-4}$alkyl;

$R^8$ is hydrogen or $C_{1-4}$alkyl;

$R^9$ and $R^{10}$ each independently represent hydrogen;

$R^{14}$ represents $C_{1-6}$alkyl, $C_{1-6}$alkoxy, fluoro$C_{1-6}$alkyl or phenyl;

X is an oxygen atom or two hydrogen atoms;

Z is $C_{1-6}$alkylene; and the broken line represents an optional double bond;

or a pharmaceutically acceptable salt thereof.

13. A compound selected from:

(5R,6S)-3-(2-methoxy-5-trifluoromethoxyphenyl)-6-phenyl-1-oxa-7-aza-spiro[4.5]dec-3-ene;

(3S,5R,6S)-3-(2-methoxy-5-trifluoromethoxyphenyl)-6-phenyl-1-oxa-7-aza-spiro[4.5]decane;

(3S,5R,6S)-3-(2-methoxy-5-trifluoromethoxyphenyl)-6-phenyl-7-(1,2,4-triazolyl-3-methylene)-1-oxa-7-aza-spiro[4.5]decane;

(5R,6S)-3-(2-isopropoxy-5-trifluoromethoxyphenyl)-6-phenyl-1-oxa-7-aza-spiro[4.5]dec-3-ene;

(5R,6S)-3-(2-allyloxy-5-trifluoromethoxyphenyl)-6-phenyl-1-oxa-7-aza-spiro[4.5]dec-3-ene;

(5R,6S)-3-(5-trifluoromethoxy-2,3-dihydrobenzofuran-7-yl)-6-phenyl-1-oxa-7-aza-spiro[4.5]dec-3-ene;

(5R,6S)-3-(2-methoxy-5-(2,2,2-trifluoroethoxy)phenyl)-6-phenyl-1-oxa-7-aza-spiro[4.5]dec-3-ene;

(5R,6S)-3-(2,5-bis(2,2,2-trifluoroethoxy)phenyl)-6-phenyl-1-oxa-7-aza-spiro[4.5]dec-3-ene;

(5R,6S)-3-(2-difluoromethoxy-5-trifluoromethoxyphenyl)-6-phenyl-1-oxa-7-aza-spiro[4.5]dec-3-ene;

(5R,6S)-3-(2-(2,2,2-trifluoroethoxy)-5-trifluoromethoxyphenyl)-6-phenyl-1-oxa-7-aza-spiro[4.5]dec-3-ene;

(3S,5R,6S)-3-(2-isopropoxy-5-trifluoromethoxyphenyl)-6-phenyl-1-oxa-7-aza-spiro[4.5]decane;

(3S,5R,6S)-3-(5-trifluoromethoxy-2,3-dihydrobenzofuran-7-yl)-6-phenyl-1-oxa-7-aza-spiro[4.5]decane;

(3S,5R,6S)-3-(2-methoxy-5-(2,2,2-trifluoroethoxy)phenyl)-6-phenyl-1-oxa-7-aza-spiro[4.5]decane;

(3S,5R,6S)-3-(2,5-bis(2,2,2-trifluoroethoxy)phenyl)-6-phenyl-1-oxa-7-aza-spiro[4.5]decane;

(3S,5R,6S)-3-(2-difluoromethoxy-5-trifluoromethoxyphenyl)-6-phenyl-1-oxa-7-aza-spiro[4.5]decane;

(3S,5R,6S)-3-(2-(2,2,2-trifluoroethoxy)-5-trifluoromethoxyphenyl)-6-phenyl-1-oxa-7-aza-spiro[4.5]decane;

(3S,5R,6S)-3-(2-(2,2,2-trifluoroethoxy)-5-fluorophenyl)-6-phenyl-1-oxa-7-aza-spiro[4.5]decane;

(5R,6S)-3-(5-methanesulfonyl-2-methoxyphenyl)-6-phenyl-1-oxa-7-aza-spiro[4.5]dec-3-ene;

(3S,5R,6S)-3-(5-methanesulfonyl-2-methoxyphenyl)-6-phenyl-1-oxa-7-aza-spiro[4.5]decane;

(5R,6S)-3-[2-(trifluoromethoxy)phenyl]-6-phenyl-1-oxa-7-aza-spiro[4.5]dec-3-ene;

(3S,5R,6S)-3-[2-(trifluoromethoxy)phenyl]-6-phenyl-1-oxa-7-aza-spiro[4.5]decane;

(5R,6S)-3-[2-cyclobutoxy-5-(trifluoromethoxy)phenyl]-6-phenyl-1-oxa-7-aza-spiro[4.5]dec-3-ene;

(3S,5R,6S)-3-[2-cyclobutoxy-5-(trifluoromethoxy)phenyl]-6-phenyl-1-oxa-7-aza-spiro[4.5]decane;

(5R,6S)-3-(2-(2-fluoroethoxy)-5-(trifluoromethoxy)phenyl)-6-phenyl-1-oxa-7-aza-spiro[4.5]dec-3-ene;

(3S,5R,6S)-3-(2-(2-fluoroethoxy)-5-(trifluoromethoxy)-6-phenyl-1-oxa-7-aza-spiro[4.5]decane;

(5R,6S)-3-(2-(ethen-1-yl)-5-(trifluoromethoxy)phenyl)-6-phenyl-1-oxa-7-aza-spiro[4.5]dec-3-ene;

(3S,5R,6S)-3-(2-ethyl-5-(trifluoromethoxy)phenyl)-6-phenyl-1-oxa-7-aza-spiro[4.5]decane;

(5R,6S)-3-(2-benzyloxy-5-(trifluoromethoxy)phenyl)-6-phenyl-1-oxa-7-aza-spiro[4.5]dec-3-ene;

(3S,5R,6S)-3-(2-hydroxy-5-(trifluoromethoxy)phenyl)-6-phenyl-1-oxa-7-aza-spiro[4.5]decane;

(3S,5R,6S)-3-(2-(ethen-1-yl)-5-(trifluoromethoxy)phenyl)-6-phenyl-1-oxa-7-aza-spiro[4.5]decane;

(5R,6S)-3-(2-methoxyphenyl)-6-phenyl-1-oxa-7-aza-spiro[4.5]dec-3-ene;

(3S,5R,6S)-3-(2-methoxyphenyl)-6-phenyl-1-oxa-7-aza-spiro[4.5]decane;

3S,5R,6S)-3-(2-methoxy-5-(trifluoromethoxy)phenyl)-6-phenyl-1-oxa-7-aza-spiro[4.5]decan-2-one;

(5R,6S)-N-[4-methoxy-3-(6-phenyl-1-oxa-7-aza-spiro[4.5]dec-3-en-3-yl)phenyl]trifluoroacetamide;

(3S,5R,6S)-N-[4-methoxy-3-(6-phenyl-1-oxa-7-aza-spiro[4.5]decan-3-yl)phenyl]trifluoroacetamide;

(3S,5R,6S)-methyl N-[4-methoxy-3-(6-phenyl-1-oxa-7-aza-spiro[4.5]decan-3-yl)phenyl]-N-(methyl)carbamate;

(5R,6S)-N-[4-methoxy-3-(6-phenyl-1-oxa-7-aza-spiro[4.5]dec-3-en-3-yl)phenyl]-N-(methyl)trifluoroacetamide;

(3S,5R,6S)-N-[4-methoxy-3-(6-phenyl-1-oxa-7-aza-spiro[4.5]decan-3-yl)phenyl]-N-(methyl)trifluoroacetamide;

(5R,6S)-N-[4-isopropoxy-3-(6-phenyl-1-oxa-7-aza-spiro[4.5]dec-3-en-3-yl)phenyl]-N-(methyl)trifluoroacetamide;

(3S,5R,6S)-N-[4-isopropoxy-3-(6-phenyl-1-oxa-7-aza-spiro[4.5]decan-3-yl)phenyl]-N-(methyl)trifluoroacetamide;

(5R,6S)-N-[4-(difluoromethoxy)-3-(6-phenyl-1-oxa-7-aza-spiro[4.5]dec-3-en-3-yl)phenyl]-N-(methyl)trifluoroacetamide;

(3S,5R,6S)-N-[4-(difluoromethoxy)-3-(6-phenyl-1-oxa-7-aza-spiro[4.5]decan-3-yl)phenyl]-N-(methyl)trifluoroacetamide;

(5R,6S)-N-[4-methoxy-3-(6-phenyl-1-oxa-7-aza-spiro[4.5]dec-3-en-3-yl)phenyl]-N-(2,2,2-trifluoroethyl)acetamide;

(3S,5R,6S)-N-[4-methoxy-3-(6-phenyl-1-oxa-7-aza-spiro[4.5]decan-3-yl)phenyl]-N-(2,2,2-trifluoroethyl)acetamide;

(3S,5R,6S)-N-[4-methoxy-3-(6-phenyl-1-oxa-7-aza-spiro[4.5]decan-3-yl)phenyl]-N-(methyl)benzamide;

(5R,6S)-3-[5-methylamino-2-(trifluoromethoxy)phenyl]-6-phenyl-1-oxa-7-aza-spiro[4.5]dec-3-ene;

(3S,5R,6S)-3-[5-methylamino-2-(trifluoromethoxy)phenyl-1-oxa-7-aza-spiro[4.5]decane;

(5R,6S)-N-methyl-N-[3-(6-phenyl-1-oxa-7-aza-spiro[4.5]dec-3-en-3-yl)-4-(trifluoromethoxy)phenyl]trifluoroacetamide;

(3S,5R,6S)-N-methyl-N-[3-(6-phenyl-1-oxa-7-aza-spiro[4.5]decan-3-yl)-4-(trifluoromethoxy)phenyl]trifluoroacetamide;

(5R,6S)-3-[2-ethoxy-5-(trifluoromethoxy)phenyl]-6-phenyl-1-oxa-7-aza-spiro[4.5]dec-3-ene;

(3S,5R,6S)-3-[2-ethoxy-5-(trifluoromethoxy)phenyl]-6-phenyl-1-oxa-7-aza-spiro[4.5]decane;

(5R,6S)-3-[2-(trifluoromethylthio)phenyl]-6-phenyl-1-oxa-7-aza-spiro[4.5]dec-3-ene;

(3S,5R,6S)-3-[2-(trifluoromethylthio)phenyl]-6-phenyl-1-oxa-7-aza-spiro[4.5]decane;

(5R,6S)-3-[2-(2,2,2-trifluoroethoxy)-5-(trifluoromethyl)phenyl)-6-phenyl-1-oxa-7-aza-spiro[4.5]dec-3-ene;

(3S,5R,6S)-3-[2-(2,2,2-trifluoroethoxy)-5-(trifluoromethyl)phenyl)-6-phenyl-1-oxa-7-aza-spiro[4.5]decane;

(5R,6S)-3-[2-isopropoxy-5-(trifluoromethyl)phenyl]-6-phenyl-1-oxa-7-aza-spiro[4.5]dec-3-ene;

(3S,5R,6S)-3-[2-isopropoxy-5-(trifluoromethyl)phenyl]-6-phenyl-1-oxa-7-aza-spiro[4.5]decane;

(3S,5R,6S)-3-[2-cyclopropyl-5-(trifluoromethoxy)phenyl]-6-phenyl-1-oxa-7-aza-spiro[4.5]decane;

(3S,5R,6S)-3-(5-bromo-2-isopropoxyphenyl)-6-phenyl-1-oxa-7-aza-spiro[4.5]decane;

(3S,5R,6S)-3-(5-cyano-2-isopropoxyphenyl)-6-phenyl-1-oxa-7-aza-spiro[4.5]decane;

(3S,5R,6S)-3-[5-cyano-2-(difluoromethoxy)phenyl]-6-phenyl-1-oxa-7-aza-spiro[4.5]decane;

(3S,5R,6S)-3-[5-cyano-2-(2,2,2-trifluoroethoxy)phenyl]-6-phenyl-1-oxa-7-aza-spiro[4.5]decane;

(3S,5R,6S)-3-[5-cyano-2-(cyclobutyloxy)-phenyl]-6-phenyl-1-oxa-7-aza-spiro[4.5]decane;

(5R,6S)-3-[2-cyano-5-(trifluoromethoxy)phenyl]-6-phenyl-1-oxa-7-aza-spiro[4.5]dec-3-ene;

(3S,5R,6S)-3-[2-(cyclopropylmethyloxy)-5-(trifluoromethoxy)phenyl]-6-phenyl-1-oxa-7-aza-spiro[4.5]decane;

(3S,5R,6S)-3-[2-methoxy-5-(trifluoromethyl)phenyl]-6-phenyl-1-oxa-7-aza-spiro[4.5]decane;

(3S,5R,6S)-3-[2-methoxy-5-(trifluoromethyl)phenyl]-6-phenyl-1-oxa-7-(1,2,4-triazolyl-3-methyl)-7-aza-spiro[4.5]decane;

(5R,6S)-3-(2-methanesulfonylphenyl)-6-phenyl-1-oxa-7-aza-spiro[4.5]dec-3-ene;

(3S,5R,6S)-3-(2-methanesulfonylphenyl)-6-phenyl-1-oxa-7-aza-spiro[4.5]decane;

(5R,6S)-methyl [4-hydroxy-3-(6-phenyl-1-oxa-7-aza-spiro[4.5]dec-3-en-3-yl)phenyl]ethanoate;

(3S,5R,6S)-methyl [4-hydroxy-3-(6-phenyl-1-oxa-7-aza-spiro[4.5]decan-3-yl)phenyl]ethanoate;

(3S,5R,6S)-3-[5-(cyanomethyl)-2-methoxyphenyl]-6-phenyl-1-oxa-7-aza-spiro[4.5]decane;

(5R,6S)-[4-methoxy-3-(6-phenyl-1-oxa-7-aza-spiro[4.5]dec-3-en-3-yl)phenyl]carboxamide;

(3S,5R,6S)-[4-methoxy-3-(6-phenyl-1-oxa-7-aza-spiro[4.5]decan-3-yl)phenyl]carboxamide;

(3S,5R,6S)-3-(5-cyano-2-methoxyphenyl)-6-phenyl-1-oxa-7-aza-spiro[4.5]decane;

(5R,6S)-methyl [4-methoxy-3-(6-phenyl-1-oxa-7-aza-spiro[4.5]dec-3-en-3-yl)phenyl]ethanoate;

(3S,5R,6S)-methyl [4-methoxy-3-(6-phenyl-1-oxa-7-aza-spiro[4.5]decan-3-yl)phenyl]ethanoate;

(3S,5R,6S)-3-(5-(trifluoromethoxy)-2-(trifluoromethylsulfonyloxy)phenyl)-6-phenyl-1-oxa-7-aza-spiro[4.5]decane;

(3S,5R,6S)-7-{[5-(dimethylaminomethyl)-1H-[1,2,3]triazol-4-yl]methyl}-3-[2-isopropoxy-5-(trifluoromethyl)phenyl]-6-phenyl-1-oxa-7-aza-spiro[4.5]decane;

(3S,5R,6S)-3-[5-fluoro-2-(2,2,2-trifluoroethoxy)phenyl)-6-phenyl-1-oxa-7-(1,2,4-triazolyl-3-methyl)-7-aza-spiro[4.5]decane;

(5R,6S)-3-[2-dimethylamino-5-(trifluoromethoxy)phenyl]-6-phenyl-1-oxa-7-aza-spiro[4.5]dec-3-ene;

(3S,5R,6S)-3-[2-dimethylamino-5-(trifluoromethoxy)phenyl]-6-phenyl-1-oxa-7-aza-spiro[4.5]decane;

or a pharmaceutically acceptable salt thereof.

14. A compound selected from:

(3R,5R,6S)-3-(2-methoxy-5-(trifluoromethoxy)phenyl)-6-phenyl-1-oxa-7-aza-spiro[4.5]decane;

(3R,5R,6S)-3,6-bis(phenyl)-1-oxa-7-aza-spiro[4.5]decane;

(3R,5R,6S)-3-(2-methoxyphenyl)-6-phenyl-1-oxa-7-aza-spiro[4.5]decane;

(3R,5R,6S)-7-benzyl-3-(2-methoxy-5-trifluoromethoxyphenyl)-6-phenyl-1-oxa-7-aza-spiro[4.5]decane;

(3R,5R,6S)-3-(2-methoxy-5-(trifluoromethyl)phenyl)-6-phenyl-1-oxa-7-aza-spiro[4.5]decane;

(3R,5R,6S)-3-[2-hydroxy-5-(trifluoromethoxy)phenyl]-6-phenyl-1-oxa-7-aza-spiro[4.5]decane;

(3R,5R,6S)-3-(5-hydroxy-2-isopropoxyphenyl)-6-phenyl-1-oxa-7-aza-spiro[4.5]decane;
(3R,5R,6S)-3-[2,4-bis(methoxy)phenyl]-6-phenyl-1-oxa-7-aza-spiro[4.5]decane;
(3R,5R,6S)-3-[2-difluoromethoxy-5-(trifluoromethoxy)phenyl]-6-phenyl-1-oxa-7-aza-spiro[4.5]decane;
(3R,5R,6S)-3-[2-isopropoxy-5-(trifluoromethoxy)phenyl]-6-phenyl-1-oxa-7-aza-spiro[4.5]decane;
(3R,5R,6S)-3-[2-(ethen-1-yl)-5-(trifluoromethoxy)phenyl]-6-phenyl-1-oxa-7-aza-spiro[4.5]decane;
(3R,5R,6S)-3-[2-(2,2,2-trifluoroethoxy)-5-(trifluoromethyl)phenyl]-6-phenyl-1-oxa-7-aza-spiro[4.5]decane;
(3R,5R,6S)-3-[2,5-bis(difluoromethoxy)phenyl]-6-phenyl-1-oxa-7-aza-spiro[4.5]decane;
(3R,5R,6S)-3-[5-fluoro-2-(difluoromethoxy)phenyl]-6-phenyl-1-oxa-7-aza-spiro[4.5]decane;
(3R,5R,6S)-3-[5-fluoro-2-(2,2,2-trifluoroethoxy)phenyl]-6-phenyl-1-oxa-7-aza-spiro[4.5]decane;
(3R,5R,6S)-3-(5-fluoro-2-isopropoxyphenyl)-6-phenyl-1-oxa-7-aza-spiro[4.5]decane;
(3R,5R,6S)-3-[2-isopropoxy-5-(2,2,2-trifluoroethoxy)phenyl]-6-phenyl-1-oxa-7-aza-spiro[4.5]decane;
(3R,5R,6S)-3-[2,5-bis(isopropoxy)phenyl]-6-phenyl-1-oxa-7-aza-spiro[4.5]decane;
(3R,5R,6S)-3-(5-chloro-2-methoxyphenyl)-6-phenyl-1-oxa-7-aza-spiro[4.5]decane;
(3R,5R,6S)-3-[2-(2,2,2-trifluoroethoxy)-5-(trifluoromethoxy)phenyl]-6-phenyl-1-oxa-7aza-spiro[4.5]decane;
(3R,5R,6S)-3-[2-(cyclopropylmethoxy)-5-(trifluoromethoxy)phenyl]-6-phenyl-1-oxa-7-aza-spiro[4.5]decane;
(3R,5R,6S)-3-[2-benzyloxy-5-(trifluoromethoxy)phenyl]-6-phenyl-1-oxa-7-aza-spiro[4.5]decane;
(3R,5R,6S)-3-[5-(difluoromethoxy)-2-(2,2,2-trifluoroethoxy)phenyl]-6-phenyl-1-oxa-7-aza-spiro[4.5]decane;
(3R,5R,6S)-3-[2-(2,2-difluoroethoxy)-5-(difluoromethoxy)phenyl]-6-phenyl-1-oxa-7-aza-spiro[4.5]decane;
(3R,5R,6S)-3-[2-(cyclobutoxy)-5-(trifluoromethoxy)phenyl]-6-phenyl-1-oxa-7-aza-spiro[4.5]decane;
(3R,5R,6S)-3-[2-(2-methoxyethoxy)-5-(trifluoromethoxy)phenyl]-6-phenyl-1-oxa-7-aza-spiro[4.5]decane;
(3R,5R,6S)-3-[5-(trifluoromethoxy)-2-(trifluoromethylsulfonyloxy)phenyl]-6-phenyl-1-oxa-7-aza-spiro[4.5]decane;
(3R,5R,6S)-3-[2-(2,2-difluoroethoxy)-5-(trifluoromethoxy)phenyl]-6-phenyl-1-oxa-7-aza-spiro[4.5]decane;
(3R,5R,6S)-3-[2-cyclopropyl-5-(trifluoromethoxy)phenyl]-6-phenyl-1-oxa-7-aza-spiro[4.5]decane;
(3R,5R,6S)-3-(5-cyano-2-hydroxyphenyl)-6-phenyl-1-oxa-7-aza-spiro[4.5]decane;
(3R,5R,6S)-3-[5-cyano-2-(2,2,2-trifluoroethoxy)phenyl]-6-phenyl-1-oxa-7-aza-spiro[4.5]decane;
(3R,5R,6S)-3-(5-cyano-2-isopropoxyphenyl)-6-phenyl-1-oxa-7-aza-spiro[4.5]decane;
(3R,5R,6S)-3-[2-(ethen-1-yl)-5-(trifluoromethoxy)phenyl]-6-phenyl-1-oxa-7-aza-spiro[4.5]decane;
(3R,5R,6S)-3-[2-acetyl-5-(trifluoromethoxy)phenyl]-6-phenyl-1-oxa-7-aza-spiro[4.5]decane;
(3R,5R,6S)-3-[2-formyl-5-(trifluoromethoxy)phenyl]-6-phenyl-1-oxa-7-aza-spiro[4.5]decane;
(3R,5R,6S)-3-(3-fluoro-2-methoxy-5-(trifluoromethoxy)phenyl)-6-phenyl-1-oxa-7aza-spiro[4.5]decane;
(3R,5R,6S)-3-[2-cyano-5-(trifluoromethoxy)phenyl]-6-phenyl-1-oxa-7-aza-spiro[4.5]decane;
(3R,5R,6S)-3-[2-ethyl-5-(trifluoromethoxy)phenyl]-6-phenyl-1-oxa-7-aza-spiro[4.5]decane;
(3R,5R,6S)-3-(6-fluoro-2-methoxyphenyl)-6-phenyl-1-oxa-7-aza-spiro[4.5]decane;

or a pharmaceutically acceptable salt thereof.

15. A compound selected from:
(3S,5R,6S)-3-(2-cyclopropoxy-5-(trifluoromethoxy)phenyl)-6-phenyl-1-oxa-7-aza-spiro[4.5]decane;
(3R,5R,6S)-3-[2-cyclopropoxy-5-(trifluoromethoxy)phenyl]-6-phenyl-1-oxa-7-aza-spiro[4.5]decane;
(3S,5R,6S)-3-[2-cyclopropoxy-5-(trifluoromethyl)phenyl]-6-phenyl-1-oxa-7-aza-spiro[4.5]decane;
(3R,5R,6S)-3-[2-cyclopropoxy-5-(difluoromethoxy)phenyl]-6-phenyl-1-oxa-7-aza-spiro[4.5]decane;
(3R,5R,6S)-3-[2-cyclopropoxy-5-(trifluoromethoxy)phenyl]-6-(4-fluorophenyl)-1-oxa-7-aza-spiro[4.5]decane;
(3R,5R,6S)-3-[2-cyclopropoxy-5-(trifluoromethyl)phenyl]-6-phenyl-1-oxa-7-aza-spiro[4.5]decane;

or a pharmaceutically acceptable salt thereof.

16. A pharmaceutical composition comprising an effective amount of a compound as claimed in claim 1 in association with a pharmaceutically acceptable carrier or excipient.

17. A method for the treatment of physiological disorders associated with an excess of tachykinins, which method comprises administration to a patient in need thereof of a tachykinin reducing amount of a compound according to claim 1.

18. A method according to claim 17 for the treatment or prevention of pain or inflammation.

19. A method according to claim 17 for the treatment or prevention of pain or inflammation associated with migraine.

20. A method according to claim 17 for the treatment or prevention of pain or inflammation associated with postherpetic neuralgia.

21. A method according to claim 17 for the treatment or prevention of emesis.

22. A process for the preparation of a compound as claimed in claim 1 which comprises:

(A.1), where the double bond represented by the broken line is absent, reducing by catalytic hydrogenation or with trifluoroacetic acid and triethylsilane a compound of formula (IIA)

(IIA)

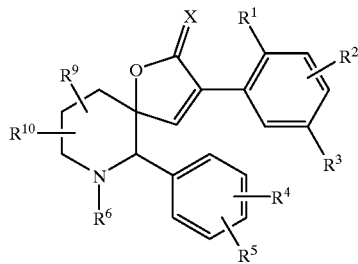

wherein $R^1$, $R^2$, $R^3$, $R^4$, $R^5$, $R^6$, $R^9$, $R^{10}$ and X are as defined in claim 1; or (A.2), where the double bond represented by the broken line is absent and X is two hydrogen atoms, reducing by catalytic hydrogenation or with trifluoroacetic acid and triethylsilane a compound of formula (IIB)

(IIB)

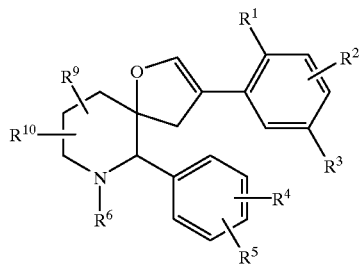

or (B), where the broken line represents a double bond, reacting a compound of formula (III)

(III)

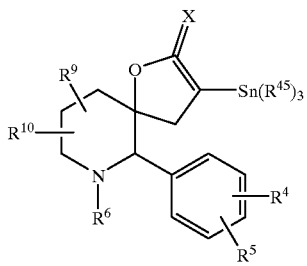

wherein each $R^{45}$ is a $C_{1-4}$ alkyl group, with a compound of formula (IV)

(IV)

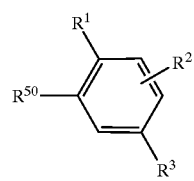

wherein $R^{50}$ is a leaving group; or (C), reacting a compound of formula (V)

(V)

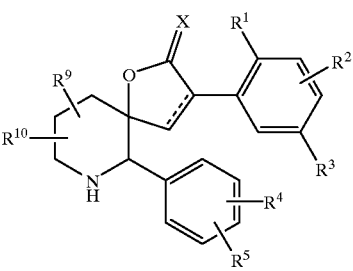

with a compound of formula (VI):

$$LG\text{—}R^{6a} \qquad (VI)$$

where $R^{6a}$ is a group of the formula $R^6$ as defined in claim 1 (other than H) or a precursor therefor and LG is a leaving group; and, if $R^{6a}$ is a precursor group, converting it to a group $R^6$; or (D), where $R^1$ is $C_{1-6}$alkoxy, fluoro$C_{1-6}$alkoxy, $C_{2-6}$alkenoxy, $C_{3-7}$cycloalkoxy, $C_{3-7}$cycloalkyl$C_{1-4}$alkoxy or benzyloxy, reacting a compound of formula (VII)

(VII)

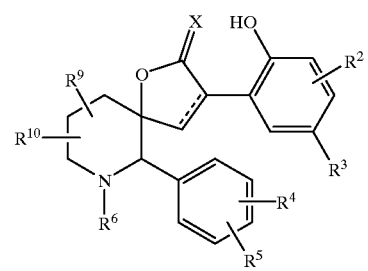

with an appropriate alkyl-, fluoroalkyl-, alkenyl-, cycloalkyl-, cycloalkylalkyl- or aralkyl-halide, in the presence of a base selected from an alkali metal hydride; or (E), cyclising a compound of formula (VIII)

(VIII)

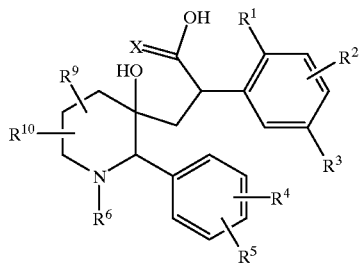

using hydrating reagents selected from methanesulfonyl chloride or phenylsulfonyl chloride; or (F), where the broken line represents a double bond, dehydrating of a compound of formula (IX)

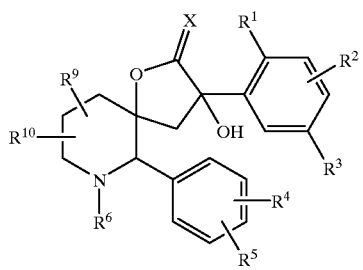

(IX)

using an acid such as trifluoroacetic acid; or (G), where the double bond represented by the broken line is absent, reacting a compound of formula (X)

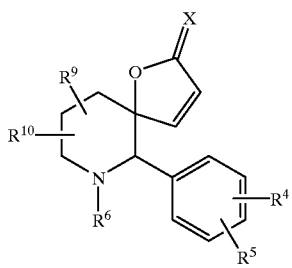

(X)

with a compound of formula (IV), under the conditions of a reductive Heck reaction; or (H), reacting a compound of formula (XX)

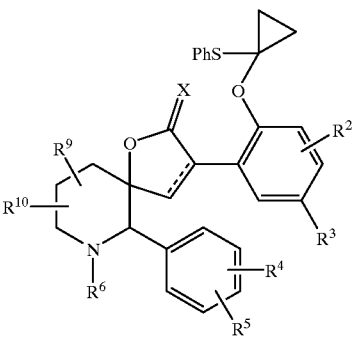

(XX)

with lithium naphthalenide;

each process being followed, where necessary, by the removal of any protecting group where present;

and when the compound of formula (I) is obtained as a mixture of enantiomers or diastereoisomers, optionally resolving the mixture to obtain the desired enantiomer;

and/or, if desired, converting the resulting compound of formula (I) or a salt thereof, into a pharmaceutically acceptable salt thereof.

23. A compound which is:

(3R,5R,6S)-3-[2-cyclopropoxy-5-(trifluoromethoxy) phenyl]-6-phenyl-1-oxa-7aza-spiro[4.5]decane;

or a pharmaceutically acceptable salts thereof.

24. A compound which is:

(3R,5R,6S)-3-[2-cyclopropoxy-5-(trifluoromethoxy) phenyl]-6-phenyl-1-oxa-7aza-spiro[4,5]decane hydrochloride.

* * * * *